US009546385B2

(12) United States Patent
Argyros et al.

(10) Patent No.: US 9,546,385 B2
(45) Date of Patent: Jan. 17, 2017

(54) GENETICALLY MODIFIED CLOSTRIDIUM THERMOCELLUM ENGINEERED TO FERMENT XYLOSE

(75) Inventors: Aaron Argyros, White River Junction, VT (US); Trisha Barrett, Bradford, VT (US); Nicky Caiazza, Rancho Santa Fe, CA (US); Dave Hogsett, Grantham, NH (US)

(73) Assignee: Enchi Corporation, Wellesley Hills, MA (US)

( * ) Notice: Subject to any disclaimer, the term of this patent is extended or adjusted under 35 U.S.C. 154(b) by 82 days.

(21) Appl. No.: 13/995,402

(22) PCT Filed: Dec. 22, 2011

(86) PCT No.: PCT/US2011/066968
§ 371 (c)(1),
(2), (4) Date: Aug. 28, 2013

(87) PCT Pub. No.: WO2012/088467
PCT Pub. Date: Jun. 28, 2012

(65) Prior Publication Data
US 2014/0370561 A1 Dec. 18, 2014

Related U.S. Application Data

(60) Provisional application No. 61/426,151, filed on Dec. 22, 2010.

(51) Int. Cl.
| | | |
|---|---|---|
| C12P 7/06 | (2006.01) |
| C12N 9/12 | (2006.01) |
| C12N 15/74 | (2006.01) |
| C12N 1/20 | (2006.01) |
| C12N 9/92 | (2006.01) |
| C12P 7/54 | (2006.01) |
| C12P 7/10 | (2006.01) |

(52) U.S. Cl.
CPC . *C12P 7/06* (2013.01); *C12N 1/20* (2013.01); *C12N 9/1205* (2013.01); *C12N 9/92* (2013.01); *C12N 15/74* (2013.01); *C12P 7/065* (2013.01); *C12P 7/10* (2013.01); *C12P 7/54* (2013.01); *C12Y 207/01017* (2013.01); *C12Y 503/01005* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| 7,704,719 B2 | 4/2010 | Wang et al. |
|---|---|---|
| 2008/0113415 A1 | 5/2008 | Wang et al. |
| 2008/0305529 A1 | 12/2008 | Wang et al. |
| 2009/0221048 A1 | 9/2009 | Wang et al. |
| 2010/0028966 A1 | 2/2010 | Blanchard et al. |
| 2010/0159536 A1 | 6/2010 | Sweeney et al. |
| 2010/0297721 A1 | 11/2010 | Hogsett et al. |
| 2010/0306881 A1 | 12/2010 | Harris et al. |

FOREIGN PATENT DOCUMENTS

| WO | WO 2006/009434 A1 | 1/2006 |
|---|---|---|
| WO | WO 2008/141174 A2 | 11/2008 |
| WO | WO 2010/056450 A2 | 5/2010 |
| WO | WO 2010/105194 A2 | 9/2010 |
| WO | WO 2011/022651 A1 | 2/2011 |
| WO | WO 2011/140386 A2 | 11/2011 |
| WO | WO 2012/088467 | 6/2012 |

OTHER PUBLICATIONS

Accession ABX4188. Nov. 20, 2007.*
Accession ADL69946. Aug. 16, 2010.*
Fan et al. Biotechnol Lett. May 2009;31(5):751-7. Epub Jan. 25, 2009*
Chica et al. Curr Opin Biotechnol. Aug. 2005;16(4):378-84.*
Sen et al. Appl Biochem Biotechnol. Dec. 2007;143(3):212-23.*
Accession ABX41884. Nov. 20, 2007.*
Accession AAQ93072. Oct. 14, 2003.*
Accession AEE48998. Feb. 9, 2006.*
Accession D9TTQ7. Oct. 5, 2010.*
Argyros, D.A., et al., "High Ethanol Titers from Cellulose by Using Metabolically Engineered Thermophilic Anaerobic Microbes," *Applied and Environmental Microbiology* 77(23):8288-8294, American Society for Microbiology, United States (Dec. 2011).
Bowie, J.U., et al., "Deciphering the Message in Protein Sequences: Tolerance to Amino Acid Substitutions," *Science* 247:1306-1310, American Association for the Advancement of Science, United States (1990).
Brutlag, D.L., et al., "Improved Sensitivity of Biological Sequence Database Searches," *Comp. App. Biosci.* 6(3):237-245, Oxford University Press, United Kingdom (1990).
Cunningham, B.C. and Wells, J.A., "High-Resolution Epitope Mapping of hGH-Receptor Interactions by Alanine-Scanning Mutagenesis," *Science* 244:1081-1085, American Association for the Advancement of Science, United States (1989).

(Continued)

*Primary Examiner* — Christian Fronda
(74) *Attorney, Agent, or Firm* — Sterne, Kessler, Goldstein & Fox P.L.L.C.

(57) ABSTRACT

One aspect of the invention relates to industrial bioconversion of the xylose portion of biomass materials into fuels and chemicals. Another aspect of the invention relates to industrial bioconversion of the xylan portion of biomass materials into fuels and chemicals. In one embodiment, the invention is directed to the bacterium *Clostridium thermocellum*, a highly cellulolytic organism that has much potential as a biocatalyst in a consolidated bioprocess configuration. In some embodiments, the invention is a genetic modification that confers the ability to ferment xylose to *C. thermocellum* and the strains created with this modification. In some embodiments, the genetic modification is composed of two genes contained in an operon from *T. saccharolyticum*. The genes express proteins with xylose isomerase (XI) and xylulokinase activites (XK). In other embodiments, the invention relates to a recombinant *Clostridium thermocellum* host cell capable of fermenting xylan.

26 Claims, 10 Drawing Sheets

(56) References Cited

OTHER PUBLICATIONS

Gu, Y., et al., "Reconstruction of xylose utilization pathway and regulons in Firmicutes," *BMC Genomics* 11:255, 14 pages, BioMed Central Ltd., England (Apr. 2010).

Jeppsson M., et al. "Reduced Oxidative Pentose Phosphate Pathway Flux in Recombinant Xylose-Utilizing *Saccharomyces cerevisiae* Strains Improves the Ethanol Yield from Xylose," *Appl. Environ. Microbiol.* 68(4):1604-1609, American Society for Microbiology, Washington, United States (2002).

Karhumaa, K., et al., "Comparison of the xylose reductase-xylitol dehydrogenase and the xylose isomerase pathways for xylose fermentation by recombinant *Saccharomyces cerevisiae*," *Microbiol Cell Factories* 6(5):1-10, BioMed Central, England (2007).

Ladisch, M.R., et al., "Symposium on Fuels and Chemicals from Biomass," *Biotechnology and Bioengineering XXV(1)*:1-2, John Wiley & Sons, Inc., England (1983).

Nakamura, Y., et al., "Codon Usage Tabulated from International DNA Sequence Databases: Status for the Year 2000," *Nucl. Acids Res.* 28(0:292, Oxford University Press, United Kingdom (2000).

Van Walsum, G.P. and Lynd, L.R., "Allocation of ATP to Synthesis of Cells and Hydrolytic Enzymes in Cellulolytic Fermentative Microorganisms: Bioenergetics, Kinetics, and Bioprocessing," *Biotechnol Bioeng* 58:316-320, John Wiley & Sons, Inc., England (1998).

Xiao, H., at al., "Confirmation and Elimination of Xylose Metabolism Bottlenecks in Glucose Phosphoenolpyruvate-Dependent Phosphotransferase System-Deficient *Clostridium acetobutylicum* for Simultaneous Utilization of Glucose, Xylose, and Arabinose," *Applied Environmental Microbiology* 77(22):7886-7895, American Society for Microbiology, United States (Nov. 2011).

"backtranseq," accessed at http://ernboss.bioinformatics.nl/cgi-bin/emboss/backtranseq on Aug. 15, 2013.

"Codon optimization tool," accessed at http://www.entelechon.com/2008/10/backtranslation-tool/ on Aug. 15, 2013.

"Codon Usage Database" accessed at http://www.kazusa.or.jp/codon/ on Apr. 23, 2013.

International Search Report for International Application No. PCT/US2011/066968, USPTO, United States, mailed Jun. 22, 2012.

International Preliminary Report on Patentability and Written Opinion for International Application No. PCT/US2011/066968, USPTO, United States, mailed Jun. 22, 2012.

\* cited by examiner

```
                        SEQUENCE LISTING

<160> NUMBER OF SEQ ID NOS: 62

<210> SEQ ID NO 1
<211> LENGTH: 1323
<212> TYPE: DNA
<213> ORGANISM: Thermoanaerobacterium saccharolyticum
<220> FEATURE:
<221> NAME/KEY: misc_feature
<222> LOCATION: (1)..(1323)
<223> OTHER INFORMATION: Xylose isomerase

<400> SEQUENCE: 1
atgaataaat attttgagaa cgtatctaaa ataaaatatg aaggaccaaa atcaaacaat      60
ccttattctt ttaaatttta caatccagaa gaagtaatcg atggcaagac gatggaggag    120
catctacgct tttctatagc ttactggcac acttttactg ctgatggaac agatcaattt    180
ggcaaagcta ccatgcaaag accatggaac cactacacag atcctatgga catagcaaag    240
gcaagggtag aagcagcatt tgagtttttt gataagataa atgcaccttt cttctgcttc    300
catgacaggg atattgcacc tgaaggagac actcttagag agacaaacaa aaacttagat    360
acaatagttg ccatgataaa ggattacttg aagaccagca agacgaaagt tttgtggggc    420
accgcaaatc ttttctccaa tccgagattt gtacatggtg catcaacatc ctgcaatgct    480
gatgttttcg catattctgc agctcaagtt aaaaaagctc ttgagattac taaggagctt    540
ggcggcgaaa actacgtatt ctggggtggc agagaaggat atgaaacact tctcaataca    600
gacatggagt ttgagcttga caactttgca agattttgc acatggctgt tgactacgcg    660
aaggaaatcg gctttgaagg ccagttcttg attgagccga agccaaagga gcctacgaaa    720
caccaatacg actttgacgt ggcaaatgta ttggcattct tgagaaaata cggccttgac    780
aaatatttca aagtgaatat cgaggcaaac catgcgacat tggcattcca cgacttccaa    840
catgagctaa gatacgccag aataaacggt gtattaggat caattgacgc aaatacaggc    900
gatatgcttt taggatggga tacagaccag ttccctacag atatacgcat gacaacgctt    960
gctatgtatg aagtcataaa gatgggtgga tttgacaaag gcggccttaa cttcgatgca   1020
aaagtaagac gtgcttcatt tgaaccagaa gatctttct taggtcatat agccggaatg   1080
gatgcctttg caaaaggctt caaagttgct tacaaacttg tgaaagatgg cgtatttgac   1140
aagttcatcg aggaaagata cgcaagctac aaagacggca ttggcgctga cattgtaagc   1200
gggaaagctg acttcaagag ccttgaaaag tacgcattag agcacagcca gattgtcaac   1260
aaatcaggca ggcaagagct gttagaatca atcctaaatc agtatttgtt tgcagaataa   1320
```

-continued

```
tga                                                           1323
```

<210> SEQ ID NO 2
<211> LENGTH: 1506
<212> TYPE: DNA
<213> ORGANISM: Thermoanaerobacterium saccharolyticum
<220> FEATURE:
<221> NAME/KEY: misc_feature
<222> LOCATION: (1)..(1506)
<223> OTHER INFORMATION: Xylulokinase

<400> SEQUENCE: 2

```
atgtattttt tagggataga tttagggaca tcatcagtta agataatact gatgaatgaa       60
agcggcaatg tggtatcaag cgtttcaaaa gaatatcctg tgtactatcc agagccaggc      120
tgggctgagc aaaatccaga agattggtgg aatggcacaa gggatggaat aagagagatt      180
attgcgaaaa gcggcgtaaa tggcgatgaa ataaaggggtg ttggcttaag cgggcagatg      240
catggactgg tgcttttaga caaagacaat aacgttttaa cgccagccat actttggtgt      300
gaccagagga cacaggaaga atgcgactac atcacagaga aaataggaaa agaaggcctt      360
ttgaagtaca cagggaataa agcattgaca ggttttactg caccaaagat attatgggta      420
aagaagcacc ttaaagacgt atatgaaaga tcgctcata tccttttgcc aaaagattat      480
ataaggttta aattgacagg tgagtacgct acagaagttt cagatgcatc aggtacactt      540
cttttcgatg tggaaaatag aagatggtca aggaaatga tagacatatt tgaaataccg      600
gaaaaagccc ttcctaagtg ctacgaatca acagatgtca cagggtatgt caccaaagag      660
gcagcagatt tgacagggct tcatgaaggg actattgtcg taggcggtgg tggtgaccaa      720
gccagcggcg ctgtaggcac tggcacggtg aaaagcggca tagtgtccat cgcattagga      780
acttcaggct tcgtatttgc atcacaggac aagtacgcag cagatgatga gcttaggctt      840
cactcattct gccatgcaaa cggcaaatgg catgtgatgg tgtcatgct ttcggctgca      900
tcatgtctta atggtgggt agatgatgta aataattaca agaccgatgt tatgacattt      960
gatggactct tagaagaagc agagaaggtg aagccaggca gtgatggatt gatattcttg     1020
ccatacctga tgggtgaaag gaccccttac agcgatcctt atgcgagagg cagctttgta     1080
ggtttaacaa ttacacacaa tagaagccac atgacaagat ctatattaga aggcgtcgca     1140
tttggactta gggattcgct ggagcttata aaggctttaa atatacctgt aaatgaagcc     1200
agggtaagtg gtggtggtgc taaaagcagg cttttggagc aaatacttgc cgatgtattc     1260
aatgtaagga tagacatgat aaatgctaca gaaggacctt catttggtgc agcaataatg     1320
gcgtctgtgg gatatggcct ttacaaaaat gtagatgatg catgcaatag tttaataaaa     1380
gttacagaca gcgtatatcc aatcaaagaa aacgtcgaaa agtacaacaa actgtatcca     1440
atctacgtga gcttgtattc aaggcttaaa ggcgcctttg aagaaattgg gaagttggat     1500
ttgtaa                                                                1506
```

<210> SEQ ID NO 3
<211> LENGTH: 439
<212> TYPE: PRT
<213> ORGANISM: Thermoanaerobacterium saccharolyticum
<220> FEATURE:
<221> NAME/KEY: misc_feature
<222> LOCATION: (1)..(439)
<223> OTHER INFORMATION: Xylose isomerase

<400> SEQUENCE: 3

Met Asn Lys Tyr Phe Glu Asn Val Ser Lys Ile Lys Tyr Glu Gly Pro

-continued

```
1               5                   10                  15
Lys Ser Asn Asn Pro Tyr Ser Phe Lys Phe Tyr Asn Pro Glu Glu Val
                20                  25                  30
Ile Asp Gly Lys Thr Met Glu Glu His Leu Arg Phe Ser Ile Ala Tyr
                35                  40                  45
Trp His Thr Phe Thr Ala Asp Gly Thr Asp Gln Phe Gly Lys Ala Thr
            50                  55                  60
Met Gln Arg Pro Trp Asn His Tyr Thr Asp Pro Met Asp Ile Ala Lys
65                  70                  75                  80
Ala Arg Val Glu Ala Ala Phe Glu Phe Phe Asp Lys Ile Asn Ala Pro
                85                  90                  95
Phe Phe Cys Phe His Asp Arg Asp Ile Ala Pro Glu Gly Asp Thr Leu
                100                 105                 110
Arg Glu Thr Asn Lys Asn Leu Asp Thr Ile Val Ala Met Ile Lys Asp
                115                 120                 125
Tyr Leu Lys Thr Ser Lys Thr Lys Val Leu Trp Gly Thr Ala Asn Leu
            130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                165                 170                 175
Thr Lys Glu Leu Gly Gly Glu Asn Tyr Val Phe Trp Gly Gly Arg Glu
            180                 185                 190
Gly Tyr Glu Thr Leu Leu Asn Thr Asp Met Glu Phe Glu Leu Asp Asn
            195                 200                 205
Phe Ala Arg Phe Leu His Met Ala Val Asp Tyr Ala Lys Glu Ile Gly
210                 215                 220
Phe Glu Gly Gln Phe Leu Ile Glu Pro Lys Pro Lys Glu Pro Thr Lys
225                 230                 235                 240
His Gln Tyr Asp Phe Asp Val Ala Asn Val Leu Ala Phe Leu Arg Lys
                245                 250                 255
Tyr Gly Leu Asp Lys Tyr Phe Lys Val Asn Ile Glu Ala Asn His Ala
                260                 265                 270
Thr Leu Ala Phe His Asp Phe Gln His Glu Leu Arg Tyr Ala Arg Ile
            275                 280                 285
Asn Gly Val Leu Gly Ser Ile Asp Ala Asn Thr Gly Asp Met Leu Leu
            290                 295                 300
Gly Trp Asp Thr Asp Gln Phe Pro Thr Asp Ile Arg Met Thr Thr Leu
305                 310                 315                 320
Ala Met Tyr Glu Val Ile Lys Met Gly Gly Phe Asp Lys Gly Gly Leu
                325                 330                 335
Asn Phe Asp Ala Lys Val Arg Arg Ala Ser Phe Glu Pro Glu Asp Leu
                340                 345                 350
Phe Leu Gly His Ile Ala Gly Met Asp Ala Phe Ala Lys Gly Phe Lys
            355                 360                 365
Val Ala Tyr Lys Leu Val Lys Asp Gly Val Phe Asp Lys Phe Ile Glu
            370                 375                 380
Glu Arg Tyr Ala Ser Tyr Lys Asp Gly Ile Gly Ala Asp Ile Val Ser
385                 390                 395                 400
Gly Lys Ala Asp Phe Lys Ser Leu Glu Lys Tyr Ala Leu Glu His Ser
                405                 410                 415
Gln Ile Val Asn Lys Ser Gly Arg Gln Glu Leu Leu Glu Ser Ile Leu
                420                 425                 430
```

Asn Gln Tyr Leu Phe Ala Glu
        435

<210> SEQ ID NO 4
<211> LENGTH: 501
<212> TYPE: PRT
<213> ORGANISM: Thermoanaerobacterium saccharolyticum
<220> FEATURE:
<221> NAME/KEY: misc_feature
<222> LOCATION: (1)..(501)
<223> OTHER INFORMATION: Xylulokinase

<400> SEQUENCE: 4

```
Met Tyr Phe Leu Gly Ile Asp Leu Gly Thr Ser Ser Val Lys Ile Ile
1               5                   10                  15

Leu Met Asn Glu Ser Gly Asn Val Val Ser Ser Val Ser Lys Glu Tyr
            20                  25                  30

Pro Val Tyr Tyr Pro Glu Pro Gly Trp Ala Glu Gln Asn Pro Glu Asp
        35                  40                  45

Trp Trp Asn Gly Thr Arg Asp Gly Ile Arg Glu Ile Ile Ala Lys Ser
    50                  55                  60

Gly Val Asn Gly Asp Glu Ile Lys Gly Val Gly Leu Ser Gly Gln Met
65                  70                  75                  80

His Gly Leu Val Leu Leu Asp Lys Asp Asn Asn Val Leu Thr Pro Ala
                85                  90                  95

Ile Leu Trp Cys Asp Gln Arg Thr Gln Glu Glu Cys Asp Tyr Ile Thr
            100                 105                 110

Glu Lys Ile Gly Lys Glu Gly Leu Leu Lys Tyr Thr Gly Asn Lys Ala
        115                 120                 125

Leu Thr Gly Phe Thr Ala Pro Lys Ile Leu Trp Val Lys Lys His Leu
    130                 135                 140

Lys Asp Val Tyr Glu Arg Ile Ala His Ile Leu Leu Pro Lys Asp Tyr
145                 150                 155                 160

Ile Arg Phe Lys Leu Thr Gly Glu Tyr Ala Thr Glu Val Ser Asp Ala
                165                 170                 175

Ser Gly Thr Leu Leu Phe Asp Val Glu Asn Arg Arg Trp Ser Lys Glu
            180                 185                 190

Met Ile Asp Ile Phe Glu Ile Pro Glu Lys Ala Leu Pro Lys Cys Tyr
        195                 200                 205

Glu Ser Thr Asp Val Thr Gly Tyr Val Thr Lys Glu Ala Ala Asp Leu
    210                 215                 220

Thr Gly Leu His Glu Gly Thr Ile Val Val Gly Gly Gly Asp Gln
225                 230                 235                 240

Ala Ser Gly Ala Val Gly Thr Gly Thr Val Lys Ser Gly Ile Val Ser
                245                 250                 255

Ile Ala Leu Gly Thr Ser Gly Val Val Phe Ala Ser Gln Asp Lys Tyr
            260                 265                 270

Ala Ala Asp Asp Glu Leu Arg Leu His Ser Phe Cys His Ala Asn Gly
        275                 280                 285

Lys Trp His Val Met Gly Val Met Leu Ser Ala Ala Ser Cys Leu Lys
    290                 295                 300

Trp Trp Val Asp Asp Val Asn Asn Tyr Lys Thr Asp Val Met Thr Phe
305                 310                 315                 320

Asp Gly Leu Leu Glu Glu Ala Glu Lys Val Lys Pro Gly Ser Asp Gly
                325                 330                 335
```

Leu Ile Phe Leu Pro Tyr Leu Met Gly Glu Arg Thr Pro Tyr Ser Asp
            340                 345                 350

Pro Tyr Ala Arg Gly Ser Phe Val Gly Leu Thr Ile Thr His Asn Arg
        355                 360                 365

Ser His Met Thr Arg Ser Ile Leu Glu Gly Val Ala Phe Gly Leu Arg
    370                 375                 380

Asp Ser Leu Glu Leu Ile Lys Ala Leu Asn Ile Pro Val Asn Glu Ala
385                 390                 395                 400

Arg Val Ser Gly Gly Ala Lys Ser Arg Leu Trp Arg Gln Ile Leu
            405                 410                 415

Ala Asp Val Phe Asn Val Arg Ile Asp Met Ile Asn Ala Thr Glu Gly
        420                 425                 430

Pro Ser Phe Gly Ala Ala Ile Met Ala Ser Val Gly Tyr Gly Leu Tyr
        435                 440                 445

Lys Asn Val Asp Asp Ala Cys Asn Ser Leu Ile Lys Val Thr Asp Ser
    450                 455                 460

Val Tyr Pro Ile Lys Glu Asn Val Glu Lys Tyr Asn Lys Leu Tyr Pro
465                 470                 475                 480

Ile Tyr Val Ser Leu Tyr Ser Arg Leu Lys Gly Ala Phe Glu Glu Ile
            485                 490                 495

Gly Lys Leu Asp Leu
            500

<210> SEQ ID NO 5
<211> LENGTH: 1560
<212> TYPE: DNA
<213> ORGANISM: Clostridium phytofermentans
<220> FEATURE:
<221> NAME/KEY: misc_feature
<222> LOCATION: (1)..(1560)
<223> OTHER INFORMATION: xylanase

<400> SEQUENCE: 5
atgctacaaa aaatgaacgg aaaggttaaa aagattcttg aattagtat cgcatttctt      60 atgttgatca tggtaattcc aacatcaatc gcaaaagcag caaccaataa gacctatgat    120
tttaattcga tgacttatca atccacatgg ggagttacat attctatcag taatggatca    180
ggaacattta atttcactgg tcaataccgt gaaattaagt tcaatcttcc ggaaacgcta    240
gatatgtctc aatgtactag tgtaacattc aatgcttcca gtccaaatgg acagattgca    300
tttaagcttt acgatacttc tggaaatcag gtggctgtag tgtataactt taattccaat    360
acctcagact gtaccttcgc accaaatagt acggcaaagg taaacagtat tggaataatg    420
gcgcaaggga caaataacta ctcagcagtt gtgaatcgag ttacatttac aatgacagga    480
gggtcttctg gcactggttc ttcaactta ttaaacactt atggaaatat attaaaaaac    540
tctggaactg ctgttaattt aagtcagctg caaaattcaa atacactaag tgtgattaag    600
acgcaatata atagtatcac attagagaat gaaatgaagc cagatgcagt tcttggaagt    660
tcatcaacat taatgactgt tgctcaagca aaatcgaatg gttattatat tccttctagc    720
tacacggaaa gtacagttcc aactcttaaa tttagtacca tcgatgcagt tctacagatt    780
tgctacaata acgggctaaa gcttagagga catacattag tatggcattc ccaaacaccg    840
gattggttct ttagaacagg ttatagttct agtggatcgt atgttagcca agctgttatg    900
gatgcaagaa tggaaatgtt tattaggtct tatatgagtc atatttataa tggaagctat    960
ggaagtgtag tatatgcttg ggatgttgta aatgagtatt tgcatgcttc tacctctgga   1020

```
tggtctcaag tttatggatc caaccttggt accacaccat cttatgtaaa gaaagctttc     1080
cagtatgcgt atgattgtct tagcagtttt ggattaacga attcagtaaa attgttttat     1140
aatgattaca acacatatga ggttacagat cagatcctat cattagtaaa ttttattaac     1200
tctggtacga aactttgcgc tggtgttgga atgcagtctc acttaaatac ctcctatcct     1260
tctgtatcgg catataaaac agctatgcag aagttcttga atgcaggata tgaagtacag     1320
gttactgaac ttgatgttac gaatacatca gcttccacac aagctactta tgtatatgat     1380
ttgatgactg ctattctttc tctaaagaaa gcaggtggga atatcactgg tattacatgg     1440
tggggactat atgatagcgt atcttggcgt gcctcccaaa atcctttgtt attcagtaat     1500
ttaactactc caaaagaatc ttataataaa gcgttacaag catttacaga tgcaggatat     1560
```

<210> SEQ ID NO 6
<211> LENGTH: 2268
<212> TYPE: DNA
<213> ORGANISM: Clostridium phytofermentans
<220> FEATURE:
<221> NAME/KEY: misc_feature
<222> LOCATION: (1)..(2268)
<223> OTHER INFORMATION: xylanase

<400> SEQUENCE: 6

```
atgttttTca agaaactagt tgcactcgca atggctgttg ccattgtcat tccaatgaac       60
gttaataaca tacaaaaggt tgaggcggaa tctacaaatg aagcagtagt atatggtaat      120
ctaatttatc acgactttga agcaagcacc aatgggtggg gaccaagagg tgacaatgca      180
gaggttgtgg cacaaagtac agaagaggca tattcagggt tacatagttt aaaaattagc      240
aaacgcacgc aaacatggca tggtgctacc tgcgatttga caaggaact tacgattgga       300 gaaacttatg tatttggaat ttatttaaaa tataaaggta gctcttattc caatacacaa      360
aagtttagct acaatttca gtacaatgat ggtgtgaatg atcagtacaa aacaattaag      420
actttagaag taaccaaaga taatggaca ttaattcaag gtgagtatac agttccagca       480
gatgccgcta atgcaaaggt ctatgtcgaa acagaatata agagttcacc atcaagtcaa      540
gatctcttag actttacat tgatgatttc actgcaacgc cagcaacttt accacagatt       600
caaaaagata ttcctagttt aaaggatgta ttttcaagtt acttctttgt tggtggagcg      660
gcaactgcag gtgagattgc accagctccg gcaaaagatt tagtagcgaa acattacaat      720
aggttaactc ctggtaatga gttaaaacca gactctgtat tagattactc tgcaaccata      780
gcctatatgg atgcaaatgg tggtaatcaa gtgaatcctc aggtgaatct tagagctgcg      840
aaaactttac tggaatatgc aagagacaat aatataccag tgcgtggaca taccttagta      900
tggcatagcc agacaccaga ttggttcttt aaggtaaact attctcagga ttcaaatgca      960
gcgtgggttt ccaaggaagt gatgctccaa agactagaaa actacatcaa aaatgtgatg     1020
cagctgatct catcaaccta tcctacagta agttctatg cttgggatgt ggtgaatgaa      1080
gcagtagatc caaatactTc tacaggtatg agaaatcctg atcgaataa cgtaacatct      1140 ggtaattctc catggatgca aaccataggt gaggaatata ttcaaagagc tttgaatac       1200 gcaagaaat atgctccaac tggttgtaa actgttttata atgattataa cgagtatgag     1260
gatagaaaga gtacctttat ctttaatatc ctgaaaggat taaagataa gggcttagtg      1320 gatggtatgg aatgcagtc tcattgggtt atgattatc caagtattag tatgttgag       1380 acagctgttc gtaatataa actttTagga ttagaattac aactaacgga gttagatata      1440
aagcagccag acaatagtac atctgcttta gctgctcagg cagacagata taaactTttg     1500
```

```
ataaataagg tcattagttt gaaaaaagag ggcatgaaca ttacaggagt tatcttctgg    1560
ggtgtaacgg ataagactag ttggttaggt ggatatccat tattatttga tggaaattat    1620
caagcaaagt cagcatacta ttctatcatt gatgggatta ccccaacagt aacgccatca    1680
ataactccaa ctgtaacacc aaaaccaacg ataacaccta cagtaacacc aactgtaacg    1740
ccaaaaccaa cgataacacc tacagtaaca ccaactgtaa caccaaagcc aacaataact    1800
cctaccataa caccaacagt aacgccaaaa ccaacaatag ctccgacacc aactcctact    1860
acagtaccag tggagggagc aaaaccggtg gtagtagtaa ctacgaaaaa caatgggaac    1920
acgataagcc agcaatacac aataaatgca cttggtggaa cgattgattt gtcaaaggta    1980
tctattgagt ttactgccga tggaatcatc aatcaagagc ataatgtttg ggtagataac    2040
gctgcgttgc aattaacagt tgaaccatat tacacaccgt taaatggtta tgtttctggg    2100
cagttgacga atcaaaaact tgtggttagc atcagtaaga gtacgatgct gtcagaagga    2160
acaggaaagc ttgttcttga tttacgattt gctaagaagg attggacgga ttttggtacg    2220
atatccaatg aagtgttaaa ggtttactat aatggagtca aagttcaa                 2268
```

<210> SEQ ID NO 7
<211> LENGTH: 636
<212> TYPE: DNA
<213> ORGANISM: Clostridium phytofermentans
<220> FEATURE:
<221> NAME/KEY: misc_feature
<222> LOCATION: (1)..(636)
<223> OTHER INFORMATION: xylanase

<400> SEQUENCE: 7

```
atgtttaaat taaataagaa agttttttgca ttagtttctg taattgcatt aggtttttct     60
agcttattta catcaactgc tcatgcagca actgattact ggcagaattg gactgatggt    120
ggtggaacag tgaacgctac caatggttct ggtggtaact acagtgttaa ctggacgaat    180
tgtggtaatt ttgttgtagg taaaggttgg ggtactggaa atgcatcaag agttgtaaat    240
tacaatgctg gtgtattttc accatctggt aatggttatt taactttcta tggttggacg    300
agaaattcac tcattgaata ttatgttgtt gatagttggg gtacttatag accaactgga    360
actttaaagg gtacagtttc tagcgatggt ggaacatatg atatttatac aagtacgaga    420
actaatgcac cttccatcga tggtactcag actttccaac aatactggag tgttagacag    480
tctaagagag ctaccggaag taacgtagca attacttttta gtaaccatgt taatgcttgg    540
aagagtaaag gaatgaactt aggaagcagc tgggcttatc aagcattatg cgtagaagga    600
tatcaaagca gtggtagtgc taatgtaacg gtttgg                              636
```

<210> SEQ ID NO 8
<211> LENGTH: 2418
<212> TYPE: DNA
<213> ORGANISM: Clostridium phytofermentans
<220> FEATURE:
<221> NAME/KEY: misc_feature
<222> LOCATION: (1)..(2418)
<223> OTHER INFORMATION: xylanase

<400> SEQUENCE: 8

```
atgggtaaaa aagtaatagc tttattaaca tgtgttatgc tttcgcttac gctgattccg     60
ggtatcggca taagagcac tgcacaagcc gctgaaacca acatctataa agtagattgg    120 agcaaatta atgagggtga caaaatcagc ggtcccatgg agggtttagg tagatcaggc    180
```

```
ggagcagata tcacggttac gggctcctct accaaatcat tttacatatc taatcgtaaa        240
gataactggg atgcacttga tattcagaac gatcttttga agttagatcg agatgcaacc        300
tatgaaatca cagttaccgg tcatgttgac agcaatgtag atactaagaa tgctagtgtc        360
aagcttggcg gtgtaacaag gaaaacgggc gaggatgatg gatacccaga gttcaaaaaa        420
gagaaactac aatcgggcaa gagttttgta ctaacctatg aacttaaact ttctgatcaa        480
attccggacg cttcaagaaa tctgtgggtg ctccgtgttc agaccgacga accaagcgga        540
agtagggccg gagatcttgt accgttctat gtggatgata tcgtgattat tcaaacaaag        600
gcatccactg ctcctgtagc tgtgactggt gaccttatgt cactttacga acttaatgcg        660
gacaaaactc tcaaggttgg agaatcatta tcaagtccag ctctgaaagt ttctggtaat        720
gctaagatag ttgttgtaga aggcaccgat ggtaccgtgt cattacaact gaaagaccgt        780
gttaataatt atgacggtgt agacatcctt cgtgatgcac tgaaaataaa cgataaattt        840
atgtctggta catacacgat tgaggtaaaa ggccatgtag aggatggttc tgatttaagt        900
aaatcccagt ttgttatggg tatgaccgaa tctccatggg gcgaactcac ttcaagagtg        960
acgccaagta gtgacggtag ctttgtaata acttatacca aagcatacac cggaagtgaa       1020
ttgacaggcc taggttatag ctaccgagtt cagacacctc caagcgttct cacatcgttt       1080
tatatcgata acattaccgt tacggttcag ggagctgaag aagaagatga gtcaactgtg       1140
gttatacctg aatgggattt aacccttgat tccattaaag atgcatacgc tgattacttc       1200
atgataggta atattatgga accaggtcag atacaggata cagaaaccac cgaaatgttt       1260
aagcatcatt ataatgttgt taccgcagaa aatgccatga accagggaa tatttccaag       1320 gtaaaaggcg aatacaattt tgacaatgct gataagcttg ttacgtgggc taaagaaaat       1380
ggtttaaaag tccacggtca tactttagtt tggcactctc agtcagctcc atggttgact       1440
acaaatgcgg atggaacacc tctaacacgt gcagaagcaa gagctaatat ggaagattat       1500
attaagaacg ttgcaggaca ttacgcaggg aaggtgattt catgggatgt attaaatgaa       1560 gcattttttgc caggtgtatc cgaaatccct gctggctgga gggatgtatt acgcaaattt       1620
gaagataacg gaaatggttc tccttggtat caagcctatg aaaacggtgc tgataagagc       1680
aagggcgagg atggctctga ttatatctat gacgcttttcg tgtttacacg tcttgccgct       1740
cctgatgcag tgctgtatta taacgacttc aatgagacag aggcaggtaa gtgtgaagcg       1800
atcgccttga tggtggaaga attaaacaca aagtggaaga ccgataaacg gaacactgag       1860
cctgacagat tgctcatcga aggaatcgga atgcaggcac attattggac cggagattta       1920 aaggttttcca ctgtagaagc tagcatcaag cgtttcataa aaacaggtgc taagatcagt       1980
gtatctgagc tggatgttcc tcatggcgat tacatgacct acaagcaacg tactgactct       2040
cctacaaagg aagaagagaa acttcaggcg gatttataca agcagttgtt tgaagtatac       2100
aaaaaatatg cggacaacat cgaacgtgtc accttctggg gtaaaacaga tcctcaaagc       2160
tggcgtttcc aaggttatcc attactgttt gataaaaatt ttgctccaaa ggacgcattc       2220
tttgctgtaa ttgatgtagc aaaggaaaag gtagcagagg aaaaggctgt tgaaaccata       2280
cctggtaaag atatcccgaa aacagggaa gacagcagta agcaaatgat tttgactgca       2340
gtagctattc tgattatatt ggtattcgta ccagttacga tcttaacaaa acgaagagag       2400
aagaatataa agaatata                                                    2418
```

<210> SEQ ID NO 9
<211> LENGTH: 1185

```
<212> TYPE: DNA
<213> ORGANISM: Thermobifida fusca
<220> FEATURE:
<221> NAME/KEY: misc_feature
<222> LOCATION: (1)..(1185)
<223> OTHER INFORMATION: xylanase

<400> SEQUENCE: 9
atgggtctcc ccgtctccgt ccacaggagt gacacaaaaa tgagggtggg ccgatacatc      60
gccatcacgg ttggggcctc cgcgctgctc gtctccgggg tggcgccggc ggcggcgggt     120
acgctgccga cgtccgggac ggccgccggc gcggcgtcgc aggccgggca cgatcagaag     180
caggtaccgc tccgcaaggt ggcgccgaag ggcttcgcga tcggcgtggc cgtcgcgggt     240
ggtggccacc atctggacca ggagtacccg acccccttca gtacgacga ggagtaccgg      300
ggggtgctcg ccaagcactt caactcggtc actcccgaga accacttgaa gtgggacttc     360
gtgcacccgg agcggaaaaa gtacaacttc gggcctgctg accagatcgt caagtttgcc     420
cagagcaacg gcagaaggt gcgcggccac acgctggtct ggcacagcca gaaccccgac      480
tggctcacca agggaagtt cagcaagaag gagctccgca agatcctcaa ggagcacatc      540
atcacggtgg tgggccgcta ccggggcaag atccaccagt gggacgtggc caacgagatc     600
ttcgacgaca acggtaagct ccgcacgaac gagaacatct ggctgaagaa cttcggaccg     660
gagatcatcg ccgacgcgtt ccgctgggcc caccaggccg acccgaaggc gaagctgttc     720
ctcaacgact acggcgccga gggcatcaac aagcgcagcg acgcctacct caagttcatg     780
aaggagctgc gcaagaaggg cgtgccggta cacggcttcg gcgtgcaggg gcacctgagc     840
ctggcctacc cgttcccggg cgacatggcg aagaacctca gcggttctc ggacgccggg       900
ttcgaggtcg cggtcaccga ggtcgacgtg cgcatcccgc tcaacggcgg cgacgccact     960
gaagcccagc tcaagaccca ggccgactac taccgccgcg ccctggaggc ctgcctgagc    1020
gtcaagagct gcaactcctt caccctctgg ggcaccacga caagtactc gtgggtgccg     1080
gtgttcttcc cggacgaggg cgaggcgacg atcttctggg acgacttctc ccccaagccc    1140
gcgtacaccg ccctgcagga ggccctggcg aaggcccgcc gccgc                    1185

<210> SEQ ID NO 10
<211> LENGTH: 1014
<212> TYPE: DNA
<213> ORGANISM: Thermobifida fusca
<220> FEATURE:
<221> NAME/KEY: misc_feature
<222> LOCATION: (1)..(1014)
<223> OTHER INFORMATION: xylanase

<400> SEQUENCE: 10
atgaaccatg cccccgccag tctgaagagc cggagacgct tccggcccag actgctcatc      60
ggcaaggcgt tcgccgcggc actcgtcgcg gtcgtcacga tgatcccag tactgccgcc     120
cacgcggccc tgacctccaa cgagaccggg taccacgacg ggtacttcta ctcgttctgg     180
accgacgcgc ccggaacggt ctccatggag ctgggccctg gcggaaacta cagcacctcc     240
tggcggaaca ccgggaactt cgtcgccggt aagggatggg ccaccggtgg ccgccggacc     300
gtgacctact ccgccagctt caaccccgtcg ggtaacgcct acctgaccct ctacgggtgg     360
acgcggaacc cgctcgtgga gtactacatc gtcgaaagct ggggcaccta ccggcccacc     420
ggtacctaca tggcacggt gaccaccgac ggtggtacct acgacatcta caagaccacg     480
cggtacaacg cgccctccat cgaaggcacc cggaccttcg accagtactg gagcgtccgc     540
```

-continued

```
cagtccaagc ggaccagcgg taccatcacc gcggggaacc acttcgacgc gtgggcccgc    600
cacggtatgc acctcggaac ccacgactac atgatcatgg cgaccgaggg ctaccagagc    660
agcggatcct ccaacgtgac gttgggcacc agcggcggtg acaaccccgg tggggcaac     720 ccccccggtg gcggcaaccc cccggtggc ggtggctgca cggcgacgct gtccgcgggc     780
cagcagtgga acgaccgcta caacctcaac gtcaacgtca gcggctccaa caactggacc    840
gtgaccgtga cgttccgtg gccggcgagg atcatcgcca cctggaacat ccacgccagc     900
tacccggact cccagacctt ggttgcccgg cctaacggca cggcaacaa ctggggcatg     960 acgatcatgc acaacggcaa ctggacgtgg cccacggtgt cctgcagcgc caac         1014
```

<210> SEQ ID NO 11
<211> LENGTH: 1965
<212> TYPE: DNA
<213> ORGANISM: Clostridium stercorarium
<220> FEATURE:
<221> NAME/KEY: misc_feature
<222> LOCATION: (1)..(1965)
<223> OTHER INFORMATION: xylanase

<400> SEQUENCE: 11

```
atgaagcgta aggttaagaa gatggcagct atggcaacga gtataattat ggctatcatg     60
atcatcctac atagtatacc agtactcgcc gggcgaataa tttacgacaa tgagacaggc    120
acacatggag gctacgacta tgagctctgg aaagactacg gaaatacgat tatggaactt    180
aacgacggtg gtacttttag ttgtcaatgg agtaatatcg gtaatgcact atttagaaaa    240
gggagaaaat ttaattccga caaaacctat caagaattag gagatatagt agttgaatat    300
ggctgtgatt acaatccaaa cggaaattcc tatttgtgtg tttacggttg gacaagaaat    360
ccactggttg aatattacat tgtagaaagc tgggggcagct ggcgtccacc tggagcaaca    420
cccaaaggaa ccatcacagt ggatggcggt acttatgaaa tatatgaaac tacccgggta    480
aatcagcctt ccatcgatgg aactgcgaca ttccaacaat attggagtgt tcgtacatcc    540
aagagaacaa gcggaacaat atctgtcact gaacatttta acagtgggaa agaatgggc    600 atgcgaatgg gtaagatgta tgaagttgct cttaccgttg aaggttatca gagcagtggg    660
tacgctaatg tatacaagaa tgaaatcaga ataggtgcaa atccaactcc tgccccatct    720
caaagcccaa ttagaagaga tgcatttta ataatcgaag cggaagaata taacagcaca    780
aattcctcca ctttacaagt gattggaacg ccaaataatg gcagaggaat tggttatatt    840
gaaaatggta taccgtaac ttacagcaat atagattttg gtagtggtgc aacagggttc    900
tctgcaactg ttgcaacgga ggttaatacc tcaattcaaa tccgttctga cagtcctacc    960
ggaactctac ttggtacctt atatgtaagt tctaccggca gctggaatac atatcaaacc    1020
gtatctacaa acatcagcaa aattaccggc gttcatgata ttgtatggt attctcaggt    1080 ccagtcaatg tggacaactt catatttagc agaagttcac cagtgcctgc acctggtgat    1140
aacacaagag acgcatattc tatcattcag gccgaggatt atgacagcag ttatggcccc    1200
aaccttcaaa tctttagctt accaggcggt ggcagcgcca ttggctatat tgaaaatggt    1260
tattccacta cctataataa cgttaatttc gccaacggct aagttctat aacagcaaga    1320 gttgccactc agatctcaac ttccattcag gtgagagcag gaggagcaac cggtacttta    1380
cttggtacaa tatatgttcc ttcgacaaat agttgggatt cttatcagaa tgtaactgcc    1440
aaccttagca atattacagg tgtgcatgat attacccttg tcttttcagg accagtgaat    1500
gtggactact tcgtatttac accagcaaat gtaaattcag ggcctacctc ccctgtcgga    1560
```

-continued

```
ggtacaagaa gtgcatttc caatattcaa gccgaagatt atgacagcag ttatggtccc      1620
aaccttcaaa tctttagctt accaggtggt ggcagcgcca ttggctatat tgaaaatggt      1680
tattccacta cctataaaaa tattgatttt ggtgacggcg caacgtccgt aacagcaaga      1740
gtagctaccc agaatgctac taccattcag gtaagattgg gaagtccatc gggtacatta      1800
cttggaacaa tttacgtggg gtccacagga agctttgata cttataggga tgtatccgct      1860
accattagta atactgcggg tgtaaaagat attgttcttg tattctcagg tcctgttaat      1920
gttgactggt ttgtattctc aaaattcagg aacttaaggg tatag                     1965
```

<210> SEQ ID NO 12
<211> LENGTH: 1164
<212> TYPE: DNA
<213> ORGANISM: Clostridium stercorarium
<220> FEATURE:
<221> NAME/KEY: misc_feature
<222> LOCATION: (1)..(1164)
<223> OTHER INFORMATION: xylanase

<400> SEQUENCE: 12

```
atgaataaat tcttaaacaa aaaatggagc ttaattttaa ccatgggagg tatttttctg       60
atggcgactt tatcattgat ttttgcaacg gggaaaaagg cctttaacga tcaaacttct      120
gctgaagaca tcccatcgct tgctgaggct ttcagagact atttccgat ggagcggcc       180 attgagcctg gtataccac aggccaaata gccgaactgt ataagaaaca cgtgaacatg      240
ctcgtggcgg aaaatgcaat gaaaccggcg tcacttcagc cgacggaagg taattttcag      300
tgggcagacg ctgacagaat tgtgcagttt gcgaaagaaa acggtatgga actgcgcttc      360
cacactcttg tgtggcataa tcagacgccg actggttttt ccttggataa agaaggaaaa      420
ccaatggtgg aggagactga tccacagaag cgtgaagaaa caggaaact tctgctgcaa      480 cggcttgaga attatattcg tgctgtggtt ttacgctaca aagacgacat aaagtcatgg      540
gatgtggtga atgaggtaat tgaacccaat gatcccggcg gtatgagaaa cagtccttgg      600
tatcagatta ccggtaccga gtacatcgaa gtggcattcc gtgcggcaag ggaagcggga      660
ggatccgata ttaagcttta tatcaacgat tacaatacag atgaccctgt caagagagat      720
atactgtatg aattagtgaa aaatttgctg gagaagggtg tgccgattga cggggtggga      780
catcagacac atattgatat ttacaatccg cctgtcgagc gaataataga gtctataaaa      840
aaatttgccg gactgggact ggacaacata attaccgaac tggacatgag catatattca      900
tggaatgacc gcagcgatta cggcgatagt atacccgatt atatcctgac tttacaggcc      960
aaacgttatc aggaactgtt tgatgcgtta aggaaaata aggacattgt aagcgcagtg     1020
gtgttttggg gcatttcgga caaatattcc tggttgaacg ggtttcctgt aaaacgtacc     1080
aatgccccgc tgctgttcga cagaaatttc atgccgaaac cagctttctg ggcgatagtt     1140
gatccttcac ggttgcggga ataa                                             1164
```

<210> SEQ ID NO 13
<211> LENGTH: 3099
<212> TYPE: DNA
<213> ORGANISM: Clostridium stercorarium
<220> FEATURE:
<221> NAME/KEY: misc_feature
<222> LOCATION: (1)..(3099)
<223> OTHER INFORMATION: xylanase

<400> SEQUENCE: 13

```
atgaatggcc gtaatggggg taaaagacct atagcgagcc tgcttgtgct cacacttgca    60
tttttattca ttccggtaac gaaggcagaa acaacggttt atcatgagac ttttgccgaa   120
ggaaagggag cggcggtaca gtcaggcggg gcgaccatta cgcacgttac cggaaaattt   180
tttgacggca acggggacgg agcggcactg tacatatcca acagagtgaa caactgggac   240
gctgcagatt tcagattcag cgacataggt cttcaggacg gaagaattta taaaataacg   300
gtaaagggat atgtggatcc cgatgttcat gtaccgaggg ttcccagat atggcttcag    360
accgttaaca gctatgggtg gtggggcagt accgacataa aggccggtga agcctttact   420
ctgacgggcg tatataaggt ggatacaacc aatgattatg ctctgaggat tcagtccaat   480
gacaccggag catttgttcc gttttatatc ggtgaaatat tgatcaccga agaaacggtt   540
cctcaggatg cagccgaaa tgggaataaa actcatgctg agaagttcac acccataacc    600
tttgaggacc aaaccacagg cggatttaca ggcagggcag gaaccgaaat tcttacggta   660
accgatgagg caaccatac cgatggcgga agatattcgc ttaaagtcgg gggaaggaac    720
gacacatggc atgcccggc gttgggtgtg gaaaaatacg tggatcaggg ttacgaatat    780
aaagtggcgg tttatgtcag gctgatttca cctgaaagtg cacaactgca actgtcaacg   840
caaattggtg aaggcacatc ggcaagttac gtaaaccttg cgaaaagaa tgttgcaatc    900
agtgacggct gggttctgct ggaaggtaca taccgctacg acaatcttgg cggagggtac   960
ctgacaatat atgtggagag ccctgacagc cctgaggcat cattttatat tgacgacatc  1020
aactttgaac ccacgggcat gaaatctgaa gagattgaaa aaggtttaaa atccttgaag  1080
gatgtgtata aggataattt tctcaccggc acgcgatat cattgcgtga cctggaaggt    1140
gtaaggtttg agcttctgaa aaaacatttc aatgcggtaa ctgcggaaaa tgcaatgaag   1200
ccttccgaat tgcagcgtga aggggaaat tttacctttg acggggcaga caggcttgta    1260
aacgccgcaa taagtgcagg aatgaaagta cacgggcata cgctggtatg gcaccagcag   1320
accccccgcgt ggatgaatat taagttggat agcggaggaa atattgtata cctcagcagg  1380
gaagaagcgc ttgaaaatat gagaaatcat ataagaaccg ttattgagca ttttggcgac   1440
aaggttatat cgtgggatgt tgtaaacgaa gcaatgagcg acaatccttc caatccttcc   1500
gactggagag gatcactgcg taaatcgcct tggtattatg ccattggcga agactacgtg   1560
gaacaggctt ccttgccgc gagagaggtg ctggatgaac ccccgaatg ggatattaag     1620
ctttactaca acgattacaa ccttgataac cagaacaaag ctttggctgt ttacaacatg   1680
gtaagagaac ttaacgaaaa ataccagaaa actcatccgg gaaaactcct tatcgacggt   1740
ataggcatgc agggacatta ttctgtaaat acaaatccga agaatgttga actgtcactg   1800
aagcggttta ccgaactggg tgtggaggtc agcataagcg aactggatat ccgtgcgggc   1860
agcaattatc agctcaccga gaaagaggcg aatgcccagg cctacctta cgctcagttg    1920
ttcaaaattt tccgtgaata ttccgacagt attgcacggg ttacgttctg gggaatggat   1980
gacggtacaa gctggagggc ggaagaaagc ccgctgctgt ttgacaggac cctaaaagcc   2040
aaacctgcgt attacgctgt tgcagatccg gacgaattca ttgagaaata taagcctgaa   2100
acaatagaag ccaaccgggc atatgcggtt tacggcacac ctgaaattga cggaaaaacc   2160
gatgaagttt ggaacaaggc acctgagctg aaaattaaca ggtaccagac cgcttggcat   2220
ggcgccgacg gcaccgcaag ggttctttac gacgaaaaca acctgtacgt tctgatcaag   2280
gttaatgaca cacagcttga taaaggaagc ccaaatccat gggagcagga ttcggttgaa   2340
atatttatag acgaaaataa tgcaaaaaca tcattttatg aggaagacga cggccagtac   2400
```

```
agggttaact tgaaaacga gacatccttt aatccggaaa gtatagccgg cggttttgaa    2460
tcggccgcgg aagtttcggg aacaaactat accttggaag tgaaaatacc gttcaggacc    2520
gtgaaacccg tcagcaatat gcaaatcgga tttgacgtgc agattaacga cggaaaaaac    2580
ggagtgcggc agagcattgc aacatggaat gacccgactg gaaatgcatg gcaggatact    2640
tcggttttcg gtattcttac tttgaaatca aaaaatccgg ttacccgcgg tgaagccatt    2700
gtaaaaatta tgaaggctta tgatatggaa ccactggaaa actggaacga caatttctcc    2760
gatgcttcgg gaagctacgc gggatattac ccgagagcaa aggaaacggg ttttgtcagc    2820
ggtatcgggg acaataagat aggtgctgaa attccgctta cccgggaaat gttttttaca    2880
atgatttata atatcgaacg aataacaggg aaaatgcagg ggatagatat ttcagacgcg    2940
gaacttacac ttttcagcga ttataacgac ttgtcggagt gggccgaaga ggcagttaag    3000
gcattggtta aatcaggcag gatcaaaatt aacggcgatt tattgccgaa gcggcttatg    3060
gacgctgaag aagtggaggc attttttaaga ttaagataa                          3099

<210> SEQ ID NO 14
<211> LENGTH: 1266
<212> TYPE: DNA
<213> ORGANISM: Bacillus subtilis
<220> FEATURE:
<221> NAME/KEY: misc_feature
<222> LOCATION: (1)..(1266)
<223> OTHER INFORMATION: xylanase

<400> SEQUENCE: 14
atgattccac gcataaaaaa aacaaatttgt gtactattag tatgttttcac tatgctgtca     60 gtcatgttag ggccaggcgc tactgaagtt ttggcagcaa gtgatgtaac agttaatgta    120
tctgcagaga aacaagtgat cgcggttttt ggagggatga atcatccggc ttgggctggg    180
gatcttacag cagctcaaag agaaactgct tttggcaatg acagaaacca gttaggattt    240
tcaatcttaa gaattcatgt agatgaaaat cgaataatt ggtataaaga ggtggagact     300
gcaaagagtg cggtcaaaca cggagcaatc gttttttgctt ctccttggaa tcctccaagt    360
gatatggttg agacctttaa tcggaatggt gacacatcgg ctaaacggct gaaatacaac    420
aagtacgcag catacgcgca gcatcttaac gattttgtta ccttcatgaa gaataatggt    480
gtgaatcttt acgcgatttc ggtccaaaac gagcctgatt acgctcacga gtggacgtgg    540
tggacgccgc aagaaatact tcgctttatg agagaaaacg ccggctcgat caatgcccgc    600
gtcattgcgc ctgagtcatt tcaatacttg aagaatttgt cggacccgat cttgaacgat    660
ccgcaggctc ttgccaatat ggatattctc ggaactcacc tgtacggcac ccaggtcagc    720
caattccctt atcctctttt caaacaaaaa ggagcgggga aggaccttg gatgacggaa    780 gtatactatc aaacagtga taccaactcg gcggatcgat ggcctgaggc attggatgtt    840
tcacagcata ttcacaatgc gatggtagag ggggactttc aagcttatgt atggtggtac    900
atccgaagat catatggacc tatgaaagaa gatggtacga tcagcaaacg cggctacaat    960
atggctcatt tctcaaagtt tgtgcgtccc ggctatgtaa ggattgatgc aacgaaaaac   1020
cctaatgcga acgtttacgt gtcagcctat aaaggtgaca caaggtcgt tattgttgcc   1080 atcaataaaa gcaacacagg agtcaaccaa actttgtttt tgcagaatgg atctgcttca   1140
aacgtatcta gatggatcac gagcagcagc agcaatctac aacctggaac gaatctcact   1200
gtatcaggca atcattttg ggctcatctt ccagctcaaa gcgtgacaac atttgttgta   1260
``` aatcgt 1266

<210> SEQ ID NO 15
<211> LENGTH: 1539
<212> TYPE: DNA
<213> ORGANISM: Bacillus subtilis
<220> FEATURE:
<221> NAME/KEY: misc_feature
<222> LOCATION: (1)..(1539)
<223> OTHER INFORMATION: xylanase

<400> SEQUENCE: 15

```
atgaggaaaa agtgtagcgt atgtttatgg attctagttt tattattgag ctgcttatct      60
gggaagtctg cgtatgctgc cactagtact acaattgcaa acatataggg aattcaaat      120
ccgcttatcg accatcattt gggagcggat ccggttgcgc tgacctataa cggaagagtc     180
tacatctata tgtcaagtga tgactatgaa tataatagca acggaacaat taaagataat     240
tcatttgcca atttgaatag agtattcgtc atatcttcag cggatatggt gaactggaca     300
gaccacggag ccattccggt agcaggtgcc aatggagcta atggaggccg tggaattgca     360
aaatgggcag gtgcgtcatg ggcaccgtca atcgcagtta aaaaaattaa tggcaaggat     420
aaattcttcc tttatttcgc aaacagcggc ggaggtatcg gggttctcac cgcagacagc     480
ccgattggtc catggaccga cccaatcgga aaaccgctcg taacgccaag tacgccagga     540
atgtctggtg ttgtatggct ttttgatccg gcagtatttg tagatgacga cggaaccggt     600
tacctgtatg ccggcggagg cgttcctggc gtttcaaatc aacgcaggg acaatgggcc      660
aatcctaaaa cggctagagt cataaaattg gggcctgata tgacgagtgt tgttggaagt     720
gcatctacaa ttgatgcgcc tttcatgttt gaagattcgg gattgcacaa gtataacgga     780
acatattatt actcctattg catcaatttc ggcggcacgc acccggccga taaaccccg      840
ggtgagatcg gctacatgac cagttcaagt cccatgggtc cctttacata tagagggcac     900
ttcctgaaaa atccgggtgc attttcggga ggtggcggaa acaaccatca tgctgttttc     960
aattttaaaa acgagtggta tgtggtgtac catgcgcaaa ctgtcagttc cgctctgttc    1020
ggggccggca aaggataccg ctctccccat attaataagc tggtgcataa tgcagatgga    1080
tctattcaag aggtagcggc aaattatgca ggtgtaacac aaatttccaa tttaaacca     1140
tataaccggg tagaagctga aacgtttgct tggaatggac gcattttgac agagaagtcc    1200
acagcacccg gcgggccagt aaataatcag catgtaacaa gcattcaaaa tggagactgg    1260
attgctgtag gaaatgcaga cttcggagcg ggcggtgcca ggtcatttaa agcaaatgta    1320
gcatccactt taggcgggaa aatagaagtg cgcctcgaca gtgcagacgg taagcttgtt    1380
ggaactctga atgtgccttc aacaggcgga gcgcaaacgt ggagggaaat agaaactgcg    1440
gtaagcgggg caaccggtgt gcacaaagta ttctttgtat ttaccggaac aggtacagga    1500
aacttgttta attttgatta ctggcagttt acgcaaaga                            1539
```

<210> SEQ ID NO 16
<211> LENGTH: 639
<212> TYPE: DNA
<213> ORGANISM: Bacillus subtilis
<220> FEATURE:
<221> NAME/KEY: misc_feature
<222> LOCATION: (1)..(639)
<223> OTHER INFORMATION: xylanase

<400> SEQUENCE: 16

```
atgtttaagt ttaaaaagaa tttcttagtt ggattatcgg cagctttaat gagtattagc     60
```

```
ttgttttcgg caaccgcctc tgcagctagc acagactact ggcaaaattg gactgatggg      120
ggcggtatag taaacgctgt caatgggtct ggcgggaatt acagtgttaa ttggtctaat      180
accggaaatt tgttgttgg taaaggttgg actacaggtt cgccatttag gacgataaac       240
tataatgccg gagtttgggc gccgaatggc aatggatatt taactttata tggttggacg      300
agatcacctc tcatagaata ttatgtagtg gattcatggg gtacttatag acctactgga      360
acgtataaag gtactgtaaa aagtgatggg ggtacatatg acatatatac aactacacgt      420
tataacgcac cttccattga tggcgatcgc actacttta cgcagtactg gagtgttcgc       480
cagtcgaaga gaccaaccgg aagcaacgct acaatcactt tcagcaatca tgtgaacgca      540
tggaagagcc atggaatgaa tctgggcagt aattgggctt accaagtcat ggcgacagaa      600
ggatatcaaa gtagtggaag ttctaacgta acagtgtgg                             639
```

<210> SEQ ID NO 17
<211> LENGTH: 1599
<212> TYPE: DNA
<213> ORGANISM: Bacillus subtilis
<220> FEATURE:
<221> NAME/KEY: misc_feature
<222> LOCATION: (1)..(1599)
<223> OTHER INFORMATION: xylanase

<400> SEQUENCE: 17

```
atgaagatta ccaatcccgt acttaaagga ttcaatcccg atccaagtat tgtagagca       60 ggagaggatt attatatcgc tgtatctaca tttgagtggt ttccgggagt ccagatacac      120
cactcaaaag atttagtaaa ttggcactta gttgcacatc cattacagag agtttcacaa      180
ttagacatga aaggaaaccc aaattcaggt ggagtttggg caccatgttt aagctatagt      240
gatgggaagt tttggctgat ctatacggat gttaaggtag tagatggcgc atggaaagat      300
tgtcacaatt atttagttac ttgtgaaacg attaatggtg attggagtga gccgattaaa      360
ttaaatagct cggggtttga tgcttctttg ttccatgata cggatggaaa aaagtatta     420 ttaaatatgt tatgggatca ccgtattgat cggcactcat ttggaggaat tgttatacag      480
gaatattctg ataaagagca aaaattaatc ggtaaaccaa aagttatatt tgaaggaact      540
gatagaaaac tgacagaagc tccgcatctt tatcatatcg gaactatta ttatttatta      600 actgcagaag gaggaacacg gtacgaacat gctgctacaa ttgctcgttc tgcaaatatt      660
gaggggccat atgaagttca tcccgataat ccaattttaa cgtcatggca tgacccagga     720
aatccattgc aaaaatgtgg tcatgcatcc attgttcaaa cacatacaga tgagtggtat      780
ttagctcatt taacgggacg tcctattcat cctgacgatg attcaattt tcagcagaga      840 ggatactgtc ctttgggcag agaaacagct attcaaaaac tttactggaa agatgaatgg      900
ccctatgtag taggtggaaa agaaggaagc ttggaggtag atgcaccttc tatacccgaa      960
acaatatttg aagcaacgta cccggaagtt gatgaatttg aggattcaac attaaatata      1020
aattttcaaa ctttaaggat tccattcacg aatgaattag gttcattgac tcaagcgcca     1080
aatcatttac gattattcgg tcatgaatca ttgacctcga catttactca ggcatttgta     1140
gccagacgct ggcaaagtct ccatttttgaa gccgaaactg ctgttgagtt ttatccggaa    1200
aattttcaac aagccgctgg gttggtgaat tactacaata cagagaactg gacggctctt     1260
caagtcacgc atgatgaaga acttgggcgc attcttgaat taacaatatg tgacaacttt    1320 tcttttttcac agccattaaa taataaaatt gttattcctc gtgaagtaaa gtatgtatat    1380
```

-continued

| | | |
|---|---|---|
| ttaagagtaa atattgaaaa ggacaaatat tattatttct attcttttaa caaagaagat | 1440 | |
| tggcacaaaa ttgacattgc actggaatcg aaaaaattat cagatgatta tatccgtggg | 1500 | |
| ggaggattct tcacaggggc cttttgtaggg atgcaatgcc aagataccag tggtaatcat | 1560 | |
| attccggccg actttagata ttttcgttat aaagaaaaa | 1599 | |

<210> SEQ ID NO 18
<211> LENGTH: 4299
<212> TYPE: DNA
<213> ORGANISM: Thermoanaerobacterium saccharolyticum
<220> FEATURE:
<221> NAME/KEY: misc_feature
<222> LOCATION: (1)..(4299)
<223> OTHER INFORMATION: xylanase

<400> SEQUENCE: 18

| | | |
|---|---|---|
| atgaagagta ttgtaaacag agttgtatct atcgttacag ctttaataat gattttgggg | 60 | |
| acatcactgt tttcacaaca cataagggca tttgctgatg acactaatac aaatctggtt | 120 | |
| tctaatgggg actttgagac aggcacaatt gatggctgga ttaagcaagg taatcctaca | 180 | |
| ttagaagtaa ctactgaaca agcaattggg caatacagta tgaaagttac gggtagaaca | 240 | |
| cagacatatg aaggacctgc atatagcttt ttaggaaaaa tgcagaaagg tgaatcatat | 300 | |
| aatgtatcgc ttaaagttag acttgtttct gaacaaaatt catctaatcc ttttattacc | 360 | |
| gtgactatgt ttagagaaga tgacaatggc aagcattatg tacaatagt ttggcaaaaa | 420 | |
| caagtttctg aagattcatg gactactgta agcgggactt atacattaga ttatactgga | 480 | |
| acattaaaaa cattatacat gtatgtagaa tcacccgatc caacgctgga atactatatt | 540 | |
| gatgatgttg tagtgacacc acaaaatcca atacaagtag gaatgtgat taccaatgga | 600 | |
| actttgaaa atgaaatac ttcaggatgg gttggaacag gctcatctgt tgttaaggca | 660 | |
| gtgtatggag tggctcatag cggaggttat agtttattga cgacagggag aacagctaat | 720 | |
| tggaatggtc ctagctatga tttgactggc aaaatagtac caggtcaaca atacaatgtt | 780 | |
| gattttgggg tgaaatttgt taatggcaat gatacagaac aaataaaggc tactgttaaa | 840 | |
| gcgacttctg acaaagacaa ttatatacaa gttaatgatt ttgcaaatgt aaataaaggc | 900 | |
| gaatggacag aaataaaagg cagttttact ttacctgtgg cagattacag cggtgtcagc | 960 | |
| atctatgtag aatctcaaaa tcctacttta gagttttaca ttgatgattt ttctgtaata | 1020 | |
| ggtgaaattt caaataatca gattacaata caaaatgata ttccggattt atattcagta | 1080 | |
| ttcaaagatt atttcccccat cggtgttgca gttgatccga gtagattaaa tgatgctgat | 1140 | |
| ccacatgctc aattgactgc taaacatttt aatatgcttg ttgcagaaaa tgccatgaaa | 1200 | |
| ccggaaagct tgcagcctac agagggaaac tttaccttg ataatgctga taagattgtt | 1260 | |
| gattatgcaa tagcacataa tatgaagatg agaggtcata cattgctttg gcataatcag | 1320 | |
| gttccggatt ggttttcca ggacccatct gatccgtcta aaccagcttc aagggatctg | 1380 | |
| ctgcttcaaa gattaagaac gcacataaca actgtgttag atcattttaa aacaaaatac | 1440 | |
| ggttctcaaa atccaataat cggatgggat gttgtaaatg aggttcttga tgataatggc | 1500 | |
| aatttaagaa attctaagtg gttacaaatt ataggacctg attatataga aaaagccttt | 1560 | |
| gaatatgcgc atgaggcaga tccatctatg aaattgttta ttaatgatta caacatcgaa | 1620 | |
| aataatggcg ttaaaacaca ggcaatgtat gatttagtga aaaagttaaa aaatgaaggt | 1680 | |
| gtgcctataa acggaatagg catgcaaatg cacataagca taaattcaaa tatagacaat | 1740 | |
| ataaaagctt ctatagaaaa acttgcatca ttaggtgtgg aaatacaggt aactgaatta | 1800 | |

```
gatatgaaca tgaatggtga tgtatctaac gacgcattgc ttaagcaagc gagattgtat    1860
aaacaattat ttgacttgtt taaagcagaa aaacaatata taactgctgt agtttttggg    1920
ggagtttcag atgatgtaag ttggcttagt aagccaaatg ctccgctact ttttgattca    1980
aagttacagg caaagccagc atactgggca attgtagatc caggcaaagc catacctgac    2040
attcaatctg caaaagcttt agaaggatca ccgacgattg gtgcaaatgt tgatagttct    2100
tggaaacttg taaaaccatt gtatgctaat acttatgtga aaggaactat ggagcaact     2160 gctgctgtta atctatgtg ggatactaaa aacttatatt tgttagtaca aatttcagac     2220
aatactccat ctaataatga tggcatcgag atttttgtgg ataagaatga caacaaatct    2280
actacctatg aaagtgacga tgaacattat atagttaaga gggatggtac agggagttca    2340
aatattacaa agtatgtaat gtctaatgct gatggctatg tagcacagat agctattcca    2400
attgaagaca ttagtcctgt gctgaatgat aaaattggat ttgatatcag aataaatgat    2460
gaccaaggca gtggcaatgt aaatgcgata acagtttgga atgattatac aaacagtcaa    2520
gatactaata cggcatattt tggagattta gtattatcaa aacctgcaca gattgcaaca    2580
gctatatatg gcactcctgt tattgacggt aaagtagatg gcgtttggaa taatgctgaa    2640
gctatttcga caaatacatg ggtcttgggt tcaaatggtg ctactgcaac agcaaaaatg    2700
atgtgggacg ataaatatct ttatatattg gcagatgtaa cagataacaa tttaaataaa    2760
tccagtgtaa atccttatga acaggattct gtggaagttt ttgtagatca gaataatgat    2820
aagcaacttt attatgaaaa tgatgatggg cagtttagag ttaactatga taatgaacaa    2880
agttttggag aagcactaa ttcaaatgga tttaagtcgg caacaagtct tacacaaaat    2940
ggatatattg tagaagaagc tattccttgg acgagtatta ctccgttaaa tggtactatc    3000 ataggtttg acttgcaagt taacgatgca gatgaaaatg gtaagaggac aggtattgtc    3060
acatggtgtg atccaagcgg aaattcatgg caagatactt ctggatttgg aaacttgatg    3120
cttacaggta agccatcttg gggcagtaca agtaattcgg gaactacaag cagtagcagt    3180
aatacaagca gtacaatagg tgtaatcaca aagaacggca acgttattac attgatactt    3240
gatgcaggaa aagctaaaga ccttatagta aattcaaagg acaagaaagt cgtatttgac    3300
ataacaacaa taggtgaagg acaacagaaa gttgtgcaga tttctaagga cattttagac    3360
acaagtgctg ccaacggcaa agacatcgtc ataaaatcag acaatgcatc gatagcactc    3420
acgaaagatg cacttaatca aaaccagata caaaacggtg tcaatgtatc aataaaagac    3480
aatgaaaagc ctaatgtgac aaaattatgt acgctttcta atgtagtaga tataacaata    3540
agcggtagca gtgggaatgt agcattggca aaaccagtag aggtgacatt aaatatatca    3600
aaagctaaca atccaagaaa agtagcagtt tactactaca acccaacaac aaatcaatgg    3660
gagtacgtag ggggtaaagt agacgcatca tctggaacaa taacattcaa tgcaacgcac    3720
ttttcacaat atgcagcatt tgagtatgac aagacattta tgacataaa agacaattgg     3780 gcgaaagacg taatagaagt attagcatca aggcatatag tagaaggaat gacagataca    3840
cagtatgaac caaacaagac agtgacgaga gcagaattta cagcaatgat actgaggctt    3900
ctaaacataa agaagaagc atacagtgga gaatttagcg atgtaaaaag tggagactgg    3960
tatgcaaacg cgatagaagc agcatacaaa gcagggataa tcgaaggtga cggaaagaac    4020
gcaaggccaa atgacagcat aacaagagaa gagatgacag caatagccat gagggcatac    4080
gagatgctga cacagtacaa agaagagaat ataggtgcga caacatttag cgacgacaaa    4140
```

| | |
|---|---|
| tccataagcg attgggcaag aaatgtagtg gcaaatgcag cgaaattagg aatagtaaat | 4200 |
| ggtgagccaa ataacgtatt tgcacctaaa ggaaatgcca caagagcaga agcagcagct | 4260 |
| atcatatacg gcttattaga aaaaacaaat aatcttttaa | 4299 |

<210> SEQ ID NO 19
<211> LENGTH: 963
<212> TYPE: DNA
<213> ORGANISM: Thermoanaerobacterium saccharolyticum
<220> FEATURE:
<221> NAME/KEY: misc_feature
<222> LOCATION: (1)..(963)
<223> OTHER INFORMATION: xylanase

<400> SEQUENCE: 19

| | |
|---|---|
| atgggacttt tcgacatgcc attacaaaaa cttagagaat acactggtac aaatccatgc | 60 |
| cctgaagatt tcgatgagta ttggaatagg gcttagatg agatgaggtc agttgatcct | 120 |
| aaaattgaat tgaaagaaag tagctttcaa gtatcctttg cagaatgcta tgacttgtac | 180 |
| tttacaggtg ttcgtggtgc cagaattcat gcaaagtata aaaacctaa gacagaaggg | 240 |
| aaacatccag cgttgataag atttcatgga tattcgtcaa attcaggcga ctggaacgac | 300 |
| aaattaaatt acgtggcggc aggcttcacc gttgtggcta tggatgtaag aggtcaagga | 360 |
| gggcagtctc aagatgttgg cggtgtaact gggaatactt taaatgggca tattataaga | 420 |
| gggctagacg atgatgctga taatatgctt ttcaggcata ttttcttaga cactgcccaa | 480 |
| ttggctggaa tagttatgaa catgccagaa gttgatgaag atagagtggg agtcatggga | 540 |
| ccttctcaag gcggagggct gtcgttggcg tgtgctgcat ggagccaag ggtacgcaaa | 600 |
| gtagtatctg aatatccttt tttatctgac tacaagagag tttgggactt agaccttgca | 660 |
| aaaaacgcct atcaagagat tacgactat ttcaggcttt ttgacccaag gcatgaaagg | 720 |
| gagaatgagg tatttacaaa gcttggatat atagacgtta aaaaccttgc gaaaaggata | 780 |
| aaaggcgatg tcttaatgtg cgttgggctt atggaccaag tatgtccgcc atcaactgtt | 840 |
| tttgcagcct acaacaacat acagtcaaaa aaagatataa aagtgtatcc tgattatgga | 900 |
| catgaaccta tgagaggatt tggagattta gcgatgcagt ttatgctgga gctaaattca | 960 |
| taa | 963 |

<210> SEQ ID NO 20
<211> LENGTH: 2043
<212> TYPE: DNA
<213> ORGANISM: Thermoanaerobacterium saccharolyticum
<220> FEATURE:
<221> NAME/KEY: misc_feature
<222> LOCATION: (1)..(2043)
<223> OTHER INFORMATION: xylanase

<400> SEQUENCE: 20

| | |
|---|---|
| atgataagta aatcttttta tgcgcatcac agcgcatttg gcgctttctc aagttttgta | 60 |
| atcggtaaat gcggtaaagg cggtggcgtc gtactaaatg atgttcggcc gcctgaaaac | 120 |
| aacgtctaca ttggatacaa aagagatggt gttataagct tgctgccatt tattaaagat | 180 |
| gatacaaaaa atgctgaaga agagtttaca ggagaagtct ctacaagcaa aaaagaaaaa | 240 |
| aacataaaaa tctttgggga agatgagata gaaagagagt tatgctgggc atcagacact | 300 |
| tggacagcag gagacttcaa attttccatc atcactccat ttggatacgt aaaagatcct | 360 |
| tcggtgatga atggagacga aaagaaactt gcactggcac ctgtcatatt tgtacagttg | 420 |
| acaatggata atactgacag cgataaggat gctgagatga tatttggctt tgaaggtccg | 480 |

```
aaaaggatat tatctgagct tacagatgga aaatacttag gaggagtata cggcagaaaa      540
tacggttttg ctatcaaaaa aagcgatgat gtaagagagc tttcaaggct tgatattttg      600
acatcatggg caaatgacaa ctatcaaaat catgggcttg cagagcgcc gtctttgata       660 tttaaagtgc cgagagggga gaaaaggaca tatactgtgg cattggcaac gtatcaaagc      720
ggcgtcataa caacaggaat cgatgctgaa ttttactaca catctgtttt taagtcattg      780
gaagaagtat tatcctttgg acttgacaat caagattatt acttaaattt agcaaaggaa      840
agagatgaag agcttaagaa aagcggttta aatgaataca ggcagttttt attggcacat      900
gcagcccaca gttactatgc cagcacggag cttttaaaga gagacgatgg tatgcctctt      960
tgggtggtaa acgaaggcga atacattatg ataaatacat ttgatttgac ggttgatcat     1020
gtcttctggg aaatgaggtt ccatccttgg acgattacaa atacattgga tctgtactat     1080
gaaaagtaca gctacaggga tcaagcaggt cttgccttta cgcatgatat gggtgtcgca     1140
gatggttttt ctaaagaagg ctattcatct tacgagcttc caaacctgac tggatgtttt     1200
agctacatga cacatgagga gcttttgaat tgggttttga caggttctgt ctatgcaata     1260
aaaataaatg ataagaatg gttaaagaaa aacatgggtg tattcgaaga ttgtttcgat      1320
tctcttgtgg caagagataa aaataatgat ggaataatgg acgttgacag ttcaaggtgt     1380
gagacggggt cggaaataac gacttacgat agccttgacg aaagcttggg acaggcgaga     1440
aacaatctat accttggtgt taagacatgg gcagcttacg tgatgttgca tggtttgttt     1500
aaagaaaatg atcttagtga aaaggcagaa aaagctttag aaaaggcaag acaggctgct     1560
aatactatcg ttgccaagtt tgacgaagaa aatcagtata tacctgcagt atttgagaat     1620
ggcaacacat caaggataat acctgctgta gaggcattgg tatatccata tgttgtagga     1680
tatactgact ttgtaagtga agatggtgta tttggtgggc ttataaaagc cttaagaag      1740 catgtaatga cgattatgaa gcctggtata tgcatagatg aagtatctgg aggttggaag     1800
ctttcgtcaa ccagcaagaa cacatggaat agtaaaattt tcttatgcca atatgtgata     1860
aaagatgtgc ttaatataga ctttggagac aaagagattg agtgggacaa agtcacgca      1920 atgtggcaac aggtgtcttg cagtgaagat tgcgctacag atcaggtaaa cagcgataca     1980
ggtacgccaa gaggaagccg cttgtatccg agacttgtga caagtgtatt gtggatgaaa     2040
tag                                                                   2043
```

<210> SEQ ID NO 21
<211> LENGTH: 1503
<212> TYPE: DNA
<213> ORGANISM: Thermoanaerobacterium saccharolyticum
<220> FEATURE:
<221> NAME/KEY: misc_feature
<222> LOCATION: (1)..(1503)
<223> OTHER INFORMATION: xylanase

<400> SEQUENCE: 21

```
atgattaaag tgatagtgcc agattttttcc gataagaagt tttctgatag gtggagatat       60
tgtgttggaa caggcagact tggccttgcg ctacaaaagg aatacatcga tacattaaaa      120
tatgtgaaag aaaacataga ctttaagtat ataagaggac atggccttttt gtgtgacgat      180 gtaggaatat acagagaaga tgtggtaggc gatgaaataa agccttttta caattttacc      240
tatatagata ggattttga ctcatttta gaaatcggaa taaggccatt tgtggaaatc        300
ggatttatgc ctaaaagatt agcatctggt acacaggcgg tatttattg ggagggaat        360
```

```
gtcactcctc ccaaggatta taaaaagtgg gagaaccctca taaaagctgt cgtttcgcat    420
ttcatatcaa ggtacggaat agatgaagtg gcaaaatggc catttgaaat ttggaatgag    480
ccgaacttaa aagagttttg gaaagatgct gacgagaagg agtattttaa gctgtacaag    540
ataactgcaa aggctataaa ggaagtaaat gagaatataa aagtaggagg acctgctata    600
tgtggtggtg ctgactattg gatagaagat tttttgaatt tctgctatga ggaaaatgtt    660
cctgtagatt ttgtgtcgcg acatgcgtat acgtctaagc aaggcgaata tacgccgcac    720
ttaatatacc aagagatcat gccgtcggaa tacatgctaa acgaatttaa aacggtgaga    780
gatatcatta aaaactcgca ttttccaaac cttccgtttc acataactga atacaataca    840
tcttacagtc ctcaaaatcc tgtacatgat acgccattta atgctgccta tattgccagg    900
atttttaagcg aaggcggaga ttatgttgat tcatttttctt actggacgtt tagcgacgtt    960
ttcgaagaaa gagatgtgcc gcgatcgcaa tttcatggag gatttggact tgtggctcta   1020
aatatggtac caaagcctac cttttacaca tttaaatttt ttaatgctat gggagaggaa   1080
atgctttata gagatgagca tatgattgtg acgagaaggg atgatggctc tgttgcgctc   1140
atagcgtgga atgaagtcat ggataagact gaaaatccag ataaagagta tgaagtccag   1200
ataccagttg gattcaaaga tgtgtttatt aaaagacaat taattgatga agaacatggc   1260
aatccatggg gaacgtggat acacatgggt aggccgaggt atcccagcaa aaaagagata   1320
aatacgctta gagaaattgc aaagccggag attatgacaa gccatgctgt taccaatgat   1380
ggatacttaa atctaaagtt taaattaggc aaaaatgcgg ttgtgctttta tgaattgaca   1440
gaaaggattg acgaatcgag cacatatata ggacttgatg atagcaagat aaacggatat   1500
tga                                                                 1503
```

<210> SEQ ID NO 22
<211> LENGTH: 520
<212> TYPE: PRT
<213> ORGANISM: Clostridium phytofermentans
<220> FEATURE:
<221> NAME/KEY: misc_feature
<222> LOCATION: (1)..(520)
<223> OTHER INFORMATION: xylanase

<400> SEQUENCE: 22

```
Met Leu Gln Lys Met Asn Gly Lys Val Lys Lys Ile Leu Gly Ile Ser
1               5                   10                  15

Ile Ala Phe Leu Met Leu Ile Met Val Ile Pro Thr Ser Ile Ala Lys
            20                  25                  30

Ala Ala Thr Asn Lys Thr Tyr Asp Phe Asn Ser Met Thr Tyr Gln Ser
        35                  40                  45

Thr Trp Gly Val Thr Tyr Ser Ile Ser Asn Gly Ser Gly Thr Phe Asn
    50                  55                  60

Phe Thr Gly Gln Tyr Arg Glu Ile Lys Phe Asn Leu Pro Glu Thr Leu
65                  70                  75                  80

Asp Met Ser Gln Cys Thr Ser Val Thr Phe Asn Ala Ser Ser Pro Asn
                85                  90                  95

Gly Gln Ile Ala Phe Lys Leu Tyr Asp Thr Ser Gly Asn Gln Val Ala
            100                 105                 110

Val Val Tyr Asn Phe Asn Ser Asn Thr Ser Asp Cys Thr Phe Ala Pro
        115                 120                 125

Asn Ser Thr Ala Lys Val Asn Ser Ile Gly Ile Met Ala Gln Gly Thr
    130                 135                 140
```

```
Asn Asn Tyr Ser Ala Val Val Asn Arg Val Thr Phe Thr Met Thr Gly
145                 150                 155                 160

Gly Ser Ser Gly Thr Gly Ser Ser Thr Leu Leu Asn Thr Tyr Gly Asn
            165                 170                 175

Ile Leu Lys Asn Ser Gly Thr Ala Val Asn Leu Ser Gln Leu Gln Asn
            180                 185                 190

Ser Asn Thr Leu Ser Val Ile Lys Thr Gln Tyr Asn Ser Ile Thr Leu
            195                 200                 205

Glu Asn Glu Met Lys Pro Asp Ala Val Leu Gly Ser Ser Ser Thr Leu
210                 215                 220

Met Thr Val Ala Gln Ala Lys Ser Asn Gly Tyr Tyr Ile Pro Ser Ser
225                 230                 235                 240

Tyr Thr Glu Ser Thr Val Pro Thr Leu Lys Phe Ser Thr Ile Asp Ala
            245                 250                 255

Val Leu Gln Ile Cys Tyr Asn Asn Gly Leu Lys Leu Arg Gly His Thr
            260                 265                 270

Leu Val Trp His Ser Gln Thr Pro Asp Trp Phe Phe Arg Thr Gly Tyr
            275                 280                 285

Ser Ser Ser Gly Ser Tyr Val Ser Gln Ala Val Met Asp Ala Arg Met
290                 295                 300

Glu Met Phe Ile Arg Ser Tyr Met Ser His Ile Tyr Asn Gly Ser Tyr
305                 310                 315                 320

Gly Ser Val Val Tyr Ala Trp Asp Val Asn Glu Tyr Leu His Ala
            325                 330                 335

Ser Thr Ser Gly Trp Ser Gln Val Tyr Gly Ser Asn Leu Gly Thr Thr
            340                 345                 350

Pro Ser Tyr Val Lys Lys Ala Phe Gln Tyr Ala Tyr Asp Cys Leu Ser
            355                 360                 365

Ser Phe Gly Leu Thr Asn Ser Val Lys Leu Phe Tyr Asn Asp Tyr Asn
            370                 375                 380

Thr Tyr Glu Val Thr Asp Gln Ile Leu Ser Leu Val Asn Phe Ile Asn
385                 390                 395                 400

Ser Gly Thr Lys Leu Cys Ala Gly Val Gly Met Gln Ser His Leu Asn
            405                 410                 415

Thr Ser Tyr Pro Ser Val Ser Ala Tyr Lys Thr Ala Met Gln Lys Phe
            420                 425                 430

Leu Asn Ala Gly Tyr Glu Val Gln Val Thr Glu Leu Asp Val Thr Asn
            435                 440                 445

Thr Ser Ala Ser Thr Gln Ala Thr Tyr Val Tyr Asp Leu Met Thr Ala
450                 455                 460

Ile Leu Ser Leu Lys Lys Ala Gly Gly Asn Ile Thr Gly Ile Thr Trp
465                 470                 475                 480

Trp Gly Leu Tyr Asp Ser Val Ser Trp Arg Ala Ser Gln Asn Pro Leu
            485                 490                 495

Leu Phe Ser Asn Leu Thr Thr Pro Lys Glu Ser Tyr Asn Lys Ala Leu
            500                 505                 510

Gln Ala Phe Thr Asp Ala Gly Tyr
            515                 520

<210> SEQ ID NO 23
<211> LENGTH: 756
<212> TYPE: PRT
<213> ORGANISM: Clostridium phytofermentans
<220> FEATURE:
<221> NAME/KEY: misc_feature
```

<222> LOCATION: (1)..(756)
<223> OTHER INFORMATION: xylanase

<400> SEQUENCE: 23

```
Met Phe Phe Lys Lys Leu Val Ala Leu Ala Met Ala Val Ala Ile Val
1               5                   10                  15

Ile Pro Met Asn Val Asn Asn Ile Gln Lys Val Glu Ala Glu Ser Thr
            20                  25                  30

Asn Glu Ala Val Val Tyr Gly Asn Leu Ile Tyr His Asp Phe Glu Ala
        35                  40                  45

Ser Thr Asn Gly Trp Gly Pro Arg Gly Asp Asn Ala Glu Val Val Ala
    50                  55                  60

Gln Ser Thr Glu Glu Ala Tyr Ser Gly Leu His Ser Leu Lys Ile Ser
65                  70                  75                  80

Lys Arg Thr Gln Thr Trp His Gly Ala Thr Cys Asp Leu Thr Lys Glu
                85                  90                  95

Leu Thr Ile Gly Glu Thr Tyr Val Phe Gly Ile Tyr Leu Lys Tyr Lys
            100                 105                 110

Gly Ser Ser Tyr Ser Asn Thr Gln Lys Phe Ser Leu Gln Phe Gln Tyr
        115                 120                 125

Asn Asp Gly Val Asn Asp Gln Tyr Lys Thr Ile Lys Thr Leu Glu Val
130                 135                 140

Thr Lys Asp Lys Trp Thr Leu Ile Gln Gly Glu Tyr Thr Val Pro Ala
145                 150                 155                 160

Asp Ala Ala Asn Ala Lys Val Tyr Val Glu Thr Glu Tyr Lys Ser Ser
                165                 170                 175

Pro Ser Ser Gln Asp Leu Leu Asp Phe Tyr Ile Asp Asp Phe Thr Ala
            180                 185                 190

Thr Pro Ala Thr Leu Pro Gln Ile Gln Lys Asp Ile Pro Ser Leu Lys
        195                 200                 205

Asp Val Phe Ser Ser Tyr Phe Phe Val Gly Gly Ala Ala Thr Ala Gly
210                 215                 220

Glu Ile Ala Pro Ala Pro Ala Lys Asp Leu Val Ala Lys His Tyr Asn
225                 230                 235                 240

Arg Leu Thr Pro Gly Asn Glu Leu Lys Pro Asp Ser Val Leu Asp Tyr
                245                 250                 255

Ser Ala Thr Ile Ala Tyr Met Asp Ala Asn Gly Gly Asn Gln Val Asn
            260                 265                 270

Pro Gln Val Asn Leu Arg Ala Ala Lys Thr Leu Leu Glu Tyr Ala Arg
        275                 280                 285

Asp Asn Asn Ile Pro Val Arg Gly His Thr Leu Val Trp His Ser Gln
290                 295                 300

Thr Pro Asp Trp Phe Phe Lys Val Asn Tyr Ser Gln Asp Ser Asn Ala
305                 310                 315                 320

Ala Trp Val Ser Lys Glu Val Met Leu Gln Arg Leu Glu Asn Tyr Ile
                325                 330                 335

Lys Asn Val Met Gln Leu Ile Ser Ser Thr Tyr Pro Thr Val Lys Phe
            340                 345                 350

Tyr Ala Trp Asp Val Val Asn Glu Ala Val Asp Pro Asn Thr Ser Thr
        355                 360                 365

Gly Met Arg Asn Pro Gly Ser Asn Val Thr Ser Gly Asn Ser Pro
370                 375                 380

Trp Met Gln Thr Ile Gly Glu Glu Tyr Ile Gln Arg Ala Phe Glu Tyr
385                 390                 395                 400
```

Ala Arg Lys Tyr Ala Pro Thr Gly Cys Lys Leu Phe Tyr Asn Asp Tyr
            405                 410                 415

Asn Glu Tyr Glu Asp Arg Lys Ser Thr Phe Ile Phe Asn Ile Leu Lys
        420                 425                 430

Gly Leu Lys Asp Lys Gly Leu Val Asp Gly Met Gly Met Gln Ser His
            435                 440                 445

Trp Val Met Asp Tyr Pro Ser Ile Ser Met Phe Glu Thr Ala Val Arg
    450                 455                 460

Lys Tyr Asn Thr Leu Gly Leu Glu Leu Gln Leu Thr Glu Leu Asp Ile
465                 470                 475                 480

Lys Gln Pro Asp Asn Ser Thr Ser Ala Leu Ala Gln Ala Asp Arg
                485                 490                 495

Tyr Lys Leu Leu Ile Asn Lys Val Ile Ser Leu Lys Lys Glu Gly Met
                500                 505                 510

Asn Ile Thr Gly Val Ile Phe Trp Gly Val Thr Asp Lys Thr Ser Trp
            515                 520                 525

Leu Gly Gly Tyr Pro Leu Leu Phe Asp Gly Asn Tyr Gln Ala Lys Ser
    530                 535                 540

Ala Tyr Tyr Ser Ile Ile Asp Gly Ile Thr Pro Thr Val Thr Pro Ser
545                 550                 555                 560

Ile Thr Pro Thr Val Thr Pro Lys Pro Thr Ile Thr Pro Thr Val Thr
                565                 570                 575

Pro Thr Val Thr Pro Lys Pro Thr Ile Thr Pro Thr Val Thr Pro Thr
            580                 585                 590

Val Thr Pro Lys Pro Thr Ile Thr Pro Thr Ile Thr Pro Thr Val Thr
        595                 600                 605

Pro Lys Pro Thr Ile Ala Pro Thr Pro Thr Pro Thr Thr Val Pro Val
    610                 615                 620

Glu Gly Ala Lys Pro Val Val Val Thr Thr Lys Asn Asn Gly Asn
625                 630                 635                 640

Thr Ile Ser Gln Gln Tyr Thr Ile Asn Ala Leu Gly Gly Thr Ile Asp
                645                 650                 655

Leu Ser Lys Val Ser Ile Glu Phe Thr Ala Asp Gly Ile Ile Asn Gln
            660                 665                 670

Glu His Asn Val Trp Val Asp Asn Ala Ala Leu Gln Leu Thr Val Glu
        675                 680                 685

Pro Tyr Tyr Thr Pro Leu Asn Gly Tyr Val Ser Gly Gln Leu Thr Asn
    690                 695                 700

Gln Lys Leu Val Val Ser Ile Ser Lys Ser Thr Met Leu Ser Glu Gly
705                 710                 715                 720

Thr Gly Lys Leu Val Leu Asp Leu Arg Phe Ala Lys Lys Asp Trp Thr
                725                 730                 735

Asp Phe Gly Thr Ile Ser Asn Glu Val Leu Lys Val Tyr Tyr Asn Gly
            740                 745                 750

Val Lys Val Gln
        755

<210> SEQ ID NO 24
<211> LENGTH: 212
<212> TYPE: PRT
<213> ORGANISM: Clostridium phytofermentans
<220> FEATURE:
<221> NAME/KEY: misc_feature
<222> LOCATION: (1)..(212)
<223> OTHER INFORMATION: xylanase

<400> SEQUENCE: 24

Met Phe Lys Leu Asn Lys Val Phe Ala Leu Val Ser Val Ile Ala
1               5                   10                  15

Leu Gly Phe Ser Ser Leu Phe Thr Ser Thr Ala His Ala Ala Thr Asp
                20                  25                  30

Tyr Trp Gln Asn Trp Thr Asp Gly Gly Gly Thr Val Asn Ala Thr Asn
                35                  40                  45

Gly Ser Gly Gly Asn Tyr Ser Val Asn Trp Thr Asn Cys Gly Asn Phe
    50                  55                  60

Val Val Gly Lys Gly Trp Gly Thr Gly Asn Ala Ser Arg Val Val Asn
65                  70                  75                  80

Tyr Asn Ala Gly Val Phe Ser Pro Ser Gly Asn Gly Tyr Leu Thr Phe
                85                  90                  95

Tyr Gly Trp Thr Arg Asn Ser Leu Ile Glu Tyr Tyr Val Val Asp Ser
                100                 105                 110

Trp Gly Thr Tyr Arg Pro Thr Gly Thr Leu Lys Gly Thr Val Ser Ser
                115                 120                 125

Asp Gly Gly Thr Tyr Asp Ile Tyr Thr Ser Thr Arg Thr Asn Ala Pro
130                 135                 140

Ser Ile Asp Gly Thr Gln Thr Phe Gln Gln Tyr Trp Ser Val Arg Gln
145                 150                 155                 160

Ser Lys Arg Ala Thr Gly Ser Asn Val Ala Ile Thr Phe Ser Asn His
                165                 170                 175

Val Asn Ala Trp Lys Ser Lys Gly Met Asn Leu Gly Ser Ser Trp Ala
                180                 185                 190

Tyr Gln Ala Leu Cys Val Glu Gly Tyr Gln Ser Ser Gly Ser Ala Asn
                195                 200                 205

Val Thr Val Trp
            210

<210> SEQ ID NO 25
<211> LENGTH: 806
<212> TYPE: PRT
<213> ORGANISM: Clostridium phytofermentans
<220> FEATURE:
<221> NAME/KEY: misc_feature
<222> LOCATION: (1)..(806)
<223> OTHER INFORMATION: xylanase

<400> SEQUENCE: 25

Met Gly Lys Lys Val Ile Ala Leu Leu Thr Cys Val Met Leu Ser Leu
1               5                   10                  15

Thr Leu Ile Pro Gly Ile Gly Ile Lys Ser Thr Ala Gln Ala Ala Glu
                20                  25                  30

Thr Asn Ile Tyr Lys Val Asp Trp Ser Lys Phe Asn Glu Gly Asp Lys
                35                  40                  45

Ile Ser Gly Pro Met Glu Gly Leu Gly Arg Ser Gly Gly Ala Asp Ile
    50                  55                  60

Thr Val Thr Gly Ser Ser Thr Lys Ser Phe Tyr Ile Ser Asn Arg Lys
65                  70                  75                  80

Asp Asn Trp Asp Ala Leu Asp Ile Gln Asn Asp Leu Leu Lys Leu Asp
                85                  90                  95

Arg Asp Ala Thr Tyr Glu Ile Thr Val Thr Gly His Val Asp Ser Asn
                100                 105                 110

Val Asp Thr Lys Asn Ala Ser Val Lys Leu Gly Gly Val Thr Arg Lys

```
            115                 120                 125
Thr Gly Glu Asp Asp Gly Tyr Pro Glu Phe Lys Lys Glu Lys Leu Gln
    130                 135                 140

Ser Gly Lys Ser Phe Val Leu Thr Tyr Glu Leu Lys Leu Ser Asp Gln
145                 150                 155                 160

Ile Pro Asp Ala Ser Arg Asn Leu Trp Val Leu Arg Val Gln Thr Asp
                165                 170                 175

Glu Pro Ser Gly Ser Arg Ala Gly Asp Leu Val Pro Phe Tyr Val Asp
                180                 185                 190

Asp Ile Val Ile Ile Gln Thr Lys Ala Ser Thr Ala Pro Val Ala Val
            195                 200                 205

Thr Gly Asp Leu Met Ser Leu Tyr Glu Leu Asn Ala Asp Lys Thr Leu
    210                 215                 220

Lys Val Gly Glu Ser Leu Ser Ser Pro Ala Leu Lys Val Ser Gly Asn
225                 230                 235                 240

Ala Lys Ile Val Val Glu Gly Thr Asp Gly Thr Val Ser Leu Gln
                245                 250                 255

Leu Lys Asp Arg Val Asn Asn Tyr Asp Gly Val Asp Ile Leu Arg Asp
                260                 265                 270

Ala Leu Lys Ile Asn Asp Lys Phe Met Ser Gly Thr Tyr Thr Ile Glu
            275                 280                 285

Val Lys Gly His Val Glu Asp Gly Ser Asp Leu Ser Lys Ser Gln Phe
    290                 295                 300

Val Met Gly Met Thr Glu Ser Pro Trp Gly Glu Leu Thr Ser Arg Val
305                 310                 315                 320

Thr Pro Ser Ser Asp Gly Ser Phe Val Ile Thr Tyr Thr Lys Ala Tyr
                325                 330                 335

Thr Gly Ser Glu Leu Thr Gly Leu Gly Tyr Ser Tyr Arg Val Gln Thr
                340                 345                 350

Pro Pro Ser Val Leu Thr Ser Phe Tyr Ile Asp Asn Ile Thr Val Thr
            355                 360                 365

Val Gln Gly Ala Glu Glu Glu Asp Glu Ser Thr Val Val Ile Pro Glu
    370                 375                 380

Trp Asp Leu Thr Leu Asp Ser Ile Lys Asp Ala Tyr Ala Asp Tyr Phe
385                 390                 395                 400

Met Ile Gly Asn Ile Met Glu Pro Gly Gln Ile Gln Asp Thr Glu Thr
                405                 410                 415

Thr Glu Met Phe Lys His His Tyr Asn Val Val Thr Ala Glu Asn Ala
                420                 425                 430

Met Lys Pro Gly Asn Ile Ser Lys Val Lys Gly Glu Tyr Asn Phe Asp
            435                 440                 445

Asn Ala Asp Lys Leu Val Thr Trp Ala Lys Glu Asn Gly Leu Lys Val
    450                 455                 460

His Gly His Thr Leu Val Trp His Ser Gln Ser Ala Pro Trp Leu Thr
465                 470                 475                 480

Thr Asn Ala Asp Gly Thr Pro Leu Thr Arg Ala Glu Ala Arg Ala Asn
                485                 490                 495

Met Glu Asp Tyr Ile Lys Asn Val Ala Gly His Tyr Ala Gly Lys Val
                500                 505                 510

Ile Ser Trp Asp Val Leu Asn Glu Ala Phe Leu Pro Gly Val Ser Glu
            515                 520                 525

Ile Pro Ala Gly Trp Arg Asp Val Leu Arg Lys Phe Glu Asp Asn Gly
    530                 535                 540
```

```
Asn Gly Ser Pro Trp Tyr Gln Ala Tyr Glu Asn Gly Ala Asp Lys Ser
545                 550                 555                 560

Lys Gly Glu Asp Gly Ser Asp Tyr Ile Tyr Asp Ala Phe Val Phe Thr
            565                 570                 575

Arg Leu Ala Ala Pro Asp Ala Val Leu Tyr Tyr Asn Asp Phe Asn Glu
        580                 585                 590

Thr Glu Ala Gly Lys Cys Glu Ala Ile Ala Leu Met Val Glu Glu Leu
    595                 600                 605

Asn Thr Lys Trp Lys Thr Asp Lys Arg Asn Thr Glu Pro Asp Arg Leu
610                 615                 620

Leu Ile Glu Gly Ile Gly Met Gln Ala His Tyr Trp Thr Gly Asp Leu
625                 630                 635                 640

Lys Val Ser Thr Val Glu Ala Ser Ile Lys Arg Phe Ile Lys Thr Gly
                645                 650                 655

Ala Lys Ile Ser Val Ser Glu Leu Asp Val Pro His Gly Asp Tyr Met
            660                 665                 670

Thr Tyr Lys Gln Arg Thr Asp Ser Pro Thr Lys Glu Glu Lys Leu
        675                 680                 685

Gln Ala Asp Leu Tyr Lys Gln Leu Phe Glu Val Tyr Lys Lys Tyr Ala
    690                 695                 700

Asp Asn Ile Glu Arg Val Thr Phe Trp Gly Lys Thr Asp Pro Gln Ser
705                 710                 715                 720

Trp Arg Phe Gln Gly Tyr Pro Leu Leu Phe Asp Lys Asn Phe Ala Pro
                725                 730                 735

Lys Asp Ala Phe Phe Ala Val Ile Asp Val Ala Lys Glu Lys Val Ala
            740                 745                 750

Glu Glu Lys Ala Val Glu Thr Ile Pro Gly Lys Asp Ile Pro Lys Thr
        755                 760                 765

Gly Glu Asp Ser Ser Lys Gln Met Ile Leu Thr Ala Val Ala Ile Leu
    770                 775                 780

Ile Ile Leu Val Phe Val Pro Val Thr Ile Leu Thr Lys Arg Arg Glu
785                 790                 795                 800

Lys Asn Ile Lys Asn Ile
            805

<210> SEQ ID NO 26
<211> LENGTH: 395
<212> TYPE: PRT
<213> ORGANISM: Thermobifida fusca
<220> FEATURE:
<221> NAME/KEY: misc_feature
<222> LOCATION: (1)..(395)
<223> OTHER INFORMATION: xylanase

<400> SEQUENCE: 26

Met Gly Leu Pro Val Ser Val His Arg Ser Asp Thr Lys Met Arg Val
1               5                   10                  15

Gly Arg Tyr Ile Ala Ile Thr Val Gly Ala Ser Ala Leu Leu Val Ser
            20                  25                  30

Gly Val Ala Pro Ala Ala Ala Gly Thr Leu Pro Thr Ser Gly Thr Ala
        35                  40                  45

Ala Gly Ala Ala Ser Gln Ala Gly His Asp Gln Lys Gln Val Pro Leu
    50                  55                  60

Arg Lys Val Ala Pro Lys Gly Phe Ala Ile Gly Val Ala Val Ala Gly
65                  70                  75                  80
```

```
Gly Gly His His Leu Asp Gln Glu Tyr Pro Asp Pro Phe Lys Tyr Asp
                 85                  90                  95

Glu Glu Tyr Arg Gly Val Leu Ala Lys His Phe Asn Ser Val Thr Pro
            100                 105                 110

Glu Asn His Leu Lys Trp Asp Phe Val His Pro Glu Arg Lys Lys Tyr
        115                 120                 125

Asn Phe Gly Pro Ala Asp Gln Ile Val Lys Phe Ala Gln Ser Asn Gly
    130                 135                 140

Gln Lys Val Arg Gly His Thr Leu Val Trp His Ser Gln Asn Pro Asp
145                 150                 155                 160

Trp Leu Thr Lys Gly Lys Phe Ser Lys Lys Glu Leu Arg Lys Ile Leu
                165                 170                 175

Lys Glu His Ile Ile Thr Val Val Gly Arg Tyr Arg Gly Lys Ile His
                180                 185                 190

Gln Trp Asp Val Ala Asn Glu Ile Phe Asp Asp Asn Gly Lys Leu Arg
            195                 200                 205

Thr Asn Glu Asn Ile Trp Leu Lys Asn Phe Gly Pro Glu Ile Ile Ala
    210                 215                 220

Asp Ala Phe Arg Trp Ala His Gln Ala Asp Pro Lys Ala Lys Leu Phe
225                 230                 235                 240

Leu Asn Asp Tyr Gly Ala Glu Gly Ile Asn Lys Arg Ser Asp Ala Tyr
                245                 250                 255

Leu Lys Phe Met Lys Glu Leu Arg Lys Lys Gly Val Pro Val His Gly
                260                 265                 270

Phe Gly Val Gln Gly His Leu Ser Leu Ala Tyr Pro Phe Pro Gly Asp
            275                 280                 285

Met Ala Lys Asn Leu Lys Arg Phe Ser Asp Ala Gly Phe Glu Val Ala
    290                 295                 300

Val Thr Glu Val Asp Val Arg Ile Pro Leu Asn Gly Gly Asp Ala Thr
305                 310                 315                 320

Glu Ala Gln Leu Lys Thr Gln Ala Asp Tyr Tyr Arg Arg Ala Leu Glu
                325                 330                 335

Ala Cys Leu Ser Val Lys Ser Cys Asn Ser Phe Thr Leu Trp Gly Thr
            340                 345                 350

Thr Asn Lys Tyr Ser Trp Val Pro Val Phe Phe Pro Asp Glu Gly Glu
        355                 360                 365

Ala Thr Ile Phe Trp Asp Asp Phe Ser Pro Lys Pro Ala Tyr Thr Ala
    370                 375                 380

Leu Gln Glu Ala Leu Ala Lys Ala Arg Arg
385                 390                 395

<210> SEQ ID NO 27
<211> LENGTH: 338
<212> TYPE: PRT
<213> ORGANISM: Thermobifida fusca
<220> FEATURE:
<221> NAME/KEY: misc_feature
<222> LOCATION: (1)..(338)
<223> OTHER INFORMATION: xylanase

<400> SEQUENCE: 27

Met Asn His Ala Pro Ala Ser Leu Lys Ser Arg Arg Phe Arg Pro
1               5                   10                  15

Arg Leu Leu Ile Gly Lys Ala Phe Ala Ala Leu Val Ala Val Val
            20                  25                  30

Thr Met Ile Pro Ser Thr Ala Ala His Ala Ala Val Thr Ser Asn Glu
```

```
                 35                  40                  45
Thr Gly Tyr His Asp Gly Tyr Phe Tyr Ser Phe Trp Thr Asp Ala Pro
 50                  55                  60

Gly Thr Val Ser Met Glu Leu Gly Pro Gly Gly Asn Tyr Ser Thr Ser
 65                  70                  75                  80

Trp Arg Asn Thr Gly Asn Phe Val Ala Gly Lys Gly Trp Ala Thr Gly
                 85                  90                  95

Gly Arg Arg Thr Val Thr Tyr Ser Ala Ser Phe Asn Pro Ser Gly Asn
                100                 105                 110

Ala Tyr Leu Thr Leu Tyr Gly Trp Thr Arg Asn Pro Leu Val Glu Tyr
                115                 120                 125

Tyr Ile Val Glu Ser Trp Gly Thr Tyr Arg Pro Thr Gly Thr Tyr Met
                130                 135                 140

Gly Thr Val Thr Thr Asp Gly Gly Thr Tyr Asp Ile Tyr Lys Thr Thr
145                 150                 155                 160

Arg Tyr Asn Ala Pro Ser Ile Glu Gly Thr Arg Thr Phe Asp Gln Tyr
                165                 170                 175

Trp Ser Val Arg Gln Ser Lys Arg Thr Ser Gly Thr Ile Thr Ala Gly
                180                 185                 190

Asn His Phe Asp Ala Trp Ala Arg His Gly Met His Leu Gly Thr His
                195                 200                 205

Asp Tyr Met Ile Met Ala Thr Glu Gly Tyr Gln Ser Ser Gly Ser Ser
                210                 215                 220

Asn Val Thr Leu Gly Thr Ser Gly Gly Asp Asn Pro Gly Gly Gly Asn
225                 230                 235                 240

Pro Pro Gly Gly Gly Asn Pro Pro Gly Gly Gly Cys Thr Ala Thr
                245                 250                 255

Leu Ser Ala Gly Gln Gln Trp Asn Asp Arg Tyr Asn Leu Asn Val Asn
                260                 265                 270

Val Ser Gly Ser Asn Asn Trp Thr Val Thr Val Asn Val Pro Trp Pro
                275                 280                 285

Ala Arg Ile Ile Ala Thr Trp Asn Ile His Ala Ser Tyr Pro Asp Ser
                290                 295                 300

Gln Thr Leu Val Ala Arg Pro Asn Gly Asn Gly Asn Asn Trp Gly Met
305                 310                 315                 320

Thr Ile Met His Asn Gly Asn Trp Thr Trp Pro Thr Val Ser Cys Ser
                325                 330                 335

Ala Asn

<210> SEQ ID NO 28
<211> LENGTH: 654
<212> TYPE: PRT
<213> ORGANISM: Clostridium stercorarium
<220> FEATURE:
<221> NAME/KEY: misc_feature
<222> LOCATION: (1)..(654)
<223> OTHER INFORMATION: xylanase

<400> SEQUENCE: 28

Met Lys Arg Lys Val Lys Lys Met Ala Ala Met Ala Thr Ser Ile Ile
 1               5                  10                  15

Met Ala Ile Met Ile Ile Leu His Ser Ile Pro Val Leu Ala Gly Arg
                20                  25                  30

Ile Ile Tyr Asp Asn Glu Thr Gly Thr His Gly Gly Tyr Asp Tyr Glu
                35                  40                  45
```

```
Leu Trp Lys Asp Tyr Gly Asn Thr Ile Met Glu Leu Asn Asp Gly Gly
 50                  55                  60

Thr Phe Ser Cys Gln Trp Ser Asn Ile Gly Asn Ala Leu Phe Arg Lys
 65                  70                  75                  80

Gly Arg Lys Phe Asn Ser Asp Lys Thr Tyr Gln Glu Leu Gly Asp Ile
                 85                  90                  95

Val Val Glu Tyr Gly Cys Asp Tyr Asn Pro Asn Gly Asn Ser Tyr Leu
            100                 105                 110

Cys Val Tyr Gly Trp Thr Arg Asn Pro Leu Val Glu Tyr Tyr Ile Val
        115                 120                 125

Glu Ser Trp Gly Ser Trp Arg Pro Pro Gly Ala Thr Pro Lys Gly Thr
    130                 135                 140

Ile Thr Val Asp Gly Gly Thr Tyr Glu Ile Tyr Glu Thr Thr Arg Val
145                 150                 155                 160

Asn Gln Pro Ser Ile Asp Gly Thr Ala Thr Phe Gln Gln Tyr Trp Ser
                165                 170                 175

Val Arg Thr Ser Lys Arg Thr Ser Gly Thr Ile Ser Val Thr Glu His
            180                 185                 190

Phe Lys Gln Trp Glu Arg Met Gly Met Arg Met Gly Lys Met Tyr Glu
        195                 200                 205

Val Ala Leu Thr Val Glu Gly Tyr Gln Ser Ser Gly Tyr Ala Asn Val
    210                 215                 220

Tyr Lys Asn Glu Ile Arg Ile Gly Ala Asn Pro Thr Pro Ala Pro Ser
225                 230                 235                 240

Gln Ser Pro Ile Arg Arg Asp Ala Phe Ser Ile Ile Glu Ala Glu Glu
                245                 250                 255

Tyr Asn Ser Thr Asn Ser Ser Thr Leu Gln Val Ile Gly Thr Pro Asn
            260                 265                 270

Asn Gly Arg Gly Ile Gly Tyr Ile Glu Asn Gly Asn Thr Val Thr Tyr
        275                 280                 285

Ser Asn Ile Asp Phe Gly Ser Gly Ala Thr Gly Phe Ser Ala Thr Val
    290                 295                 300

Ala Thr Glu Val Asn Thr Ser Ile Gln Ile Arg Ser Asp Ser Pro Thr
305                 310                 315                 320

Gly Thr Leu Leu Gly Thr Leu Tyr Val Ser Ser Thr Gly Ser Trp Asn
                325                 330                 335

Thr Tyr Gln Thr Val Ser Thr Asn Ile Ser Lys Ile Thr Gly Val His
            340                 345                 350

Asp Ile Val Leu Val Phe Ser Gly Pro Val Asn Val Asp Asn Phe Ile
        355                 360                 365

Phe Ser Arg Ser Ser Pro Val Pro Ala Pro Gly Asp Asn Thr Arg Asp
    370                 375                 380

Ala Tyr Ser Ile Ile Gln Ala Glu Asp Tyr Asp Ser Ser Tyr Gly Pro
385                 390                 395                 400

Asn Leu Gln Ile Phe Ser Leu Pro Gly Gly Gly Ser Ala Ile Gly Tyr
                405                 410                 415

Ile Glu Asn Gly Tyr Ser Thr Thr Tyr Asn Asn Val Asn Phe Ala Asn
            420                 425                 430

Gly Leu Ser Ser Ile Thr Ala Arg Val Ala Thr Gln Ile Ser Thr Ser
        435                 440                 445

Ile Gln Val Arg Ala Gly Gly Ala Thr Gly Thr Leu Leu Gly Thr Ile
    450                 455                 460

Tyr Val Pro Ser Thr Asn Ser Trp Asp Ser Tyr Gln Asn Val Thr Ala
```

```
                    465                 470                 475                 480
Asn Leu Ser Asn Ile Thr Gly Val His Asp Ile Thr Leu Val Phe Ser
                    485                 490                 495

Gly Pro Val Asn Val Asp Tyr Phe Val Phe Thr Pro Ala Asn Val Asn
                500                 505                 510

Ser Gly Pro Thr Ser Pro Val Gly Gly Thr Arg Ser Ala Phe Ser Asn
                515                 520                 525

Ile Gln Ala Glu Asp Tyr Asp Ser Ser Tyr Gly Pro Asn Leu Gln Ile
                530                 535                 540

Phe Ser Leu Pro Gly Gly Ser Ala Ile Gly Tyr Ile Glu Asn Gly
545                 550                 555                 560

Tyr Ser Thr Thr Tyr Lys Asn Ile Asp Phe Gly Asp Gly Ala Thr Ser
                565                 570                 575

Val Thr Ala Arg Val Ala Thr Gln Asn Ala Thr Thr Ile Gln Val Arg
                580                 585                 590

Leu Gly Ser Pro Ser Gly Thr Leu Leu Gly Thr Ile Tyr Val Gly Ser
                595                 600                 605

Thr Gly Ser Phe Asp Thr Tyr Arg Asp Val Ser Ala Thr Ile Ser Asn
                610                 615                 620

Thr Ala Gly Val Lys Asp Ile Val Leu Val Phe Ser Gly Pro Val Asn
625                 630                 635                 640

Val Asp Trp Phe Val Phe Ser Lys Phe Arg Asn Leu Arg Val
                645                 650

<210> SEQ ID NO 29
<211> LENGTH: 387
<212> TYPE: PRT
<213> ORGANISM: Clostridium stercorarium
<220> FEATURE:
<221> NAME/KEY: misc_feature
<222> LOCATION: (1)..(387)
<223> OTHER INFORMATION: xylanase

<400> SEQUENCE: 29

Met Asn Lys Phe Leu Asn Lys Lys Trp Ser Leu Ile Leu Thr Met Gly
1               5                   10                  15

Gly Ile Phe Leu Met Ala Thr Leu Ser Leu Ile Phe Ala Thr Gly Lys
                20                  25                  30

Lys Ala Phe Asn Asp Gln Thr Ser Ala Glu Asp Ile Pro Ser Leu Ala
            35                  40                  45

Glu Ala Phe Arg Asp Tyr Phe Pro Ile Gly Ala Ala Ile Glu Pro Gly
        50                  55                  60

Tyr Thr Thr Gly Gln Ile Ala Glu Leu Tyr Lys Lys His Val Asn Met
65                  70                  75                  80

Leu Val Ala Glu Asn Ala Met Lys Pro Ala Ser Leu Gln Pro Thr Glu
                85                  90                  95

Gly Asn Phe Gln Trp Ala Asp Ala Asp Arg Ile Val Gln Phe Ala Lys
            100                 105                 110

Glu Asn Gly Met Glu Leu Arg Phe His Thr Leu Val Trp His Asn Gln
        115                 120                 125

Thr Pro Thr Gly Phe Ser Leu Asp Lys Glu Gly Lys Pro Met Val Glu
    130                 135                 140

Glu Thr Asp Pro Gln Lys Arg Glu Glu Asn Arg Lys Leu Leu Leu Gln
145                 150                 155                 160

Arg Leu Glu Asn Tyr Ile Arg Ala Val Val Leu Arg Tyr Lys Asp Asp
                165                 170                 175
```

```
Ile Lys Ser Trp Asp Val Val Asn Glu Val Ile Glu Pro Asn Asp Pro
            180                 185                 190

Gly Gly Met Arg Asn Ser Pro Trp Tyr Gln Ile Thr Gly Thr Glu Tyr
            195                 200                 205

Ile Glu Val Ala Phe Arg Ala Arg Glu Ala Gly Gly Ser Asp Ile
210                 215                 220

Lys Leu Tyr Ile Asn Asp Tyr Asn Thr Asp Asp Pro Val Lys Arg Asp
225                 230                 235                 240

Ile Leu Tyr Glu Leu Val Lys Asn Leu Leu Glu Lys Gly Val Pro Ile
            245                 250                 255

Asp Gly Val Gly His Gln Thr His Ile Asp Ile Tyr Asn Pro Pro Val
            260                 265                 270

Glu Arg Ile Ile Glu Ser Ile Lys Lys Phe Ala Gly Leu Gly Leu Asp
            275                 280                 285

Asn Ile Ile Thr Glu Leu Asp Met Ser Ile Tyr Ser Trp Asn Asp Arg
            290                 295                 300

Ser Asp Tyr Gly Asp Ser Ile Pro Asp Tyr Ile Leu Thr Leu Gln Ala
305                 310                 315                 320

Lys Arg Tyr Gln Glu Leu Phe Asp Ala Leu Lys Glu Asn Lys Asp Ile
            325                 330                 335

Val Ser Ala Val Val Phe Trp Gly Ile Ser Asp Lys Tyr Ser Trp Leu
            340                 345                 350

Asn Gly Phe Pro Val Lys Arg Thr Asn Ala Pro Leu Leu Phe Asp Arg
            355                 360                 365

Asn Phe Met Pro Lys Pro Ala Phe Trp Ala Ile Val Asp Pro Ser Arg
            370                 375                 380

Leu Arg Glu
385

<210> SEQ ID NO 30
<211> LENGTH: 1032
<212> TYPE: PRT
<213> ORGANISM: Clostridium stercorarium
<220> FEATURE:
<221> NAME/KEY: misc_feature
<222> LOCATION: (1)..(1032)
<223> OTHER INFORMATION: xylanase

<400> SEQUENCE: 30

Met Asn Gly Arg Asn Gly Gly Lys Arg Pro Ile Ala Ser Leu Leu Val
1               5                   10                  15

Leu Thr Leu Ala Phe Leu Phe Ile Pro Val Thr Lys Ala Glu Thr Thr
            20                  25                  30

Val Tyr His Glu Thr Phe Ala Glu Gly Lys Gly Ala Ala Val Gln Ser
            35                  40                  45

Gly Gly Ala Thr Ile Thr His Val Thr Gly Lys Phe Phe Asp Gly Asn
        50                  55                  60

Gly Asp Gly Ala Ala Leu Tyr Ile Ser Asn Arg Val Asn Asn Trp Asp
65                  70                  75                  80

Ala Ala Asp Phe Arg Phe Ser Asp Ile Gly Leu Gln Asp Gly Arg Ile
                85                  90                  95

Tyr Lys Ile Thr Val Lys Gly Tyr Val Asp Pro Asp Val His Val Pro
            100                 105                 110

Glu Gly Ser Gln Ile Trp Leu Gln Thr Val Asn Ser Tyr Gly Trp Trp
            115                 120                 125
```

```
Gly Ser Thr Asp Ile Lys Ala Gly Glu Ala Phe Leu Thr Gly Val
    130                 135                 140
Tyr Lys Val Asp Thr Thr Asn Asp Tyr Ala Leu Arg Ile Gln Ser Asn
145                 150                 155                 160
Asp Thr Gly Ala Phe Val Pro Phe Tyr Ile Gly Glu Ile Leu Ile Thr
                    165                 170                 175
Glu Glu Thr Val Pro Gln Asp Asp Ser Arg Asn Gly Asn Lys Thr His
                180                 185                 190
Ala Glu Lys Phe Thr Pro Ile Thr Phe Glu Asp Gln Thr Thr Gly Gly
            195                 200                 205
Phe Thr Gly Arg Ala Gly Thr Glu Ile Leu Thr Val Thr Asp Glu Ala
210                 215                 220
Asn His Thr Asp Gly Gly Arg Tyr Ser Leu Lys Val Gly Gly Arg Asn
225                 230                 235                 240
Asp Thr Trp His Gly Pro Ala Leu Gly Val Glu Lys Tyr Val Asp Gln
                245                 250                 255
Gly Tyr Glu Tyr Lys Val Ala Val Tyr Val Arg Leu Ile Ser Pro Glu
            260                 265                 270
Ser Ala Gln Leu Gln Leu Ser Thr Gln Ile Gly Glu Gly Thr Ser Ala
            275                 280                 285
Ser Tyr Val Asn Leu Ala Lys Lys Asn Val Ala Ile Ser Asp Gly Trp
    290                 295                 300
Val Leu Leu Glu Gly Thr Tyr Arg Tyr Asp Asn Leu Gly Gly Gly Tyr
305                 310                 315                 320
Leu Thr Ile Tyr Val Glu Ser Pro Asp Ser Pro Glu Ala Ser Phe Tyr
                325                 330                 335
Ile Asp Asp Ile Asn Phe Glu Pro Thr Gly Met Lys Ser Glu Glu Ile
                340                 345                 350
Glu Lys Gly Leu Lys Ser Leu Lys Asp Val Tyr Lys Asp Asn Phe Leu
            355                 360                 365
Thr Gly Thr Ala Ile Ser Leu Arg Asp Leu Glu Gly Val Arg Phe Glu
            370                 375                 380
Leu Leu Lys Lys His Phe Asn Ala Val Thr Ala Glu Asn Ala Met Lys
385                 390                 395                 400
Pro Ser Glu Leu Gln Arg Glu Lys Gly Asn Phe Thr Phe Asp Gly Ala
                405                 410                 415
Asp Arg Leu Val Asn Ala Ala Ile Ser Ala Gly Met Lys Val His Gly
                420                 425                 430
His Thr Leu Val Trp His Gln Gln Thr Pro Ala Trp Met Asn Ile Lys
            435                 440                 445
Leu Asp Ser Gly Gly Asn Ile Val Tyr Leu Ser Arg Glu Glu Ala Leu
450                 455                 460
Glu Asn Met Arg Asn His Ile Arg Thr Val Ile Glu His Phe Gly Asp
465                 470                 475                 480
Lys Val Ile Ser Trp Asp Val Val Asn Glu Ala Met Ser Asp Asn Pro
                485                 490                 495
Ser Asn Pro Ser Asp Trp Arg Gly Ser Leu Arg Lys Ser Pro Trp Tyr
                500                 505                 510
Tyr Ala Ile Gly Glu Asp Tyr Val Glu Gln Ala Phe Leu Ala Ala Arg
            515                 520                 525
Glu Val Leu Asp Glu His Pro Glu Trp Asp Ile Lys Leu Tyr Tyr Asn
530                 535                 540
Asp Tyr Asn Leu Asp Asn Gln Asn Lys Ala Leu Ala Val Tyr Asn Met
```

-continued

```
           545                 550                 555                 560
Val Arg Glu Leu Asn Glu Lys Tyr Gln Lys Thr His Pro Gly Lys Leu
               565                 570                 575
Leu Ile Asp Gly Ile Gly Met Gln Gly His Tyr Ser Val Asn Thr Asn
               580                 585                 590
Pro Lys Asn Val Glu Leu Ser Leu Lys Arg Phe Thr Glu Leu Gly Val
               595                 600                 605
Glu Val Ser Ile Ser Glu Leu Asp Ile Arg Ala Gly Ser Asn Tyr Gln
               610                 615                 620
Leu Thr Glu Lys Glu Ala Asn Ala Gln Ala Tyr Leu Tyr Ala Gln Leu
625                 630                 635                 640
Phe Lys Ile Phe Arg Glu Tyr Ser Asp Ser Ile Ala Arg Val Thr Phe
                   645                 650                 655
Trp Gly Met Asp Asp Gly Thr Ser Trp Arg Ala Glu Glu Ser Pro Leu
                   660                 665                 670
Leu Phe Asp Arg Thr Leu Lys Ala Lys Pro Ala Tyr Tyr Ala Val Ala
                   675                 680                 685
Asp Pro Asp Glu Phe Ile Glu Lys Tyr Lys Pro Glu Thr Ile Glu Ala
               690                 695                 700
Asn Arg Ala Tyr Ala Val Tyr Gly Thr Pro Glu Ile Asp Gly Lys Thr
705                 710                 715                 720
Asp Glu Val Trp Asn Lys Ala Pro Glu Leu Lys Ile Asn Arg Tyr Gln
                   725                 730                 735
Thr Ala Trp His Gly Ala Asp Gly Thr Ala Arg Val Leu Tyr Asp Glu
                   740                 745                 750
Asn Asn Leu Tyr Val Leu Ile Lys Val Asn Asp Thr Gln Leu Asp Lys
               755                 760                 765
Gly Ser Pro Asn Pro Trp Glu Gln Asp Ser Val Glu Ile Phe Ile Asp
               770                 775                 780
Glu Asn Asn Ala Lys Thr Ser Phe Tyr Glu Glu Asp Asp Gly Gln Tyr
785                 790                 795                 800
Arg Val Asn Phe Glu Asn Glu Thr Ser Phe Asn Pro Glu Ser Ile Ala
                   805                 810                 815
Gly Gly Phe Glu Ser Ala Ala Glu Val Ser Gly Thr Asn Tyr Thr Leu
                   820                 825                 830
Glu Val Lys Ile Pro Phe Arg Thr Val Lys Pro Val Ser Asn Met Gln
                   835                 840                 845
Ile Gly Phe Asp Val Gln Ile Asn Asp Gly Lys Asn Gly Val Arg Gln
850                 855                 860
Ser Ile Ala Thr Trp Asn Asp Pro Thr Gly Asn Ala Trp Gln Asp Thr
865                 870                 875                 880
Ser Val Phe Gly Ile Leu Thr Leu Lys Ser Lys Asn Pro Val Thr Arg
                   885                 890                 895
Gly Glu Ala Ile Val Lys Ile Met Lys Ala Tyr Asp Met Glu Pro Leu
                   900                 905                 910
Glu Asn Trp Asn Asp Asn Phe Ser Asp Ala Ser Gly Ser Tyr Ala Gly
                   915                 920                 925
Tyr Tyr Pro Arg Ala Lys Glu Thr Gly Phe Val Ser Gly Ile Gly Asp
                   930                 935                 940
Asn Lys Ile Gly Ala Glu Ile Pro Leu Thr Arg Glu Met Phe Phe Thr
945                 950                 955                 960
Met Ile Tyr Asn Ile Glu Arg Ile Thr Gly Lys Met Gln Gly Ile Asp
                   965                 970                 975
```

```
Ile Ser Asp Ala Glu Leu Thr Leu Phe Ser Asp Tyr Asn Asp Leu Ser
            980                 985                 990

Glu Trp Ala Glu Glu Ala Val Lys  Ala Leu Val Lys Ser  Gly Arg Ile
            995                 1000                1005

Lys Ile  Asn Gly Asp Leu Leu  Pro Lys Arg Leu Met  Asp Ala Glu
            1010                1015                1020

Glu Val  Glu Ala Phe Leu Arg  Leu Arg
            1025                1030

<210> SEQ ID NO 31
<211> LENGTH: 422
<212> TYPE: PRT
<213> ORGANISM: Bacillus subtilis
<220> FEATURE:
<221> NAME/KEY: misc_feature
<222> LOCATION: (1)..(422)
<223> OTHER INFORMATION: xylanase

<400> SEQUENCE: 31

Met Ile Pro Arg Ile Lys Lys Thr Ile Cys Val Leu Leu Val Cys Phe
1               5                   10                  15

Thr Met Leu Ser Val Met Leu Gly Pro Gly Ala Thr Glu Val Leu Ala
            20                  25                  30

Ala Ser Asp Val Thr Val Asn Val Ser Ala Glu Lys Gln Val Ile Arg
        35                  40                  45

Gly Phe Gly Gly Met Asn His Pro Ala Trp Ala Gly Asp Leu Thr Ala
    50                  55                  60

Ala Gln Arg Glu Thr Ala Phe Gly Asn Gly Gln Asn Gln Leu Gly Phe
65                  70                  75                  80

Ser Ile Leu Arg Ile His Val Asp Glu Asn Arg Asn Asn Trp Tyr Lys
                85                  90                  95

Glu Val Glu Thr Ala Lys Ser Ala Val Lys His Gly Ala Ile Val Phe
            100                 105                 110

Ala Ser Pro Trp Asn Pro Pro Ser Asp Met Val Glu Thr Phe Asn Arg
        115                 120                 125

Asn Gly Asp Thr Ser Ala Lys Arg Leu Lys Tyr Asn Lys Tyr Ala Ala
    130                 135                 140

Tyr Ala Gln His Leu Asn Asp Phe Val Thr Phe Met Lys Asn Asn Gly
145                 150                 155                 160

Val Asn Leu Tyr Ala Ile Ser Val Gln Asn Glu Pro Asp Tyr Ala His
                165                 170                 175

Glu Trp Thr Trp Trp Thr Pro Gln Glu Ile Leu Arg Phe Met Arg Glu
            180                 185                 190

Asn Ala Gly Ser Ile Asn Ala Arg Val Ile Ala Pro Glu Ser Phe Gln
        195                 200                 205

Tyr Leu Lys Asn Leu Ser Asp Pro Ile Leu Asn Asp Pro Gln Ala Leu
    210                 215                 220

Ala Asn Met Asp Ile Leu Gly Thr His Leu Tyr Gly Thr Gln Val Ser
225                 230                 235                 240

Gln Phe Pro Tyr Pro Leu Phe Lys Gln Lys Gly Ala Gly Lys Asp Leu
                245                 250                 255

Trp Met Thr Glu Val Tyr Tyr Pro Asn Ser Asp Thr Asn Ser Ala Asp
            260                 265                 270

Arg Trp Pro Glu Ala Leu Asp Val Ser Gln His Ile His Asn Ala Met
        275                 280                 285
```

```
Val Glu Gly Asp Phe Gln Ala Tyr Val Trp Trp Tyr Ile Arg Arg Ser
    290                 295                 300

Tyr Gly Pro Met Lys Glu Asp Gly Thr Ile Ser Lys Arg Gly Tyr Asn
305                 310                 315                 320

Met Ala His Phe Ser Lys Phe Val Arg Pro Gly Tyr Val Arg Ile Asp
                325                 330                 335

Ala Thr Lys Asn Pro Asn Ala Asn Val Tyr Val Ser Ala Tyr Lys Gly
                340                 345                 350

Asp Asn Lys Val Val Ile Val Ala Ile Asn Lys Ser Asn Thr Gly Val
                355                 360                 365

Asn Gln Asn Phe Val Leu Gln Asn Gly Ser Ala Ser Asn Val Ser Arg
370                 375                 380

Trp Ile Thr Ser Ser Ser Asn Leu Gln Pro Gly Thr Asn Leu Thr
385                 390                 395                 400

Val Ser Gly Asn His Phe Trp Ala His Leu Pro Ala Gln Ser Val Thr
                405                 410                 415

Thr Phe Val Val Asn Arg
            420

<210> SEQ ID NO 32
<211> LENGTH: 513
<212> TYPE: PRT
<213> ORGANISM: Bacillus subtilis
<220> FEATURE:
<221> NAME/KEY: misc_feature
<222> LOCATION: (1)..(513)
<223> OTHER INFORMATION: xylanase

<400> SEQUENCE: 32

Met Arg Lys Lys Cys Ser Val Cys Leu Trp Ile Leu Val Leu Leu Leu
1               5                   10                  15

Ser Cys Leu Ser Gly Lys Ser Ala Tyr Ala Ala Thr Ser Thr Thr Ile
                20                  25                  30

Ala Lys His Ile Gly Asn Ser Asn Pro Leu Ile Asp His His Leu Gly
                35                  40                  45

Ala Asp Pro Val Ala Leu Thr Tyr Asn Gly Arg Val Tyr Ile Tyr Met
50                  55                  60

Ser Ser Asp Asp Tyr Glu Tyr Asn Ser Asn Gly Thr Ile Lys Asp Asn
65                  70                  75                  80

Ser Phe Ala Asn Leu Asn Arg Val Phe Val Ile Ser Ser Ala Asp Met
                85                  90                  95

Val Asn Trp Thr Asp His Gly Ala Ile Pro Val Ala Gly Ala Asn Gly
                100                 105                 110

Ala Asn Gly Gly Arg Gly Ile Ala Lys Trp Ala Gly Ala Ser Trp Ala
                115                 120                 125

Pro Ser Ile Ala Val Lys Lys Ile Asn Gly Lys Asp Lys Phe Phe Leu
130                 135                 140

Tyr Phe Ala Asn Ser Gly Gly Gly Ile Gly Val Leu Thr Ala Asp Ser
145                 150                 155                 160

Pro Ile Gly Pro Trp Thr Asp Pro Ile Gly Lys Pro Leu Val Thr Pro
                165                 170                 175

Ser Thr Pro Gly Met Ser Gly Val Val Trp Leu Phe Asp Pro Ala Val
                180                 185                 190

Phe Val Asp Asp Asp Gly Thr Gly Tyr Leu Tyr Ala Gly Gly Gly Val
                195                 200                 205

Pro Gly Val Ser Asn Pro Thr Gln Gly Gln Trp Ala Asn Pro Lys Thr
```

```
                210                 215                 220
Ala Arg Val Ile Lys Leu Gly Pro Asp Met Thr Ser Val Val Gly Ser
225                 230                 235                 240

Ala Ser Thr Ile Asp Ala Pro Phe Met Phe Glu Asp Ser Gly Leu His
                245                 250                 255

Lys Tyr Asn Gly Thr Tyr Tyr Ser Tyr Cys Ile Asn Phe Gly Gly
                260                 265                 270

Thr His Pro Ala Asp Lys Pro Pro Gly Glu Ile Gly Tyr Met Thr Ser
                275                 280                 285

Ser Ser Pro Met Gly Pro Phe Thr Tyr Arg Gly His Phe Leu Lys Asn
290                 295                 300

Pro Gly Ala Phe Phe Gly Gly Gly Asn Asn His His Ala Val Phe
305                 310                 315                 320

Asn Phe Lys Asn Glu Trp Tyr Val Val Tyr His Ala Gln Thr Val Ser
                325                 330                 335

Ser Ala Leu Phe Gly Ala Gly Lys Gly Tyr Arg Ser Pro His Ile Asn
                340                 345                 350

Lys Leu Val His Asn Ala Asp Gly Ser Ile Gln Glu Val Ala Ala Asn
                355                 360                 365

Tyr Ala Gly Val Thr Gln Ile Ser Asn Leu Asn Pro Tyr Asn Arg Val
                370                 375                 380

Glu Ala Glu Thr Phe Ala Trp Asn Gly Arg Ile Leu Thr Glu Lys Ser
385                 390                 395                 400

Thr Ala Pro Gly Gly Pro Val Asn Asn Gln His Val Thr Ser Ile Gln
                405                 410                 415

Asn Gly Asp Trp Ile Ala Val Gly Asn Ala Asp Phe Gly Ala Gly Gly
                420                 425                 430

Ala Arg Ser Phe Lys Ala Asn Val Ala Ser Thr Leu Gly Gly Lys Ile
                435                 440                 445

Glu Val Arg Leu Asp Ser Ala Asp Gly Lys Leu Val Gly Thr Leu Asn
450                 455                 460

Val Pro Ser Thr Gly Gly Ala Gln Thr Trp Arg Glu Ile Glu Thr Ala
465                 470                 475                 480

Val Ser Gly Ala Thr Gly Val His Lys Val Phe Phe Val Phe Thr Gly
                485                 490                 495

Thr Gly Thr Gly Asn Leu Phe Asn Phe Asp Tyr Trp Gln Phe Thr Gln
                500                 505                 510

Arg

<210> SEQ ID NO 33
<211> LENGTH: 213
<212> TYPE: PRT
<213> ORGANISM: Bacillus subtilis
<220> FEATURE:
<221> NAME/KEY: misc_feature
<222> LOCATION: (1)..(213)
<223> OTHER INFORMATION: xylanase

<400> SEQUENCE: 33

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Thr Asp
                20                  25                  30

Tyr Trp Gln Asn Trp Thr Asp Gly Gly Gly Ile Val Asn Ala Val Asn
                35                  40                  45
```

Gly Ser Gly Gly Asn Tyr Ser Val Asn Trp Ser Asn Thr Gly Asn Phe
 50                 55                  60

Val Val Gly Lys Gly Trp Thr Thr Gly Ser Pro Phe Arg Thr Ile Asn
65              70                  75                  80

Tyr Asn Ala Gly Val Trp Ala Pro Asn Gly Asn Gly Tyr Leu Thr Leu
            85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
            115                 120                 125

Asp Gly Gly Thr Tyr Asp Ile Tyr Thr Thr Thr Arg Tyr Asn Ala Pro
130                 135                 140

Ser Ile Asp Gly Asp Arg Thr Thr Phe Thr Gln Tyr Trp Ser Val Arg
145                 150                 155                 160

Gln Ser Lys Arg Pro Thr Gly Ser Asn Ala Thr Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
            195                 200                 205

Asn Val Thr Val Trp
210

<210> SEQ ID NO 34
<211> LENGTH: 533
<212> TYPE: PRT
<213> ORGANISM: Bacillus subtilis
<220> FEATURE:
<221> NAME/KEY: misc_feature
<222> LOCATION: (1)..(533)
<223> OTHER INFORMATION: xylanase

<400> SEQUENCE: 34

Met Lys Ile Thr Asn Pro Val Leu Lys Gly Phe Asn Pro Asp Pro Ser
1               5                   10                  15

Ile Cys Arg Ala Gly Glu Asp Tyr Tyr Ile Ala Val Ser Thr Phe Glu
            20                  25                  30

Trp Phe Pro Gly Val Gln Ile His His Ser Lys Asp Leu Val Asn Trp
        35                  40                  45

His Leu Val Ala His Pro Leu Gln Arg Val Ser Gln Leu Asp Met Lys
    50                  55                  60

Gly Asn Pro Asn Ser Gly Gly Val Trp Ala Pro Cys Leu Ser Tyr Ser
65                  70                  75                  80

Asp Gly Lys Phe Trp Leu Ile Tyr Thr Asp Val Lys Val Val Asp Gly
                85                  90                  95

Ala Trp Lys Asp Cys His Asn Tyr Leu Val Thr Cys Glu Thr Ile Asn
            100                 105                 110

Gly Asp Trp Ser Glu Pro Ile Lys Leu Asn Ser Ser Gly Phe Asp Ala
        115                 120                 125

Ser Leu Phe His Asp Thr Asp Gly Lys Lys Tyr Leu Leu Asn Met Leu
130                 135                 140

Trp Asp His Arg Ile Asp Arg His Ser Phe Gly Gly Ile Val Ile Gln
145                 150                 155                 160

Glu Tyr Ser Asp Lys Glu Gln Lys Leu Ile Gly Lys Pro Lys Val Ile
                165                 170                 175

Phe Glu Gly Thr Asp Arg Lys Leu Thr Glu Ala Pro His Leu Tyr His

```
                    180                 185                 190
Ile Gly Asn Tyr Tyr Tyr Leu Leu Thr Ala Glu Gly Gly Thr Arg Tyr
            195                 200                 205
Glu His Ala Ala Thr Ile Ala Arg Ser Ala Asn Ile Glu Gly Pro Tyr
        210                 215                 220
Glu Val His Pro Asp Asn Pro Ile Leu Thr Ser Trp His Asp Pro Gly
225                 230                 235                 240
Asn Pro Leu Gln Lys Cys Gly His Ala Ser Ile Val Gln Thr His Thr
                245                 250                 255
Asp Glu Trp Tyr Leu Ala His Leu Thr Gly Arg Pro Ile His Pro Asp
            260                 265                 270
Asp Asp Ser Ile Phe Gln Gln Arg Gly Tyr Cys Pro Leu Gly Arg Glu
        275                 280                 285
Thr Ala Ile Gln Lys Leu Tyr Trp Lys Asp Glu Trp Pro Tyr Val Val
290                 295                 300
Gly Gly Lys Glu Gly Ser Leu Glu Val Asp Ala Pro Ser Ile Pro Glu
305                 310                 315                 320
Thr Ile Phe Glu Ala Thr Tyr Pro Glu Val Asp Glu Phe Glu Asp Ser
                325                 330                 335
Thr Leu Asn Ile Asn Phe Gln Thr Leu Arg Ile Pro Phe Thr Asn Glu
            340                 345                 350
Leu Gly Ser Leu Thr Gln Ala Pro Asn His Leu Arg Leu Phe Gly His
        355                 360                 365
Glu Ser Leu Thr Ser Thr Phe Thr Gln Ala Phe Val Ala Arg Arg Trp
    370                 375                 380
Gln Ser Leu His Phe Glu Ala Glu Thr Ala Val Glu Phe Tyr Pro Glu
385                 390                 395                 400
Asn Phe Gln Gln Ala Ala Gly Leu Val Asn Tyr Asn Thr Glu Asn
                405                 410                 415
Trp Thr Ala Leu Gln Val Thr His Asp Glu Glu Leu Gly Arg Ile Leu
            420                 425                 430
Glu Leu Thr Ile Cys Asp Asn Phe Ser Phe Ser Gln Pro Leu Asn Asn
        435                 440                 445
Lys Ile Val Ile Pro Arg Glu Val Lys Tyr Val Tyr Leu Arg Val Asn
    450                 455                 460
Ile Glu Lys Asp Lys Tyr Tyr Tyr Phe Tyr Ser Phe Asn Lys Glu Asp
465                 470                 475                 480
Trp His Lys Ile Asp Ile Ala Leu Glu Ser Lys Lys Leu Ser Asp Asp
                485                 490                 495
Tyr Ile Arg Gly Gly Gly Phe Phe Thr Gly Ala Phe Val Gly Met Gln
            500                 505                 510
Cys Gln Asp Thr Ser Gly Asn His Ile Pro Ala Asp Phe Arg Tyr Phe
        515                 520                 525
Arg Tyr Lys Glu Lys
    530

<210> SEQ ID NO 35
<211> LENGTH: 1432
<212> TYPE: PRT
<213> ORGANISM: Thermoanaerobacterium saccharolyticum
<220> FEATURE:
<221> NAME/KEY: misc_feature
<222> LOCATION: (1)..(1432)
<223> OTHER INFORMATION: xylanase

<400> SEQUENCE: 35
```

```
Met Lys Ser Ile Val Asn Arg Val Val Ser Ile Val Thr Ala Leu Ile
1               5                   10                  15

Met Ile Phe Gly Thr Ser Leu Phe Ser Gln His Ile Arg Ala Phe Ala
            20                  25                  30

Asp Asp Thr Asn Thr Asn Leu Val Ser Asn Gly Asp Phe Glu Thr Gly
            35                  40                  45

Thr Ile Asp Gly Trp Ile Lys Gln Gly Asn Pro Thr Leu Glu Val Thr
        50                  55                  60

Thr Glu Gln Ala Ile Gly Gln Tyr Ser Met Lys Val Thr Gly Arg Thr
65                  70                  75                  80

Gln Thr Tyr Glu Gly Pro Ala Tyr Ser Phe Leu Gly Lys Met Gln Lys
                85                  90                  95

Gly Glu Ser Tyr Asn Val Ser Leu Lys Val Arg Leu Val Ser Glu Gln
            100                 105                 110

Asn Ser Ser Asn Pro Phe Ile Thr Val Thr Met Phe Arg Glu Asp Asp
            115                 120                 125

Asn Gly Lys His Tyr Asp Thr Ile Val Trp Gln Lys Gln Val Ser Glu
130                 135                 140

Asp Ser Trp Thr Thr Val Ser Gly Thr Tyr Thr Leu Asp Tyr Thr Gly
145                 150                 155                 160

Thr Leu Lys Thr Leu Tyr Met Tyr Val Glu Ser Pro Asp Pro Thr Leu
                165                 170                 175

Glu Tyr Tyr Ile Asp Asp Val Val Thr Pro Gln Asn Pro Ile Gln
                180                 185                 190

Val Gly Asn Val Ile Thr Asn Gly Thr Phe Glu Asn Gly Asn Thr Ser
            195                 200                 205

Gly Trp Val Gly Thr Gly Ser Ser Val Val Lys Ala Val Tyr Gly Val
    210                 215                 220

Ala His Ser Gly Gly Tyr Ser Leu Leu Thr Thr Gly Arg Thr Ala Asn
225                 230                 235                 240

Trp Asn Gly Pro Ser Tyr Asp Leu Thr Gly Lys Ile Val Pro Gly Gln
            245                 250                 255

Gln Tyr Asn Val Asp Phe Trp Val Lys Phe Val Asn Gly Asn Asp Thr
            260                 265                 270

Glu Gln Ile Lys Ala Thr Val Lys Ala Thr Ser Asp Lys Asp Asn Tyr
        275                 280                 285

Ile Gln Val Asn Asp Phe Ala Asn Val Asn Lys Gly Glu Trp Thr Glu
        290                 295                 300

Ile Lys Gly Ser Phe Thr Leu Pro Val Ala Asp Tyr Ser Gly Val Ser
305                 310                 315                 320

Ile Tyr Val Glu Ser Gln Asn Pro Thr Leu Glu Phe Tyr Ile Asp Asp
                325                 330                 335

Phe Ser Val Ile Gly Glu Ile Ser Asn Asn Gln Ile Thr Ile Gln Asn
            340                 345                 350

Asp Ile Pro Asp Leu Tyr Ser Val Phe Lys Asp Tyr Phe Pro Ile Gly
        355                 360                 365

Val Ala Val Asp Pro Ser Arg Leu Asn Asp Ala Asp Pro His Ala Gln
370                 375                 380

Leu Thr Ala Lys His Phe Asn Met Leu Val Ala Glu Asn Ala Met Lys
385                 390                 395                 400

Pro Glu Ser Leu Gln Pro Thr Glu Gly Asn Phe Thr Phe Asp Asn Ala
            405                 410                 415
```

```
Asp Lys Ile Val Asp Tyr Ala Ile Ala His Asn Met Lys Met Arg Gly
            420                 425                 430

His Thr Leu Leu Trp His Asn Gln Val Pro Asp Trp Phe Phe Gln Asp
        435                 440                 445

Pro Ser Asp Pro Ser Lys Pro Ala Ser Arg Asp Leu Leu Leu Gln Arg
    450                 455                 460

Leu Arg Thr His Ile Thr Thr Val Leu Asp His Phe Lys Thr Lys Tyr
465                 470                 475                 480

Gly Ser Gln Asn Pro Ile Ile Gly Trp Asp Val Val Asn Glu Val Leu
                485                 490                 495

Asp Asp Asn Gly Asn Leu Arg Asn Ser Lys Trp Leu Gln Ile Ile Gly
            500                 505                 510

Pro Asp Tyr Ile Glu Lys Ala Phe Glu Tyr Ala His Glu Ala Asp Pro
        515                 520                 525

Ser Met Lys Leu Phe Ile Asn Asp Tyr Asn Ile Glu Asn Asn Gly Val
    530                 535                 540

Lys Thr Gln Ala Met Tyr Asp Leu Val Lys Lys Leu Lys Asn Glu Gly
545                 550                 555                 560

Val Pro Ile Asn Gly Ile Gly Met Gln Met His Ile Ser Ile Asn Ser
                565                 570                 575

Asn Ile Asp Asn Ile Lys Ala Ser Ile Glu Lys Leu Ala Ser Leu Gly
            580                 585                 590

Val Glu Ile Gln Val Thr Glu Leu Asp Met Asn Met Asn Gly Asp Val
        595                 600                 605

Ser Asn Asp Ala Leu Leu Lys Gln Ala Arg Leu Tyr Lys Gln Leu Phe
    610                 615                 620

Asp Leu Phe Lys Ala Glu Lys Gln Tyr Ile Thr Ala Val Val Phe Trp
625                 630                 635                 640

Gly Val Ser Asp Asp Val Ser Trp Leu Ser Lys Pro Asn Ala Pro Leu
                645                 650                 655

Leu Phe Asp Ser Lys Leu Gln Ala Lys Pro Ala Tyr Trp Ala Ile Val
            660                 665                 670

Asp Pro Gly Lys Ala Ile Pro Asp Ile Gln Ser Ala Lys Ala Leu Glu
        675                 680                 685

Gly Ser Pro Thr Ile Gly Ala Asn Val Asp Ser Ser Trp Lys Leu Val
    690                 695                 700

Lys Pro Leu Tyr Ala Asn Thr Tyr Val Lys Gly Thr Ile Gly Ala Thr
705                 710                 715                 720

Ala Ala Val Lys Ser Met Trp Asp Thr Lys Asn Leu Tyr Leu Leu Val
                725                 730                 735

Gln Ile Ser Asp Asn Thr Pro Ser Asn Asn Asp Gly Ile Glu Ile Phe
            740                 745                 750

Val Asp Lys Asn Asp Asn Lys Ser Thr Thr Tyr Glu Ser Asp Asp Glu
        755                 760                 765

His Tyr Ile Val Lys Arg Asp Gly Thr Gly Ser Ser Asn Ile Thr Lys
    770                 775                 780

Tyr Val Met Ser Asn Ala Asp Gly Tyr Val Ala Gln Ile Ala Ile Pro
785                 790                 795                 800

Ile Glu Asp Ile Ser Pro Val Leu Asn Asp Lys Ile Gly Phe Asp Ile
                805                 810                 815

Arg Ile Asn Asp Asp Gln Gly Ser Gly Asn Val Asn Ala Ile Thr Val
            820                 825                 830

Trp Asn Asp Tyr Thr Asn Ser Gln Asp Thr Asn Thr Ala Tyr Phe Gly
```

```
                    835                 840                 845
Asp Leu Val Leu Ser Lys Pro Ala Gln Ile Ala Thr Ala Ile Tyr Gly
            850                 855                 860
Thr Pro Val Ile Asp Gly Lys Val Asp Gly Val Trp Asn Asn Ala Glu
865                 870                 875                 880
Ala Ile Ser Thr Asn Thr Trp Val Leu Gly Ser Asn Gly Ala Thr Ala
                    885                 890                 895
Thr Ala Lys Met Met Trp Asp Asp Lys Tyr Leu Tyr Ile Leu Ala Asp
                900                 905                 910
Val Thr Asp Asn Asn Leu Asn Lys Ser Ser Val Asn Pro Tyr Glu Gln
                915                 920                 925
Asp Ser Val Glu Val Phe Val Asp Gln Asn Asn Asp Lys Thr Thr Tyr
            930                 935                 940
Tyr Glu Asn Asp Asp Gly Gln Phe Arg Val Asn Tyr Asp Asn Glu Gln
945                 950                 955                 960
Ser Phe Gly Gly Ser Thr Asn Ser Asn Gly Phe Lys Ser Ala Thr Ser
                    965                 970                 975
Leu Thr Gln Asn Gly Tyr Ile Val Glu Glu Ala Ile Pro Trp Thr Ser
                980                 985                 990
Ile Thr Pro Leu Asn Gly Thr Ile Ile Gly Phe Asp Leu Gln Val Asn
                995                1000                1005
Asp Ala Asp Glu Asn Gly Lys Arg Thr Gly Ile Val Thr Trp Cys
        1010                1015                1020
Asp Pro Ser Gly Asn Ser Trp Gln Asp Thr Ser Gly Phe Gly Asn
        1025                1030                1035
Leu Met Leu Thr Gly Lys Pro Ser Trp Gly Ser Thr Ser Asn Ser
        1040                1045                1050
Gly Thr Thr Ser Ser Ser Ser Asn Thr Ser Ser Thr Ile Gly Val
        1055                1060                1065
Ile Thr Lys Asn Gly Asn Val Ile Thr Leu Ile Leu Asp Ala Gly
        1070                1075                1080
Lys Ala Lys Asp Leu Ile Val Asn Ser Lys Asp Lys Val Val
        1085                1090                1095
Phe Asp Ile Thr Thr Ile Gly Glu Gly Gln Gln Lys Val Val Gln
        1100                1105                1110
Ile Ser Lys Asp Ile Leu Asp Thr Ser Ala Ala Asn Gly Lys Asp
        1115                1120                1125
Ile Val Ile Lys Ser Asp Asn Ala Ser Ile Ala Leu Thr Lys Asp
        1130                1135                1140
Ala Leu Asn Gln Asn Gln Ile Gln Asn Gly Val Asn Val Ser Ile
        1145                1150                1155
Lys Asp Asn Gly Lys Pro Asn Val Thr Asn Tyr Val Thr Leu Ser
        1160                1165                1170
Asn Val Val Asp Ile Thr Ile Ser Gly Ser Ser Gly Asn Val Ala
        1175                1180                1185
Leu Ala Lys Pro Val Glu Val Thr Leu Asn Ile Ser Lys Ala Asn
        1190                1195                1200
Asp Pro Arg Lys Val Ala Val Tyr Tyr Tyr Asn Pro Thr Thr Asn
        1205                1210                1215
Gln Trp Glu Tyr Val Gly Gly Lys Val Asp Ala Ser Ser Gly Thr
        1220                1225                1230
Ile Thr Phe Asn Ala Thr His Phe Ser Gln Tyr Ala Ala Phe Glu
        1235                1240                1245
```

```
Tyr Asp Lys Thr Phe Asn Asp Ile Lys Asp Asn Trp Ala Lys Asp
    1250                1255                1260

Val Ile Glu Val Leu Ala Ser Arg His Ile Val Glu Gly Met Thr
    1265                1270                1275

Asp Thr Gln Tyr Glu Pro Asn Lys Thr Val Thr Arg Ala Glu Phe
    1280                1285                1290

Thr Ala Met Ile Leu Arg Leu Leu Asn Ile Lys Glu Glu Ala Tyr
    1295                1300                1305

Ser Gly Glu Phe Ser Asp Val Lys Ser Gly Asp Trp Tyr Ala Asn
    1310                1315                1320

Ala Ile Glu Ala Ala Tyr Lys Ala Gly Ile Ile Glu Gly Asp Gly
    1325                1330                1335

Lys Asn Ala Arg Pro Asn Asp Ser Ile Thr Arg Glu Glu Met Thr
    1340                1345                1350

Ala Ile Ala Met Arg Ala Tyr Glu Met Leu Thr Gln Tyr Lys Glu
    1355                1360                1365

Glu Asn Ile Gly Ala Thr Thr Phe Ser Asp Asp Lys Ser Ile Ser
    1370                1375                1380

Asp Trp Ala Arg Asn Val Val Ala Asn Ala Ala Lys Leu Gly Ile
    1385                1390                1395

Val Asn Gly Glu Pro Asn Asn Val Phe Ala Pro Lys Gly Asn Ala
    1400                1405                1410

Thr Arg Ala Glu Ala Ala Ala Ile Ile Tyr Gly Leu Leu Glu Lys
    1415                1420                1425

Thr Asn Asn Leu
    1430

<210> SEQ ID NO 36
<211> LENGTH: 320
<212> TYPE: PRT
<213> ORGANISM: Thermoanaerobacterium saccharolyticum
<220> FEATURE:
<221> NAME/KEY: misc_feature
<222> LOCATION: (1)..(320)
<223> OTHER INFORMATION: xylanase

<400> SEQUENCE: 36

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
                20                  25                  30

Asp Glu Met Arg Ser Val Asp Pro Lys Ile Glu Leu Lys Glu Ser Ser
            35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
    130                 135                 140
```

```
Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
            165                 170                 175

Gly Val Met Gly Pro Ser Gln Gly Gly Leu Ser Leu Ala Cys Ala
        180                 185                 190

Ala Leu Glu Pro Arg Val Arg Lys Val Val Ser Glu Tyr Pro Phe Leu
    195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Asn Ser
305                 310                 315                 320

<210> SEQ ID NO 37
<211> LENGTH: 680
<212> TYPE: PRT
<213> ORGANISM: Thermoanaerobacterium saccharolyticum
<220> FEATURE:
<221> NAME/KEY: misc_feature
<222> LOCATION: (1)..(680)
<223> OTHER INFORMATION: xylanase

<400> SEQUENCE: 37

Met Ile Ser Lys Ser Phe Tyr Ala His His Ser Ala Phe Gly Ala Phe
1               5                   10                  15

Ser Ser Phe Val Ile Gly Lys Cys Gly Lys Gly Gly Val Val Leu
            20                  25                  30

Asn Asp Val Arg Pro Pro Glu Asn Asn Val Tyr Ile Gly Tyr Lys Arg
        35                  40                  45

Asp Gly Val Ile Ser Leu Leu Pro Phe Ile Lys Asp Thr Lys Asn
    50                  55                  60

Ala Glu Glu Glu Phe Thr Gly Glu Val Ser Thr Ser Lys Lys Glu Lys
65                  70                  75                  80

Asn Ile Lys Ile Phe Gly Glu Asp Glu Ile Glu Arg Glu Leu Cys Trp
                85                  90                  95

Ala Ser Asp Thr Trp Thr Ala Gly Asp Phe Lys Phe Ser Ile Ile Thr
            100                 105                 110

Pro Phe Gly Tyr Val Lys Asp Pro Ser Val Met Asn Gly Asp Glu Lys
        115                 120                 125

Lys Leu Ala Leu Ala Pro Val Ile Phe Val Gln Leu Thr Met Asp Asn
    130                 135                 140

Thr Asp Ser Asp Lys Asp Ala Glu Met Ile Phe Gly Phe Glu Gly Pro
145                 150                 155                 160

Lys Arg Ile Leu Ser Glu Leu Thr Asp Gly Lys Tyr Leu Gly Gly Val
                165                 170                 175

Tyr Gly Arg Lys Tyr Gly Phe Ala Ile Lys Lys Ser Asp Asp Val Arg
```

```
                180                 185                 190
Glu Leu Ser Arg Leu Asp Ile Leu Thr Ser Trp Ala Asn Asp Asn Tyr
            195                 200                 205
Gln Asn His Gly Leu Gly Arg Ala Pro Ser Leu Ile Phe Lys Val Pro
            210                 215                 220
Arg Gly Glu Lys Arg Thr Tyr Thr Val Ala Leu Ala Thr Tyr Gln Ser
225                 230                 235                 240
Gly Val Ile Thr Thr Gly Ile Asp Ala Glu Phe Tyr Tyr Thr Ser Val
                245                 250                 255
Phe Lys Ser Leu Glu Glu Val Leu Ser Phe Gly Leu Asp Asn Gln Asp
            260                 265                 270
Tyr Tyr Leu Asn Leu Ala Lys Glu Arg Asp Glu Glu Leu Lys Lys Ser
            275                 280                 285
Gly Leu Asn Glu Tyr Arg Gln Phe Leu Leu Ala His Ala Ala His Ser
            290                 295                 300
Tyr Tyr Ala Ser Thr Glu Leu Leu Lys Arg Asp Asp Gly Met Pro Leu
305                 310                 315                 320
Trp Val Val Asn Glu Gly Glu Tyr Ile Met Ile Asn Thr Phe Asp Leu
                325                 330                 335
Thr Val Asp His Val Phe Trp Glu Met Arg Phe His Pro Trp Thr Ile
            340                 345                 350
Thr Asn Thr Leu Asp Leu Tyr Tyr Glu Lys Tyr Ser Tyr Arg Asp Gln
            355                 360                 365
Ala Gly Leu Ala Phe Thr His Asp Met Gly Val Ala Asp Gly Phe Ser
            370                 375                 380
Lys Glu Gly Tyr Ser Ser Tyr Glu Leu Pro Asn Leu Thr Gly Cys Phe
385                 390                 395                 400
Ser Tyr Met Thr His Glu Glu Leu Leu Asn Trp Val Leu Thr Gly Ser
                405                 410                 415
Val Tyr Ala Ile Lys Ile Asn Asp Lys Glu Trp Leu Lys Lys Asn Met
            420                 425                 430
Gly Val Phe Glu Asp Cys Phe Asp Ser Leu Val Ala Arg Asp Lys Asn
            435                 440                 445
Asn Asp Gly Ile Met Asp Val Asp Ser Ser Arg Cys Glu Thr Gly Ser
            450                 455                 460
Glu Ile Thr Thr Tyr Asp Ser Leu Asp Glu Ser Leu Gly Gln Ala Arg
465                 470                 475                 480
Asn Asn Leu Tyr Leu Gly Val Lys Thr Trp Ala Ala Tyr Val Met Leu
                485                 490                 495
His Gly Leu Phe Lys Glu Asn Asp Leu Ser Glu Lys Ala Glu Lys Ala
            500                 505                 510
Leu Glu Lys Ala Arg Gln Ala Ala Asn Thr Ile Val Ala Lys Phe Asp
            515                 520                 525
Glu Glu Asn Gln Tyr Ile Pro Ala Val Phe Glu Asn Gly Asn Thr Ser
            530                 535                 540
Arg Ile Ile Pro Ala Val Glu Ala Leu Val Tyr Pro Tyr Val Val Gly
545                 550                 555                 560
Tyr Thr Asp Phe Val Ser Glu Asp Gly Val Phe Gly Gly Leu Ile Lys
                565                 570                 575
Ala Leu Lys Lys His Val Met Thr Ile Met Lys Pro Gly Ile Cys Ile
            580                 585                 590
Asp Glu Val Ser Gly Gly Trp Lys Leu Ser Ser Thr Ser Lys Asn Thr
            595                 600                 605
```

```
Trp Asn Ser Lys Ile Phe Leu Cys Gln Tyr Val Ile Lys Asp Val Leu
610                 615                 620

Asn Ile Asp Phe Gly Asp Lys Glu Ile Glu Trp Asp Lys Val His Ala
625                 630                 635                 640

Met Trp Gln Gln Val Ser Cys Ser Glu Asp Cys Ala Thr Asp Gln Val
            645                 650                 655

Asn Ser Asp Thr Gly Thr Pro Arg Gly Ser Arg Leu Tyr Pro Arg Leu
            660                 665                 670

Val Thr Ser Val Leu Trp Met Lys
            675                 680
```

<210> SEQ ID NO 38
<211> LENGTH: 500
<212> TYPE: PRT
<213> ORGANISM: Thermoanaerobacterium saccharolyticum
<220> FEATURE:
<221> NAME/KEY: misc_feature
<222> LOCATION: (1)..(500)
<223> OTHER INFORMATION: xylanase

<400> SEQUENCE: 38

```
Met Ile Lys Val Ile Val Pro Asp Phe Ser Asp Lys Lys Phe Ser Asp
1               5                   10                  15

Arg Trp Arg Tyr Cys Val Gly Thr Gly Arg Leu Gly Leu Ala Leu Gln
            20                  25                  30

Lys Glu Tyr Ile Asp Thr Leu Lys Tyr Val Lys Glu Asn Ile Asp Phe
            35                  40                  45

Lys Tyr Ile Arg Gly His Gly Leu Leu Cys Asp Asp Val Gly Ile Tyr
50                  55                  60

Arg Glu Asp Val Val Gly Asp Glu Ile Lys Pro Phe Tyr Asn Phe Thr
65                  70                  75                  80

Tyr Ile Asp Arg Ile Phe Asp Ser Phe Leu Glu Ile Gly Ile Arg Pro
            85                  90                  95

Phe Val Glu Ile Gly Phe Met Pro Lys Arg Leu Ala Ser Gly Thr Gln
            100                 105                 110

Ala Val Phe Tyr Trp Glu Gly Asn Val Thr Pro Pro Lys Asp Tyr Lys
            115                 120                 125

Lys Trp Glu Asn Leu Ile Lys Ala Val Val Ser His Phe Ile Ser Arg
130                 135                 140

Tyr Gly Ile Asp Glu Val Ala Lys Trp Pro Phe Glu Ile Trp Asn Glu
145                 150                 155                 160

Pro Asn Leu Lys Glu Phe Trp Lys Asp Ala Asp Glu Lys Glu Tyr Phe
            165                 170                 175

Lys Leu Tyr Lys Ile Thr Ala Lys Ala Ile Lys Glu Val Asn Glu Asn
            180                 185                 190

Ile Lys Val Gly Gly Pro Ala Ile Cys Gly Gly Ala Asp Tyr Trp Ile
            195                 200                 205

Glu Asp Phe Leu Asn Phe Cys Tyr Glu Glu Asn Val Pro Val Asp Phe
210                 215                 220

Val Ser Arg His Ala Tyr Thr Ser Lys Gln Gly Glu Tyr Thr Pro His
225                 230                 235                 240

Leu Ile Tyr Gln Glu Ile Met Pro Ser Glu Tyr Met Leu Asn Glu Phe
            245                 250                 255

Lys Thr Val Arg Asp Ile Ile Lys Asn Ser His Phe Pro Asn Leu Pro
            260                 265                 270
```

Phe His Ile Thr Glu Tyr Asn Thr Ser Tyr Ser Pro Gln Asn Pro Val
             275                 280                 285

His Asp Thr Pro Phe Asn Ala Ala Tyr Ile Ala Arg Ile Leu Ser Glu
        290                 295                 300

Gly Gly Asp Tyr Val Asp Ser Phe Ser Tyr Trp Thr Phe Ser Asp Val
305                 310                 315                 320

Phe Glu Glu Arg Asp Val Pro Arg Ser Gln Phe His Gly Gly Phe Gly
                325                 330                 335

Leu Val Ala Leu Asn Met Val Pro Lys Pro Thr Phe Tyr Thr Phe Lys
            340                 345                 350

Phe Phe Asn Ala Met Gly Glu Glu Met Leu Tyr Arg Asp Glu His Met
        355                 360                 365

Ile Val Thr Arg Arg Asp Asp Gly Ser Val Ala Leu Ile Ala Trp Asn
370                 375                 380

Glu Val Met Asp Lys Thr Glu Asn Pro Asp Lys Glu Tyr Glu Val Gln
385                 390                 395                 400

Ile Pro Val Gly Phe Lys Asp Val Phe Ile Lys Arg Gln Leu Ile Asp
                405                 410                 415

Glu Glu His Gly Asn Pro Trp Gly Thr Trp Ile His Met Gly Arg Pro
            420                 425                 430

Arg Tyr Pro Ser Lys Lys Glu Ile Asn Thr Leu Arg Glu Ile Ala Lys
        435                 440                 445

Pro Glu Ile Met Thr Ser His Ala Val Thr Asn Asp Gly Tyr Leu Asn
    450                 455                 460

Leu Lys Phe Lys Leu Gly Lys Asn Ala Val Val Leu Tyr Glu Leu Thr
465                 470                 475                 480

Glu Arg Ile Asp Glu Ser Ser Thr Tyr Ile Gly Leu Asp Asp Ser Lys
                485                 490                 495

Ile Asn Gly Tyr
            500

<210> SEQ ID NO 39
<211> LENGTH: 1107
<212> TYPE: DNA
<213> ORGANISM: Thermoanaerobacterium thermosaccharolyticum
<220> FEATURE:
<221> NAME/KEY: misc_feature
<222> LOCATION: (1)..(1107)
<223> OTHER INFORMATION: xylose transporter

<400> SEQUENCE: 39
atgggtaaaa atgcaaaaaa agctttgttg tcggtgatac ttatacttag tatgttgttt      60
acgttttcgg cgtgtgctac aacaaatcct aatcaatcaa atctaataa tcaaacaagc     120 caaacgacca atacatctga caactcaggc aaaattaaaa ttggctttag ttttgatact     180
ctaaatctag agatggcaca catgataga gactattttg ttcaagggc taaagagtta     240 ggagctgatg tattagtaca gtcagctaat agtgattcac aaacacaata ttcgcaatgt     300
caaaatttaa tagcgcaagg cataaaagtt ttagtaataa ttccacatga tggaagtgca     360
atagcaccaa tcgttgaaga agctcataaa gctggagtaa aggttttagc atacgataga     420
ttaattatga acgcagatgt agatgcatac gtgtcgtttg acaatgaaaa agttggtgaa     480
ttacaagctg aagcaataac aaaactggta ccaaaaggaa attatttctt acttgaaggt     540
tcacctacag ataataatgc taaattgttt gaacaaggtc aaagaaggt tttcaaccg     600 ttagttgata aaggcgatat aaaaatagtt ggagagcaat gggcgcaaga ttggcttaca     660

```
caaaatgctt acaatattat gcaaaatgca ctaacagcta ataacaataa aattgatgca      720
gtagttgatg cgaatgacag tactgcttta ggagcgatta gggctttaca agaacaaaat      780
cttgctggaa aagttgcaat atccggtcaa gatgctgatc tagcaaattg tcagttgatt      840
gttgaaggca acaatcaat gactgtgtat aagccagtaa aggaagaagc aacaaaaggt      900
gctgatgtag cggttgcctt agcaaaaggt gaagacatca atgcaaacgg aaaggtcaat      960
aatggaaaaa ttgacgtacc atctgtattg cttacacctg tagccgtaga taagaacaat     1020
atggtagata ctatcataaa agacggattc catagccttg atgaagttta taaaaatgtt     1080
cctaaagatc aatggccaaa acaatag                                         1107
```

<210> SEQ ID NO 40
<211> LENGTH: 1527
<212> TYPE: DNA
<213> ORGANISM: Thermoanaerobacterium thermosaccharolyticum
<220> FEATURE:
<221> NAME/KEY: misc_feature
<222> LOCATION: (1)..(1527)
<223> OTHER INFORMATION: xylose transporter

<400> SEQUENCE: 40

```
atggatatgg gtgatttcat actagaaatg aaaaatataa caaggatttt ttccggtgtt       60
aaagctttag acaatgtgaa tttgaaagtc aaaaaggag aaatacacgg actatgtggt      120
gaaaatggtg cgggaaagtc aacacttatg aaaattttaa gcggtgtata tccatatggt      180 acttttctg gagagataat atttgatgga aaagaattaa aattaaataa tattaaagat      240
gcagaagatg cagggatagg tataatttat caggagttgt cattagttaa agaattgtct      300
gtcagtgaaa atatatttat tgggaatgag cctaataaaa atgggataat tgattttgac      360
aggatgtact atgaaactaa aatcttactt gataaattga atttgaatat taatcctaat      420
gtaccagtaa agaatttggg cattggacag caacaattag ttgaaattgc caaagcttta      480
tctaaaaatg ttagcttgtt gatattggat gagccaacat catctcttac agatgctgat      540
gttgagatat tgtttaatat attaagacag ttaaagata atggtgttac atgtatatat      600
atatctcata aattaaatga agtaatgaa ataacggatc ggataacagt tcagagagat      660
ggaaaaacaa taggttcaga agatacaaaa aatcttacag agagtgaaat tataaaaatg      720
atggttgggc gtgaacttac gaatcttttc ccaaaagagg aacatcaaat tggaaaagaa      780
atattggaag taaaaaattt cagtgtttat gattcgaaat catctagcaa aaaaattgta      840
gacaatgtca gctttacttt aaaagaaggt gagatattag aatagcagg ccttattgga      900 gctggaagaa ctgaacttgt ttctagtatt ttcggatcat atccaggaag acatgaaggt      960
gaaatctatt tagaaggtaa aaaaattaat ataagaaatc ctgatgaagc cttggattat     1020
ggaattgcaa tggttccaga agatagaaaa ggtcaagggt taataaatat attatctgta     1080
agagataata tgacattatc taatatagaa agttataaaa ataactttgg ctcagttgac     1140
gtaaataaag aaatagtgga tgttaaaaaa tatatcgaaa tgttgaaaat aaagtttca     1200 cattttgact tagcagtaaa aaatttaagc ggtggaaatc aacagaaagt ggttttggct     1260 aaaaattttat taagaaatcc taaaatattg atattagatg aacctactcg tggaattgat     1320
gtcggtgcaa aatatgagat atataaatta atttatgaat tggttaaaag cggtatttca     1380
ataataatgg tatcatcaga actgccagaa ataataggat taagtgatag aattgtcgta     1440
atgcatgaag gtaaaagaa gggtgaattt gtcaataaag atgtcactca agaaatgata     1500
atgcaatgtg cgataggagg taaataa                                        1527
```

<210> SEQ ID NO 41
<211> LENGTH: 1167
<212> TYPE: DNA
<213> ORGANISM: Thermoanaerobacterium thermosaccharolyticum
<220> FEATURE:
<221> NAME/KEY: misc_feature
<222> LOCATION: (1)..(1167)
<223> OTHER INFORMATION: xylose transporter

<400> SEQUENCE: 41

```
atggtgaatt cgaaaggttt taagaaaaat aatgtatcga taaataaaaa attttcattt      60
aatttaaaat tatatacgat gataatagca ttagtcggta tttggattat ttttgcaatt     120
gctacaaaag gtgactttt aacttctaga aatatgtcaa atcttttag gcaaatggtt      180 tctacggcgg tttagccat agggatggtt tttgtaataa tagctggtca gattgatctt      240
tcagttggat cgcttttagg tctgactggt ggtatagctg caattgctaa tgtctggttt     300
catattaatg gcatcctttc aataattatt gcgttagcga ttggtttgat tttaggaacg     360
tggaatggct ggtgggtagc ttataaaaat gttccatcgt ttattgtaac gttagcaggc    420
atgctggtat ttagaggaat attgattggt ataactaatg ttatactat agcaccattg     480 agtagtgatt ttcagtttat aggtcaagct tatttaactc cagtaagtgg ctatttactc     540
ggtataattg tattactagt aggagcctat actatatatt cacaaaggaa atcaaaaatt     600
aagtatgggt tagaagtttc accttttat ttagatattg ctaaaataat acttatgatt     660
gtattgattg gactatttgt attcacgcta aattcctata atggaattcc tttttcagta    720
ttaattttgg cgattttagt tgcaatattt acttatattg catcaaagac agttttggg    780 agaagagttt atgcattagg tggtaatatc gaggctgcaa aattatcagg tatcaatgtt     840
aagaagataa cacttattt atttgcaatt aatggattgc ttgcagcagt atcaggcgtt     900
gttcttacat caactttaaa tgctggatca acatctgcag gtcagaatgc ggagatggat     960
gcaatcgcgt cttgtgtaat tggtggagca agccttatgg gaggcgttgg atcagttatt    1020
ggtgctataa taggcgcatt agttatggca agtatcaaca atggaatgag cttacttaat    1080
tccgcaccat tttggcaata tgttgttaag ggattgatat tactattagc tgtttatgta    1140
gatgtagcct cgaaaaataa agaataa                                        1167
```

<210> SEQ ID NO 42
<211> LENGTH: 1086
<212> TYPE: DNA
<213> ORGANISM: Thermoanaerobacter mathranii
<220> FEATURE:
<221> NAME/KEY: misc_feature
<222> LOCATION: (1)..(1086)
<223> OTHER INFORMATION: xylose transporter

<400> SEQUENCE: 42

```
atggtaaagt ctaaaaaatt gttggcattt ttcttggtta tgatattgac attgtctgtt      60
gtattagcag gatgtactag ttcaaagaca atgagacga caaacactac ttcaagtaat     120
ggttcaagta gcacagaaac taaaaaaata aaaatcggtt tttctcttcc aacaatgaga    180
gaagaaaggt atcaaagaga tagagatgca tttgttgaag aagcagaaaa acttggagca    240
gaagttttag tacaaggtgc aaataacgat gaaaaccttc agaatagcca agtagaaaac    300
cttatcaccc aaggaataga cgtattagtt cttgatccac aaaatgctgc ttctgcagct    360
accttggttg aaaaagctca tcaagcgggg attaaggtta tctcttatga cagacttata    420
```

```
ttaaattctg aaccagacgt gtatatctct tttgataatg aaagagtagg agagttacag     480
ggagaattcc tcacaaagtt ggtaccaaag ggaacttatt tcatatttgc tggtgctcca     540
actgacaaca atgctacatt gttcaaaaaa ggagcaatga aatatattca acctcttgtt     600
gacaaaggag atataaaaat agcttttgac caggcaataa aagactggga cccaaatgag     660
gctttaaaac ttgctgaaaa cgctcttact gctaacaaaa acaaagtgga tgctattctt     720
gcacctaacg atggcactgc aggtggtata atacaggcct tagcagaaca aaaattggct     780
ggtaaagtgc caattacagg tcaagatgca gaacttgcag cagtgaagag gattgtggaa     840
ggcacacaat caatgacagt gttcaaagat gtaagagttc ttgctagaaa ggctgctcaa     900
attgctgtaa tgttagctca agggaaagaa gtaaaagata taccggaaat taataagact     960
gtaaacaatc aaaagataga tgttccatca ttgttgttga caccagttgt tataacaaag    1020
gacaacattg ataaagagct tattgacagt ggttggttta caagggaaca agtgtacggt    1080
aagtaa                                                              1086

<210> SEQ ID NO 43
<211> LENGTH: 1518
<212> TYPE: DNA
<213> ORGANISM: Thermoanaerobacter ethanolicus
<220> FEATURE:
<221> NAME/KEY: misc_feature
<222> LOCATION: (1)..(1518)
<223> OTHER INFORMATION: xylose transporter

<400> SEQUENCE: 43
atgagcgagt atattcttga aatgagaaac ataacaaagg aatttcctgg agttaaagca      60
ttggataatg taaatttcaa agttaaaaga ggggaaattc acgcgttagt aggagaaaat     120
ggagcgggaa agtctacctt gatgaagata ttaagtggtg tttatcctta tggaacttat     180
aaaggagaca taatcataga tggtgaagtg aagcaatttc gaaatattaa agatagtgaa     240
aaaagtggta tagcgattat ttatcaggag ctcactctgg taaagtatat gacagtaggc     300
gaaaacatat ttttaggtga agagcctgta aaaggcggaa taattgattg atgaaagtt     360 tactctgaga cttatagact tttgaaagag ttgcagatta atgtaaaccc ctatacaaaa     420
gttatgaatt taggaattgg gcatcaacaa atggtagaaa tagcgaaggc tcttttcaaaa     480 aaagcgagga ttttaatatt agatgagcct acttctgcat tgacagaaag cgaaacagaa     540
catcttctca atattttgaa agatttgaag aaaaatggtg taacttgtat atacatttct     600
cacaagctta atgaagtatt tgaaattgca gattcaatca ctgtattaag agatggcaaa     660
acgataatga cggacaaaaa agaaaatttc acagaaaaca aggtaatttc tttaatggta     720
gggcgtgagc ttacacagag attccccaaga gctaagcata cgccagggga agtggttttc     780
gaggttaaaa attacacagt ttatgaccat gaaataccgg gcaagaaaat tattgacaat     840
gtaagcttta aagccaggag aggcgagata ttaggtattg caggacttat gggagcaggg     900
aggacagaac ttgctgctag tatatttggt gcatttaaag gtagaaaaga aggggaaata     960
tatttaaatg gcaaaaaaat tgaaataaac actcccagcg atgcgataaa acatggaatt    1020
gcctatcttt cagaggatag gaaaaggttt ggccttgtga ctttgatgga tgtacaagaa    1080
aatatagcac ttcctaacta tgacagacta tcaaaattta gtattataaa taacaatgca    1140
aaaattaaac atgcagaaaa gtatgtaaaa gagttaaaaa taaaaacacc aaccataaga    1200
caaagggttg ctaatttaag tggaggaaac cagcaaaaag tggttattgc aaagtggctt    1260
atgtcagacc caaaagtttt gatactggac gaaccaacta gaggaataga tgtgggagct    1320
```

```
aagtttgaaa tatataatct aatgaataaa ttggttgata tgggcgtgtg tgtaataatg    1380
atatcttcag aactgcctga atattggga atgagtgata gaatactggt aattcatgaa    1440
ggaaaaatca atggagaatt tccaatagaa gaagcagacc aagaaaaaat catgtactgt    1500
gcaactggag gtaagtaa                                                  1518
```

<210> SEQ ID NO 44
<211> LENGTH: 1167
<212> TYPE: DNA
<213> ORGANISM: Thermoanaerobacter ethanolicus
<220> FEATURE:
<221> NAME/KEY: misc_feature
<222> LOCATION: (1)..(1167)
<223> OTHER INFORMATION: xylose transporter

<400> SEQUENCE: 44

```
atgatggaaa gcaaagtgag caaaacaact gaaaagcgca ttttaaatca tttcaagata     60
gatataaggt catatactat gatattagct ttattgggga tatggattat tttttcaata   120
ttgacccatg gcgattttct atctccgaga aacttgtcca tgcttgccag gcaaatgtct   180
ataacagcaa ttttagcttc aggtatggtt ttagttatag ttgctgggca tatagactta   240
tctgttggtt ctgtggcagg gtttacagga gctatagctg caattcttca ggtgatatat   300
cattgggata cagtgccgac aataatagtg actcttatgg ctgggcttgc tattggagtt   360
tggcaaggat tttggatagc ctatagaaaa gtgcctgctt ttatagtgac cttaagctca   420
atgcttgttt ttagaggtgg aatttttatta attacaaaag gtgttactat atctccttta   480
aaacaggact tcacagtcgt aggacaggga tatattcctc cattgtttag cgttattctt   540
gctgtggtgg caggtgtttt gtatgtaatc atggaccttta agaatagaaa ttctcgaatt   600
aaatacggct aagtgtgtc cagctgggga atagaactgg caaaaattgc aggagtattg   660
attttcatcg ctttgtttac aagtgttatg atatcttatg aaggaattcc tgtgccagta   720
ttacttgttt tggtaattgt gattttgctt acttttgtgg ctcaaaatac gacttttgga   780
cgttatgttt atgcgatagg cggaaataaa gaagcagcag cttactcagg aataaacata   840
gctaagacga acatgacgat tttcttgatt atgggggttt tatcggcaat tgcaggtata   900
gttttgactt caaggttaaa tgctgctaca actagtgcag gaaatttgtt tgagctggat   960
gctatagctt cggcaattat cggtggaaca agcacgttag gaggagaagg aacagtacca  1020
ggagcgattt taggtgctct tattatggct agcatagata atggcatgag tcttatgaat  1080
atagattatt ctatattgac aattgtaaag ggccttgtat tagtacttgc agtgtgggtg  1140
gatatttcaa caaagaagag gggataa                                     1167
```

<210> SEQ ID NO 45
<211> LENGTH: 1398
<212> TYPE: DNA
<213> ORGANISM: Clostridium beijerinckii
<220> FEATURE:
<221> NAME/KEY: misc_feature
<222> LOCATION: (1)..(1398)
<223> OTHER INFORMATION: xylose transporter

<400> SEQUENCE: 45

```
atgaaaataa aaattagtaa ctctgtaata tatattttcg ctgcacttag tgggcttttg     60
tttggttatg atactggagt tatttcagga gctattttat ttattcaaga acaaatgcac   120
cttgattcat ggcagcaagg atgggttgta agttctgtat tattaggagc tattcttggg   180
```

```
gctgcaatca ttggtcctat gtctgataaa tatggccgta taaagctaat tcttacatcg    240
gctgttatct tctttgtcgg cgcacttgga tcagcatttg ctccagaaat ttggtcatta    300
attatattta gaatcattct tggtgtcgca gttggtgcat cttcagctct aattccaact    360
tatttagctg aattatcacc atctgaaaaa cgtggaacca tatcaagttt gtttcagcta    420
atggttatga gcggaattct attggcttat attacgaatt atgcattttc agatttatat    480
actggttggc gagtgatgtt agggttcgca gctattccag cagcagttct tttaataggt    540
gcacttgtgt taccagaaag tcctagattt ttagtaaaag atggacgagc agatgaagca    600
agaagtatac tagaacatat gaataaacat gataaaggtg ctgttaatta tgaattagct    660
caaataaaaa aacaagccga gattaaaagt ggtggagtta aagagctatt tagcgaattt    720
gtacgcccgg cattagtcat aggctttggt ttggctgttt ttcagcagat tatgggttgt    780
aacacagttc tttattatgc accaactata tttactgatg ttggatttgg ggtgcaagca    840
gctttactcg ctcatattgg aattggagtt tttaatataa taattactgc tatagctgta    900
gctattatgg ataaaattga tcgtaaaaag atgcttattt atggtgctat tggaatgggc    960
gtttcgctct tgattatgag tatttcaatg aaattctcta atggatcttt cgttgcctca   1020
atcatatgtg ttattgcatt aactatttac attgctttct tttcagctac ttggggacct   1080
gtaatgtggg tcatggtagg agaagtattt ccattaaata ttcgcggctt aggtaattca   1140
ttcagtagtg taattaattg gagtgctaat atgatggtat cattgacatt tccagtatta   1200
ttgaattact ttggtacagg tagtttgttt ataggttatg gtgtaatatg ttttgcagca   1260
atttggtttg ttcagtctaa ggtatttgaa acacgtaatc gttcacttga agatatagaa   1320
gctgaactta gatcatataa aggagtagaa aaactccaaa aggatatctg cactcaagat   1380
gctacaacta aggcttag                                                 1398

<210> SEQ ID NO 46
<211> LENGTH: 1455
<212> TYPE: DNA
<213> ORGANISM: Clostridium carboxidivorans
<220> FEATURE:
<221> NAME/KEY: misc_feature
<222> LOCATION: (1)..(1455)
<223> OTHER INFORMATION: xylose transporter

<400> SEQUENCE: 46
ttataatttt attgattggt cagggatttc ctctactaac tcaaccaaac aatttctttt     60
atcattttta tgtcttatat ctagttcagc cattatatca gctactcttt cttctgttaa    120
attatagaat atcatgaata tgagcaatgt aactacacag acaacagctg gcaaaataga    180
tgtcataatt aaaattccat tcaacgattt tgcagtttga gttacattag aatatatcc     240 aacattagct aatatcaatg taggtataac tcccccctact gctaatgaaa cctttaatcc    300
aagagtaata agtgagtaca caactgcggc atgtctttg ccagtattgt actcagcata    360
ctcaactgca tccggaatga ttaccacaa actgcccata gtatgccat agccaaatgc     420 agctactgat ttagctatca tcattactgt aatttgtgaa actggaatga tatataaagc    480
tgctgatcca agggcaccta aactcaaacc aagtacaaca gttttttttct ttttgatatg    540 tctaaaaagc gcaggcacaa aaggaactgc cacgactgaa ggtaaaacgt tcaacataga    600
aaataaagca actaaatctt ttctatttac gttataagtc atataataaa ttcctgaagc    660
tgattgtata gatgaaaatg cataaacacc tacaaacagt aaaaataata tgacacctgg    720
ctgattatgt gtaatctgat taataaaccc tttgaaagta actggatcta aatgagattt    780
```

```
tactctgata cgttcatgca aagtagtata actataaagc aatatggatg cacaaataac    840
agaaagtaaa ataatagtca tctgataacc ttttgctgaa tcacctctgc cgaaaacctg    900
tgataaaata ggaataaaata gagcaactat taccaccct gactgagcaa acatcattct    960
tatggaattt agcctagttc tctccatagg atctgctgtc atgacagttg tacaagatac   1020
atatggatta atgatgaaag tatataatgt aagtagtaaa ttgtacgtag catatgccca   1080
tatcaatttg cccgtatgtc ccaaattggg tactgtaaaa gtcaaaatac ctgcaagtgc   1140
aaaaggaaca gctccataaa taagataact tttgtactta ccatgctttg gattcattct   1200
ctctgcaata atacccatgg tagggtccca tatcatatcc catcctctag atataagaaa   1260
cataacagaa acttctgcag cagttaatcc ataaacatca gtataataaa atgtcaaaaa   1320
cattaaaatt gactgaaaaa ctaaattcat tccaccatct acaagggaat atcccactac   1380
ttctttggta ggaagtttat aaaagccagg attatcacca cttttttcat acaaatttat   1440 tgttttgcc tccat                                                    1455
```

<210> SEQ ID NO 47
<211> LENGTH: 1368
<212> TYPE: DNA
<213> ORGANISM: Clostridium acetobutylicum
<220> FEATURE:
<221> NAME/KEY: misc_feature
<222> LOCATION: (1)..(1368)
<223> OTHER INFORMATION: xylose transporter

<400> SEQUENCE: 47

```
atgaataaaa aaatatctcc agcactaatt tatttctttg gagccttcgg tggatttatg     60
tttggatatg atattggaat aattaatggt gctttacctg gaattaatgc aacttggcac    120
gtaagttctt ggttagaagg attatcact tctggattgt ttgttggagc tatgatagga    180
gcctcattaa tggcttcact agcagatagg tttggtcgtc gtagaatgat tatgtggagt    240
gcaattgtgt ttgcacttgg tgcattaggt tctgccgttt ctactagtac taatctttta    300
atcggtgctc gtgttatttt aggagtagcc gtaggtggag cttctgcttt agttccaatg    360
tatatgggag aaattagccc tgctgaaaca cgtggaaaac tatctggttt aaatcaatta    420
atgataactg ttggaatgct tttctcatat ggtgtaaatt ttgcgtttgc tggtgcattt    480
gaaggatggc gttggatgct tggaggagct atggtacctg caatggtact attaattgga    540
acatttatac ttccagagtc accaagattt ttagctagaa taggaaagac agaattagca    600
aaacaagtac ttcagacttt acgttcaaag gaagaggcag aaactgaata tcaagagatt    660
attaattcaa aacatactga aacaggttct tttggagatt tatttgcaaa acaggctttg    720
ccagctgtaa ttgcaggctg tgggttaaca cttcttcaac aaattcaagg tgcaaacact    780
attttctact attcatcaca aattttatcc aatgttttg gatcagcaaa tggtggaact    840
attagtactg ttggaattgg tgtggttcta gtattagcaa ctattgtaac tttattggtt    900
gtagacaaat tcaaacgtcg tacattattt atgactggtt ctattggaat gggcgcatct    960
ctattattag ttggattaat ttatccatac tctgaagcta acatgcgtgt ggcaacttgg   1020
ttagtattct tcttcatatg ttataacgtt gttttctatg catactcttg ggcagctact   1080
acatggattg ttgttggaga attattccca gtaatgttta gggacttgc aacaggtatt   1140 gcatcagcag taaactggtt tggtaacatt ttagttgctt tattcttccc agtatacttt   1200
gaaactgtag gtttatctgt aatcttcttc ggttttgctg caatttgtat cataggatttt  1260
```

| ttatttgcaa aatatgttct ttatgaaaca aaaggaaaat ctttagaaga aattgagaca | 1320 |
| tatttgtaca atcgttctat tggaaaagtt agaggattaa atgagtag | 1368 |

<210> SEQ ID NO 48
<211> LENGTH: 1377
<212> TYPE: DNA
<213> ORGANISM: Clostridium acetobutylicum
<220> FEATURE:
<221> NAME/KEY: misc_feature
<222> LOCATION: (1)..(1377)
<223> OTHER INFORMATION: xylose transporter

<400> SEQUENCE: 48

| atgataggaa gttttaaaat taaaatgagg gaaaaaatag gctatgcatc tggagattta | 60 |
| gcaagtaact tgatatatca aaccatttca atttatttgc tattttttcta tactaacgtt | 120 |
| ttcggcttat ctgctggtca ggccggtgta atgtttcttg tggtaagatt tatcgacgca | 180 |
| attaatgacc caattattgg aactttagtc gacaaaacca atacgcgttt tggaagattt | 240 |
| agaccatact tattatatgg agctgctcct tttgcagttt tagcttttct gtgttttacc | 300 |
| actcctaatt tttcagcaac aggtaaatta atttacgctt atgttactta cgtaggcctt | 360 |
| tcaattactt atacttgtat aaatgttcct tatggtgcat tgacatcagc tattacagat | 420 |
| gataatcagg aaattgttag cttgacctca gtaagaatgt tttttgctaa tctaggcggt | 480 |
| gtaatcgttt cctactttgt tcctgtactt tcggcatatt tcacaaaatc atttggtctt | 540 |
| tcaggtggtt ggcaaataac tatgagtatt ctaggtatag caggtgcctt cctattgcta | 600 |
| ttttgttttt caagtactaa ggaaagagta aaaagcgtta accaagatca taagattaaa | 660 |
| ttctctgatc tctttgaaca attcaaaact aatagacctc ttattgtatt aagtatttcc | 720 |
| tttgtactga tatttggaat aaattcaatt aatagttcaa taggcatata ttacattacc | 780 |
| tataacgttg gtcgtgctga cttagtacaa tggtatacgg tattagggtc tctccctgca | 840 |
| tttgtttgta taccactaat accaaaaatc aacagaaaaa ttggaaaaaa gcctttatta | 900 |
| attagttctc ttttaataac agtgcttggt accttatctc tgttagtaat tccaactcat | 960 |
| gcagtagcat taatattagt ttctcgtgtg attacatcaa taggttcatt gactgccgga | 1020 |
| gcatttatgt ggtcattaat tccagaaaca attgaatatg gtgaatacac aacaggaaaa | 1080 |
| cgtttaagcg gcttaattta tgctattatc ggattctttt tcaagtgcgg aatggcatta | 1140 |
| ggcggagctg taccaggaat aatactcggt aactttgggt atgtagccaa taaaacccaa | 1200 |
| actcctcatg ccctaacggg tatacttcta actgccacag tcgttcctgc cgtactcatg | 1260 |
| atattagctt taatagatat taccttctac aacttagatg ataaaaaata taatcatatt | 1320 |
| atagctactt taaaagaaag agctaaatta aatagagggg agaatttaaa tttatga | 1377 |

<210> SEQ ID NO 49
<211> LENGTH: 1350
<212> TYPE: DNA
<213> ORGANISM: Thermoanaerobacterium thermosaccharolyticum
<220> FEATURE:
<221> NAME/KEY: misc_feature
<222> LOCATION: (1)..(1350)
<223> OTHER INFORMATION: xylose transporter

<400> SEQUENCE: 49

| atgaaaaatt ttgaaacaac ttggaaagaa aggatcagtt atgggcttag tgacactgct | 60 |
| tctaatttag tttatcagat gattaccact tatttaatgt ttttttacac tgatgttttt | 120 |
| ggaataagtg ctgcagctgt cggaacactt tttttagtag caaggatcat cgacgcattt | 180 |

```
gatggaccat tttttggcat tctaatagat catacaaata caaagtgggg aaaatgcaga      240
ccatactttc tttggttatc aattccatat ggagtattag caatactagc atttacgact      300
ccaagtttta atgcttctgg taaattaatt tatgcttatg ttacatatat tcttttagga      360
attatctact ctggaattaa tataccaatt acatcaattt taccgagttt aacagataat      420
ttagaagaaa gaaatatatt ggttagtacc agaatgattt tagctacagt tggtgctacg      480
attgtcagtg taggaacgtt gcctctagtt aaagtattcg gcaatggtaa tcagcaaaaa      540
ggctttatga tgactatgac tttgtttgct gtgttagctg ttatattatt cctagtaacc      600 ttttcaata ctagagaaaa agtaaacgaa gcaaaagatc aatcaattac tttaaaagaa       660
gaactaaaag cattgaaagg aaatactcct tggtttatac ttttctttgt agcttttata      720
aatttcatag cttttataat gaaagctcaa acgacagttt attatttgac atataattta      780
aagatgccta acttaatcag tatagcttta ggattaggct cactgaatgt tgtttcatta      840
cttatcatgc catttttagc aaagaaaata ggaaaaagaa atgtcatgat tacgggatttt     900 acttttcaa tattagcaca atttatattg tatttatcat cattgacatc aagtgcatttt      960 atatttttag taggcactgt aattgcagct tttggaaatg gatttgttat gggagcaatg     1020
ttttctatga cagcagatac agttgactac ggtgagtgga atcgggtgt tagagctcaa      1080 ggacttcttt cagctacacc agcttttggg gtcaaagcag gaatgggaat aggtggggct     1140
ttagcaggtt ggatattatc aattggtaaa tatgttccag atcatccgca aaccttatcc     1200
gcattaaaag cgatagaaat taactttatt tggctaccgt taattggttt tattatcagt     1260
gctgtattac ttctattcta taatttagat aaacaacaag aacagatgac taaagaatta     1320
aatgaaagaa gagctaagtt aagcgcatga                                       1350
```

<210> SEQ ID NO 50
<211> LENGTH: 1362
<212> TYPE: DNA
<213> ORGANISM: Thermodesulfobium narugense
<220> FEATURE:
<221> NAME/KEY: misc_feature
<222> LOCATION: (1)..(1362)
<223> OTHER INFORMATION: xylose transporter

<400> SEQUENCE: 50

```
atggttgaga aaaatttaga cgaactaaaa ctaagcaagc accacttaaa agcgatgttt       60
gtttcaggaa tggggttttt tactgatgca tatgatctct tcattattgg tgtagcttta      120
tctttaattg ctccggtgtg gggacttaca agttcagaaa ttgcactcct tggtagtagt      180
tctcttttgg ctgctttgtt tggttcgatt ttttttggta gatttgcaga taattttggt      240
agaaagaaga tttatggttt agaagctctg ataatgacaa ttggcgcttt aatgtcagca      300
ttttcgccaa attttttgtt tcttctcttc tcaagattca ttttgggttt aggcattggt      360
ggagattatc ctgttagtgc tgttattatg agtgaatatt caaatagatc tgatcgaggg      420
aaattggttg ggttagtttt ttctatgcaa gcacttggtc ttataattgg tcctcttgtt      480
gccttaagct tattattgtt acacattcca cttgactttg catggcgttt aatgcttggg      540
ttaggagcgc ttccttcact tatggttatt tatttaagga gaaaattacc agaatctcct      600
cgctatcttt cacaaatagt tggcgataaa aaagcagctt taactgcttt tgtaaatttt      660
actggtaatg gtaataagag ctatgaaccg atacatttaa atccgaaaat taatcatagg      720
ttaaaagatt ttttttcaaa caaacaacat actttgactt tatttgggac agctggtagc      780
```

```
tggttttttgc ttgattgggc ttattatggt aacacaattt ctactccaat tgtaatgaat      840
gcaatttgtg atagttcttc tttagaactg aagatgattt attctcttgt aatatttgtt      900
gttttcgctt taccaggata tattttatca ataatattta tggatataat tggaagaaaa      960
tatattcagc ttatgggttt tggcattatg gcattttcat ttttattatt aggattaata     1020
cctgatatag aaagtaatgt tacaggattt cttatacttt atgggcttag ctatcttttt     1080
actgagtttg gacctaatac taccactttt gtccttccct cagagctttt cccaaccgaa     1140
tataggacaa caggtcatgg cttgtctgca ggaattggga acttggagc ttttttttgga     1200 gtgttatttt tccctattac cgagtctttt ttgggactaa atatgacatt tgttattgtt     1260
tcgattatat gttttatggg aattataacc acgtctgttc tgactgaacc aaagggaaag     1320
agcctcgaag actgttcgta ttctaaaata gtaggcaaat aa                        1362
```

<210> SEQ ID NO 51
<211> LENGTH: 368
<212> TYPE: PRT
<213> ORGANISM: Thermoanaerobacterium thermosaccharolyticum
<220> FEATURE:
<221> NAME/KEY: misc_feature
<222> LOCATION: (1)..(368)
<223> OTHER INFORMATION: xylose transporter

<400> SEQUENCE: 51

```
Met Gly Lys Asn Ala Lys Lys Ala Leu Leu Ser Val Ile Leu Ile Leu
1               5                   10                  15

Ser Met Leu Phe Thr Phe Ser Ala Cys Ala Thr Thr Asn Pro Asn Gln
            20                  25                  30

Ser Lys Ser Asn Asn Gln Thr Ser Gln Thr Thr Asn Thr Ser Asp Asn
        35                  40                  45

Ser Gly Lys Ile Lys Ile Gly Phe Ser Phe Asp Thr Leu Asn Leu Glu
    50                  55                  60

Arg Trp Gln His Asp Arg Asp Tyr Phe Val Gln Arg Ala Lys Glu Leu
65                  70                  75                  80

Gly Ala Asp Val Leu Val Gln Ser Ala Asn Ser Asp Ser Gln Thr Gln
                85                  90                  95

Tyr Ser Gln Cys Gln Asn Leu Ile Ala Gln Gly Ile Lys Val Leu Val
            100                 105                 110

Ile Ile Pro His Asp Gly Ser Ala Ile Ala Pro Ile Val Glu Glu Ala
        115                 120                 125

His Lys Ala Gly Val Lys Val Leu Ala Tyr Asp Arg Leu Ile Met Asn
    130                 135                 140

Ala Asp Val Asp Ala Tyr Val Ser Phe Asp Asn Glu Lys Val Gly Glu
145                 150                 155                 160

Leu Gln Ala Glu Ala Ile Thr Lys Leu Val Pro Lys Gly Asn Tyr Phe
                165                 170                 175

Leu Leu Glu Gly Ser Pro Thr Asp Asn Asn Ala Lys Leu Phe Glu Gln
            180                 185                 190

Gly Gln Lys Lys Val Leu Gln Pro Leu Val Asp Lys Gly Asp Ile Lys
        195                 200                 205

Ile Val Gly Glu Gln Trp Ala Gln Asp Trp Leu Thr Gln Asn Ala Tyr
    210                 215                 220

Asn Ile Met Gln Asn Ala Leu Thr Ala Asn Asn Lys Ile Asp Ala
225                 230                 235                 240

Val Val Asp Ala Asn Asp Ser Thr Ala Leu Gly Ala Ile Arg Ala Leu
                245                 250                 255
```

```
Gln Glu Gln Asn Leu Ala Gly Lys Val Ala Ile Ser Gly Gln Asp Ala
            260                 265                 270

Asp Leu Ala Asn Cys Gln Leu Ile Val Glu Gly Lys Gln Ser Met Thr
            275                 280                 285

Val Tyr Lys Pro Val Lys Glu Glu Ala Thr Lys Gly Ala Asp Val Ala
            290                 295                 300

Val Ala Leu Ala Lys Gly Glu Asp Ile Asn Ala Asn Gly Lys Val Asn
305                 310                 315                 320

Asn Gly Lys Ile Asp Val Pro Ser Val Leu Thr Pro Val Ala Val
                325                 330                 335

Asp Lys Asn Asn Met Val Asp Thr Ile Ile Lys Asp Gly Phe His Ser
            340                 345                 350

Leu Asp Glu Val Tyr Lys Asn Val Pro Lys Asp Gln Trp Pro Lys Gln
            355                 360                 365

<210> SEQ ID NO 52
<211> LENGTH: 508
<212> TYPE: PRT
<213> ORGANISM: Thermoanaerobacterium thermosaccharolyticum
<220> FEATURE:
<221> NAME/KEY: misc_feature
<222> LOCATION: (1)..(508)
<223> OTHER INFORMATION: xylose transporter

<400> SEQUENCE: 52

Met Asp Met Gly Asp Phe Ile Leu Glu Met Lys Asn Ile Thr Lys Asp
1               5                   10                  15

Phe Ser Gly Val Lys Ala Leu Asp Asn Val Asn Leu Lys Val Lys Lys
            20                  25                  30

Gly Glu Ile His Gly Leu Cys Gly Glu Asn Gly Ala Gly Lys Ser Thr
        35                  40                  45

Leu Met Lys Ile Leu Ser Gly Val Tyr Pro Tyr Gly Thr Phe Ser Gly
50                  55                  60

Glu Ile Ile Phe Asp Gly Lys Glu Leu Lys Leu Asn Asn Ile Lys Asp
65                  70                  75                  80

Ala Glu Asp Ala Gly Ile Gly Ile Ile Tyr Gln Glu Leu Ser Leu Val
                85                  90                  95

Lys Glu Leu Ser Val Ser Glu Asn Ile Phe Ile Gly Asn Glu Pro Asn
            100                 105                 110

Lys Asn Gly Ile Ile Asp Phe Asp Arg Met Tyr Tyr Glu Thr Lys Ile
        115                 120                 125

Leu Leu Asp Lys Leu Asn Leu Asn Ile Asn Pro Asn Val Pro Val Lys
    130                 135                 140

Asn Leu Gly Ile Gly Gln Gln Gln Leu Val Glu Ile Ala Lys Ala Leu
145                 150                 155                 160

Ser Lys Asn Val Ser Leu Leu Ile Leu Asp Glu Pro Thr Ser Ser Leu
            165                 170                 175

Thr Asp Ala Asp Val Glu Ile Leu Phe Asn Ile Leu Arg Gln Leu Lys
            180                 185                 190

Asp Asn Gly Val Thr Cys Ile Tyr Ile Ser His Lys Leu Asn Glu Val
        195                 200                 205

Met Glu Ile Thr Asp Arg Ile Thr Val Gln Arg Asp Gly Lys Thr Ile
    210                 215                 220

Gly Ser Glu Asp Thr Lys Asn Leu Thr Glu Ser Glu Ile Ile Lys Met
225                 230                 235                 240
```

```
Met Val Gly Arg Glu Leu Thr Asn Leu Phe Pro Lys Glu Glu His Gln
                245                 250                 255

Ile Gly Lys Glu Ile Leu Glu Val Lys Asn Phe Ser Val Tyr Asp Ser
            260                 265                 270

Lys Ser Ser Lys Lys Ile Val Asp Asn Val Ser Phe Thr Leu Lys
        275                 280                 285

Glu Gly Glu Ile Leu Gly Ile Ala Gly Leu Ile Gly Ala Gly Arg Thr
        290                 295                 300

Glu Leu Val Ser Ser Ile Phe Gly Ser Tyr Pro Gly Arg His Glu Gly
305                 310                 315                 320

Glu Ile Tyr Leu Glu Gly Lys Lys Ile Asn Ile Arg Asn Pro Asp Glu
            325                 330                 335

Ala Leu Asp Tyr Gly Ile Ala Met Val Pro Glu Asp Arg Lys Gly Gln
            340                 345                 350

Gly Leu Ile Asn Ile Leu Ser Val Arg Asp Asn Met Thr Leu Ser Asn
        355                 360                 365

Ile Glu Ser Tyr Lys Asn Asn Phe Gly Ser Val Asp Val Asn Lys Glu
        370                 375                 380

Ile Val Asp Val Lys Lys Tyr Ile Glu Met Leu Lys Ile Lys Val Ser
385                 390                 395                 400

His Phe Asp Leu Ala Val Lys Asn Leu Ser Gly Gly Asn Gln Gln Lys
                405                 410                 415

Val Val Leu Ala Lys Asn Leu Leu Arg Asn Pro Lys Ile Leu Ile Leu
            420                 425                 430

Asp Glu Pro Thr Arg Gly Ile Asp Val Gly Ala Lys Tyr Glu Ile Tyr
            435                 440                 445

Lys Leu Ile Tyr Glu Leu Val Lys Ser Gly Ile Ser Ile Met Val
        450                 455                 460

Ser Ser Glu Leu Pro Glu Ile Ile Gly Leu Ser Asp Arg Ile Val Val
465                 470                 475                 480

Met His Glu Gly Lys Lys Gly Glu Phe Val Asn Lys Asp Val Thr
                485                 490                 495

Gln Glu Met Ile Met Gln Cys Ala Ile Gly Gly Lys
        500                 505
```

<210> SEQ ID NO 53
<211> LENGTH: 388
<212> TYPE: PRT
<213> ORGANISM: Thermoanaerobacterium thermosaccharolyticum
<220> FEATURE:
<221> NAME/KEY: misc_feature
<222> LOCATION: (1)..(388)
<223> OTHER INFORMATION: xylose transporter

<400> SEQUENCE: 53

```
Met Val Asn Ser Lys Gly Phe Lys Glu Asn Asn Val Ser Ile Asn Lys
1               5                   10                  15

Lys Phe Ser Phe Asn Leu Lys Leu Tyr Thr Met Ile Ile Ala Leu Val
            20                  25                  30

Gly Ile Trp Ile Ile Phe Ala Ile Ala Thr Lys Gly Asp Phe Leu Thr
        35                  40                  45

Ser Arg Asn Met Ser Asn Leu Phe Arg Gln Met Val Ser Thr Ala Val
    50                  55                  60

Leu Ala Ile Gly Met Val Phe Val Ile Ala Gly Gln Ile Asp Leu
65                  70                  75                  80

Ser Val Gly Ser Leu Leu Gly Leu Thr Gly Gly Ile Ala Ala Ile Ala
```

85                  90                  95
Asn Val Trp Phe His Ile Asn Gly Ile Leu Ser Ile Ile Ala Leu
                100                 105                 110

Ala Ile Gly Leu Ile Leu Gly Thr Trp Asn Gly Trp Trp Val Ala Tyr
            115                 120                 125

Lys Asn Val Pro Ser Phe Ile Val Thr Leu Ala Gly Met Leu Val Phe
            130                 135                 140

Arg Gly Ile Leu Ile Gly Ile Thr Asn Gly Tyr Thr Ile Ala Pro Leu
145                 150                 155                 160

Ser Ser Asp Phe Gln Phe Ile Gly Gln Ala Tyr Leu Thr Pro Val Ser
                165                 170                 175

Gly Tyr Leu Leu Gly Ile Ile Val Leu Leu Val Gly Ala Tyr Thr Ile
                180                 185                 190

Tyr Ser Gln Arg Lys Ser Lys Ile Lys Tyr Gly Leu Glu Val Ser Pro
                195                 200                 205

Phe Tyr Leu Asp Ile Ala Lys Ile Ile Leu Met Ile Val Leu Ile Gly
            210                 215                 220

Leu Phe Val Phe Thr Leu Asn Ser Tyr Asn Gly Ile Pro Phe Ser Val
225                 230                 235                 240

Leu Ile Leu Ala Ile Leu Val Ala Ile Phe Thr Tyr Ile Ala Ser Lys
                245                 250                 255

Thr Val Phe Gly Arg Arg Val Tyr Ala Leu Gly Asn Ile Glu Ala
                260                 265                 270

Ala Lys Leu Ser Gly Ile Asn Val Lys Lys Ile Thr Leu Ile Leu Phe
            275                 280                 285

Ala Ile Asn Gly Leu Leu Ala Ala Val Ser Gly Val Val Leu Thr Ser
            290                 295                 300

Thr Leu Asn Ala Gly Ser Thr Ser Ala Gly Gln Asn Ala Glu Met Asp
305                 310                 315                 320

Ala Ile Ala Ser Cys Val Ile Gly Gly Ala Ser Leu Met Gly Gly Val
                325                 330                 335

Gly Ser Val Ile Gly Ala Ile Ile Gly Ala Leu Val Met Ala Ser Ile
                340                 345                 350

Asn Asn Gly Met Ser Leu Leu Asn Ser Ala Pro Phe Trp Gln Tyr Val
            355                 360                 365

Val Lys Gly Leu Ile Leu Leu Ala Val Tyr Val Asp Val Ala Ser
            370                 375                 380

Lys Asn Lys Glu
385

<210> SEQ ID NO 54
<211> LENGTH: 361
<212> TYPE: PRT
<213> ORGANISM: Thermoanaerobacter mathranii
<220> FEATURE:
<221> NAME/KEY: misc_feature
<222> LOCATION: (1)..(361)
<223> OTHER INFORMATION: xylose transporter

<400> SEQUENCE: 54

Met Val Lys Ser Lys Lys Leu Leu Ala Phe Phe Leu Val Met Ile Leu
1               5                   10                  15

Thr Leu Ser Val Val Leu Ala Gly Cys Thr Ser Ser Lys Thr Asn Glu
                20                  25                  30

Thr Thr Asn Thr Thr Ser Ser Asn Gly Ser Ser Ser Thr Glu Thr Lys
            35                  40                  45

```
Lys Ile Lys Ile Gly Phe Ser Leu Pro Thr Met Arg Glu Glu Arg Tyr
        50                  55                  60

Gln Arg Asp Arg Asp Ala Phe Val Glu Ala Glu Lys Leu Gly Ala
 65                  70                  75                  80

Glu Val Leu Val Gln Gly Ala Asn Asn Asp Glu Asn Leu Gln Asn Ser
                85                  90                  95

Gln Val Glu Asn Leu Ile Thr Gln Gly Ile Asp Val Leu Val Leu Asp
                100                 105                 110

Pro Gln Asn Ala Ala Ser Ala Ala Thr Leu Val Glu Lys Ala His Gln
                115                 120                 125

Ala Gly Ile Lys Val Ile Ser Tyr Asp Arg Leu Ile Leu Asn Ser Glu
                130                 135                 140

Pro Asp Val Tyr Ile Ser Phe Asp Asn Glu Arg Val Gly Glu Leu Gln
145                 150                 155                 160

Gly Glu Phe Leu Thr Lys Leu Val Pro Lys Gly Thr Tyr Phe Ile Phe
                165                 170                 175

Ala Gly Ala Pro Thr Asp Asn Asn Ala Thr Leu Phe Lys Lys Gly Ala
                180                 185                 190

Met Lys Tyr Ile Gln Pro Leu Val Asp Lys Gly Asp Ile Lys Ile Ala
                195                 200                 205

Phe Asp Gln Ala Ile Lys Asp Trp Asp Pro Asn Glu Ala Leu Lys Leu
210                 215                 220

Ala Glu Asn Ala Leu Thr Ala Asn Lys Asn Lys Val Asp Ala Ile Leu
225                 230                 235                 240

Ala Pro Asn Asp Gly Thr Ala Gly Gly Ile Ile Gln Ala Leu Ala Glu
                245                 250                 255

Gln Lys Leu Ala Gly Lys Val Pro Ile Thr Gly Gln Asp Ala Glu Leu
                260                 265                 270

Ala Ala Val Lys Arg Ile Val Glu Gly Thr Gln Ser Met Thr Val Phe
                275                 280                 285

Lys Asp Val Arg Val Leu Ala Arg Lys Ala Ala Gln Ile Ala Val Met
290                 295                 300

Leu Ala Gln Gly Lys Glu Val Lys Asp Ile Pro Glu Ile Asn Lys Thr
305                 310                 315                 320

Val Asn Asn Gln Lys Ile Asp Val Pro Ser Leu Leu Leu Thr Pro Val
                325                 330                 335

Val Ile Thr Lys Asp Asn Ile Asp Lys Glu Leu Ile Asp Ser Gly Trp
                340                 345                 350

Phe Thr Arg Glu Gln Val Tyr Gly Lys
                355                 360

<210> SEQ ID NO 55
<211> LENGTH: 505
<212> TYPE: PRT
<213> ORGANISM: Thermoanaerobacter ethanolicus
<220> FEATURE:
<221> NAME/KEY: misc_feature
<222> LOCATION: (1)..(505)
<223> OTHER INFORMATION: xylose transporter

<400> SEQUENCE: 55

Met Ser Glu Tyr Ile Leu Glu Met Arg Asn Ile Thr Lys Glu Phe Pro
 1               5                  10                  15

Gly Val Lys Ala Leu Asp Asn Val Asn Phe Lys Val Lys Arg Gly Glu
                20                  25                  30
```

```
Ile His Ala Leu Val Gly Glu Asn Gly Ala Gly Lys Ser Thr Leu Met
         35                  40                  45

Lys Ile Leu Ser Gly Val Tyr Pro Tyr Gly Thr Tyr Lys Gly Asp Ile
 50                  55                  60

Ile Ile Asp Gly Glu Val Lys Gln Phe Arg Asn Ile Lys Asp Ser Glu
 65                  70                  75                  80

Lys Ser Gly Ile Ala Ile Ile Tyr Gln Glu Leu Thr Leu Val Lys Tyr
                 85                  90                  95

Met Thr Val Gly Glu Asn Ile Phe Leu Gly Glu Pro Val Lys Gly
                100                 105                 110

Gly Ile Ile Asp Trp Met Lys Val Tyr Ser Glu Thr Tyr Arg Leu Leu
                115                 120                 125

Lys Glu Leu Gln Ile Asn Val Asn Pro Tyr Thr Lys Val Met Asn Leu
130                 135                 140

Gly Ile Gly His Gln Gln Met Val Glu Ile Ala Lys Ala Leu Ser Lys
145                 150                 155                 160

Lys Ala Arg Ile Leu Ile Leu Asp Glu Pro Thr Ser Ala Leu Thr Glu
                165                 170                 175

Ser Glu Thr Glu His Leu Leu Asn Ile Leu Lys Asp Leu Lys Lys Asn
                180                 185                 190

Gly Val Thr Cys Ile Tyr Ile Ser His Lys Leu Asn Glu Val Phe Glu
                195                 200                 205

Ile Ala Asp Ser Ile Thr Val Leu Arg Asp Gly Lys Thr Ile Met Thr
210                 215                 220

Asp Lys Lys Glu Asn Phe Thr Glu Asn Lys Val Ile Ser Leu Met Val
225                 230                 235                 240

Gly Arg Glu Leu Thr Gln Arg Phe Pro Arg Ala Lys His Thr Pro Gly
                245                 250                 255

Glu Val Val Phe Glu Val Lys Asn Tyr Thr Val Tyr Asp His Glu Ile
                260                 265                 270

Pro Gly Lys Lys Ile Ile Asp Asn Val Ser Phe Lys Ala Arg Arg Gly
                275                 280                 285

Glu Ile Leu Gly Ile Ala Gly Leu Met Gly Ala Gly Arg Thr Glu Leu
290                 295                 300

Ala Ala Ser Ile Phe Gly Ala Phe Lys Gly Arg Lys Glu Gly Glu Ile
305                 310                 315                 320

Tyr Leu Asn Gly Lys Lys Ile Glu Ile Asn Thr Pro Ser Asp Ala Ile
                325                 330                 335

Lys His Gly Ile Ala Tyr Leu Ser Glu Asp Arg Lys Arg Phe Gly Leu
                340                 345                 350

Val Thr Leu Met Asp Val Gln Glu Asn Ile Ala Leu Pro Asn Tyr Asp
                355                 360                 365

Arg Leu Ser Lys Phe Ser Ile Ile Asn Asn Asn Ala Lys Ile Lys His
370                 375                 380

Ala Glu Lys Tyr Val Lys Glu Leu Lys Ile Lys Thr Pro Thr Ile Arg
385                 390                 395                 400

Gln Arg Val Ala Asn Leu Ser Gly Gly Asn Gln Gln Lys Val Val Ile
                405                 410                 415

Ala Lys Trp Leu Met Ser Asp Pro Lys Val Leu Ile Leu Asp Glu Pro
                420                 425                 430

Thr Arg Gly Ile Asp Val Gly Ala Lys Phe Glu Ile Tyr Asn Leu Met
                435                 440                 445

Asn Lys Leu Val Asp Met Gly Val Cys Val Ile Met Ile Ser Ser Glu
```

```
                    450                 455                 460
Leu Pro Glu Ile Leu Gly Met Ser Asp Arg Ile Leu Val Ile His Glu
465                 470                 475                 480

Gly Lys Ile Asn Gly Glu Phe Pro Ile Glu Glu Ala Asp Gln Glu Lys
                    485                 490                 495

Ile Met Tyr Cys Ala Thr Gly Gly Lys
                    500                 505

<210> SEQ ID NO 56
<211> LENGTH: 388
<212> TYPE: PRT
<213> ORGANISM: Thermoanaerobacter ethanolicus
<220> FEATURE:
<221> NAME/KEY: misc_feature
<222> LOCATION: (1)..(388)
<223> OTHER INFORMATION: xylose transporter

<400> SEQUENCE: 56

Met Met Glu Ser Lys Val Ser Lys Thr Thr Glu Lys Arg Ile Leu Asn
1               5                   10                  15

His Phe Lys Ile Asp Ile Arg Ser Tyr Thr Met Ile Leu Ala Leu Leu
                20                  25                  30

Gly Ile Trp Ile Ile Phe Ser Ile Leu Thr His Gly Asp Phe Leu Ser
            35                  40                  45

Pro Arg Asn Leu Ser Met Leu Ala Arg Gln Met Ser Ile Thr Ala Ile
50                  55                  60

Leu Ala Ser Gly Met Val Leu Ile Val Ala Gly His Ile Asp Leu
65                  70                  75                  80

Ser Val Gly Ser Val Ala Gly Phe Thr Gly Ala Ile Ala Ala Ile Leu
                85                  90                  95

Gln Val Ile Tyr His Trp Asp Thr Val Pro Thr Ile Ile Val Thr Leu
                100                 105                 110

Met Ala Gly Leu Ala Ile Gly Val Trp Gln Gly Phe Trp Ile Ala Tyr
            115                 120                 125

Arg Lys Val Pro Ala Phe Ile Val Thr Leu Ser Ser Met Leu Val Phe
130                 135                 140

Arg Gly Gly Ile Leu Leu Ile Thr Lys Gly Val Thr Ile Ser Pro Leu
145                 150                 155                 160

Lys Gln Asp Phe Thr Val Val Gly Gln Gly Tyr Ile Pro Pro Leu Phe
                165                 170                 175

Ser Val Ile Leu Ala Val Val Ala Gly Val Leu Tyr Val Ile Met Asp
            180                 185                 190

Leu Lys Asn Arg Asn Ser Arg Ile Lys Tyr Gly Leu Ser Val Ser Ser
        195                 200                 205

Trp Gly Ile Glu Leu Ala Lys Ile Ala Gly Val Leu Ile Phe Ile Ala
        210                 215                 220

Leu Phe Thr Ser Val Met Ile Ser Tyr Glu Gly Ile Pro Val Pro Val
225                 230                 235                 240

Leu Leu Val Leu Val Ile Val Ile Leu Leu Thr Phe Val Ala Gln Asn
                245                 250                 255

Thr Thr Phe Gly Arg Tyr Val Tyr Ala Ile Gly Gly Asn Lys Glu Ala
                260                 265                 270

Ala Ala Tyr Ser Gly Ile Asn Ile Ala Lys Thr Asn Met Thr Ile Phe
            275                 280                 285

Leu Ile Met Gly Val Leu Ser Ala Ile Ala Gly Ile Val Leu Thr Ser
        290                 295                 300
```

```
Arg Leu Asn Ala Ala Thr Thr Ser Ala Gly Asn Leu Phe Glu Leu Asp
305                 310                 315                 320

Ala Ile Ala Ser Ala Ile Ile Gly Gly Thr Ser Thr Leu Gly Gly Glu
            325                 330                 335

Gly Thr Val Pro Gly Ala Ile Leu Gly Ala Leu Ile Met Ala Ser Ile
        340                 345                 350

Asp Asn Gly Met Ser Leu Met Asn Ile Asp Tyr Ser Ile Leu Thr Ile
            355                 360                 365

Val Lys Gly Leu Val Leu Val Leu Ala Val Trp Val Asp Ile Ser Thr
370                 375                 380

Lys Lys Arg Gly
385

<210> SEQ ID NO 57
<211> LENGTH: 465
<212> TYPE: PRT
<213> ORGANISM: Clostridium beijerinckii
<220> FEATURE:
<221> NAME/KEY: misc_feature
<222> LOCATION: (1)..(465)
<223> OTHER INFORMATION: xylose transporter

<400> SEQUENCE: 57

Met Lys Ile Lys Ile Ser Asn Ser Val Ile Tyr Ile Phe Ala Ala Leu
1               5                   10                  15

Ser Gly Leu Leu Phe Gly Tyr Asp Thr Gly Val Ile Ser Gly Ala Ile
            20                  25                  30

Leu Phe Ile Gln Glu Gln Met His Leu Asp Ser Trp Gln Gln Gly Trp
        35                  40                  45

Val Val Ser Ser Val Leu Leu Gly Ala Ile Leu Gly Ala Ala Ile Ile
    50                  55                  60

Gly Pro Met Ser Asp Lys Tyr Gly Arg Ile Lys Leu Ile Leu Thr Ser
65                  70                  75                  80

Ala Val Ile Phe Phe Val Gly Ala Leu Gly Ser Ala Phe Ala Pro Glu
                85                  90                  95

Ile Trp Ser Leu Ile Ile Phe Arg Ile Ile Leu Gly Val Ala Val Gly
            100                 105                 110

Ala Ser Ser Ala Leu Ile Pro Thr Tyr Leu Ala Glu Leu Ser Pro Ser
        115                 120                 125

Glu Lys Arg Gly Thr Ile Ser Ser Leu Phe Gln Leu Met Val Met Ser
130                 135                 140

Gly Ile Leu Leu Ala Tyr Ile Thr Asn Tyr Ala Phe Ser Asp Leu Tyr
145                 150                 155                 160

Thr Gly Trp Arg Val Met Leu Gly Phe Ala Ala Ile Pro Ala Ala Val
                165                 170                 175

Leu Leu Ile Gly Ala Leu Val Leu Pro Glu Ser Pro Arg Phe Leu Val
            180                 185                 190

Lys Asp Gly Arg Ala Asp Glu Ala Arg Ser Ile Leu His Met Asn
        195                 200                 205

Lys His Asp Lys Gly Ala Val Asn Tyr Glu Leu Ala Gln Ile Lys Lys
    210                 215                 220

Gln Ala Glu Ile Lys Ser Gly Val Lys Glu Leu Phe Ser Glu Phe
225                 230                 235                 240

Val Arg Pro Ala Leu Val Ile Gly Phe Gly Leu Ala Val Phe Gln Gln
                245                 250                 255
```

```
Ile Met Gly Cys Asn Thr Val Leu Tyr Tyr Ala Pro Thr Ile Phe Thr
            260                 265                 270

Asp Val Gly Phe Gly Val Gln Ala Ala Leu Leu Ala His Ile Gly Ile
            275                 280                 285

Gly Val Phe Asn Ile Ile Thr Ala Ile Ala Val Ala Ile Met Asp
            290                 295                 300

Lys Ile Asp Arg Lys Lys Met Leu Ile Tyr Gly Ala Ile Gly Met Gly
305                 310                 315                 320

Val Ser Leu Leu Ile Met Ser Ile Ser Met Lys Phe Ser Asn Gly Ser
                325                 330                 335

Phe Val Ala Ser Ile Ile Cys Val Ile Ala Leu Thr Ile Tyr Ile Ala
            340                 345                 350

Phe Phe Ser Ala Thr Trp Gly Pro Val Met Trp Val Met Val Gly Glu
            355                 360                 365

Val Phe Pro Leu Asn Ile Arg Gly Leu Gly Asn Ser Phe Ser Ser Val
            370                 375                 380

Ile Asn Trp Ser Ala Asn Met Met Val Ser Leu Thr Phe Pro Val Leu
385                 390                 395                 400

Leu Asn Tyr Phe Gly Thr Gly Ser Leu Phe Ile Gly Tyr Gly Val Ile
            405                 410                 415

Cys Phe Ala Ala Ile Trp Phe Val Gln Ser Lys Val Phe Glu Thr Arg
            420                 425                 430

Asn Arg Ser Leu Glu Asp Ile Glu Ala Glu Leu Arg Ser Tyr Lys Gly
            435                 440                 445

Val Glu Lys Leu Gln Lys Asp Ile Cys Thr Gln Asp Ala Thr Thr Lys
            450                 455                 460

Ala
465

<210> SEQ ID NO 58
<211> LENGTH: 484
<212> TYPE: PRT
<213> ORGANISM: Clostridium carboxidivorans
<220> FEATURE:
<221> NAME/KEY: misc_feature
<222> LOCATION: (1)..(484)
<223> OTHER INFORMATION: xylose transporter

<400> SEQUENCE: 58

Met Glu Ala Lys Thr Ile Asn Leu Tyr Glu Lys Ser Gly Asp Asn Pro
1               5                   10                  15

Gly Phe Tyr Lys Leu Pro Thr Lys Glu Val Val Gly Tyr Ser Leu Val
            20                  25                  30

Asp Gly Gly Met Asn Leu Val Phe Gln Ser Ile Leu Met Phe Leu Thr
            35                  40                  45

Phe Tyr Tyr Thr Asp Val Tyr Gly Leu Thr Ala Ala Glu Val Ser Val
    50                  55                  60

Met Phe Leu Ile Ser Arg Gly Trp Asp Met Ile Trp Asp Pro Thr Met
65                  70                  75                  80

Gly Ile Ile Ala Glu Arg Met Asn Pro Lys His Gly Lys Tyr Lys Ser
                85                  90                  95

Tyr Leu Ile Tyr Gly Ala Val Pro Phe Ala Leu Ala Gly Ile Leu Thr
            100                 105                 110

Phe Thr Val Pro Asn Leu Gly His Thr Gly Lys Leu Ile Trp Ala Tyr
            115                 120                 125

Ala Thr Tyr Asn Leu Leu Leu Thr Leu Tyr Thr Phe Ile Ile Asn Pro
```

```
                130                 135                 140
Tyr Val Ser Cys Thr Thr Val Met Thr Ala Asp Pro Met Glu Arg Thr
145                 150                 155                 160

Arg Leu Asn Ser Ile Arg Met Met Phe Ala Gln Ser Gly Gly Val Ile
                165                 170                 175

Val Ala Leu Phe Ile Pro Ile Leu Ser Gln Val Phe Gly Arg Gly Asp
            180                 185                 190

Ser Ala Lys Gly Tyr Gln Met Thr Ile Ile Leu Leu Ser Val Ile Cys
        195                 200                 205

Ala Ser Ile Leu Leu Tyr Ser Tyr Thr Thr Leu His Glu Arg Ile Arg
    210                 215                 220

Val Lys Ser His Leu Asp Pro Val Thr Phe Lys Gly Phe Ile Asn Gln
225                 230                 235                 240

Ile Thr His Asn Gln Pro Gly Val Ile Leu Phe Leu Leu Phe Val Gly
                245                 250                 255

Val Tyr Ala Phe Ser Ser Ile Gln Ser Ala Ser Gly Ile Tyr Tyr Met
            260                 265                 270

Thr Tyr Asn Val Asn Arg Lys Asp Leu Val Ala Leu Phe Ser Met Leu
        275                 280                 285

Asn Val Leu Pro Ser Val Val Ala Val Pro Phe Val Pro Ala Leu Phe
    290                 295                 300

Arg His Ile Lys Lys Lys Thr Val Val Leu Gly Leu Ser Leu Gly
305                 310                 315                 320

Ala Leu Gly Ser Ala Ala Leu Tyr Ile Ile Pro Val Ser Gln Ile Thr
                325                 330                 335

Val Met Met Ile Ala Lys Ser Val Ala Ala Phe Gly Tyr Gly Ile Leu
            340                 345                 350

Met Gly Ser Leu Trp Ser Ile Ile Pro Asp Ala Val Glu Tyr Ala Glu
        355                 360                 365

Tyr Asn Thr Gly Lys Arg His Ala Ala Val Val Tyr Ser Leu Ile Thr
    370                 375                 380

Leu Gly Leu Lys Val Ser Leu Ala Val Gly Gly Val Ile Pro Thr Leu
385                 390                 395                 400

Ile Leu Ala Asn Val Gly Tyr Ile Pro Asn Val Thr Gln Thr Ala Lys
                405                 410                 415

Ser Leu Asn Gly Ile Leu Ile Met Thr Ser Ile Leu Pro Ala Val Val
            420                 425                 430

Cys Val Val Thr Leu Leu Ile Phe Met Ile Phe Tyr Asn Leu Thr Glu
        435                 440                 445

Glu Arg Val Ala Asp Ile Met Ala Glu Leu Asp Ile Arg His Lys Asn
    450                 455                 460

Asp Lys Glu Asn Cys Leu Val Glu Leu Val Glu Ile Pro Asp Gln
465                 470                 475                 480

Ser Ile Lys Leu

<210> SEQ ID NO 59
<211> LENGTH: 455
<212> TYPE: PRT
<213> ORGANISM: Clostridium acetobutylicum
<220> FEATURE:
<221> NAME/KEY: misc_feature
<222> LOCATION: (1)..(455)
<223> OTHER INFORMATION: xylose transporter

<400> SEQUENCE: 59
```

Met Asn Lys Lys Ile Ser Pro Ala Leu Ile Tyr Phe Phe Gly Ala Phe
1               5                   10                  15

Gly Gly Phe Met Phe Gly Tyr Asp Ile Gly Ile Ile Asn Gly Ala Leu
            20                  25                  30

Pro Gly Ile Asn Ala Thr Trp His Val Ser Ser Trp Leu Glu Gly Phe
            35                  40                  45

Ile Thr Ser Gly Leu Phe Val Gly Ala Met Ile Gly Ala Ser Leu Met
50                      55                  60

Ala Ser Leu Ala Asp Arg Phe Gly Arg Arg Met Ile Met Trp Ser
65                  70                  75                  80

Ala Ile Val Phe Ala Leu Gly Ala Leu Gly Ser Ala Val Ser Thr Ser
                85                  90                  95

Thr Asn Leu Leu Ile Gly Ala Arg Val Ile Leu Gly Val Ala Val Gly
                100                 105                 110

Gly Ala Ser Ala Leu Val Pro Met Tyr Met Gly Glu Ile Ser Pro Ala
            115                 120                 125

Glu Thr Arg Gly Lys Leu Ser Gly Leu Asn Gln Leu Met Ile Thr Val
            130                 135                 140

Gly Met Leu Phe Ser Tyr Gly Val Asn Phe Ala Phe Ala Gly Ala Phe
145                 150                 155                 160

Glu Gly Trp Arg Trp Met Leu Gly Gly Ala Met Val Pro Ala Met Val
                165                 170                 175

Leu Leu Ile Gly Thr Phe Ile Leu Pro Glu Ser Pro Arg Phe Leu Ala
            180                 185                 190

Arg Ile Gly Lys Thr Glu Leu Ala Lys Gln Val Leu Gln Thr Leu Arg
            195                 200                 205

Ser Lys Glu Glu Ala Glu Thr Glu Tyr Gln Glu Ile Ile Asn Ser Lys
            210                 215                 220

His Thr Glu Thr Gly Ser Phe Gly Asp Leu Phe Ala Lys Gln Ala Leu
225                 230                 235                 240

Pro Ala Val Ile Ala Gly Cys Gly Leu Thr Leu Leu Gln Gln Ile Gln
                245                 250                 255

Gly Ala Asn Thr Ile Phe Tyr Tyr Ser Ser Gln Ile Leu Ser Asn Val
            260                 265                 270

Phe Gly Ser Ala Asn Gly Gly Thr Ile Ser Thr Val Gly Ile Gly Val
            275                 280                 285

Val Leu Val Leu Ala Thr Ile Val Thr Leu Leu Val Val Asp Lys Phe
            290                 295                 300

Lys Arg Arg Thr Leu Phe Met Thr Gly Ser Ile Gly Met Gly Ala Ser
305                 310                 315                 320

Leu Leu Leu Val Gly Leu Ile Tyr Pro Tyr Ser Glu Ala Lys His Ala
                325                 330                 335

Trp Ala Thr Trp Leu Val Phe Phe Ile Cys Leu Tyr Val Val Phe
            340                 345                 350

Tyr Ala Tyr Ser Trp Ala Ala Thr Thr Trp Ile Val Val Gly Glu Leu
            355                 360                 365

Phe Pro Ser Asn Val Arg Gly Leu Ala Thr Gly Ile Ala Ser Ala Val
            370                 375                 380

Asn Trp Phe Gly Asn Ile Leu Val Ala Leu Phe Pro Val Leu Leu
385                 390                 395                 400

Glu Thr Val Gly Leu Ser Val Ile Phe Phe Gly Phe Ala Ala Ile Cys
                405                 410                 415

Ile Ile Gly Phe Leu Phe Ala Lys Tyr Val Leu Tyr Glu Thr Lys Gly

```
                420             425             430
Lys Ser Leu Glu Glu Ile Glu Thr Tyr Leu Tyr Asn Arg Ser Ile Gly
            435                 440                 445
Lys Val Arg Gly Leu Asn Glu
    450                 455

<210> SEQ ID NO 60
<211> LENGTH: 458
<212> TYPE: PRT
<213> ORGANISM: Clostridium acetobutylicum
<220> FEATURE:
<221> NAME/KEY: misc_feature
<222> LOCATION: (1)..(458)
<223> OTHER INFORMATION: xylose transporter

<400> SEQUENCE: 60

Met Ile Gly Ser Phe Lys Ile Lys Met Arg Glu Lys Ile Gly Tyr Ala
1               5                   10                  15
Ser Gly Asp Leu Ala Ser Asn Leu Ile Tyr Gln Thr Ile Ser Ile Tyr
            20                  25                  30
Leu Leu Phe Phe Tyr Thr Asn Val Phe Gly Leu Ser Ala Gly Gln Ala
        35                  40                  45
Gly Val Met Phe Leu Val Val Arg Phe Ile Asp Ala Ile Asn Asp Pro
    50                  55                  60
Ile Ile Gly Thr Leu Val Asp Lys Thr Asn Thr Arg Phe Gly Arg Phe
65                  70                  75                  80
Arg Pro Tyr Leu Leu Tyr Gly Ala Ala Pro Phe Ala Val Leu Ala Phe
                85                  90                  95
Leu Cys Phe Thr Thr Pro Asn Phe Ser Ala Thr Gly Lys Leu Ile Tyr
            100                 105                 110
Ala Tyr Val Thr Tyr Val Gly Leu Ser Ile Thr Tyr Thr Cys Ile Asn
        115                 120                 125
Val Pro Tyr Gly Ala Leu Thr Ser Ala Ile Thr Asp Asp Asn Gln Glu
    130                 135                 140
Ile Val Ser Leu Thr Ser Val Arg Met Phe Phe Ala Asn Leu Gly Gly
145                 150                 155                 160
Val Ile Val Ser Tyr Phe Val Pro Val Leu Ser Ala Tyr Phe Thr Lys
                165                 170                 175
Ser Phe Gly Leu Ser Gly Gly Trp Gln Ile Thr Met Ser Ile Leu Gly
            180                 185                 190
Ile Ala Gly Ala Phe Leu Leu Leu Phe Cys Phe Ser Ser Thr Lys Glu
        195                 200                 205
Arg Val Lys Ser Val Asn Gln Asp His Lys Ile Lys Phe Ser Asp Leu
    210                 215                 220
Phe Glu Gln Phe Lys Thr Asn Arg Pro Leu Ile Val Leu Ser Ile Phe
225                 230                 235                 240
Phe Val Leu Ile Phe Gly Ile Asn Ser Ile Asn Ser Ser Ile Gly Ile
                245                 250                 255
Tyr Tyr Ile Thr Tyr Asn Val Gly Arg Ala Asp Leu Val Gln Trp Tyr
            260                 265                 270
Thr Val Leu Gly Ser Leu Pro Ala Phe Val Cys Ile Pro Leu Ile Pro
        275                 280                 285
Lys Ile Asn Arg Lys Ile Gly Lys Lys Pro Leu Leu Ile Ser Ser Leu
    290                 295                 300
Leu Ile Thr Val Leu Gly Thr Leu Ser Leu Leu Val Ile Pro Thr His
305                 310                 315                 320
```

```
Ala Val Ala Leu Ile Leu Val Ser Arg Val Ile Thr Ser Ile Gly Ser
                325                 330                 335

Leu Thr Ala Gly Ala Phe Met Trp Ser Leu Ile Pro Glu Thr Ile Glu
                340                 345                 350

Tyr Gly Glu Tyr Thr Thr Gly Lys Arg Leu Ser Gly Leu Ile Tyr Ala
                355                 360                 365

Ile Ile Gly Phe Phe Phe Lys Cys Gly Met Ala Leu Gly Gly Ala Val
                370                 375                 380

Pro Gly Ile Ile Leu Gly Asn Phe Gly Tyr Val Ala Asn Lys Thr Gln
385                 390                 395                 400

Thr Pro His Ala Leu Thr Gly Ile Leu Leu Thr Ala Thr Val Val Pro
                405                 410                 415

Ala Val Leu Met Ile Leu Ala Leu Ile Asp Ile Thr Phe Tyr Asn Leu
                420                 425                 430

Asp Asp Lys Lys Tyr Asn His Ile Ile Ala Thr Leu Lys Glu Arg Ala
                435                 440                 445

Lys Leu Asn Arg Gly Glu Asn Leu Asn Leu
        450                 455

<210> SEQ ID NO 61
<211> LENGTH: 449
<212> TYPE: PRT
<213> ORGANISM: Thermoanaerobacterium thermosaccharolyticum
<220> FEATURE:
<221> NAME/KEY: misc_feature
<222> LOCATION: (1)..(449)
<223> OTHER INFORMATION: xylose transporter

<400> SEQUENCE: 61

Met Lys Asn Phe Glu Thr Thr Trp Lys Glu Arg Ile Ser Tyr Gly Leu
1               5                   10                  15

Ser Asp Thr Ala Ser Asn Leu Val Tyr Gln Met Ile Thr Thr Tyr Leu
                20                  25                  30

Met Phe Phe Tyr Thr Asp Val Phe Gly Ile Ser Ala Ala Ala Val Gly
                35                  40                  45

Thr Leu Phe Leu Val Ala Arg Ile Ile Asp Ala Phe Asp Gly Pro Phe
        50                  55                  60

Phe Gly Ile Leu Ile Asp His Thr Asn Thr Lys Trp Gly Lys Cys Arg
65                  70                  75                  80

Pro Tyr Phe Leu Trp Leu Ser Ile Pro Tyr Gly Val Leu Ala Ile Leu
                85                  90                  95

Ala Phe Thr Thr Pro Ser Phe Asn Ala Ser Gly Lys Leu Ile Tyr Ala
                100                 105                 110

Tyr Val Thr Tyr Ile Leu Leu Gly Ile Ile Tyr Ser Gly Ile Asn Ile
                115                 120                 125

Pro Ile Thr Ser Ile Leu Pro Ser Leu Thr Asp Asn Leu Glu Glu Arg
        130                 135                 140

Asn Ile Leu Val Ser Thr Arg Met Ile Leu Ala Thr Val Gly Ala Thr
145                 150                 155                 160

Ile Val Ser Val Gly Thr Leu Pro Leu Val Lys Val Phe Gly Asn Gly
                165                 170                 175

Asn Gln Gln Lys Gly Phe Met Met Thr Met Thr Leu Phe Ala Val Leu
                180                 185                 190

Ala Val Ile Leu Phe Leu Val Thr Phe Phe Asn Thr Arg Glu Lys Val
                195                 200                 205
```

-continued

```
Asn Glu Ala Lys Asp Gln Ser Ile Thr Leu Lys Glu Leu Lys Ala
210                 215                 220

Leu Lys Gly Asn Thr Pro Trp Phe Ile Leu Phe Val Ala Phe Ile
225                 230                 235                 240

Asn Phe Ile Ala Phe Ile Met Lys Ala Gln Thr Thr Val Tyr Tyr Leu
                    245                 250                 255

Thr Tyr Asn Leu Lys Met Pro Asn Leu Ile Ser Ile Ala Leu Gly Leu
                260                 265                 270

Gly Ser Leu Asn Val Val Ser Leu Ile Met Pro Phe Leu Ala Lys
                275                 280                 285

Lys Ile Gly Lys Arg Asn Val Met Ile Thr Gly Phe Thr Phe Ser Ile
290                 295                 300

Leu Ala Gln Phe Ile Leu Tyr Leu Ser Ser Leu Thr Ser Ser Ala Phe
305                 310                 315                 320

Ile Phe Leu Val Gly Thr Val Ile Ala Ala Phe Gly Asn Gly Phe Val
                325                 330                 335

Met Gly Ala Met Phe Ser Met Thr Ala Asp Thr Val Asp Tyr Gly Glu
                340                 345                 350

Trp Lys Ser Gly Val Arg Ala Gln Gly Leu Leu Ser Ala Thr Pro Ala
                355                 360                 365

Phe Gly Val Lys Ala Gly Met Gly Ile Gly Gly Ala Leu Ala Gly Trp
370                 375                 380

Ile Leu Ser Ile Gly Lys Tyr Val Pro Asp His Pro Gln Thr Leu Ser
385                 390                 395                 400

Ala Leu Lys Ala Ile Glu Ile Asn Phe Ile Trp Leu Pro Leu Ile Gly
                405                 410                 415

Phe Ile Ile Ser Ala Val Leu Leu Phe Tyr Asn Leu Asp Lys Gln
                420                 425                 430

Gln Glu Gln Met Thr Lys Glu Leu Asn Glu Arg Arg Ala Lys Leu Ser
                435                 440                 445

Ala
```

```
<210> SEQ ID NO 62
<211> LENGTH: 453
<212> TYPE: PRT
<213> ORGANISM: Thermodesulfobium narugense
<220> FEATURE:
<221> NAME/KEY: misc_feature
<222> LOCATION: (1)..(453)
<223> OTHER INFORMATION: xylose transporter

<400> SEQUENCE: 62
```

```
Met Val Glu Lys Asn Leu Asp Glu Leu Lys Leu Ser Lys His His Leu
1               5                   10                  15

Lys Ala Met Phe Val Ser Gly Met Gly Phe Phe Thr Asp Ala Tyr Asp
                20                  25                  30

Leu Phe Ile Ile Gly Val Ala Leu Ser Leu Ile Ala Pro Val Trp Gly
            35                  40                  45

Leu Thr Ser Ser Glu Ile Ala Leu Leu Gly Ser Ser Ser Leu Leu Ala
        50                  55                  60

Ala Leu Phe Gly Ser Ile Phe Phe Gly Arg Phe Ala Asp Asn Phe Gly
65                  70                  75                  80

Arg Lys Lys Ile Tyr Gly Leu Glu Ala Leu Ile Met Thr Ile Gly Ala
                85                  90                  95

Leu Met Ser Ala Phe Ser Pro Asn Phe Leu Phe Leu Leu Phe Ser Arg
                100                 105                 110
```

-continued

```
Phe Ile Leu Gly Leu Gly Ile Gly Gly Asp Tyr Pro Val Ser Ala Val
            115                 120                 125

Ile Met Ser Glu Tyr Ser Asn Arg Ser Asp Arg Gly Lys Leu Val Gly
        130                 135                 140

Leu Val Phe Ser Met Gln Ala Leu Gly Leu Ile Ile Gly Pro Leu Val
145                 150                 155                 160

Ala Leu Ser Leu Leu Leu Leu His Ile Pro Leu Asp Phe Ala Trp Arg
                165                 170                 175

Leu Met Leu Gly Leu Gly Ala Leu Pro Ser Leu Met Val Ile Tyr Leu
                180                 185                 190

Arg Arg Lys Leu Pro Glu Ser Pro Arg Tyr Leu Ser Gln Ile Val Gly
            195                 200                 205

Asp Lys Lys Ala Ala Leu Thr Ala Phe Val Asn Phe Thr Gly Asn Gly
            210                 215                 220

Asn Lys Ser Tyr Glu Pro Ile His Leu Asn Pro Lys Ile Asn His Arg
225                 230                 235                 240

Leu Lys Asp Phe Phe Ser Asn Lys Gln His Thr Leu Thr Leu Phe Gly
                245                 250                 255

Thr Ala Gly Ser Trp Phe Leu Leu Asp Trp Ala Tyr Tyr Gly Asn Thr
                260                 265                 270

Ile Ser Thr Pro Ile Val Met Asn Ala Ile Cys Asp Ser Ser Ser Leu
            275                 280                 285

Glu Leu Lys Met Ile Tyr Ser Leu Val Ile Phe Val Val Phe Ala Leu
            290                 295                 300

Pro Gly Tyr Ile Leu Ser Ile Ile Phe Met Asp Ile Ile Gly Arg Lys
305                 310                 315                 320

Tyr Ile Gln Leu Met Gly Phe Gly Ile Met Ala Phe Ser Phe Leu Leu
                325                 330                 335

Leu Gly Leu Ile Pro Asp Ile Glu Ser Asn Val Thr Gly Phe Leu Ile
                340                 345                 350

Leu Tyr Gly Leu Ser Tyr Leu Phe Thr Glu Phe Gly Pro Asn Thr Thr
            355                 360                 365

Thr Phe Val Leu Pro Ser Glu Leu Phe Pro Thr Glu Tyr Arg Thr Thr
        370                 375                 380

Gly His Gly Leu Ser Ala Gly Ile Gly Lys Leu Gly Ala Phe Phe Gly
385                 390                 395                 400

Val Leu Phe Phe Pro Ile Thr Glu Ser Phe Leu Gly Leu Asn Met Thr
                405                 410                 415

Phe Val Ile Val Ser Ile Ile Cys Phe Met Gly Ile Ile Thr Thr Ser
                420                 425                 430

Val Leu Thr Glu Pro Lys Gly Lys Ser Leu Glu Asp Cys Ser Tyr Ser
            435                 440                 445

Lys Ile Val Gly Lys
    450
```

GENETICALLY MODIFIED CLOSTRIDIUM THERMOCELLUM ENGINEERED TO FERMENT XYLOSE

CROSS-REFERENCE TO RELATED APPLICATIONS

This application is the National Stage of International Application Number PCT/US2011/066968, filed Dec. 22, 2011, which claims the benefit of U.S. Provisional Application No. 61/426,151, filed Dec. 22, 2010, which are incorporated by reference herein.

REFERENCE TO A SEQUENCE LISTING SUBMITTED ELECTRONICALLY VIA EFS-WEB

The content of the electronically submitted sequence listing (Name: 2608_0540001_SequenceListing_ascii.txt; Size: 209,694 bytes; and Date of Creation: Jun. 13, 2013) is herein incorporated by reference in its entirety.

BACKGROUND OF THE INVENTION

Field of the Invention

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Biomass and derivatives thereof are a resource for the biological conversion of energy to forms useful to humanity.

Biomass is biological material from living, or recently living organisms, such as wood, waste, (hydrogen) gas, and alcohol fuels. Biomass is carbon, hydrogen and oxygen based. Nitrogen and small quantities of other atoms, including alkali, alkaline earth and heavy metals can be found as well. Metals are often found in functional molecules such as the porphyrins which include chlorophyll which contains magnesium. Plants in particular combine water and carbon dioxide to sugar building blocks. The required energy is produced from light via photosynthesis based on chlorophyll. On average, between 0.1 and 1% of the available light is stored as chemical energy in plants. The sugar building blocks are the starting point for all of the major fractions found in terrestrial plants, lignin, hemicellulose and cellulose. Biomass is widely recognized as a promising source of raw material for production of renewable fuels and chemicals.

The primary obstacle impeding widespread production of energy from biomass feedstocks is the general absence of low-cost technology for overcoming the recalcitrance of these materials to conversion into useful products. Biomass contains carbohydrate fractions (e.g., cellulose and hemicellulose) as well as pentose sugars (e.g., xylose and arabinose) that can be converted into ethanol or other products such as acetate, pyruvate, lactic acid, and acetic acid. In order to convert these fractions, the cellulose, hemicellulose, xylose, and arabinose must ultimately be converted or hydrolyzed into monosaccharides; it is the hydrolysis that has historically proven to be problematic.

Biologically mediated processes are promising for energy conversion. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer, and engineering non-cellulolytic organisms that exhibit high product yields and titers to express a heterologous cellulase and hemicellulase system enabling cellulose and hemicellulose utilization.

One way to meet the demand for ethanol production is to convert sugars found in biomass, e.g., materials such as agricultural wastes, corn hulls, corncobs, cellulosic materials, and the like to produce ethanol or other products. In biomass conversion, microorganisms are used as biocatalysts to convert cellulosic materials to usable end products, such as ethanol. Efficient biomass conversion in large-scale industrial applications requires a microorganism that is able to tolerate high concentrations of sugar and ethanol, and which is able to ferment more than one sugar simultaneously.

Xylose appears in great abundance in biomass feedstocks. It can constitute as much as 40% of a lignocellulosic material (Ladisch et al., *Biotechnol Bioeng*, 25:1-2, 1983). By fermentation xylose can be converted to ethanol which can be used as a liquid fuel or a chemical feedstock. Enzymatically or as a by-product of fermentation, xylose can also be converted to xylitol which is a promising natural sweetener having dental caries reducing properties. Xylitol can also be used by diabetics.

Although many bacteria have the ability to ferment simple hexose sugars, the pentose sugars, xylose and arabinose, are among the most difficult sugars in biomass to metabolize. Some bacteria can ferment pentoses to ethanol and other co-products, and bacteria with improved ethanol production from pentose sugars have been genetically engineered. See, e.g., Xiao et al., *Appl. Environ. Microbiol.*, 77:7886-7895, 2011. However, these bacteria are sensitive to low pH and high concentrations of ethanol, their use in fermentations is associated with co-product formation, and the level of ethanol produced remains too low. For at least these reasons, using these bacteria in large-scale ethanol production is not economically feasible. Therefore, there is a need in the art for a cellulolytic organism that is capable of fermenting pentose sugar to ethanol.

Organisms, such as *Thermoanaerobacterium saccharolyticum* are naturally capable of utilizing xylose by the xylose isomerase pathway. In the xylose isomerase pathway, the enzyme xylose isomerase (XI) converts xylose to xylulose. Xylulose is then phosphorylated by an ATP utilising kinase, xylulose kinase (XK), to xylulose-5-phosphate which is an intermediate of the pentose phosphate pathway. Therefore, one method of producing a xylose fermenting cellulolytic organism, that would be useful as a CBP organism, is to clone genes from the xylose isomerase pathway, required for the fermentation of xylose to ethanol, into a cellulolytic organism such that the cellulolytic organism can produce the enzymes needed to metabolize xylose.

*Clostridium thermocellum* is a highly cellulolytic organism that has much potential as a biocatalyst in a consolidated bioprocess configuration. The economic potential of *C. thermocellum* as a CBP organism is limited by its inability to ferment xylose. There are currently no known strains of *C. thermocellum* capable of fermenting xylose, engineered or otherwise. Therefore, a strain of *C. thermocellum* that is capable of fermenting xylose will have great industrial applicability as a CBP organism.

Although the genome of *C. thermocellum* has been completely sequenced and a number of *C. thermocellum* genes have been cloned into other bacteria, reliable methods have not been established for the introduction of foreign genes into this microorganism. The absence of such methods has been a significant impediment to studies of *C. thermocellum* aimed at increasing both fundamental understanding and applied capability. Due to the multiple and substantial possible genome modifications required to render *C. thermocellum* capable of fermenting xylose, as well as the difficulty and unpredictability in transforming this organism, it is currently not possible to create a *Clostridium thermocellum* strain suitable for use in the industrial production of ethanol and other products from biomass. Therefore, to date, no identified strains of *C. thermocellum* exist that have the ability to ferment xylose. Thus, there is a need in the art to develop one or more strains of *C. thermocellum* capable of fermenting xylose that can act as a biocatalyst in a consolidated bioprocess configuration.

The present invention provides, for the first time, strains of *C. thermocellum* containing genetic modifications that confer the ability to ferment xylose to *C. thermocellum*.

BRIEF SUMMARY OF THE INVENTION

In one embodiment, the invention relates to a recombinant *Clostridium thermocellum* host cell capable of fermenting xylose.

In another embodiment, the invention relates to a recombinant *Clostridium thermocellum* host cell comprising a heterologous polynucleotide, wherein the polynucleotide has a nucleotide sequence at least 90% identical to any one of the nucleotide sequences of SEQ ID NOs: 1-2 or the amino acid sequences of SEQ ID NOs: 3-4.

Another aspect of the invention relates to a fermentation broth comprising: (a) a recombinant *Clostridium thermocellum* host cell capable of fermenting xylose; and (b) a media, wherein the media comprises xylose, and wherein the media is capable of supporting the growth of the host cell.

In yet another aspect, the invention relates to a co-culture comprising the recombinant *Clostridium thermocellum* host cell of the invention capable of fermention xylose and at least one other host cell.

In another embodiment, the invention relates to a method of fermenting xylose comprising: incubating a reaction mixture comprising: (a) a biomass, wherein the biomass comprises xylose; and (b) a recombinant *Clostridium thermocellum* host cell, wherein the host cell is capable of fermenting xylose.

In still another embodiment, the invention relates to a method of making one or more xylose fermentation product comprising: incubating a reaction mixture comprising: (a) a biomass, wherein the biomass comprises xylose; and (b) a recombinant *Clostridium thermocellum* host cell, wherein the host cell is capable of fermenting xylose to yield one or more xylose fermentation products.

In another embodiment, the invention relates to a recombinant *Clostridium thermocellum* host cell capable of fermenting xylan.

Another aspect of the invention relates to a fermentation broth comprising: (a) a recombinant *Clostridium thermocellum* host cell capable of fermenting xylan; and (b) a media, wherein the media comprises xylan, and wherein the media is capable of supporting the growth of the host cell.

In yet another embodiment, the invention relates to a co-culture comprising the recombinant *Clostridium thermocellum* of the invention capable of fermention xylan and at least one other host cell.

In another embodiment, the invention relates to a method of fermenting xylan comprising: incubating a reaction mixture comprising: (a) a biomass, wherein the biomass comprises xylan; and (b) a recombinant *Clostridium thermocellum* host cell, wherein the host cell is capable of fermenting xylan.

In still another embodiment, the invention relates to a method of making one or more xylan fermentation products comprising: incubating a reaction mixture comprising: (a) a biomass, wherein the biomass comprises xylan; and (b) a recombinant *Clostridium thermocellum* host cell, wherein the host cell is capable of fermenting xylan to yield one or more xylan fermentation products.

BRIEF DESCRIPTION OF THE DRAWINGS/FIGURES

Figure 3:
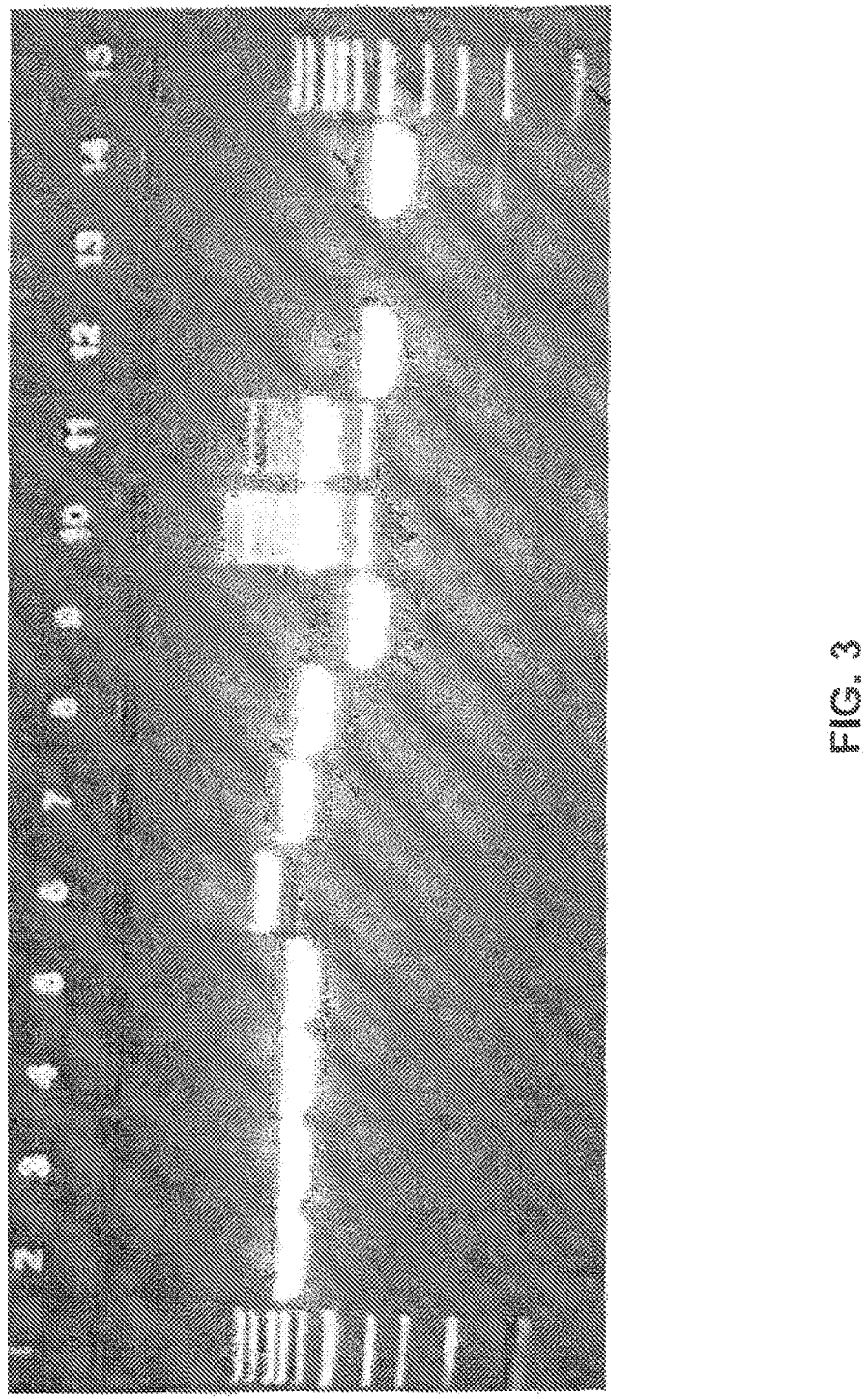

FIG. 3 depicts an image of diagnostic PCR confirmation of seamless integration of the XI/XK operon at the lactate dehydrogenase (LDH) locus. Wild type control genomic DNA was used to generate the amplicon observed in lane 14 and the expected 2.9 KB band is observed. The integrated XI/XK operon should run at 4966 bp, a size which is observed in lanes 2-5 and 8.

Figure 4:
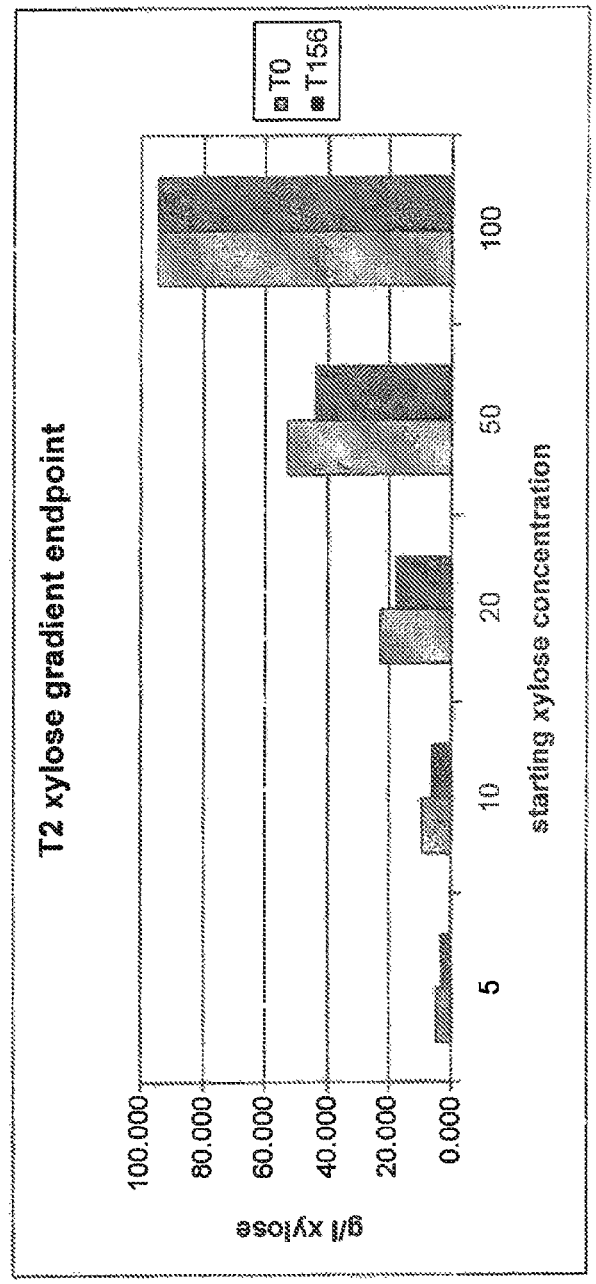

FIG. 4 depicts the endpoint analysis of xylose concentration at 156 hr in medium inoculated with a *C. thermocellum* strain T2 (Δldh::XI/XK).

Figure 5:
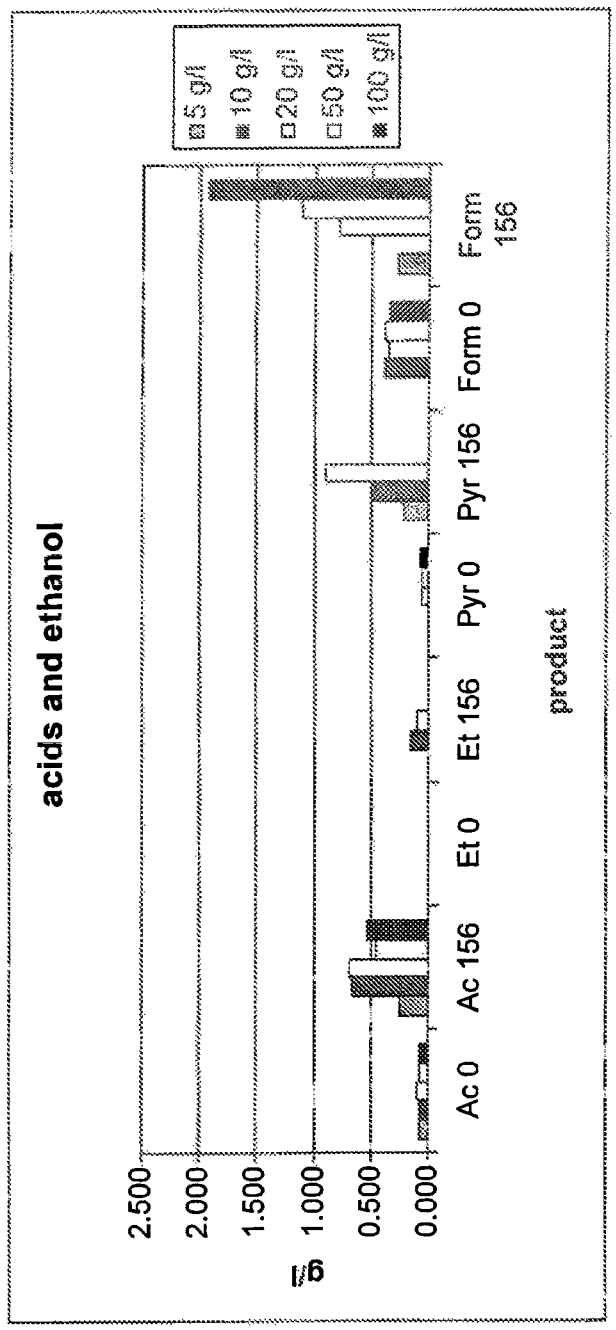

FIG. 5 depicts the end product HPLC analysis of the T2 strain.

Figure 6:
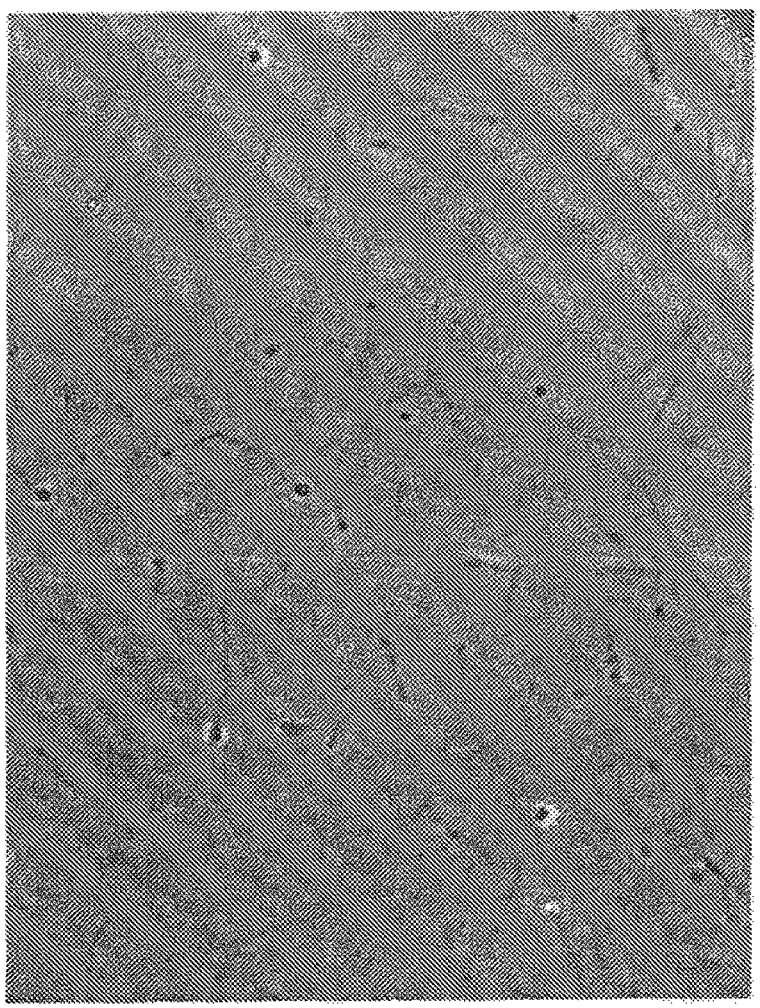

FIG. 6 shows evidence of sporulation observed in T3 cultures at 48 hrs.

Figure 7:
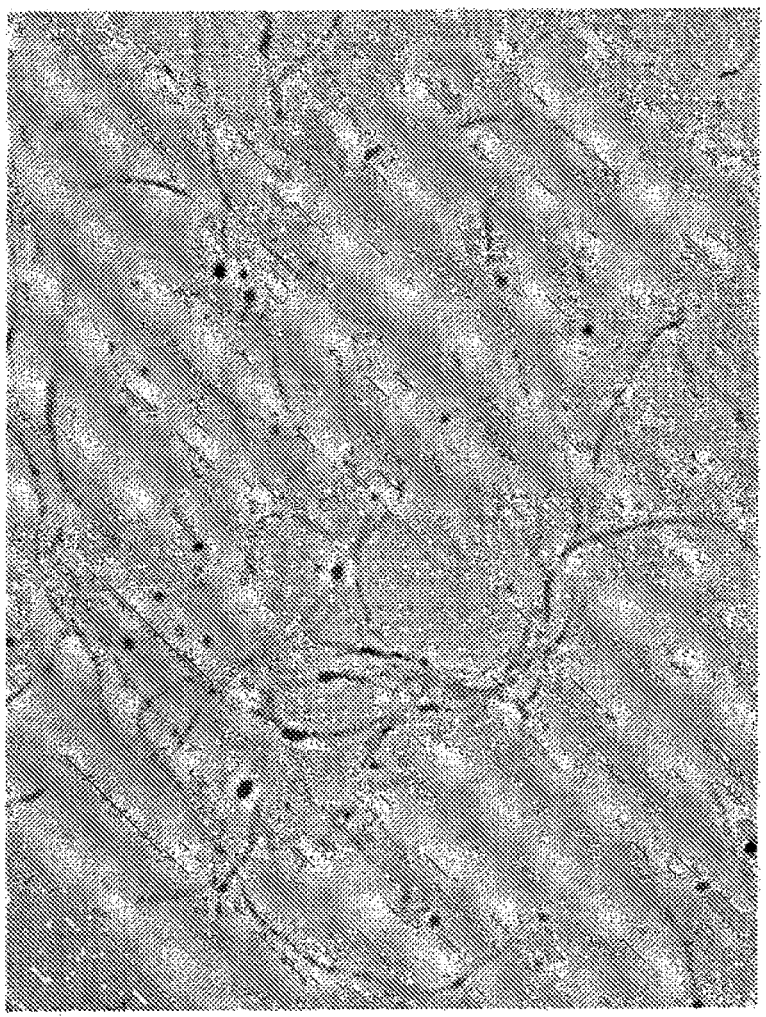

FIG. 7 shows the microscopy of T3 culture at 72 hrs.

Figure 8:
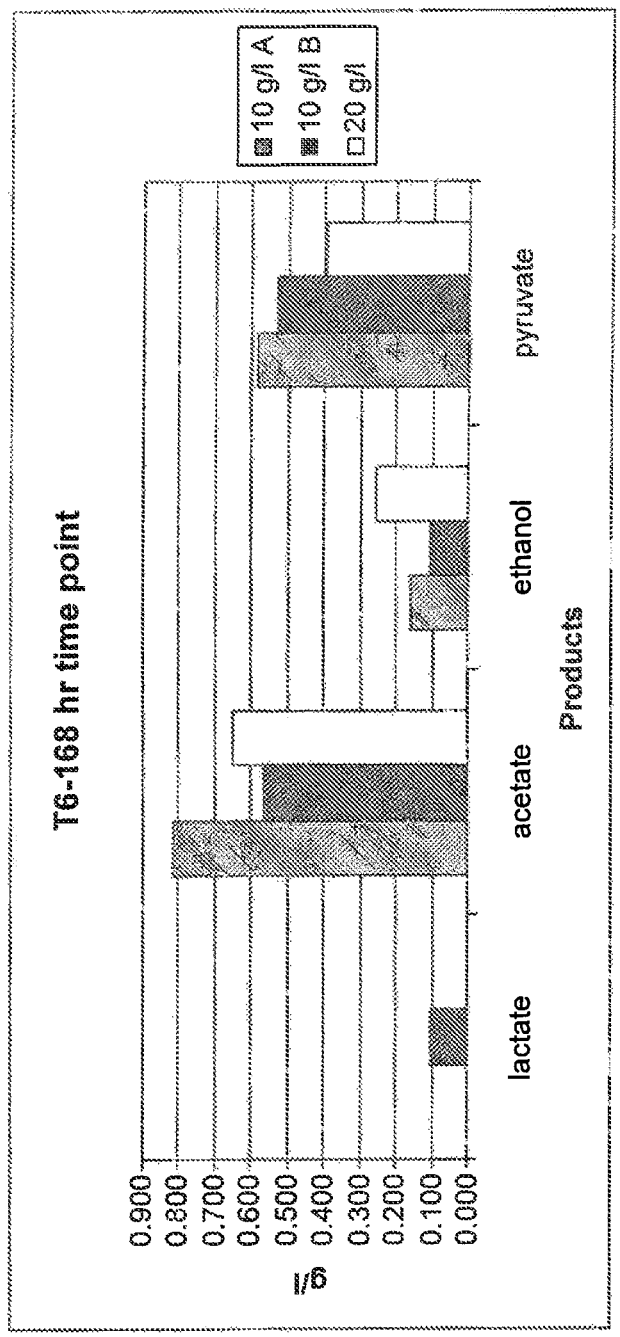

FIG. 8 depicts the endpoint analysis of T6 culture grown on 10 and 20 g/l xylose.

Figure 9:
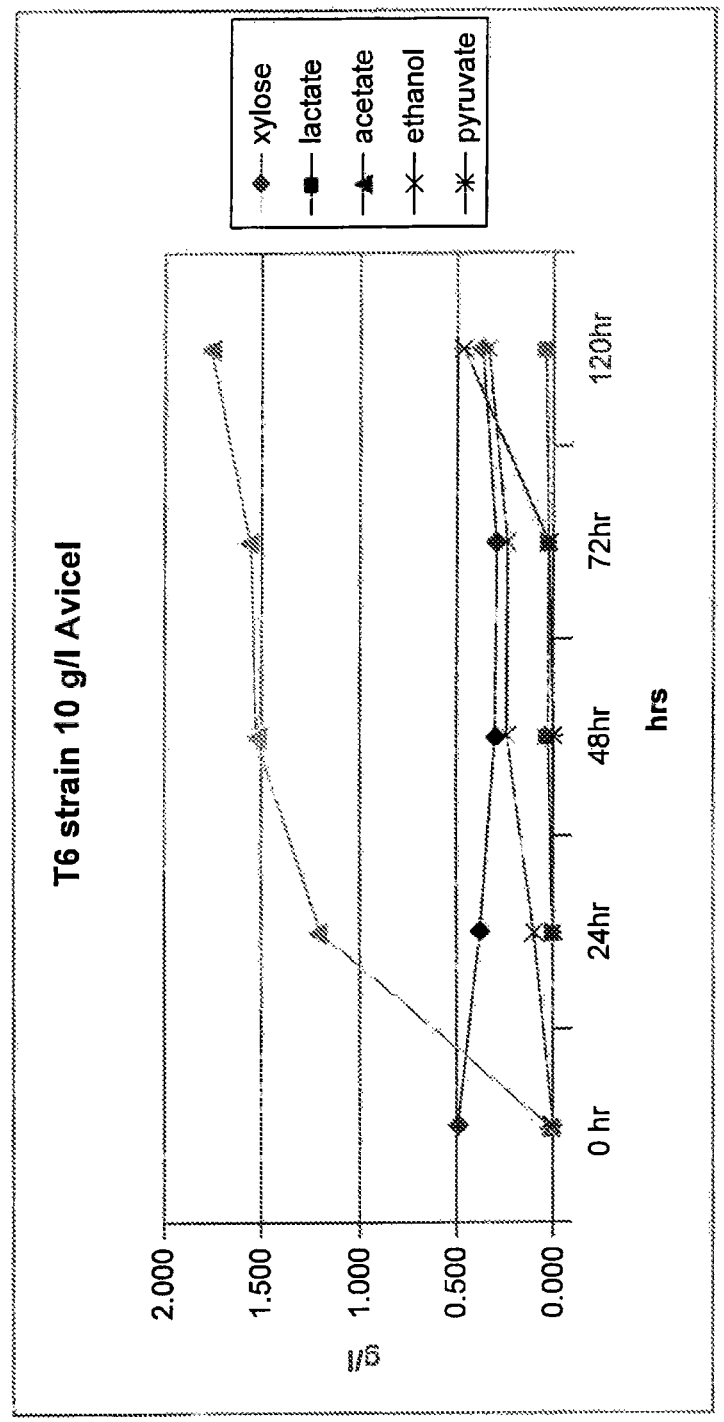

FIG. 9 shows the growth of T6 culture on 10 g/l avicel.

Figure 10:
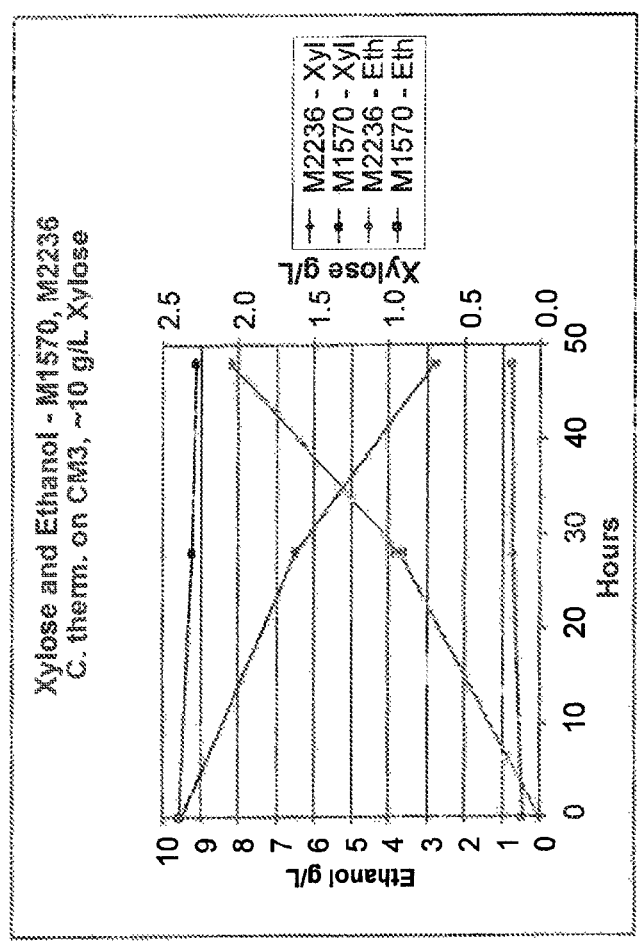

FIG. 10 shows the growth of M2236 culture on CM3 medium containing xylose as the only sugar source. Xylose is consumed and ethanol is produced by the M2236 strain, while the M1570 strain is unable to convert significant amounts of xylose to ethanol.

DETAILED DESCRIPTION OF THE INVENTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting of" and/or "consisting essentially of" are also provided.

DEFINITIONS

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is removed from the source organism and subsequently reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes. A heterologous polynucleotide, gene, polypeptide, or an enzyme may be derived from any source, e.g., eukaryotes, prokaryotes, viruses, or synthetic polynucleotide fragments. The term "heterologous" as used herein also refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

By "promoter" is meant a region of DNA that facilitates the transcription of a particular gene. Promoters are typically located near the genes they regulate, on the same strand and upstream (towards the 5' region of the sense strand). The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

As used herein, the term "terminator" or "transcription terminator" is a section of genetic sequence that marks the end of a gene or operon on genomic DNA for transcription.

As used herein, the term "operon" refers to a functioning unit of genomic material containing a cluster of genes under the control of a single regulatory signal or promoter. The genes are transcribed together into an mRNA strand and either translated together in the cytoplasm, or undergo trans-splicing to create monocistronic mRNAs that are translated separately, i.e., several strands of mRNA that each encode a single gene product. The result of this is that the genes contained in the operon are either expressed together or not at all. Originally operons were thought to exist solely in prokaryotes but since the discovery of the first operons in eukaryotes in the early 1990s, more evidence has arisen to suggest they are more common than previously assumed. Operons occur primarily in prokaryotes but also in some eukaryotes, including *Drosophila melanogaster* and *C. elegans*.

"Thermophilic" or "thermotolerant" bacteria are those bacteria whose growth temperature optimum is above about 45° C. Thermophilic bacteria offer major advantages for biotechnological processes, many of which run more rapidly and efficiently at high temperatures. Higher incubation temperatures increase the diffusion rate and solubilities of non-gaseous compounds of interest and tend to discourage non-thermophilic microbial contamination. Cell culture carried out at high temperatures also eliminates or greatly reduces cooling costs.

By "mesophilic" is meant an organism that thrives at a temperature of about 20-45° C.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of a acetate to a non-charged solvent, including but not limited to, acetone, isopropanol, ethyl acetate, or ethanol. Accordingly, the term is intended to include any gene encoding a polypeptide, such as the enzymes acetate kinase (ACK), phosphotransacetylase (PTA), lactate dehydrogenase (LDH), pyruvate formate lyase (PFL), aldehyde dehydrogenase (ADH) and/or alcohol dehydrogenase (ADH), acetyl-CoA transferase (ACS), acetaldehyde dehydrogenase, acetaldehyde/alcohol dehydrogenase, glycerol-3-phosphate dehydrogenase (GPD), acetyl-CoA synthetase, thiolase, CoA transferase, acetoacetate decarboxylase, enzymes in the D-xylose pathway, such as xylose isomerase and xylulokinase, enzymes in the L-arabinose pathway, such as L-arabinose isomerase and L-ribulose-5-phosphate 4-epimerase. The term gene is also intended to cover all copies of a particular gene, e.g., all of the DNA sequences in a cell encoding a particular gene product.

The term "expression" is intended to include the expression of a gene at least at the level of mRNA production.

The term "expression product" is intended to include the resultant product, e.g., a polypeptide, of an expressed gene.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

The term "xylanolytic activity" is intended to include the ability to hydrolyze glycosidic linkages in oligopentoses and polypentoses.

As used herein, the term "lactate dehydrogenase" or "LDH" is intended to include the enzymes capable of converting pyruvate into lactate. It is understood that LDH can also catalyze the oxidation of hydroxybutyrate. LDH includes those enzymes that correspond to Enzyme Commission Number 1.1.1.27.

As used herein the term "alcohol dehydrogenase" or "ADH" is intended to include the enzymes capable of converting acetaldehyde into an alcohol, such as ethanol. ADH also includes the enzymes capable of converting acetone to isopropanol. ADH includes those enzymes that correspond to Enzyme Commission Number 1.1.1.1.

As used herein, the term "phosphotransacetylase" or "PTA" is intended to include the enzymes capable of converting hypoxanthine to inosine monophosphate and guanine to guanosine monophosphate via transfer of the 5-phosphoribosyl group from 5-phosphoribosyl 1-pyrophosphate. This enzyme plays a central role in the generation of purine nucleotides through the purine salvage pathway. HPT includes those enzymes that correspond to Enzyme Commission Number 2.4.2.8.

As used herein, the term "hypoxanthine phosphoribosyltransferase" or "HPT" is intended to include the enzymes capable of converting acetyl-phosphate into acetyl-CoA. PTA includes those enzymes that correspond to Enzyme Commission Number 2.3.1.8.

A "xylose metabolizing enzyme" can be any enzyme involved in xylose digestion, metabolism and/or hydrolysis, including a xylose isomerase, xylulokinase, xylose reductase, xylose dehydrogenase, xylitol dehydrogenase, xylonate dehydratase, a transketolase, and a transaldolase protein. See, e.g. Gu et al., *BMC Genomics*, 11:255-268, 2010.

By "xylulokinase" (XK) is meant an enzyme that catalyzes the chemical reaction: ATP+D-xylulose ⇌ ADP+D-xylulose 5-phosphate. Thus, the two substrates of this enzyme are ATP and D-xylulose, whereas its two products are ADP and D-xylulose 5-phosphate. This enzyme belongs to the family of transferases, specifically those transferring phosphorus-containing groups (phosphotransferases) with an alcohol group as acceptor. The systematic name of this enzyme class is ATP:D-xylulose 5-phosphotransferase. Other names in common use include xylulokinase (phosphorylating), and D-xylulokinase. This enzyme participates in pentose and glucuronate interconversions. XK includes those enzymes that correspond to Enzyme Commission Number 2.7.1.17.

By "xylose isomerase" (XI) is meant an enzyme that catalyzes the chemical reaction: D-xylose ⇌ D-xylulose. This enzyme belongs to the family of isomerases, specifically those intramolecular oxidoreductases interconverting aldoses and ketoses. The systematic name of this enzyme class is D-xylose aldose-ketose-isomerase. Other names in common use include D-xylose isomerase, D-xylose ketoisomerase, and D-xylose ketol-isomerase. This enzyme participates in pentose and glucuronate interconversions and fructose and mannose metabolism. The enzyme is used industrially to convert glucose to fructose in the manufacture of high-fructose corn syrup. It is sometimes referred to as "glucose isomerase". XI includes those enzymes that correspond to Enzyme Commission Number 5.3.1.5.

As used herein, the term "xylose transport proteins" or "xylose transporter" is intended to include a membrane protein that is involved in the movement of xylose across a biological membrane, thereby facilitating xylose utilization by the host organism. See, e.g. Gu et al., *BMC Genonmics*, 11:255-268, 2010. As used herein, the term "xylose transport genes" is intended to include the genes that encode a xylose transport protein.

Certain embodiments of the present invention provide for the "inactivation" or "deletion" of certain genes or particular polynucleotide sequences within microorganisms, which "inactivation" or "deletion" of genes or particular polynucleotide sequences may be understood to encompass "genetic modification(s)" or "transformation(s)" such that the resulting strains of said microorganisms may be understood to be "genetically modified" or "transformed." In certain embodiments, strains of microorganisms may be of bacterial, fungal, or yeast origin.

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains of microorganisms may be of bacterial, fungal, or yeast origin.

The term "CBP organism" is intended to include microorganisms of the invention, e.g., microorganisms that have properties suitable for CBP.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

As used herein, the term "undesirable end products" of fermentation is intended to include products of fermentation other than ethanol and carbon dioxide. Undesirable end products may include, but are not limited to, acetate, lactate, pyruvate, and glyceraldehyde.

As used herein, "selection" or "selection methods" or "selection protocol(s)" refers to methods for putting pressure on (or challenging) a given strain to adapt to new conditions. The selection methods favor sporadic "variants" of the original strain wherein the variants undergo some genetic or epigenetic change that confers a growth advantage in the culture conditions of the embodiment.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in the D-xylose pathway and/or L-arabinose pathway. In certain embodiments of the invention, genes encoding enzymes in the conversion of acetate to a non-charged solvent, including but not limited to, acetone, isopropanol, ethyl acetate, or ethanol, may be added to a mesophilic or thermophilic organism.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination." and "knockout" are used interchangeably with the terms "deletion," "partial deletion," "substantial deletion," or "complete deletion." In certain embodiments, strains of microorganisms of interest may be engineered by site directed homologous recombination to knockout specific genes. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "expression," as used herein, refers to the transcription and stable accumulation of sense (mRNA) or antisense RNA derived from the nucleic acid fragment of the invention. Expression may also refer to translation of mRNA into a polypeptide.

The term "lignocellulose" refers to material that is comprised of lignin and cellulose.

A "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar hydrolyzing enzymes.

A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

A "cellulolytic enzyme" can be any enzyme involved in cellulose digestion, metabolism and/or hydrolysis. The term "cellulase" refers to a class of enzymes produced chiefly by fungi, bacteria, and protozoans that catalyze cellulolysis (i.e. the hydrolysis) of cellulose. However, there are also cellulases produced by other types of organisms such as plants and animals. Several different kinds of cellulases are known, which differ structurally and mechanistically. The EC number for this group of enzymes is EC 3.2.1.4. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulase digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, and feruoyl esterase protein.

An "amylolytic enzyme" can be any enzyme involved in amylase digestion, metabolism and/or hydrolysis. The term "amylase" refers to an enzyme that breaks starch down into sugar. Amylase is present in human saliva, where it begins the chemical process of digestion. Foods that contain much starch but little sugar, such as rice and potato, taste slightly sweet as they are chewed because amylase turns some of their starch into sugar in the mouth. The pancreas also makes amylase ($\alpha$-amylase) to hydrolyse dietary starch into disaccharides and trisaccharides which are converted by other enzymes to glucose to supply the body with energy. Plants and some bacteria also produce amylase. All amylases are glycoside hydrolases and act on $\alpha$-1,4-glycosidic bonds. Some amylases, such as $\gamma$-amylase (glucoamylase), also act on $\alpha$-1,6-glycosidic bonds. Amylase enzymes include $\alpha$-amylase (EC 3.2.1.1), 3-amylase (EC 3.2.1.2), and $\gamma$-amylase (EC 3.2.1.3). An amylase can be any enzyme involved in amylase digestion, metabolism and/or hydrolysis, including $\alpha$-amylase, $\beta$-amylase, glucoamylase, and alpha-glucosidase. The $\alpha$-amylases are calcium metalloenzymes, unable to function in the absence of calcium. By acting at random locations along the starch chain, $\alpha$-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In animals, it is a major digestive enzyme and its optimum pH is about 6.7-7.0. Another form of amylase, 3-amylase, is also synthesized by bacteria, fungi, and plants. Working from the non-reducing end, β-amylase catalyzes the hydrolysis of the second α-1.4 glycosidic bond, cleaving off two glucose units (maltose) at a time. Many microbes produce amylase to degrade extracellular starches. In addition to cleaving the last α(1-4) glycosidic linkages at the nonreducing end of amylose and amylopectin, yielding glucose, γ-amylase will cleave α(1-6) glycosidic linkages. Another amylolytic enzyme is pullulanase. Pullulanase is a specific kind of glucanase, an amylolytic exoenzyme, that degrades pullulan. Pullulan is regarded as a chain of maltotriose units linked by alpha-1, 6-glycosidic bonds. Pullulanase (EC 3.2.1.41) is also known as pullulan-6-glucanohydrolase (Debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

The term "xylan" includes a wide variety of highly complex polysaccharides that are found in plant cell walls and some algae. Xylans are polysaccharides made from units of xylose.

The term "xylanase" is the name given to a class of enzymes which degrade the linear polysaccharide beta-1,4-xylan into xylose, thus breaking down hemicellulose, one of the major components of plant cell walls. As such, it plays a major role in micro-organisms thriving on plant sources (mammals, conversely, do not produce xylanase). Additionally, xylanases are present in fungi for the degradation of plant matter into usable nutrients. Xylanases include those enzymes that correspond to Enzyme Commission Number 3.2.1.8. A "xylose metabolizing enzyme" can be any enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein.

A "pentose sugar hydrolyzing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

Biomass

Biomass can include any type of biomass known in the art or described herein. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan), pectins (e.g., homogalacturonans, rhamnogalacturonan I and II, and xylogalacturonan), and proteoglycans (e.g., arabinogalactan-protein, extensin, and proline-rich proteins). Biomass also includes starch and hexose and pentose sugars.

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber, stovers, such as corn stover and soybean stover; grasses, such as switch grass, reed canary grass, cord grass, and *miscanthus*; or combinations thereof.

Paper sludge is also a viable feedstock for lactate or acetate production. Paper sludge is solid residue arising from pulping and paper-making, and is typically removed from process wastewater in a primary clarifier.

Consolidated Bioprocessing

Consolidated bioprocessing (CBP) is a processing strategy for cellulosic biomass that involves consolidating into a single process step four biologically-mediated events: enzyme production, hydrolysis, hexose fermentation, and pentose fermentation. Implementing this strategy requires development of microorganisms that both utilize cellulose, hemicellulosics, and other biomass components, such as hexose and pentose sugars, while also producing a product of interest at sufficiently high yield and concentrations. The feasibility of CBP is supported by kinetic and bioenergetic analysis. See van Walsum and Lynd (1998) *Biotech. Bioeng.* 58:316.

Acetate

Acetate is produced from acetyl-CoA in two reaction steps catalyzed by phosphotransacetlyase (PTA) and acetate kinase (ACK). The reactions mediated by these enzymes are shown below:

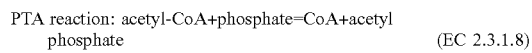

PTA reaction: acetyl-CoA+phosphate=CoA+acetyl phosphate     (EC 2.3.1.8)

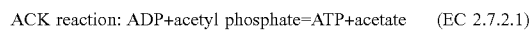

ACK reaction: ADP+acetyl phosphate=ATP+acetate     (EC 2.7.2.1)

*C. thermocellum* makes acetate under standard fermentation conditions and has well annotated genes encoding PTA and ACK.

Pyruvate

Pyruvate is an important intermediary compound of metabolism. For example, under aerobic conditions pyruvate may be oxidized to acetyl coenzyme A (acetyl-CoA), which then enters the tricarboxylic acid cycle (TCA), which in turn generates synthetic precursors, $CO_2$, and reduced cofactors. The cofactors are then oxidized by donating hydrogen equivalents, via a series of enzymatic steps, to oxygen resulting in the formation of water and ATP. This process of energy formation is known as oxidative phosphorylation.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor $NAD^+$. Because of the varying cofactors needed in this pathway and the degree to which they are available for usage, an imbalance can result in an overproduction of xylitol byproduct and an inefficient production of desirable products. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKSI, to further modify xylulose into xylulose-5-P where it then enters the pentose phosphate pathway for further catabolism.

Apart from the two major pathways mentioned above, xylose can also be catabolized by two oxidative pathways that are called the Weimberg pathway and the Dahms pathway are common in prokaryotic microorganisms. The Weimberg pathway is an oxidative pathway where the D-xylose is oxidized to D-xylono-lactone by a D-xylose dehydrogenase followed by a lactonase to hydrolyze the lactone to D-xylonic acid. A xylonate dehydratase is splitting off a water molecule resulting in 2-keto 3-deoxy-xylonate. A second dehydratase forms the 2-keto glutarate semialdehyde which is subsequently oxidised to 2-ketoglutarate. The Dahms pathway starts as the Weimberg pathway but the 2-keto-3 deoxy-xylonate is split by an aldolase to pyruvate and glycoladehyde.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene (Jeppsson et al., *Appl Environ Microbiol.* 68:1604-1609, 2002). Since the pentose phosphate pathway produces additional NADPH during metabolism, limiting this step will help to correct the already evident imbalance between NAD(P)H and $NAD^+$ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production (Karhumaa et al., *Microb Cell Fact.* 2007 Feb. 5; 6:5). See also International Publication No. WO2006/009434, incorporated herein by reference in its entirety.

Host Cells

Host cells useful in the present invention include any prokaryotic or eukaryotic cells; for example, microorganisms selected from bacterial, algal, and yeast cells. Among host cells suitable for the present invention are microorganisms, for example, of the genera *Clostridium*.

In some embodiments, the host cells are microorganisms. In one embodiment the microorganism is a thermotolerant or thermophilic microorganism.

In one embodiment, the host cells can contain antibiotic markers or can contain no antibiotic markers. In another embodiment, the host cells are bacteria selected from the genus *Clostridium* and other bacteria having characteristics resembling those of *Clostridium* species.

Cellulolytic and Xylanolytic Microorganisms

Several microorganisms that are reported in the literature to be both cellulolytic and xylanolytic have been characterized by a variety of means, including their ability to grow on microcrystalline cellulose and birchwood xylan as well as a variety of other sugars. Additionally, such organisms may be characterized by other means, including but not limited to, their ability to depolymerize and debranch cellulose and hemicellulose. In one embodiment, cellulolytic the organisms of interest is *Clostridium thermocellum*.

TABLE 1 summarizes the growth of *C. thermocellum* on Avicel®.

| Strain | DSMZ No. | T optimum; or range | pH optimum; or range | Gram Stain | Aero-tolerant | Utilizes | Products |
|---|---|---|---|---|---|---|---|
| *Clostridium thermocellum* | 1313 | 55-60 | 7 | positive | No | cellobiose, cellulose | acetic acid, lactic acid, ethanol, $H_2$, $CO_2$ |

Certain microorganisms, including, for example, *C. thermocellum*, cannot metabolize pentose sugars, such as xylose or arabinose, but are able to metabolize hexose sugars. Both xylose and arabinose are abundant sugars in biomass with xylose accounting for approximately 16-20% in soft and hard woods and L-arabinose accounting for approximately 25% in corn fiber. Accordingly, in one embodiment of the invention genetically-modified cellulolytic microorganisms are provided with the ability to metabolize pentose sugars, such as xylose and arabinose, thereby to enhance their use as biocatalysts for fermentation in the biomass-to-acetic acid or lactic acid or ethanol industries. Therefore, in one embodiment, the host cell is a *Clostridium thermocellum* strain. In another embodiment, the host cell is a *Clostridium thermocellum* strain selected from the group consisting of DSM 1313, DSM 1237 and DSM 2360.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention, the thermotolerant host cell can ferment xylose to ethanol and other products at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C. about 40° C. to 60° C., about 40° C. to 55° C. or about 40° C. to 50° C. In some embodiments of the present invention, the thermotolerant host cell can ferment xylose to ethanol and other products at temperatures from about 30° C. to 60° C., about 30° C. to 55° C., about 30° C. to 50° C., about 40° C. to 60° C., about 40° C. to 55° C. or about 40° C. to 50° C.

Figure 2:
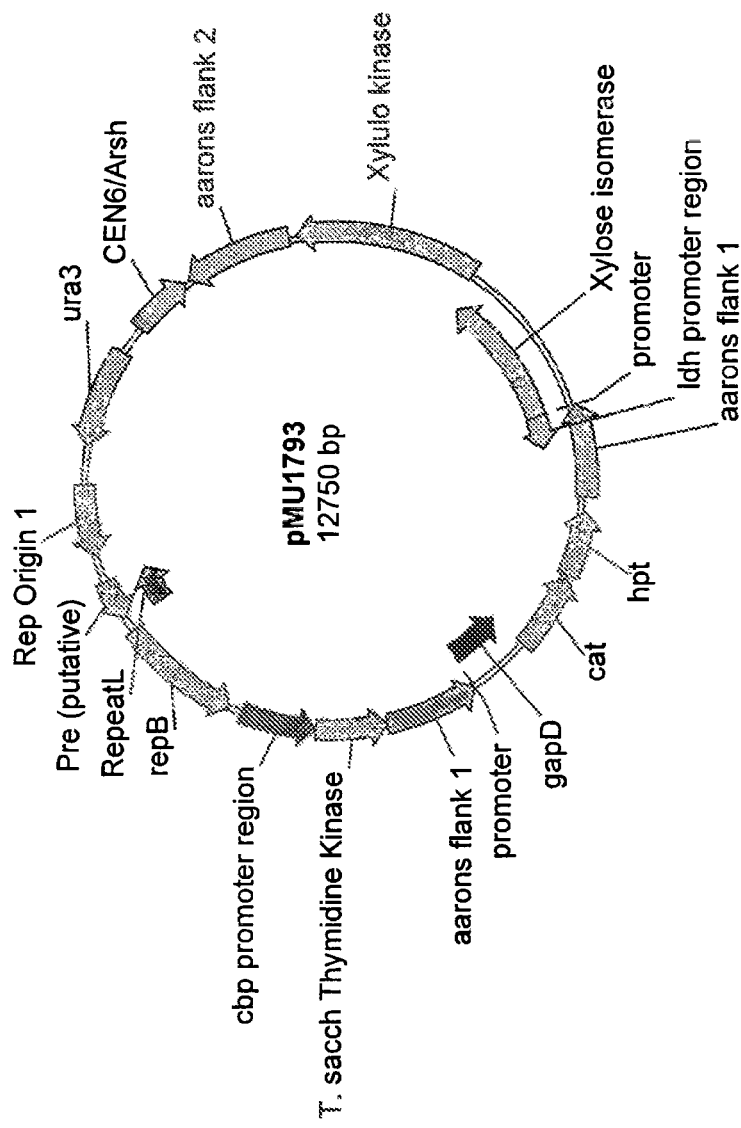
FIG. 2 depicts plasmid pMU1793 which was designed and built in order to integrate the XI/XK operon in the chromosome of *C. thermocellum* containing a deletion of the hypoxanthine phosphoribosyl transferase (HPT) gene.

The present invention provides cellulolytic microorganisms expressing enzymes that allow the microorganisms to ferment xylose. When genes encoding enzymes involved in the metabolic pathway of lactate or acetate, including, for example, xylose, arabinose, and/or xylan, are introduced into a microorganism that lacks one or more of these genes, for example, *C. thermocellum*, one may select transformed strains for growth on xylose or growth on arabinose or growth on xylan. *C. thermocellum* may lack one or more known genes or enzymes in the xylose to ethanol pathway and/or the arabinose utilization pathway. FIG. 2 depicts two key enzymes that are missing in the xylose to ethanol pathway in *C. thermocellum*. *C. thermocellum* is unable to metabolize xylulose which could reflect the absence of genes for xylose isomerase (referred to in FIG. 2 as "XI" or 5.3.1.5), which converts xylose to xylulose, and xylulokinase (also referred to in FIG. 2 as "XK" or 2.7.1.1), which converts xylulose to xylulose-5-phosphate.

In one embodiment, host cells are genetically engineered (transduced or transformed or transfected) with the polynucleotides encoding xylose metabolizing enzymes of this invention which are described in more detail below. In another embodiment, host cells are genetically engineered with the polynucleotides encoding xylanases of this invention The polynucleotides encoding xylose metabolizing enzymes or xylanases can be introduced to the host cell on a vector, which may be, for example, a cloning vector or an expression vector comprising a sequence encoding a heterologous xylose metabolizing enzyme. The host cells can comprise polynucleotides of the invention as integrated copies or plasmid copies.

In certain aspects, the present invention relates to host cells containing the polynucleotide constructs described below. The host cells of the present invention can express one or more heterologous polypeptides expressing xylose metabolizing enzymes. In another embodiment, the host cells of the present invention can express one or more heterologous polypeptides expressing xylanases. In some embodiments, the host cell comprises a combination of polynucleotides that encode heterologous xylose metabolizing enzymes or fragments, variants or derivatives thereof. In other embodiments, the host cell comprises a combination of polynucleotides that encode heterologous xylanases or fragments, variants or derivatives thereof. The host cell can, for example, comprise multiple copies of the same nucleic acid sequence, for example, to increase expression levels, or the host cell can comprise a combination of unique polynucleotides. In other embodiments, the host cell comprises a single polynucleotide that encodes a heterologous xylose metabolizing enzyme or a fragment, variant or derivative thereof. In yet other embodiments, the host cell comprises a single polynucleotide that encodes a heterologous xylanase or a fragment, variant or derivative thereof. In particular, such host cells expressing a single heterologous xylose metabolizing enzyme or a heterologous xylanase can be used in co-culture with other host cells of the invention comprising a polynucleotide that encodes at least one other heterologous xylose metabolizing enzyme or a heterologous xylanase or fragment, variant or derivative thereof. As used herein, "co-culture" refers to growing two different strains or species of host cells together in the same vessel.

Introduction of a polynucleotide encoding a heterologous xylose metabolizing enzyme or a heterologous xylanase into a host cell can be done by methods known in the art. Introduction of polynucleotides encoding heterologous xylose metabolizing enzymes or heterologous xylanases into, for example yeast host cells, can be effected by lithium acetate transformation, spheroplast transformation, or transformation by electroporation, as described in Current Protocols in Molecular Biology, 13.7.1-13.7.10. Introduction of the construct in other host cells can be effected by calcium phosphate transfection, DEAE-Dextran mediated transfection, or electroporation. (Davis, L., et al., Basic Methods in Molecular Biology, (1986)). However, as mentioned above, several species of *Clostridium*, including *Clostridium thermocellum*, are difficult to transform with heterologous polynucleotides. An example of transformation of *Clostridium thermocellum* is disclosed in International Publication No. WO 2010/056450.

In certain embodiments, xylose metabolizing gene donors may include microorganisms that confer to the host cell the ability to metabolize hexose and pentose sugars. In other embodiments, xylanase gene donors may include microorganisms that confer to the host cell the ability to metabolize xylan. In some embodiments, the xylose metabolizing gene donors are *Thermoanaerobacterium saccharolyticum*, *C. cellulolyticum*, *Caldicellulosiruptor kristjanssonii*, *C. phytofgrmentans*, and *C. stercorarium*.

In one embodiment, the donors of the xylose metabolizing genes are bacterial species, including, but not limited to, *Clostridium cellulolyticum*, *Thermoanaerobacterium saccharolyticum*, *C. stercorarium*, *Caldiscellulosiruptor kristjanssonii*, and *C. phytokirmentans*. These strains are good utilizers of xylose. In one embodiment, *Thermoanaerobacterium saccharolyticum* is the donor of the xylose metabolizing genes.

Accordingly, in one aspect of the invention, one or more microorganism strains are modified so as to optimize sugar utilization capability by, for example, introducing genes for one or more enzymes required for the production of ethanol from biomass-derived pentoses, e.g., D-xylose or L-arabinose metabolism. Promoters, including the native promoters of *C. thermocellum* such as triose phosphate isomerase (TPI), GAPDH, and LDH, can be used to express these genes. Once the gene has been cloned, codon optimization can be performed before expression. Cassettes containing, for example, the native promoter, one or more xylanolytic genes and a selectable marker can then be used to transform *C. thermocellum* and select for xylose growth on medium containing xylose as the sole carbohydrate source.

In certain other embodiments, the host cells of the present invention relate to genetically modified *Clostridium* organisms, wherein a gene or a particular polynucleotide sequence is partially, substantially, or completely deleted, silenced, inactivated, or down-regulated, which gene or polynucleotide sequence encodes for an enzyme that confers upon the organism the ability to produce organic acids as fermentation products, thereby increasing the ability of the organism to produce lactate or acetate as the major fermentation product.

The gene that confers upon the organism an ability to produce acetic acid as a fermentation product may code for expression of acetate kinase (ACK), phosphotransacetylase (PTA), pyruvate formate lyase (PFL), and/or aldehyde or alcohol dehydrogenase (ADH). The deletion or suppression of the gene(s) or particular polynucleotide sequence(s) that encode for expression of ACK, PTA, PFL, and/or ADH diminishes or eliminates the reaction scheme in the overall glycolytic pathway whereby pyruvate is converted to acetyl CoA and acetyl CoA is converted to acetic acid or ethanol. In certain embodiments, the above-mentioned genes can be disrupted, or partially or fully deleted individually or in concert in the host cell. In one embodiment, the PTA gene is deleted from the host cell. In one aspect, the deletion of the PTA gene results in the host cell fermenting xylose to ethanol as the major end product. In one aspect, the deletion of the PTA gene results in the host cell fermenting xylose to ethanol as the end product, with the virtual elimination of one or more undesirable end products (e.g. end products other than ethanol or carbon dioxide). In another aspect, the deletion of the PTA gene results in the host cell fermenting xylose to ethanol as the end product and producing no undesirable end product. In another embodiment, no, or significantly no lactate or acetate, or both, is produced.

In one embodiment, the host cell of the invention further comprises a deletion of one or more endogenous genes. In one aspect, the deletion of the one or more endogenous gene facilitates the genetic selections of the integration of one or more polynucleotides of the invention into the genome of the host cell. In certain embodiments, the one or more endogenous genes to be deleted may be selected from, but are not limited to, the hypoxanthine phosphoribosyl transferase (HPT) gene and the adenine phosphoribosyl transferase (APT) gene. In one embodiment, the endogenous gene to be deleted is the hypoxanthine phosphoribosyl transferase (HPT) gene. HPT is a transferase enzyme, which catalyzes the conversion of hypoxanthine to ionosine. The enzyme plays a central role in the generation of purine nucleotides through the purine salvage pathway.

The transformed host cells or cell cultures, as described above, can be examined for protein content of xylose metabolizing enzymes comprising a xylose isomerase, xylulokinase, xylose reductase, xylose dehydrogenase, xylitol dehydrogenase, xylonate dehydratase, a transketolase, and a transaldolase protein. These proteins can be recovered and purified from recombinant yeast cell cultures by methods including spheroplast preparation and lysis, cell disruption using glass beads, and cell disruption using liquid nitrogen for example. Additional protein purification methods include ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method or the protein assay method according to BioRad's manufacturer's protocol. Using such methods, the protein content of the xylose metabolizing enzymes can be estimated. Additionally, to accurately measure protein concentration, a heterologous xylose metabolizing enzyme can be expressed with a tag, for example a His-tag or HA-tag and purified by standard methods using, for example, antibodies against the tag or a standard nickel resin purification technique or similar approach.

The transformed host cells or cell cultures, as described above, can be further analyzed for hydrolysis of xylose, for a particular type of xylose metabolizing enzyme activity (e.g., by measuring the individual xylose isomerase, xylulokinase, xylose reductase, xylose dehydrogenase, xylitol dehydrogenase, xylonate dehydratase, transketolase, and transaldolase activity) or for total xylose metabolizing enzyme activity. The transformed host cells or cell cultures, can also be analyzed for hydrolysis of xylan, for a particular type of xylanase enzyme activity or for total xylanase enzyme activity.

One aspect of the invention is related to the efficient production of one or more xylose metabolizing enzymes to aid in the digestion of xylose and generation of products such as ethanol. Another aspect of the invention is related to the efficient production of one or more xylanase enzymes to aid in the digestion of xylan and generation of products such as ethanol.

In additional embodiments, the transformed host cells or cell cultures are assayed for ethanol production. Ethanol production can be measured by techniques known to one of ordinary skill in the art, e.g., by a standard HPLC refractive index method.

Heterologous Xylose Metabolizing Enzymes

In one embodiment, the host cells of the invention express one or more heterologous saccharolytic enzymes. In one aspect, the host cells express one or more heterologous cellulolytic enzymes. In another aspect, the host cells express one or more heterologous amylolytic enzymes. In one aspect, the host cells express one or more heterologous pentose sugar hydrolyzing enzymes. In another aspect, the host cells express one or more heterologous xylanases.

Complex biomass feedstocks contain varying amounts of starch, lignocellulosic material, and hexose and pentose sugars. Accordingly, in one embodiment, the host cells of the present invention are constructed to express different saccharolytic enzymes at different levels. In one embodiment, a host cell expresses one or more cellulolytic enzymes at a higher level than one or more amylolytic enzymes and one or more pentose sugar hydrolyzing enzymes. In another embodiment, the host cell expresses one or more amylolytic enzymes at a higher level than one or more cellulolytic enzymes and one or more pentose sugar hydrolyzing enzymes. In yet another embodiment, the host cell expresses one or more pentose sugar hydrolyzing enzymes at a higher level than one or more cellulolytic enzymes and one or more amylolytic enzymes.

In one embodiment, the one or more heterologous pentose sugar hydrolyzing enzymes expressed in a host cell comprise one or more xylose metabolizing enzymes. According to one aspect of the present invention, the expression of heterologous xylose metabolizing enzymes in a host cell can be used advantageously to produce products such as ethanol from the xylose portion of biomass sources. Xylose metabolizing enzymes from a variety of sources can be heterologously expressed to successfully increase efficiency of ethanol production, for example. The xylose metabolizing enzymes can be from fungi, bacteria, plant, protozoan or termite sources. In some embodiments, the xylose metabolizing enzyme is a *Thermnnoanaerobacterium saccharolyticum, H. grisea, T. aurantiacus, T. ernersonii, T. reesei, C. lacteus, C. formosanus, N. takasagoensis, C. acinaciformis, M. darwinensis, N. walkeri, S. fibuligera, C. hlckowense R.* speratus, Thermobfida fusca, Clostridium cellulolyticum, Clostridum josui, Bacillus pumilis, Cellulomonas fimi, Saccharophagus degradans, Piromyces equii, Neocallimastix patricarum or Arabidopsis thaliana xylose metabolizing enzyme. In one embodiment, the xylose metabolizing enzyme is a Thermoanaerobacteriumn saccharolyticum xylose metabolizing enzyme. In some embodiments, the xylose metabolizing enzyme of the invention is any xylose metabolizing enzyme known in the art. In a specific embodiment, the xylose metabolizing enzyme of the invention is an enzyme disclosed in Table 7 produced herein. In some embodiments, the xylose metabolizing enzyme is encoded by a nucleic acid sequence at least about 80%, at least about 85%, at least about 90%, at least about 95%, at least about 96%, at least about 97%, at least about 98%, at least about 99%, or 100% identical to any one of SEQ ID NOs: 1-2. In some embodiments, the xylose metabolizing enzyme has an amino acid sequence that is at least about 80%, at least about 85%, at least about 90%, at least about 95%, at least about 96%, at least about 97%, at least about 98%, at least about 99%, or 100% identical to any one of SEQ ID NOs: 3-4. In some embodiments, the xylose metabolizing enzyme of the invention is any xylose metabolizing enzyme suitable for expression in an appropriate host cell.

In some embodiments of the invention, multiple xylose metabolizing enzymes from a single organism are co-expressed in the same host cell. In some embodiments of the invention, multiple xylose metabolizing enzymes from different organisms are co-expressed in the same host cell. In particular, xylose metabolizing enzymes from two, three, four, five, six, seven, eight, nine or more organisms can be co-expressed in the same host cell. Similarly, the invention can encompass co-cultures of microorganism strains, wherein the microorganism strains express different xylose metabolizing enzymes. Co-cultures can include microorganism strains expressing heterologous xylose metabolizing enzymes from the same organism or from different organisms. Co-cultures can include microorganism strains expressing xylose metabolizing enzymes from two, three, four, five, six, seven, eight, nine or more microorganisms.

In some embodiments of the invention, multiple xylanases from a single organism are co-expressed in the same host cell. In some embodiments of the invention, multiple xylanases from different organisms are co-expressed in the same host cell. In particular, xylanases from two, three, four, five, six, seven, eight, nine or more organisms can be co-expressed in the same host cell. Similarly, the invention can encompass co-cultures of microorganism strains, wherein the microorganism strains express different xylanases. Co-cultures can include microorganism strains expressing heterologous xylanases from the same organism or from different organisms. Co-cultures can include microorganism strains expressing xylanases from two, three, four, five, six, seven, eight, nine or more microorganisms. In one embodiment, the xylanase may be of microbial origin, such as of fungal origin (e.g., Trichoderma, Meripilus, Humicola, Aspergillus, Fusarium) or from a bacterium (e.g., Bacillus). In another embodiment, the xylanase is derived from a filamentous fungus, for example from a strain of Aspergillus, such as Aspergillus aculeatus; or a strain of Humicola, such as Humicola lanuginosa. In certain embodiments, the xylanase may be an endo-1,4-beta-xylanase, or an endo-1, 4-beta-xylanase of GH10 or GH11. Examples of commercial xylanases include SHEARZYME™ and BIOFEED WHEAT™ from Novozymes A/S, Denmark. Tables 2 and 3 below list the xylanases expressed in Thermoanaerobacterium saccharolyticum, and the sources of the xylanases.

TABLE 2

DNA sequences of xylanase genes expressed in *Thermoanaerobacterium saccharolyticum*

| Organism | Sequence |
|---|---|
| *Clostridium phytofermentans* | atgctacaaaaaatgaacggaaaggttaaaaagattcttggaattagtatcgcatttcttatgttgatcatggtaat tccaacatcaatcgcaaaagcagcaaccaataagacctatgattttaattcgatgacttatcaatccacatggggag ttacatattctatcagtaatggatcaggaacatttaatttcactggtcaataccgtgaaattaagttcaatcttccg gaaacgctagatatgtctcaatgtactagtgtaacattcaatgcttccagtccaaatggacagattgcatttaagct ttacgatacttctggaaatcaggtggctgtagtgtataactttaattccaatacctcagactgtaccttcgcaccaa atagtacggcaaaggtaaacagtattggaataatggcgcaagggacaaataactactcagcagttgtgaatcgagtt acatttacaatgacaggagggtcttctggcactggttcttcaactttattaaacacttatgggaaatatattaaaaaa ctctggaactgctgttaatttaagtcagctgcaaaattcaaatacactaagtgtgattaagacgcaatataatagta tcacattagagaatgaaatgaagccagatgcagttcttggaagttcatcaacattaatgactgttgctcaagcaaaa tcgaatggttattatattccttctagctacacggaaagtacagttccaactcttaaatttagtaccatcgatgcagt tctacagatttgctacaataacgggctaaagcttagaggacatacattagtatggcattcccaaacaccggattggt tctttagaacaggttatagttctagtggatcgtatgttagccaagctgttatggatgcaagaatggaaatgtttatt aggtcttatatgagtcatatttataatggaagctatggaagtgtagtatatgcttgggatgttgtaaatgagtattt gcatgcttctacctctggatggtctcaagtttatggatccaaccttggtaccacaccatcttatgtaaagaaagctt tccagtatgcgtatgattgtcttagcagttttggattaacgaattcagtaaaattgttttataatgattacaacaca tatgaggttacagatcagatcctatcattagtaaattttattaactctggtacgaaactttgcgctggtgttggaat gcagtctcacttaaatacctcctatccttctgtatcggcatataaaacagctatgcagaagttcttgaatgcaggat atgaagtacaggttactgaacttgatgttacgaatacatcagcttccacacaagctacttatgtatatgatttgatg actgctattctttctctaaagaaagcaggtgggaatatcactggtattacatggtgggactatatgatagcgtatc ttggcgtgcctcccaaaatccttgttattcagtaatttaactactccaaaagaatcttataataaagcgttacaag catttacagatgcaggatat |
| *Clostridium phytofermentans* | atgttttcaagaaactagttgcactcgcaatggctgttgccattgtcattccaatgaacgttaataacatacaaaa ggttgaggcggaatctacaaatgaagcagtagtatatggtaatctaatttatcacgactttgaagcaagcaccaatg ggtggggaccaagaggtgacaatgcagaggttgtggcacaaagtacagaagaggcatattcagggttacatagttta aaaattagcaaacgcacgcaaacatggcatggtgctacctgcgatttgacaaaggaacttacgattggagaaactta tgtatttggaatttatttaaaatataaaggtagctcttattccaatacacaaaagtttagcttacaatttcagtaca atgatggtgtgaatgatcagtacaaaacaattaagactttagaagtaaccaaagataaatggacattaattcaaggt gagtatacagttccagcagatgccgctaatgcaaaggtctatgtcgaaacagaatataagagttcaccatcaagtca agatctcttagacttttacattgatgatttcactgcaacgccagcaactttaccacagattcaaaaagatattccta gtttaaaggatgtattttcaagttacttctttgttggtggagcggcaactgcaggtgagattgcaccagctccggca aaagatttagtagcgaaacattacaataggttaactcctggtaatgagttaaaaccagactctgtattagattactc tgcaaccatagcctatatggatgcaaatggtggtaatcaagtgaatcctcaggtgaatcttagagctgcgaaaactt |

TABLE 2-continued

DNA sequences of xylanase genes expressed in *Thermoanaerobacterium saccharolyticum*

| Organism | Sequence |
|---|---|
| | tactggaatatgcaagagacaataatataccagtgcgtggacataccttagtatggcatagccagacaccagattgg<br>ttctttaaggtaaactattctcaggattcaaatgcagcgtgggttccaaggaagtgatgctccaaagactagaaaa<br>ctacatcaaaaatgtgatgcagctgatctcatcaacctatcctacagtaaagttctatgcttgggatgtggtgaatg<br>aagcagtagatccaaatacttctacaggtatgagaaatcctggatcgaataacgtaacatctggtaattctccatgg<br>atgcaaaccataggtgaggaatatattcaaagagcttttgaatacgcaagaaaatatgctccaactggttgtaaact<br>gttttataatgattataacgagtatgaggatagaaagagtaccttatctttaatatcctgaaaggattaaaagata<br>agggcttagtggatggtatgggaatgcagtctcattgggttatggattatccaagtattagtatgtttgagacagct<br>gttcgtaaatataatactttaggattagaattacaactaacgagttagatataaagcagccagacaatagtacatc<br>tgctttagctgctcaggcagacagatataaacttttgataaataaggtcattagtttgaaaaaagagggcatgaaca<br>ttacaggagttatcttctggggtgtaacggataagactagttggttaggtggatatccattattatttgatggaaat<br>tatcaagcaaagtcagcatactattctatcattgatgggattaccccaacagtaacgccatcaataactccaactgt<br>aacaccaaaaccaacgataacacctacagtaacaccaactgtaacgccaaaaccaacgataacacctacagtaacac<br>caactgtaacaccaaagccaacaataactcctaccataacaaccaacagtaacgccaaaaccaacaatagctccgaca<br>ccaactcctactacagtaccagtggagggagcaaaaccggtggtagtagtaactacgaaaaacaatgggaacacgat<br>aagccagcaatacacaataaatgcacttggtggaacgattgatttgtcaaaggtatctattgagtttactgccgatg<br>gaatcatcaatcaagagcataatgtttgggtagataacgctgcgttgcaattaacagttgaaccatattcacaccg<br>ttaaatggttatgtttctgggcagttgacgaatcaaaaacttgtggttagcatcagtaagagtacgatgctgtcaga<br>aggaacaggaaagcttgttcttgatttgctaagaaggattggacggattttggtacgatatccaatgaag<br>tgttaaaggtttactataatggagtcaaagttcaa |
| *Clostridium phytofermentans* | atgtttaaattaaataagaaagtttttgcattagtttctgtaattgcattaggttttttctagcttatttacatcaac<br>tgctcatgcagcaactgattactggcagaattggactgatgggtggaacagtgaacgctaccaatggttctggtggt<br>aactacagtgttaactgggacgaattgtggtaattttgttgtaggtaaaggttgggtactggaaatgcatcaagagt<br>tgtaaattacaatgctggtgtattttcaccatctggtaatggttatttaacttctctatggttggacgagaaattcac<br>tcattgaatattatgttgttgatagttggggtacttatagaccaactggaacttttaaagggtacagttttctagcgat<br>ggtggaacatatgatatttatacaagtacgagaactaatgcaccttccatcgatggtactcagactttccaacaata<br>ctgagtgttagacagtctaagagagctaccgaagtaacgtagcaattactttttagtaaccatgttaatgcttgga<br>agagtaaaggaatgaacttaggaagcagctgggcttatcaagcattatgcgtagaaggatatcaaagcagtggtagt<br>gctaatgtaacggtttgg |
| *Clostridium phytofermentans* | atgggtaaaaaagtaatagctttattaacatgtgttatgctttcgcttacgctgattccgggtatcggcataaaga<br>gcactgcacaagccgctgaaaccaacatctataaagtagattggagcaaatttaatgagggtgacaaaatcagcgg<br>tcccatggagggtttaggtagatcaggcggagcagatatcacggttacgggctcctctaccaaatcattttacata<br>cttaatcgtaaagataactgggatgcacttgatattcagaacgatctctttgaagttagatcgagatgcaacctatg<br>aaatcacagttaccggtcatgttgacagcaatgtagatactaagaatgctagtgtcaagcttggcggtgtaacaag<br>gaaaacgggcgaggatgatggataccccagagttcaaaaaagagaaactacaatcgggcaagagttttgtactaacc<br>tatgaacttaaactttctgatcaaattccggacgcttcaagaaatctgtgggtgctccgtgttcagaccgacgaac<br>caagcggaagtagggccggagatctgtaccgttctatggtggatgatatcgtgattattcaaacaaaggcatccac<br>tgctcctgtagctgtgactggtgacctatgtcacttttacgaacttaatgcggacaaaactctcaaggttggagaa<br>tcattatcaagtccagctctgaaagtttctggtaatgctaagatagttgttgtagaaggcaccgatggtaccgtgt<br>cattacaactgaaagaccgtgttaataattatgacggtgtagacatccttcgtgatgcactgaaaataaacgataa<br>atttatgtctggtacatacacgattgaggtaaaaggccatggatggttctgatttaagtaaatcccagttt<br>gttatgggtatgaccgaatctccatggggcgaactcacttcaagagtgacgccaagtagtgacggtagctttgtaa<br>taacttataccaaagcatacaccggaagtgaattgacaggcctaggttatagctaccgagttcagacacctccaag<br>cgttctcacatcgttttatatcgataacattaccgttacggttcagggagctgaagaagaagatgagtcaactgtg<br>gttatacctgaatgggatttaaccttgattccattaagagtcatacgctgattacttcatgataggtaatatta<br>atggaaccaggtcagtacaggatacagaaaccaccgaaatgtttaagcatcattataatgttgttaccgcagaaaa<br>tgccatgaaaccagggaatatttccaaggtaaaaggcgaatacaattttgacaatgctgataagcttgttacgtgg<br>gctaaagaaaatggtttaaaagtccacggtcatactttagtttggcactctcagtcagctccatggttgactacaa<br>catgcggatggaacaccttaacacgtgcagaagcaagagctaatatggaagattatattaagaacgttgcaggaca<br>ttacgcagggaaggtgatttcatgggatgtattaaatgaagcattttttgccaggtgtatccgaaatccctgctggc<br>tggagggatgtattacgcaaatttgaagataacggaaatggttctccttggtatcaagcctatgaaaacggtgctg<br>ataagagcaagggcgaggatggctctgattatatctatgacgctttcgtgtttacacgtcttgccgctcctgatgc<br>agtgctgtattataacgacttcaatgagacagaggcaggtaagtgtgaagcgatcgccttgatggtggaagaatta<br>aacacaaagtggaagaccgataaacggaacactgagcctgacagattgctcatcgaaggaatcggaatgcaggcac<br>attattggaccggagatttaaaggttttccactgtagaagctagcatcaagcgtttcataaaaacaggtgctaagat<br>cagtttatctgagctggatgttcctcatggcgattacatgacctacaagcaacgtactgactctcctacaaaggaa<br>gaagagaaacttcaggcggattttatacaagcagttgtttgaagtatacaaaaaatatgcggacaacatcgaacgtg<br>tcacctctggggtaaaacagatcctcaaagctggcgtttcaaaggttatccattacttgttgataaaaattttgct<br>ccaaaggacgcattctttgctgtaattgatgtagcaaaggaaaaggtagcagaggaaaaggctgttgaaaccatac<br>ctggtaaagatatcccgaaaacaggggaagacagcagtaagcaaatgattttgactgcagtagctattctgattat<br>attggtattcgtaccagttacgatcttaacaaaacgaagagagaagaatataaagaatata |
| *Thermobifida fusca* | atgggtctccccgtctccgtccacaggagtgacacaaaaaaatgagggtgggccgatacatcgccatcacgg<br>ttggggcctccgcgctgctcgtctccggggtggcgccggcggcggcgggtaccgctgccgacgtccgggacg<br>gccgccgcgcggcgtcgcaggccgggcacgatcagaagcaggtaccgctccgcaaggtggcgccgaagggc<br>cttgcgatcggcgtggccgtcgcgggtggtggccaccatcgtgaccaggagtaccccgaccccttccaagtac<br>gacgaggagtaccggggggtgctcgccaagcacttcaactcggtcactcccgagaaccacttgaagtgggac<br>ttcgtgcacccggagcggaaaagtacaacttcgggcctgctgaccagatcgtcaagtttgcccagagcaac<br>gggcagaaggcgcgcggccacacgctggtctggcacagccagaaccccgactggctcaccaaggggaagttc<br>agcaagaaggagctccgcaagatcctcaaggagcacatcatcacggtggtgggccgctaccggggcaagatc<br>caccagtgggacgtggccaacgagatcttcgacgacaacggtaagctccgcacgaacgagaacatggctgaa<br>gaacttcgggccggagatcatcgccgacgcgttccgctgggccccaccaggccgacccgaaggcgaagctgtt<br>cctcaacgactacggcgccgagggcatcaacaagcgcagcgacgcctacctcaagttcatgaaggagctgcg<br>caagaagggcgtgccggtacacggcttcggcgtgcaggggcacctgagcctggcctacccgttcccgggcga<br>catggcgaagaacctcagcggttctcggacgccgggttcgaggtcgccggtcaccgaggtcgacgtgcgcat |

TABLE 2-continued

DNA sequences of xylanase genes expressed in *Thermoanaerobacterium saccharolyticum*

| Organism | Sequence |
|---|---|
| | cccgctcaacggcggcgacgccactgaagcccagctcaagacccaggccgactactaccgccgcgccctgga |
| | ggcctgcctgagcgtcaagagctgcaactccttcaccctctggggcaccacgaacaagtactcgtgggtgcc |
| | ggtgttcttcccggacgagggcgaggcgacgatcttctgggacgacttctcccccaagcccgcgtacaccgc |
| | cctgcaggaggccctggcgaaggcccgccgccgc |
| *Thermobifida fusca* | atgaaccatgcccccgccagtctgaagagccggagacgcttccggcccagactgctcatcggcaaggcgttcg |
| | ccgcggcactcgtcgcggtcgtcacgatgatccccagtactgccgcccacgcggccgtgacctccaacgagac |
| | cgggtaccacgacgggtacttctactcgttctggaccgacgcgcccggaacggtctccatggagctgggccct |
| | ggcggaaactacagcacctcctggcggaacaccgggaacttcgtcgccggtaagggatgggccaccggtggcc |
| | gccggaccgtgacctactccgccagcttcaacccgtcgggtaacgcctacctgaccctctacgggtggacgcg |
| | gaacccgctcgtggagtactacatcgtcgaaagctggggcaccaccggccaccggtacctacatgggcacg |
| | gtgaccaccgacggtggtacctacgacatctacaagaccacgcggtacaacgcgccctccatcgaaggcaccc |
| | ggaccttcgaccagtactggagcgtccgccagtccaagcggaccagccggtaccatcaccgcggggaaccactt |
| | cgacgcgtgggcccgccacggtatgcacctcggaacccacgactacatgatcatggcgaccgagggctaccag |
| | agcagcggatcctccattcgtgacgttgggcaccagcggcggtgacaaccccggtgggggcaaccccccggt |
| | ggcggcaaccccccggtggcggtggctgcacggcgacgctgtccgcgggccagcagtggaacgaccgctaca |
| | acctcaacgtcagcggctccaacaactggaccgtgaacgttccgtggccggcgaggatcat |
| | cgccacctggaacatccacgccagctaccccggactcccagaccttggttgcccggcctaacggcaacgcaac |
| | aactggggcatgacgatcatgcacaacggcaactggacgtggcccacggtgtcctgcagcgccaac |
| *Clostridium stercorarium* | atgaagcgtaaggttaagaagatggcagctatggcaacgagtataattatggctatcatgatcatcctacatag |
| | tataccagtactcgccgggcgaataatttacgacaatgagacaggcacacatggaggctacgactatgagctct |
| | ggaaagactacgaaatacgattatggaacttaacgacggtggtacttttagttgtcaatggagtaatatcggt |
| | aatgcactatttagaaaaggagaaaatttaattccgacaaaacctatcaagaattaggagatatagtagttga |
| | atatggctgtgattacaatccaaacggaaattcctatttgtgtgtttacggttggacaagaaatccactggttg |
| | aattacattgtagaaagctggggcagctggcgtccacctggagcaacacccaaaggaaccatcacagtggat |
| | aggcggtacttatgaatatatgaaactacccgggtaaatcagccttccatcgatgaactgcgacattccaaca |
| | catattggagtgttcgtaatccaagagaacaagcggaacaatatcgtcactgaacattttaaacagtgggaaa |
| | gaatgggcatgcgaatgggtaagatgtatgaagttgctcttaccgttgaaggttatcagagcagtgggtacgct |
| | aatgtatacaagaatgaaatcagaataggtgcaaatcccaatcctgcccatctcaaagcccaattagaagaga |
| | tgcattttcaataatcgaagcggaagaatataacagcacaaattcctccactttacaagtgattggaacgccaa |
| | tataatggcagaggaattggttatatgaaaatggtaataccgtaacttacagcaatatagatttggtagtggt |
| | ggcaacaggggttctctgcaactgttgcaacgaggttaatacctcaattcaaatccgttctgacagtcctaccgg |
| | aactctacttggtaccttatatgtaagttctaccggcagctggaatacatatcaaaccgtatctacaaacatca |
| | gcaaaattaccgcgttcatgatattgtattggtattctcaggtccagtcaatgtggacaacttcatatttagc |
| | agaagttcaccagtgcctgcacctggtgataacacaagagacgcatattctatcattcaggccgaggattatga |
| | cagcagttatggccccaaccttcaaatctttagcttaccaggcggtggcagcgccattggctatattgaaaatg |
| | gttattccactacctataataacgttaatttcgccaagagttctataacagcaagagttgccactcag |
| | atctcaacttccattcaggtgagagcaggaggagcaaccggtactttactgtgcatgatattccccttgtcttt |
| | tcaggaccagtgaatgtggactacttcgtatttacaccagcaaatgtaaattcagggcctacctcccctgtcgg |
| | aggtacaagaagtgcattttccaatattcaagccgaagattatgacagcagttatggtcccaaccttcaaatct |
| | ttagcttaccaggtggtggcagcgccattggctatattgaaaatggttattccactacctataaaaatattgat |
| | tttggtgacggcgcaacgtccgtaacagcaagagtagctacccagaatgctactaccattcaggtaagattggg |
| | aagtccatcgggtacattacttggaacaatttacgtgggtccacaggaagctttgatacttataggatgtat |
| | ccgctaccattagtaatactgcgggtgtaaaagatattgttcttgtattctcaggtcctgttaatgttgactgg |
| | tttgtattctcaaaattcaggaacttaagggtatag |
| *Clostridium stercorarium* | atgaataaatttcttaaacaaaaaatggagcttaattttaaccatggaggtattttttctgatggcgactttatcat |
| | tgattttgcaacggggaaaaaggcctttaacgatcaaacttctgctgaagacatcccatcgcttgctgaggcttt |
| | cagagactattttccgattggagcggccattggcctgggtgcctcactcagccgacggaaggtaattttcagtggg |
| | cacgtgaacatgctcgtggcggaaaatgcaatgaaaccgcgtcacttcagccgacggaaggtaattttcagtggg |
| | cagacgctgacgaattgtgcagtttgcgaaagaaaacggtatggaactgcgcttccacactcttgtgtggcataa |
| | tcagacgccgactggtttttccttggataaagaaggaaaaccaatggtggaggagactgatccacagaagcgtgaa |
| | gaaaacaggaaacttctgctgcaacggcttgagaattatattcgtgctgtggttttacgctacaaagacgacataa |
| | agtcatgggatgtggtgaatgaggtaattgaacccaatgatcccggcggtatgagaaacagtccttggtatcagat |
| | taccggtaccgagtacatcgaagtggcattccgtgcgcaagggaagcgggaggatccgatattaagctttatatc |
| | aacgattacaatacagatgaccctgtcaagagagatatactgtatgaattagtgaaaatttgctggagaagggtg |
| | tgccgattgacggggtgggacatcagacacatattgatatttacaatccgcctgtcgagcgaataatagagtctat |
| | aaaaaaatttgccggactgggactggacaacataattaccgaactggacatggcatattcatggaatgaccgc |
| | agcgattacgcgatagtataccccgattatatcctgactttacaggccaaacgttatcaggaactgtttgatgcgt |
| | taaaggaaataaggacattgtaagcgcagtggtgtttggggcatttcggacaaatattcctggttgaacgggtt |
| | tcctgtaaaacgtaccaatgccccgctgctgttcgacagaaatttcatgccgaaaccagctttctgggcgatagtt |
| | gatccttcacggttgcgggaataa |
| *Clostridium stercorarium* | atgaatgccgtaatgggggtaaaagacctatagcgagcctgcttgtgctcacacttgcatttttaucauccgg |
| | taacgaaggcagaaacaacgggtttatcatgagacttttgccgaaggaaagggagcggcggtacagtcaggcggg |
| | gcgaccattacgcacgttaccggaaaattttttgacggcaacgggacggagcggcactgtacatatccaacag |
| | agtgaacaactgggacgctgcagatttcagattcagcgacataggtcttcaggacggaagaatttataaaataa |
| | cggtaaagggatatgtggatcccgatgttcatgtaccggagggttcccagatatggcttcagaccgttaacagc |
| | tatggtggtgggcagtaccgacataaaggccggtgaagcctttactctgacgggctatataaggtggatac |
| | aaccaattgatgctctgaggattcagtccaatgacaccggagcatttgttccgttttatatcggtgaaatat |
| | tgatcaccgaagaaacggttcctcaggatgacagccgaaatggaataaaaactcatgctgagaagttcacaccc |
| | ataaccttttgaggaccaaaccacaggcggatttacaggcagggcaggaaccgaaattcttacggtaaccgatga |
| | ggcaaaccataccgatgcggaagatattcgcttaaagtcgggggaaggaacgacacatggcatggcccggcgt |
| | tgggtgtggaaaaatacgtggatcagggttacgaatataaagtggcggtttatgtcaggctgatttcacctgaa |
| | agtgcacaactgcaactgtcaacgcaaattggtgaaggcacatcggcaagttacgtaaaccttgcgaaaaagaa |

TABLE 2-continued

DNA sequences of xylanase genes expressed in *Thermoanaerobacterium saccharolyticum*

| Organism | Sequence |
|---|---|
| | tgttgcaatcagtgacggctgggttctgctggaaggtacataccgctacgacaatcttggcggagggtacctga<br>caatatatgtggagagccctgacagccctgaggcatcattttatattgacgacatcaactttgaacccacgggc<br>atgaaatctgaagagattgaaaaaggtttaaaatccttgaaggatgtgtataaggataattttctcaccggcac<br>ggcgatatcattgcgtgacctggaaggtgtaaggtttgagcttctgaaaaaacatttcaatgcggtaactgcgg<br>aaaatgcaatgaagccttccgaattgcagcgtgagaagggaaattttaccttttgacggggcagacaggcttgta<br>aacgccgcaataagtgcaggaatgaaagtacacgggcatacgctggtatggcaccagcagaccccccgcgtggat<br>gaatattaagttggatagcggaggaaatattgtatacctcagcagggaagaagcgcttgaaaatatgagaaatc<br>atataagaaccgttattgagcattttggcgacaaggttatatcgtgggatgttgtaaacgaagcaatgagcgac<br>aatccttccaatccttccgactggagaggatcactgcgtaaatcgccttggtattatgccattggcgaagacta<br>cgtggaacaggctttccttgccgcgagagaggtgctggatgaacaccccgaatggggatattaagctttactaca<br>acgattacaaccttgataaccagaacaaagctttggctgtttacaacatggtaagagaacttaacgaaaaatac<br>cagaaaactcatccgggaaaactcccttatcgacggtataggcatgcagggacattattctgtaaatacaaatcc<br>gaagaatgttgaactgtcactgaagcggtttaccgaactgggtgtggaggtcagcataagcgaactggatatcc<br>gtgcgggcagcaauatcagctcaccgagaaagaggcgaatgcccaggcctacctttacgctcagttgttcaaaa<br>ttttccgtgaatattccgacagtattgcacgggttacgttctggggaatggatgacggtacaagctggagggcg<br>gaagaaagcccgctgctgtttgacaggaccctaaaagccaaacctgcgtattacgctgttgcagatccggacga<br>attcattgagaaatataagcctgaaacaatagaagccaaccgggcatatgcggttttacggcacacctgaaattg<br>acggaaaaaccgatgaagtttggaacaaggcacctgagctgaaaattaacaggtaccagaccgcttggcatggc<br>gccgacggcaccgcaagggttcttttacgacgaaaacaacctgtacgttctgatcaaggttaatgacacacagct<br>tgataaaggaagcccaaatccatgggagcaggattcggttgaaatatttatagacgaaaataatgcaaaaacat<br>cattttatgaggaagacgacggccgatacagggttaactttgaaaacgagacatccttttaatccggaaagtata<br>gccggcggttttgaatcggccgcgaagtttcgggaacaaactataccttggaagtgaaaataccgttcaggac<br>cgtgaaacccgtcagcaatatgcaaatcggatttgacgtgcagattaacgacggaaaaaacggagtgcggcaga<br>gcattgcaacatggaatgacccgactggaaatgcatggcaggatacttcggttttcggtattcttactttgaaa<br>tcaaaaaatccggttacccgcggtgaagccattgtaaaaattatgaaggcttatgatatggaaccactggaaaa<br>ctggaacgacaatttctccgatgcttcgggaagctacgcgggatattacccgagagcaaaggaaacgggttttg<br>tcagcggtatcggggacaataagataggtgctgaaattccgcttacccgggaaatgttttttacaatgatttat<br>aatatcgaacgaataacagggaaatgcaggggatagatatttcagacgcggaacttacacttttcagcgatta<br>taacgacttgtcggagtgggccgaagaggcagttaaggcattggttaaatcaggcaggatcaaaattaacggcg<br>atttattgccgaagcggcttatggacgctgaagaagtggaggcattttaagattaagataa |
| *Bacillus subtilis* | atgattccacgcataaaaaaacaatttgtgtactattagtatgtttcactatgctgtcagtcatgttagggccagg<br>cgctactgaagttttggcagcaagtgatgtaacagttaatgtatctgcagagaaacaagtgattcgcggttttggag<br>ggatgaatcatccggcttgggctgggggatcttacagcagctcaaagagaaactgcttttggcaatggacagaaccag<br>ttaggattttcaatcttaagaattcatgtagatgaaaatcgaaataattggtataaagaggtggagactgcaaagag<br>tgccggtcaaacacggagcaatcgttttttgcttctccttggaatcctccaagtgatatggttgagacctttaatcgga<br>atggtgacacatcggctaaacgctgaaatacaacaagtacgcagcatacgcgcagcatcttaacgattttgttacc<br>ttcatgaagaataatggtgtgaatcttacgcgatttcggtccaaaacgagcctgattacgctcacgagtggacgtg<br>gtggacgccgcaagaaatacttcgctttatgagagaaaacgccggctcgatcaatgcccgcgtcattgcgcctgagt<br>cattcaatacttgaagaatttgtcggacccgatcttgaacgatccgcaggctcttgccaatatggatattctcgga<br>actcacctgtacggcacccaggtcagccaattcccttatcctcttttcaaacaaaaaggagcggggaaggaccttg<br>gatgacggaagtatactatccaaacagtgataccaactcggcggatcgatggcctgaggcattggatgtttcacagc<br>atattcacaatgcgatggtagaggggggactttcaagcttatgtatggtggtacatccgaagatcatatgggacctatg<br>aaagaagatggtacgatcagcaaacgcggctacaatatggctcatttctcaaagtttgtgcgtcccggctatgtaag<br>gattgatgcaacgaaaaaccctaatgcgaacgtttacgtgtcagcctataaaggtgacaacaaggtcgttattgttg<br>ccatcaataaaagcaacacaggagtcaaccaaaactttgttttgcagaatggatctgcttcaaacgtatctagatgg<br>atcacgacgcagcagcaatctacaacctggaacgaatctcactgtatcaggcaatcattttgggctcatcttcc<br>agctcaaagcgtgacaacatttgttgtaaatcgt |
| *Bacillus subtilis* | atgaggaaaaagtgtagcgtatgttatggattctagttttattattgagctgcttatctgggaagtctgcgtatg<br>ctgccactagtactacaattgcaaaacatatagggaattcaaatccgcttatcgaccatcatttgggagcggatcc<br>ggttgcgctgacctataacggaagagtctacatctatatgtcaagtcgatgactatgaatataatagcaacggaaca<br>attaaagataattcatttgccaatttgaatagagtattcgtcatatcttcagcggatatggtgaactggacagacc<br>acggagccattccggtagcaggtgccaatggagctaatggaggccgtggaattgcaaatgggcaggtgcgtcatg<br>ggcaccgtcaatcgcagttaaaaaaaattaatggcaaggataaattcttcctttatttcgcaaacagcggcggaggt<br>atcggggttctctcaccgcagacagcccgattggtccatggaccgacccaatcggaaaaccgctcgtaacgccaagta<br>cgccaggaatgtctggtgttgtatggcttttgatccggcagtatttgtagatgacgacggaaccggttacctgtt<br>gccggcggaggcgttcctggcgtttcaaatccaacgcagggacaatgggccaatcctaaaacggctagagtcataa<br>aattggggcctgatatgacgagtgttgtggaagtgcatctacaattgatgcgcctttcatgtttgaagattcggg<br>attgcacaagtataacggaacatattattactcctattgcatcaatttcggcggcacgcaccccggccgataaaccc<br>ccgggtgagatcggctacatgaccagttcaagtcccatgggtcccttttacatatagagggcacttcctgaaaaatc<br>cgggtgcatttttcggaggtggcggaaacaaccatcatgctgttttcaattttaaaaacgagtggtatgtggtgta<br>ccatgcgacaacctgtcagttccgctctgttccggggccggaaaggataccgctctccccatattaataagctggtg<br>cataatgcagattggatctattcaagaggtagcggcaaattatgcaggtgtaacacaaatttccaatttaaacccat<br>ataaccgggtagaagctgaaacgtttgcttggaatggacgcattttgacagagaagttccacagcacccggcgggcc<br>agtaaataatcagcatgtaacaagcattcaaaatggagactggattgctgtaggaaatgcagacttcggagcgggc<br>ggtgccagtcatttaaagcaaatgtaagcatccactttaggcgggaaaatagaagtgcgcctcgacagtgcagacg<br>gtaagcttgttggaactctgaatgtgccttcaacaggcggagcgcaaacgtggagggaaatagaaactgcggtaag<br>cgggcaaccggtgtgcacaaagtattctttgtatttaccggaacaggtacaggaaacttgtttaattttgattac<br>tggcagtttacgcaaaga |
| *Bacillus subtilis* | atgtttaagtttaaaaagaatttcttagttggattatcggcagctttaatgagtattagcttgttttcggcaacc<br>gcctctgcagctagcacagactactggcaaaattggactgatggggcggtatagtaaacgctgtcaatgggtct<br>ggcgggaattacagtgttaattggtctaataccggaaatttgttgttggtaaaggttggactacaggttcgcca<br>tttaggacgataaactataatgccggagtttgggcgccgaatggcaatggatatttaactttatatggttggacg<br>agatcacctctcatagaatattgtagtggattcatgggtacttatagacctactggaacgtataaaggtact |

TABLE 2-continued

DNA sequences of xylanase genes expressed in *Thermoanaerobacterium saccharolyticum*

| Organism | Sequence |
|---|---|
| | gtaaaaagtgatgggggtacatatgacatatatacaactacacgttataacgcaccttccattgatggcgatcgc<br>actacttttacgcagtactggagtgttcgccagtcgaagagaccaaccggaagcaacgctacaatcactttcagc<br>aatcatgtgaacgcatggaagagccatggaatgaatctgggcagtaattgggcttaccaagtcatggcgacagaa<br>ggatatcaaagtagtggaagttctaacgtaacagtgtgg |
| *Bacillus subtilis* | atgaagattaccaatcccgtacttaaaggattcaatcccgatccaagtatttgtagagcaggagaggattattatat<br>cgctgtatctacatttgagtggtttccgggagtccagatacaccactcaaaagatttagtaaattggcacttagttg<br>cacatccattacagagagtttcacaattagacatgaaaggaaacccaaattcaggtggagtttgggccaccatgttta<br>agctatagtgatgggaagttttggctgatctatacggatgttaaggtagtagatggcgcatggaaagattgtcacaa<br>ttatttagttacttgtgaaacgattaatggtgattggagtgagccgattaaattaaatagctcggggtttgatgctt<br>ctttgttccatgatacggatggaaaaaagtatttattaaatatgttatgggatcaccgtattgatcggcactcattt<br>ggaggaattgttatacaggaatattctgataaagagcaaaaattaatcggtaaaccaaaagttatatttgaaggaac<br>tgatagaaaactgacagaagctccgcatcttttatcatatcgggaactattattatttattaactgcagaaggaggaa<br>cacggtacgaacatgctgctacaattgctcgttctgcaaatattgaggggccatatgaagttcatcccgataatcca<br>atttaacgtcatggcatgacccaggaaatccattgcaaaaatgtggtcatgcatccattgttcaaacacatacaga<br>tgagtggtatttagctcatttaacgggacgtcctattcatcctgacgatgattcaatttttcagcagagaggatact<br>gtccttttgggcagagaaacagctattcaaaaactttactggaaagatgaatggcccatatgtagtaggtggaaaagaa<br>ggaagcttggaggtagatgcaccttctatacccgaaacaatatttgaagcaacgtacccggaagttgatgaatttga<br>ggattcaacattaaatataaattttcaaactttaaggattccattcacgaatgaattaggttcattgactcaagcgc<br>caaatcatttacgattattcggtcatgaatcattgacctcgacatttactcaggcatttgtagccagacgctggcaa<br>agtctccattttgaagccgaaactgctgttgagtttatccggaaaattttcaacaagccgctgggttggtgaatta<br>ctacaatacagagaactggacggctcttcaagtcacgcatgatgaagaacttgggcgcattcttgaattaacaatat<br>gtgacaacttttcttttcacagccattaaataataaaattgttattcctcgtgaagtaaagtatgtatatttaaga<br>gtaaatattgaaaaggacaaatattattatttctattcttttaacaaagaagattggcacaaaattgacattgcact<br>ggaatcgaaaaaattatcagatgattatatccgtggggaggattcttcacagggggcctttgtagggatgcaatgcc<br>aagataccagtggtaatcatattccggccgactttagatattttcgttataaagaaaaa |
| *Thermo-<br>anaerobacter-<br>ium<br>saccharolyticum* | atgaagagtattgtaaacagagttgtatctatcgttacagctttaataatgattttttgggacatcactgttttcacaa<br>cacataagggcatttgctgatgacactaatacaaatctggtttctaatggggactttgagacaggcacaattgatggc<br>tggattaagcaaggtaatcctacattagaagtaactactgaacaacaattgggcaatacagtatgaaagttacgggt<br>agaacacagacatatgaaggacctgcatatagctcttttaggaaaaatgcagaaaggtgaatcatataatgtatcgctt<br>aaagttagacttgttctgaacaaaattcatctaatccttttattaccgtgactatgtttagagaagatgacaatggc<br>aagcattatgatacaatagtttggcaaaaacaagtttctgaagattcatggactactgtaagcgggacttatacatta<br>gattatactggacacattaaaaactattaaacaccgatccaacgctggaatactatattgatgat<br>gttgtagtgacaccacaaaatccaatacaagtaggaaatgtgattaccaatggaacttttgaaaatggaaatacttca<br>ggatgggttggaacaggctcatctgttgttaaggcagtgtatggagtggctcatagcggaggttatagtttattgacg<br>acagggagaacagctaattggaatggtcctagctatgatttgactggcaaaatagtaccaggtcaacaatacaatgtt<br>gattttttgggtgaaatttgttaatggcaatgatacagaacaaataaaggctactgttaaagcgacttctgacaaagac<br>aattatatacaagttaatgattttgcaaatgtaaatacagagcgaatggacagaaataaaaggcagttttacttacct<br>gtggcagattacagcggtgtcagcatctatgtagaatctcaaaatcctactttagagttttacattgatgattttcct<br>gtaataggtgaaatttcaaataatcagattacaatacaaaatgatattccggatttatattcagtattcaaagattat<br>ttccccatcggtgttgcagttgatccgagtagattaaatgatcgtgatccacatgctcaattgactgctaaacattt<br>aatatgcttgttgcagaaaatgccatgaaaccggaaagcttgcagcctacagagggaaactttacctttgataatgct<br>gataagcttgttgattatgcaatagcacataatatgaagatgagaggtcatacattgcttggcataatcaggttccg<br>gattggttttccaggacccatctgatccgtctaaaccagcttcaaggatcgtgctgcttcaaagattaagaacgcac<br>ataacaactgtgttagatcattttaaaacaaaatacggttctcaaaatccaataatcggatgggatgttgtaaatgag<br>gttcttgatgataatggcaatttaagaaattctaagtggttacaaattataggacctgattatatagaaaaagcttt<br>gaatatgcgcatgaggcagatccatctatgaaattgtttattaatgattacaacatcgaaaataatggcgttaaaaca<br>caggcaatgtatgatttagtgaaaaagttaaaaaatgaaggtgtgcctataaacggaataggcatgcaaatgcacata<br>agcataaattcaaatatagacaatataaaagcttctatagaaaaacttgcatcattaggtgtggaaatacaggtaact<br>gaattagatatgaacatgaatggtgatgtatctaacgacgcattgcttaagcaagcagattgtataaacaattattt<br>gacttgtttaaagcagaaaaacaatatataactgctgtagtttttttggggagtttcagatgatgtaagttggcttagt<br>aagccaaatgctccgctacttttttgattcaaagttacaggcaaagccagcatactgggcaattgtagatccaggcaaa<br>gccataccctgacattcaatctgcaaaagctttagaaggatcaccgacgattggtgcaaatgttgatagttcttggaaa<br>cttgtaaaaccattgtatgctaatacttatgtgaaaggaacattggagcaactgctgctgttaaatctatgtgtggat<br>actaaaaaacttatatttgttagtacaaaatttcagacaatactccatctaataatgatggcatcgagatttttgtggat<br>aagaatgacaacaaatctactacctatgaaagtgacgatgaacattatatagttaagagggatggtacagggagttca<br>aatattacaaagtatgtaatgtctaatgctgatggctatgtagcacagatagctattccaattgaagacattagtcct<br>gtgctgaatgataaaattggatttgatatcagaataaatgatgaccaaggcagtggcaatgtaaatgcgataacagtt<br>tggaatgattatacaaacagtcaagatactaatacggcatattttggagatttagtattatcaaaacctgcacagatt<br>gcaacagctatatatggcactcctgttattgacggtaaagtagatggcgtttggaataatgctgaagctatttcgaca<br>aatacatgggtcttgggttcaaatggtgctactgcaacagcaaaaatgatgtgggacgataaatatctttatatattg<br>gcagatgtaacagataacaatttaaataaatccagtgtaaatcctttatgaacgaatgatttctgtggaagttttttgtagat<br>cagaatgatgataagacaacttattatgaaaatgatgtgggcagtttagagttaactatgataatgaacaaagttttt<br>ggaggaagcactaattcaaatggatttaagtcggcaacaagtcttacacaaaatggatatattgtagaagaagctatt<br>ccttggacgagtattactccgttaaatggtactatcatagggtttgacttgcaagttaacgatgcagatgaaaatggt<br>aagaggacaggtattgtcacatggtgtgatccaagcggaaattcatggcaagatacttctggatttggaaacttgatg<br>cttacaggtaagccatcttgggcagtacaagtaattcgggaactacaagcagtagcagtaatacaagcagtacaata<br>ggtgtaatcacaaagaacggcaacgttattacattgatacttgatgcaggaaaagctaaagaccttatagtaaattca<br>aaggacaagaaagtcgtatttgacataacaacaataggtgaaggacaacagaaagttgtgcagatttctaaggacatt<br>ttagacacaagtgctgccaacggcaaagacatcgtcataaaatcagacaatcgatcgatacactcacgaaagatgct<br>taatcaaaaccagatacaaaacggtgtcaatgtatcaatcaatcaaagacaatggaaagcctacaatgtgacaaattatgtg<br>acgctttctaatgtagtagatataacaataagcggtagcagtgggaatgtagcattggcaaaaccagtagaggtgaca<br>ttaaatatatcaaaagctaacgatccaagaaaagtagcagtttactactacaacccaacaacaaatcaatgggagtac<br>gtaggggggtaaagtagacgcatcatctggaacaataacattcaatgcaacgcacttttcacaatatgcagcatttgag<br>tatgacaagacatttaatgacataaaagacaattgggcgaaagacgtaatagaagtattagcatcaaggcatatagta |

TABLE 2-continued

DNA sequences of xylanase genes expressed in *Thermoanaerobacterium saccharolyticum*

| Organism | Sequence |
|---|---|
| | gaaggaatgacagatacacagtatgaaccaaacaagacagtgacgagagcagaatttacagcaatgatactgaggctt<br>ctaaacataaaagaagaagcatacagtggagaatttagcgatgtaaaaagtggagactggtatgcaaacgcgatagaa<br>gcagcatacaaagcagggataatcgaaggtgacggaaagaacgcaaggccaaatgacagcataacaagagaagagatg<br>acagcaatagccatgagggcatacgagatgctgacacagtacaaagaagagaatataggtgcgacaacatttagcgac<br>gacaaatccataagcgattgggcaagaaatgtagtggcaaatgcagcgaaattaggaatagtaaatggtgagccaaat<br>aacgtatttgcacctaaaggaaatgccacaagagcagaagcagcagctatcatatacggcttattagaaaaaacaaat<br>aatctttaa |
| *Thermo-anaerobacterium saccharolyticum* | atgataagtaaatcttttttatgcgcatcacagcgcatttggcgctttctcaagttttgtaatcggtaaatgcggtaa<br>aggcggtggcgtcgtactaaatgatgttcggccgcctgaaaacaacgtctacattggatacaaaagagatggtgtta<br>taagcttgctgccatttattaaagatgatacaaaaaatgctgaagaagagtttacaggagaagtctctacaagcaaa<br>aaagaaaaaaacataaaaatctttggggaagatgagatagaaagagagttatgctgggcatcagacacttggacagc<br>aggagacttcaaattttccatcatcactccatttgatacgtaaaagatccttcggtgatgaagtggagacgaaaaga<br>aacttgcactggcacctgtcatatttgtacagttgacaatggataatactgacagcgataaggatgctgagatgata<br>ttttggcttttgaaggtccgaaaaggatattatctgagcttacagatggaaaatacttaggaggagtatacggcagaaa<br>atacggttttgctatcaaaaaaagcgatgatgtaagagagctttcaaggcttgatattttgacatcatgggcaaatg<br>acaactatcaaaatcatgggcttggcagagcgccgtctttgatattttaaagtgccgagagggggagaaaaggacatat<br>actgtggcattggcaacgtatcaaagcggcgtcataacaacaggaatcgatgctgaatttttactacacatctgtttt<br>taagtcattggaagaagtattatcctttggacttgacaatcaagattattacttaaatttagcaaaggaaagagatg<br>aagagcttaagaaaagcggtttaaatgaatacaggcagttttttattggcacatgcagcccacagttactatgccagc<br>acggagcttttaaagagagacgatggtatgcctctttgggtggtaaacgaaggcgaatacattatgataaatacatt<br>tgatttgacggttgatcatgtcttctgggaaatgaggttccatccttggacgattacaaatacattggatctgtact<br>atgaaaagtacagctacagggatcaagcaggtcttgcctttacgcatgatatgggtgtcgcagatggttttttctaaa<br>gaaggctattcatcttacgagcttccaaacctgactggatgttttagctacatgacacatgaggagcttttgaattg<br>ggttttgacaggttctgtctatgcaatcaaaaataaatgataaagaatggttaaagaaaaacatgggtgtattcgaag<br>attgtttcgattctcttgtggcaagagataaaaataatgatggaataatggacgttgacagttcaaggtgtgagacg<br>gggtcggaaataacgacttacgatagccttgacgaaagcttgggacaggcgagaaacaatctataccttggtgttaa<br>gacatgggcagcttacgtgatgttgcatggtttgtttaaagaaaatgatcttagtgaaaaggcagaaaaagctttag<br>aaaaggcaagacaggctgctaatactatcgttgccaagtttgacgaagaaaatcagtatataccctgcagtatttgag<br>aatggcaacacatcaaggataatacctgctgtagaggcattggtatatccatatgttgtaggatatactgactttgt<br>aagtgaagatggtgtatttggtgggcttataaaagccttaaagaagcatgtaatgacgattatgaagcctggtatat<br>gcatagatgaagtatctggaggttggaagctttcgtcaaccagcaagaacacatgaatagtaaaattttcttatgc<br>caatatgtgataaaagatgtgcttaatatagactttggagacaaagagattgagtgggacaaagtacacgcaatgtg<br>gcaacaggtgtcttgcagtgaagattgcgctacagatcaggtaaacagcgatacaggtacgccaagaggaagccgct<br>tgtatccgagacttgtgacaagtgtattgtggatgaaatag |
| *Thermo-anaerobacterium saccharolyticum* | atgattaaagtgatagtgccagatttttccgataagaagttttctgataggtggagatattgtgttggaacaggcag<br>acttggccttgcgctacaaaaggaatacatcgatacattaaaatatgtgaaagaaaaacatagactttaagtatataa<br>gaggacatggcctttttgtgtgacgatgtaggaatatacagagaagatgtggtaggcgatgaaataaagcctttttac<br>aattttacctatatagataggattttttgactcattttttagaaatcggaataaggccatttgtggaaatcggatttat<br>gcctaaaagattagcatctggtacacaggcggtatttattgggagggggaatgtcactcctcccaaggattataaaa<br>aggggagaacctcataaaagctgtcgtttcgcatttcatatcaagttacggaatagatgaagtggcaaaatggccat<br>tgaaatttggaatgagccgaacttaaaagagttttggaaagatgctgacgagaaggagtatttttaagctgtacaag<br>ataactgcaaaggctataaaggaagtaaatgagaatataaaagtaggaggacctgctatatgtggtggtgctgacta<br>ttggatagaagatttttttgaatttctgctatgaggaaaatgttcctgtagattttgtgtcgcgacatgcgtatacgt<br>ctaagcaaggcgaatatacgccgcacttaatataccaagagatcatgccgtcggaatacatgctaaacgaatttaaa<br>acggtgagagatatcattaaaaactcgcatttttccaaaccttccgtttcacataactgaatacaatacatcttacag<br>tcctcaaaatcctgtacatgatacgccatttaatgctgcctatattgccaggattttaagcgaaggcggagattatg<br>ttgattcattttcttactggacgtttagcgacgttttcgaagaaagagatgtgccgcgatcgcaatttcatggagga<br>tttggacttgtggctctaaatatggtaccaaagcctaccttttacacatttaaattttttaatgctatgggagagga<br>aatgtatagagatgagcatatgattgtgacgagaagggatgatggctctgttgcgctcatagcgtggaatgaagtca<br>tggataacgatgaaaatccagataaagagtatgaagtccagataccagttggattcaaagatgtgttttattaaaaga<br>caattaattgatgaagaacatggcaatccatggggaacgtgatacacatgggtaggccgaggtatcccagcaaaaa<br>agagataaatacgcttagagaaattgcaaagccggagattatgacaagccatgctgttaccaatgatggatacttaa<br>atctaaagtttaaatttaggcaaaaatgcggttgtgctttatgaattgacagaaaggattgacgaatcgagcacatat<br>ataggacttgatgatagcaagataaacggatattga |

TABLE 3

Protein sequences of xylanases expressed in *Thermoanaerobacterium saccharolyticum*

| Organism | Sequence |
|---|---|
| *Clostridium phytofermentans* | mlqkmngkvkkilgisiaflmlimviptsiakaainktydfnsmtyqstwgvtysisngsgtfnftgqyreik<br>fnlpetldmsqetsvtfnasspngqiafklydtsgnqvavvynfnsntsdetfapnstakvnsigimaqgtnn<br>ysavvnrvtftmtggssgtgsstllntygnilknsgtavnlsqlqnsntlsviktqynsitlenemkpdavlgsss<br>tlmtvaqaksngyyipssytestvptlkfstidavlqicynnglklrghtlvwhsqtpdwffrtgysssgsyvsq<br>avmdarmemfirsymshiyngsygsvvyawdvvneylhastsgwsqvygsnlgttpsyvkkafqyayd<br>clssfgltnsvklfyndyntyevtdqilslvnfinsgtklcagvgmqshlntsypsvsayktamqkflnagyev<br>qvteldvtntsastqatyvvydlmtailslkkaggnitgitwwglydsvswrasqnpllfsnlttpkesynkalqa<br>ftdagy |

TABLE 3-continued

Protein sequences of xylanases expressed in *Thermoanaerobacterium saccharolyticum*

| Organism | Sequence |
|---|---|
| *Clostridium phytofermentans* | mffkklvalamavaivipmnvnniqkveaestneavvygnliyhdfeastngwgprgdnaevvaqsteea ysglhslkiskrtqtwhgatcdltkeltigetyvfgiylkykgssysntqkfsqfqyndgvndqyktiktlevtk dkwtliqgeytvpadaanakvyveteyksspssqdlldfyiddftatpatlpqiqkdipslkdvfssyffvgga atageiapapakdlvakhynrltpgnelkpdsvldysatiaymdanggnqvnpqvnlraaktlleyardnni pvrghtlvwhsqtpdwffkvnysqdsnaawvskevmlqrlenyiknvmqlisstyptvkfyawdvvnea vdpntstgmrnpgsnnvtsgnspwmqtigecyiqrafeyarkyaptgcklfyndyneyedrkstfifnilkg lkdkglvdgmgmqshwvmdypsismfetavrkyntlglelqlteldikqpdnstsalaaqadryklinkvi slkkegmnitgvifwgvtdktswlggyplllfdgnyqaksayysiidgitptvtpsitptvtpkptitptvtptvtp kptitptvtptvtpkptitptitptvtpkptiaptptpttvpvegakpvvvvttknngntisqqytinalggtidlsk vsieftadgiinqehnvwvdnaalqltvepyytplngyvsgqltnqklvvsiskstmlsegtgklvldlrfakk dwtdfgtisnevlkvyyngvkvq |
| *Clostridium phytofermentans* | mfklnkkvfalvsvialgfsslftstahaatdywqnwtdgggtvnatngsggnysvnwtncgnfvvgkgw gtgnasrvvnynagvfspsgngyltfygwtrnslieyyvvdswgtyrptgtlkgtvssdggtydiytstrtnap sidgtqtfqqywsvrqskratgsnvaitfsnhvnawkskgmnlgsswayqalcvegyqssgsanvtvw |
| *Clostridium phytofermentans* | mgkkvialltcvmlsltlipgigikstaqaaetniyvkvdwskfnegdkisgpmeglgrssgaditvtgsstksf yisnrkdnwdaldiqndllkldrdatyeitvtghvdsnvdtknasvklggvtrktgedddgypefkkeklqsgk sfvltyelklsdqipdasrnlwvlrvqtdepsgsragdlvpfyyddiviiqtkastapvavtgdlmslyelnadk tlkvgeslsspalkvsgnakivvvegtdgtvslqlkdrvnnydgvdilrdalkindkfmsgtytievkghved gsdlsksqfvmgmtespwgeltsrvtpssdqsfvitytkaytgseltglgysyrvqtppsvltsfyidnitvtvq gaeeedestvvipewdltldsikdayadyfmignimepgqiqdtettemfkhhynvvtaenamkpgnisk vkgeynfdnadklvtwakenglkvhghtlvwhsqsapwlttnadgtpltraearnmedyiknvaghyag kviswdvlneaflpgvseipagwrdvlrkfedngngspwyqayengadkskgedgsdyiydafvftrlaa pdavlyyrdhfneteagkceaialmveelntkwktdkrntepdrlliegigmqahywtgdlkvstveasikrfi ktgakisvseldvphgdymtykqrtdsptkeeeklqadlykqlfevykkyadniervtfwgktdpqswrfq gypllfdknfapkdaffavidvakekvaeekavetipgkdipktgedsskqmiltavailiilvfvpvtiltkrre knikni |
| *Thermobifida fusca* | mglpvsvhrsdtkmrvgryiaitvgasallvsgvapaaagtlptsgtaagaasqaghdkqvplrkvapkgf aigvavagggghhldqeypdpfkydeeyrgvlakhfnsvtpenhlkwdfvhperkkynfgpadqivkfaqs ngqkvrghtlvwhsqnpdwltkgkfskkelrkilkehiitvvgryrgkihqwdvaneifddngklrtneniw lknfgpeiiadafrwahqadpkaklflndygacginkrsdaylkfmkelrkkgvpvhgfgvqghlslaypf pgdmaknlkrfsdagfevavtevdvriplnggdateaqlktqadyyrraleaclsvkscnsftlwgttnkysw vpvffpdegeatifwddfspkpaytalqealakarrr |
| *Thermobifida fusca* | mnhapaslksrrrfrprlligkafaaalvavvtmipstaahaavtsnetgyhdgyfysfwtdapgtvsmelgp ggnystswrntgnfvagkgwatggrrtvtysasfnpsgnayltlygwtrnplveyyiveswgtyrptgtymg tvttdggtydiyktttrynapsiegtrtfdqywsvrqskrtsgitatagnhfdawarhgmhlgthdymimategy qssgssnvtlgtsggdnpgggnppgggnppggggctatlsagqqwndrynlnvnvsgsnnwtvtvnvp wpariiatwnihasypdsqtlvarpngngnnwgmtimhngnwtwptvscsan |
| *Clostridium stercorarium* | mkrkvkkmaamatsiimaimiilhsipvlagriiydnetgthggydyelwkdygntimelndggtfscqw snignalfrkgrkfnsdktyqelgdivveygcdynpngnsylcvygwtrnplveyyiveswgswrppgat pkgtitvdggtyeiyettrvnqpsidgtatfqqywsvrtskrtsgtisvtehfkqwermgmrmgkmyevalt vegyqssgyanvykneiriganptpapsqspirrdafsiicaecynstnsstlqvigtpnngrgigyiengntvt ysnidfgsgatgfsatvatevntsiqirsdsptgtllgtlyvsstgswntyqtvstniskitgvhdivlvfsgpvnv dnfifsrsspvpapgdntrdaysiiqaedydssygpnlqifslpgggsaigyiengysttynnvnfanglssita rvatqistsiqvraggatgllgtiyvpstnswdsyqnvtanlsnitgvhditlvfsgpvnvdyfvftpanvnsg ptspvggtrsafsniqaedydssygpnlqifslpgggsaigyiengysttyknidfgdgatsvtarvatqnattiq vrlgspsgtllgtiyvgstgsfdtyrdvsatisntagvkdivlvfsgpvnvdwfvfskfrnlrv |
| *Clostridium stercorarium* | mnkflnkkwsliltmggiflmatlslifatgkkafndqtsaedipslaeafrdyfpigaaiepgyttgqiaelyk khvnmlvaenamkpaslqptegnfqwadadrivqfakengmelrfhtlvwhnqtptgfsldkegkpmv eetdpqkreenrkllllqrlenyiravvlrykddikswdvvneviepndpggmrnspwyqitgteyievafra areaggsdiklyindyntddpvkrdilyelvknllekgvpidgvghqthidiynppveriiesikkfaglgldn iiteldmsiysvndrsdygdsipdyiltlqakryqelfdalkenkdivsavvfwgisdkyswlngfpvkrtna pllfdrnfmpkpafwaivdpsrlre |
| *Clostridium stercorarium* | mngrnggkrpiaslllvltlafllfipvtkaettvyhetfaegkgaavqsggatithvtgkffdgngdgaalyisnr vnnwdaadfrfsdiglqdgriykitvkgyvdpdvhvpegsqiwlqtvnsygwwgstdikageaftltgvyk vdttndyalriqsndtgafvpfyigeiliteetvpqddsrngnkthaekftpitfedqttggftgragteiltvtdea nhtdggryslkvggrndtwhgpalgvekyvdqgyeykvavyvrlispesaqlqlstqigegtsasyvnlakk nvaisdgwvllegtyrydnlgggyltiyvespdspeasfyiddinfeptgmkseeiekglkslkdvykdnflt gtaislrdlegvrfellkkhfnavtaenamkpselqrekgnfttdgadrlvnaaisagmkvhghtlvwhqqtp awmnikldsggnivylsreealenmrnhirtviehfgdkviswdvvneamsdnpsnpsdwrgslrkspw |

TABLE 3-continued

Protein sequences of xylanases expressed in *Thermoanaerobacterium saccharolyticum*

| Organism | Sequence |
|---|---|
| | yyaigedyveqaflaarevldehpewdiklyyndynldnqnkalavynmvrelnekyqkthpgkllidgig<br>mqghysvntnpknvelslkrftelgvevsiseldiragsnyqltekeanaqaylyaqlfkifreysdsiarvtfw<br>gmddgtswraeespllfdrtlkakpayyavadpdefiekykpetieanrayavygtpeidgktdevwnkap<br>elkinryqtawhgadgtarvlydennlyvlikvndtqldkgspnpweqdsveifidennaktsfyeeddgq<br>yrvnfenetsfnpesiaggfesaaevsgtnytlevkipfrtvkpvsnmqigfdvqindgkngvrqsiatwnd<br>ptgnawqdtsvfgiltlksknpvtrgeaivkimkaydmeplenwndnfsdasgsyagyypraketgfvsgi<br>gdnkigaeipltremfftmiynieritgkmqgidisdaeltlfsdyndlsewaecavkalvksgrikingdllp<br>krlmdaeeveaflrlr |
| *Bacillus subtilis* | miprikkticvllvcftmlsvmlgpgatevlaasdvtvnvsackqvirgfggmnhpawagdltaaqretafg<br>ngqnqlgfsilrihvdenrnnwykevetaksavkhgaivfaspwnppsdmvetfnrngdtsakrlkynky<br>aayaqhlndfvtfmknngvnlyaisvqnepdyahewtwwtpqeilrfmrenagsinarviapesfqylknl<br>sdpilndpqalanmdilgthlygtqvsqfpyplfkqkgagkdlwmtevyypnsdtnsadrwpealdvsqh<br>ihnamvegdfqayvwwyirrsygpmkedgtiskrgynmahfskfvrpgyvridatknpnanvyvsayk<br>gdnkvvivainksntgvnqnfvlqngsasnvsrwitsssnlqpgtnltvsgnhfwahlpaqsvttfvvnr |
| *Bacillus subtilis* | mrkkcsvelwilvllscslgsgksayaatsttiakhignsnplidhhlgadpvaltyngrvyiymssddyeynsn<br>gtikdnsfanlnrvfvissadmvnwtdhgaipvagangangrgiakwagaswapsiavkkingkdkffl<br>yfansgggigvltadspigpwtdpigkplvtpstpgmsgvvwlfdpavfvdddgtgylyagggvpgvsnp<br>tqggwanpktarviklgpdmtsvvgsastidapfmfedsglhkyngtyyysycinfggthpadkppgeig<br>ymtssspmgpftyrghflknpgaffgggggnnhhavfnfknewyvvyhaqtvssalfgagkgyrsphinkl<br>vhnadgsiqevaanyagvtqisnlnpynrveaetfawngriltekstapggpvnnqhvtsigngdwiavgn<br>adfgaggarsfkanvastlggkievrldsadgklvgtlnvpstggaqtwreietavsgatgvhkvffvftgtgtg<br>nlfnfdywqftqr |
| *Bacillus subtilis* | mfkfkknflvglsaalmsislfsatasaastdywqnwtdgggivnavngsggnysvnwsntgnfvvgkg<br>wttgspfrtinynagvwapngngyltlygwtrsplieyyvvdswgtyrptgtykgtvksdggtydiytttryn<br>apsidgdrttftqywsvrqskrptgsnatitfsnhvnawkshgmnlgsnwayqvmategyqssgssnvtv<br>w |
| *Bacillus subtilis* | mkitnpvlkgfnpdpsicragedyyiavstfewfpgvqihhskdlvnwhlvahplqrvsqldmkgnpnsg<br>gvwapclsysdgkfwliytdvkvvdgawkdchnylvtcetingdwsepiklnssgfdaslfhdtdgkkyll<br>nmlwdhridrhsfggiviqeysdkeqkligkpkvifegtdrklteaphlyhignyyylltacggtryehaatia<br>rsaniegpyevhpdnpiltswhdpgnplqkcghasivqthtdewylahltgrpihpdddsifqqrgycplgr<br>etaiqklywkdewpyvvggkegslevdapsisetifeatypevdefedstlninfqtlripftnelgsltqapnh<br>lrlfgheslstftqafvarrwqslhfeaetavefypenfqqaaglvnyyntenwtalqvthdeelgrileltidcn<br>fsfsqplnnkiviprevkyvylrvniekdkyyyfysfnkedwhkidialeskklsddyirgggfftgafvgm<br>qcqdtsgnhipadfryfrykek |
| *Thermoanaerobacterium saccharolyticum* | mksivnrvvsivtalimifgtslfsqhirafadddtntnlvsngdfetgtidgwikqgnptlevtteqaigqysmk<br>vtgrtqtyegpaysflgkmqkgesynvslkvrlvseqnssnpfitvtmfreddngkhydtivwqkqvseds<br>wttvsgtytldytglktlymyvespdptleyyiddvvvtpqnpiqvgnvitngtfengntsgwvgtgssvvk<br>avygvahsggyyslllttgrtanwngpsydltgkivpgqqynvdfwvkfvngndteqikatvkatsdkdnyiq<br>vndfanvnkgewteikgsftlpvadysgvsiyvesqnptlefyiddfsvigeisnnqitiqndipdlysvfkdy<br>fpigvavdpsrlndadphaqltakhfnmlvaenamkpeslqptegnfttfdnadkivdyaiahnmkmrght<br>llwhnqvpdwffqdpsdpskpasrdllllqrlrthittvldhfktkygsqnpiigwdvvnevlddngnlrnsk<br>wlqiigpdyiekafeyaheadpsmklfindynienngvktqamydlvkklknegvpingigmqmhisin<br>snidnikasieklaslgveiqvteldmnmngdvsndallkqarlykqlfdlfkaekqyitavvfwgvsddvs<br>wlskpnapllfdsklqakpaywaivdpgkaipdiqsakalegsptiganvdsswklvkplyantyvkgtiga<br>taavksmwdtknlyllvqisdntpsnndgieifvdkndnksttyesddehyivkrdgtgssnitkyvmsnad<br>gyvaqiaipiedispvlndkigfdirinddqgsgnvnaitvwndytnsqdtntayfgdlvlskpaqiataiygt<br>pvidgkvdgvwnnaeaistntwvlgsngatatakmmwddkylyiladvtdnnlnkssvnpyeqdsvevf<br>vdqnndkttyyenddgqfrvnydneqsfggstnsngfksatsltqngyiveeaipwtsitplngtiigfdlqvn<br>dadengkrtgivtwedpsgnswqdtsgfgnlmltgkpswgstsnsgttssssntsstigvitkngnvitlilda<br>gkakdlivnskdkkvvfdittigegqqkvvqiskdildtsaangkdiviksdnasialtkdalnqnqiqngvn<br>vsikdngkpnvtnyvtlsnvvditisgssgnvalakpvevtlniskandprkvavyyynpttnqweyvggk<br>vdassgtitfnathfsqyaafeydktfndikdnwakdvievlasrhivegmtdtqyepnktvtvtraeftamilrll<br>nikeeysgefsdvksgdwyanaieaaykagiiegdgknarpndsitreemtaiamrayemltqykeenig<br>attfsddksisdwarnvvanaaklgivngepnnvfapkgnatracaaaiiygllektnnl |
| *Thermoanaerobacterium saccharolyticum* | mglfdmplqklreytgtnpcpedfdeywnraldemrsvdpkielkessfqvsfaecydlyftgvrgarihak<br>yikpkteghkhpalirfhgyssnsgdwndklnyvaagftvvamdvrgqggsqdvggvtgntlnghiirgld<br>ddadnmlfrhifldtaqlagivmnmpevdedrvgvmgpsqgglslacaaleprvrkvvseypflsdykr<br>vwdldlaknayqeitdyfrlfdprherenevftklgyidvknlakrikgdvlmcvglmdqvcppctvfaayn<br>niqskkdikvypdyghepmrgfgdlamqfmlelns |
| *Thermoanaerobacterium saccharolyticum* | misksfyahhsafgafssfvigkcgkgggvvlndvrppennvyigykrdgvisllpfikddtknaeeeftge<br>vststkkeknikifgedeierelcwasdtwtagdfkfsiitpfgyvkdpsvmngdekklalapvifvqltmdnt<br>dsdkdaemifgfegpkrilseltdgkylggvygrkygfaikksddvrelsrldiltswandnyqnhglgraps<br>lifkvprgekrtytvalatyqsgvittgidaefyytsvfksleevlsfgldnqdyylnlakerdeellkksglneyr<br>qfllahaahsyyastellkrddgmplwvvnegeyimintfdltvdhvfwemrfhpwtitntldlyyekysyr<br>dqaglafthdmgvadgfskegyssyelpnltgcfsymtheellnwvltgsvyaikindkewlkknmgvfe |

TABLE 3-continued

Protein sequences of xylanases expressed in *Thermoanaerobacterium saccharolyticum*

| Organism | Sequence |
|---|---|
|  | dcfdslvardknndgimdvdssrcetgseittydsldeslgqarnnlylgvktwaayvmlhglfkendlseka<br>ekalekarqaantivakfdeenqyipavfengntsriipavealvypyvvgytdfvsedgvfgglikalkkhv<br>mtimkpgicidevsggwklsstskntwnskiflcqyvikdlvlnidfgdkeiewdkvhamwqqvscsedc<br>atdqvnsdtgtprgsrlyprlvtsvlwmk |
| *Thermoanaerobacterium saccharolyticum* | mikvivpdfsdkkfsdrwrycvgtgrlglalqkeyidtlkyvkenidfkyirghglledvgiyredvvgdei<br>kpfynftyidrifdsfleigirpfveigfmpkrlasgtqavfywegnvtppkdykkwenlikavvshfisrygi<br>devakwpfeiwnepnlkefwkdadekeyfklykitakaikevnenikvggpaicggadywiedflnfcye<br>envpvdfvsrhaytskqgcytphliyqcimpscymlnefktvrdiiknshfpnlpfhiteyntsyspqnpvh<br>dtpfnaayiarilseggdyvdsfsywtfsdvfeerdvprsqfhggfglvalnmvpkptfytfkffnamgeem<br>lyrdehmivtrrddgsvaliawnevmdktenpdkeyevqipvgfkdvfikrqlideehgnpwgtwihmg<br>rprypskkeintlreiakpeimtshavtndgylnlkfklgknavvlyelteridesstyiglddskingy |

In some embodiments of the invention, multiple xylose transporters from a single organism are co-expressed in the same host cell. In some embodiments of the invention, multiple xylose transporters from different organisms are co-expressed in the same host cell. In particular, xylose transporters from two, three, four, five, six, seven, eight, nine or more organisms can be co-expressed in the same host cell. Similarly, the invention can encompass co-cultures of microorganism strains, wherein the microorganism strains express different xylose transporters. Co-cultures can include microorganism strains expressing heterologous xylose transporters from the same organism or from different organisms. Co-cultures can include microorganism strains expressing xylose transporters from two, three, four, five, six, seven, eight, nine or more microorganisms. In one embodiment, the xylose transporter may be of microbial origin, such as of fungal origin (e.g., *Trichoderma, Meripilus, Humicola, Aspergillus, Fusarium*) or from a bacterium (e.g., *Bacillus*). In another embodiment, the xylose transporter is derived from a filamentous fungus, for example from a strain of *Aspergillus*, or a strain of *Humicola*. Tables 4 and 5 below list the xylose transporters expressed in *Thermoanaerobacterium saccharolyticum*, and the sources of the xylose transporters.

TABLE 4

DNA sequences of xylose transporter genes expressed in *Thermoanaerobacterium saccharolyticum*

| Organism | Sequence |
|---|---|
| *Thermoanaerobacterium themosaccharolyticum* | atgggtaaaaatgcaaaaaaagctttgttgtcggtgatacttatacttagtatgttgtttacgttttcggcgtgtgc<br>tacaacaaatcctaatcaatcaaaatctaataatcaaacaagccaaacgaccaatacatctgacaactcaggc<br>aaaattaaaattggctttagttagatactctaaatctagagagatggcaacatgatagagactattttgttcaaa<br>gggctaaagagttaggagctgaigtattagtacagtcagctaatagtgattcacaaacacaatattcgcaatgt<br>caaaatttaatagcgcaaggeataaaagttttagtaataattccacatgatggaagtgcaatagcaccaatcgt<br>tgaagaagctcataaagctggagtaaaggttttagcatacgatagattaattattaacgcagatgtagatgcat<br>acgtgtcgtttgacaatgaaaaagttggtgaattacaagctgaagcaataacaaaactggtaccaaaaggaa<br>attatttcttacttgaaggttcacctacagataataatgctaaattgtttgaacaaggtcaaaagaaggttttacaa<br>ccgttagttgataaagcgatataaaaatagttggagagcaatgggcgcaagattggcttcacacaaaatgctt<br>acaatattatgcaaaatgcactaacagctaataacaataaaattgatgcagtagttgatgcgaatgacagtact<br>gctttaggagcgattagggctttacaagaacaaaatcttgctggaaaagttgcaatatccggtcaagatgctg<br>atctagcaaattgtcagttgattgttgaaggcaaacaatcaatgactgtgtataagccagtaaaggaagaagc<br>aacaaaaggtgctgatgtagcggttgccttagcaaaaaggtgaagacatcaatgcaaacggaaaggtcaata<br>atggaaaaattgacgtaccatctgtattgcttacacctgtagccgtagataagaacaatatggtagatactatca<br>taaaagacggattccatagccttgatgaagtttataaaaatgttcctaaagatcaatggccaaaacaatag |
| *Thermoanaerobacterium thermosaccharolyticum* | atggatatgggtgatttcatactagaaatgaaaatataacaaaggattttccggtgttaaagctttagacaatg<br>tgaatttgaaagtcaaaaaaggagaaatacacggactatgtggtgaaaatggtgcgggaaagtcaacactta<br>tgaaaatttaagcggtgtatatccatatggtacttttttctggagagataatattttgatggaaaagaattaaaatta<br>aataatattaaagatgcagaagatgcagggataggtataatttatcaggagttgtcattagttaaagaattgtct<br>gtcagtgaaaatatatttattgggaatgagcctaataaaaatgggataattgattttgacaggatgtactatgaa<br>actaaaatcttacttgataaattgaatttgaatattaatcctaatgtaccagtaaagaatttgggcattggacagc<br>aacaattagttgaaattgccaaagcttatctaaaaatgttagcttgttgatattggatgagccaacatcatctctt<br>acagatgctgatgttgagatattgtttaatatattaagacagttaaaagataatggtgttacatgtatatatatatct<br>cataaattaaatgaagtaatggaaataacggatcggataacagttcagagagatggaaaaacaataggttca<br>gaagatacaaaaaatcttacagagagtgaaattataaaaatgatggttgggcgtgaacttacgaatcttttccc<br>aaaagaggaacatcaaattggaaaagaaatattggaagtaaaaaatttcagtgtttatgattcgaaatcatcta<br>gcaaaaaaattgtagacaatgtcagctttacttttaaaagaaggtgagatattaggaatagcaggccttattgga<br>gctggaagaactgaacttgtttctagtattttcggatcatatccaggaagacatgaaggtgaaatctatttagaa<br>ggtaaaaaaattaataaagaaatcctgatgaagccttggattatggaattgcaatggttccagaagatagaaa<br>aggtcaagggttaataaatatattatctgtaagagataatatgacattatctaatatagaaagttataaaaataac<br>tttggctcagttgacgtaaataaagaaatagtggatgttaaaaaatatatcgaaatgttgaaaataaaagtttca<br>catttttgacttagcagtaaaaaatttaagcggtggaaatcaacagaaagtggttttggctaaaaatttattaaga<br>aatcctaaaatattgatattagatgaacctactcgtggaattgatgtcggtgcaaaatgagatatataaattaa<br>tttatgaattggttaaaagcggtatttcaataataatggtatcatcagaactgccagaaataataggattaagtga<br>tagaattgtcgtaatgcatgaaggtaaaaagaagggtgaatttgtcaataaagatgtcacteaagaaatgata<br>atgcaatgtgcgataggaggtaaataa |

TABLE 4-continued

DNA sequences of xylose transporter genes expressed in
*Thermoanaerobacterium saccharolyticum*

| Organism | Sequence |
|---|---|
| *Thermoanaerobacterium thermosaccharolyticum* | atggtgaattcgaaaggttttaaagaaaataatgtatcgataaataaaaaattttcatttaatttaaaattatatacg atgataatagcattagtcggtatttggattatttttgcaattgctacaaaaggtgacttttttaacttctagaaatatgt caaatcttttttaggcaaatggtttctacggcggttttagccatagggatggttttttgtaataatagctggtcagatt gatctttcagttggatcgcttttaaggtctgactggtggtatagctgcaattgctaatgtctggttcatattaatggc atcctttcaataattattgcgttagcgattggtttgattttaggaacgtggaatggctggtgggtagcttataaaa atgttccatcgtttattgtaacgttagcaggcatgctggtatttagaggaatattgattggtataactaatggttat actatagcaccattgagtagtgatttcagtttataggtcaagcttatttaactccagtaagtgggctatttactcgg tataattgtattactagtaggagcctatactatatattcacaaaggaaatcaaaaattaagtatgggttagaagttt caccttttatttagatattgctaaaataatacttatgattgtattgattggactatttgtattcacgctaaattcctata atggaattcctttttcagtattaattttggcgatttagttgcaatatttacttatattgcatcaaagacagttttggg agaagagtttatgcattaggtggtaatatcgaggctgcaaaattatcaggtatcaatgttaagaagataacactt atttttatttgcaattaatggattgcttgcagcagtatcaggcgttgttcttacatcaacttttaaatgctggatcaaca tctgcaggtcagaatgcggagatggatgcaatcgcgtccttgtgtaattggtggagcaagccttatgggaggc gttggatcagttattggtgctataataggcgcattagttatggcaagtatcaacaatgagattgaggcttacttaatt ccgcacccattttggcaatatgttgttaagggattgatattactattagctgtttatgtagatgtagcctcgaaaaat aaagaataa |
| *Thermoanaerobacter mathranii* | atggtaaagtctaaaaaaattgttggcattttttcttggttatgatattgacattgtctgttgtattagcaggatgtacta gttcaaagacaaatgagacgacaaacactacttcaagtaatggttcaagtagcacagaaactaaaaaaataa aaatcggtttttctcttccaacaatgagagaagaaaggtatcaaaagatagagatgcatttgttgaagaagc agaaaaacttggageagaagttttagtacaaggtgcaaataacgatgaaaaccttcagaatagccaagtaga aaaccttatcacccaaggaatagacgtattagttcttgatccacaaaatgctgcttctgcagctaccttggttga aaaagctcatcaagcggggattaaggttatctcttatgacagacttatattaaattctgaaccagacgtgtatat ctcttttgataatgaaagagtaggagttacagggagaatccctcacaaagttggtaccaaagggaacttatt tcatatttgctggctccaactgacaacaatgctacattgttcaaaaaaggagcaatgaaatatattcaacctc ttgttgacaaaggagatataaaaatagctttgaccaggcaataaaaagactgggacccaaatgaggcttttaaa acttgctgaaaacgctcttactgctaacaaaaacaaagtggatgctattcttgcacctaacgatggcactgca ggtggtataatacaggccttagcagaacaaaaattggctggtaaagtgccaattacaggtcaagatgcagaa cttgcagcagtgaagaggattggaaggcacacaatcaatgacagtgttcaaagatgtaagagttcttgcta gaaaggctgctcaaattgctgtaatgttagctcaagggaaagaagtaaaagatataccggaaattaataaga ctgtaaacaatcaaaagatagatgttccatcattgttgttgacaccagttgttataacaaaggacaacattgata aagagcttattgacagtggttggtttacaagggaacaagtgtacggtaagtaa |
| *Thermoanaerobacter ethanolicus* | atgagcgagtatattcttgaaatgagaaacataacaaaggaatttcctggagttaaagcattggataatgtaaa tttcaaagttaaaagaggggaaattcacgcgttagtaggagaaaatggagcgggaaagtctaccttgatgaa gatattaagtggtgtttatccttatggaacttataaaggagacataatcatagatggtgaagtgaagcaatttcg aaatattaaagatagtgaaaaaagtggtatagcgattatttatcaggagctcactctggtaaagtatatgacagt aggcgaaaacatattttaggtgaagagcctgtaaaaggcggaataattgattggtgaaagtttactctgag acttatagacttttgaaagagttgcagattaatgtaaaccctatacaaaagttatgaatttaggaattgggcatc aacaaatggtagaaatagcgaaggctctttcaaaaaaagcgaggatttttaatattagatgagcctacttctgca ttgacagaaagcgaaacagaacatcttctcaatattttgaaagatttgaagaaaaatggtgtaacttgtatatac atttctcacaagcttaatgaagtatttgaaattgcagattcaatcactgtatttaagagatggcaaaacgataatg acggacaaaaagaaaatttcacagaaaacaaggtaatttcttaatggtaggggcgtgagcttacacagaga ttcccaagagctaagcatacgccaggggaagtggttttcgaggttaaaaattacacagtttatgaccatgaaa taccgggcaagaaaattattgacaatgtaagcttttaaagccaggagaggcgagatattaggtattgcaggac ttatgggagcagggaggacagaacttgctgctagtatatttggtgcatttaaaggtagaaaagaagggggaaa tatatttaaatggcaaaaaaattgaaataaaacactcccagcgatgcgataaaacatggaattgcctatctttcag aggataggaaaggtttggccttgtgactttgatggatgtacaagaaaatatagcacttcctaactatgacaga ctatcaaaatttagtattataaataacaatgcaaaaatttaaacatgcagaaaaagtatgtaaaagagttaaaaata aaaacaccaaccataagacaaagggttgctaattaagtggaggaaaccagcaaaaagtggttattgcaaa gtggcttatgtcagacccaaaagttttgatactggacgaaccaactagaggaatagatgtgggagctaagttt gaaatatataatctaatgaataaattggttgatatgggcgtgtgtgtaataatgatatcttcagaactgcctgaaa tattgggaatgagtgatagaatactggtaattcatgaaggaaaaatcaatggagaatttccaatagaagaagc agaccaagaaaaaatcatgtactgtgcaactggaggtaaa |
| *Thermoanaerobacter ethanolicus* | atgatggaaagcaaagtgagcaaaacaactgaaaagcgcatttaaatcatttcaagatagatataaggtcat atactatgatattagctttattggggatatggattatttatcaatattgacccatggcgattttctatctccgagaaa cttgtccatgcttgccaggcaaatgtctataacagcaatttgacttcaggtatggtttttagttatagttgctgggc atatagacttatctgttggttctgtggcagggtttacaggagctatagctgcaattcttcaggtgatatatcattg ggatacagtgccgacaataatagtgactcttatggctgggcttgctattggagtttggcaaggattttggatag cctatagaaagtgcctgcttttatagtgaccttaagctcaatgcttgtttttagaggtggaatttattaattacaa aaggtgttactatatctcctttaaaacaggacttcacagtcgtaggacagggatatattcctccattgtttagcgt tattcttgctgtggtggcaggtgttttgtatgtaatcatgaccttaagaatagaaattctcgaatttaaatacggct taagtgtgtccagctggggaatagaactggcaaaaattgcaggagtattgattttcatcgctttgtttacaagtg ttatgatatcttatgaaggaattcctgtgccagtattacttgttttggtaattgtgattttgcttacttttgtggctcaa aatacgactttggacgttatgtttatgcgataggcggaaaattaaagaagcagcagcttactcaggaataaaca tagctaagacgaacatgacgattttcttgattatggggggttttatcggcaattgcaggtatagttttttgacttcaag gttaaatgctgctacaactagtgcaggaaatttgtttgagctggatgctatagcttcggcaattatcggtggaac aagcacgttaggaggagaaggaacagtaccaggagcgattttaggtgctcttattatggctagcatagataat ggcatgagtcttatgaatatagattattctatattgacaattgtaaagggccttgtattagtacttgcagtgtgggt ggatatttcaacaaagaagaggggataa |
| *Clostridium beijerinckii* | atgaaaataaaaatagtaactctgtaatatatatttcgctgcacttagtgggctttttgtttggttatgatactgga gttatttcaggagctatttttatttattcaagaacaaatgcaccttgattcatggcagcaaggatgggItgtaagtt ctgtattattaggagctattcttggggctgcaatcattggtcctatgtctgataaatatggccgtataaagctaatt |

TABLE 4-continued

DNA sequences of xylose transporter genes expressed in
*Thermoanaerobacterium saccharolyticum*

| Organism | Sequence |
|---|---|
| | cttacatcggctgttatcttctttgtcggcgcacttggatcagcatttgctccagaaatttggtcattaattatattta<br>gaatcattcttggtgtcgcagttggtgcatcttcagctctaattccaacttatttagctgaattatcaccatctgaa<br>aaacgtggaaccatatcaagtttgtttcagctaatggttatgagcggaattctattggcttatattacgaattatgc<br>attttcagatttatatactggttggcgagtgatgttagggttcgcagctattccagcagcagttcttttaataggtg<br>cacttgtgttaccagaaagtcctagatttttagtaaaagatggacgagcagatgaagcaagaagtatactaga<br>acatatgaataaacatgataaaggtgctgttaattatgaattagctcaaataaaaaaacaagccgagattaaaa<br>gtggtggagttaaagagctatttagcgaatttgtacgcccggcattagtcataggctttggtttggctgttttttca<br>gcagattatgggttgtaacacagttcttttattatgcaccaactatatttactgatgttggatttggggtgcaagca<br>gctttactcgctcatattggaattggagttttaatataataattactgctatagctgtagctattatggataaaattg<br>atcgtaaaaagatgcttatttatggtgctattggaatgggcgtttcgctcttgattatgagtatttcaatgaaattct<br>ctaatggatctttcgttgcctcaatcatatgtgttattgcattaactatttacattgctttcttttcagctacttgggga<br>cctgtaatgtgggtcatggtaggagaagtatttccattaaatattcgcggcttaggtaattcattcagtagtgtaa<br>ttaattggagtgctaatatgatggtatcattgacatttccagtattattgaattactttggtacaggtagtttgtttata<br>ggtatggtgtaatatgttttgcagcaatttggtttgttcagtctaaggtatttgaaacacgtaatcgttcacttgaa<br>gatatagaagctgaacttagatcatataaaggagtagaaaaactccaaaaggatatctgcactcaagatgcta<br>caactaaggcttag |
| *Clostridium carboxidivorans* | ttataattttattgattggtcagggatttcctctactaactcaaccaaacaattttctttatcattttatgtcttatat<br>ctagttcagccattatatcagctactcttctttctgttaaattatagaatatcatgaatatgagcaatgtaactacaca<br>gacaacagctggcaaaatagatgtcataattaaaattccattcaacgattttgcagtttgagttacattaggaat<br>atatccaacattagctaatatcaatgtaggtataactccccctactgctaatgaaaccttttaatccaagagtaata<br>agtgagtacacaactgcggcatgtcttttgccagtattgtactcagcatactcaactgcatccggaatgattga<br>ccacaaactgcccataagtatgccatagccaaatgcagctactgatttagctatcatcattacttgaatttgtga<br>aactggaatgatatataaactgctgatccaagggcacctaaactcaaaccaagtacaacagttttttttctttttg<br>atatgtctaaaaagcgcaggcacaaaaggaactgccacgactgaaggtaaaacgttcaacatagaaaataa<br>agcaactaaatcttttctatttacgttataagtcatataataaattcctgaagctgattgtatagatgaaaatgcata<br>aacacctacaaacagtaaaaataatatgacacctggctgattatgtgtaatctgattaataaacccttttgaaagt<br>aactggatctaaatgagattttactctgatacgttcatgcaaagtagtataactataaagcaatatggatgcaca<br>aataacagaaagtaaaataatagtcatctgataacctttttgctgaatcacctctgccgaaaacctgtgataaaat<br>aggaataaaatagagcaactattacaccacctgactgagcaaacatcattcttatggaatttagcctagttctctc<br>cataggatctgctgtcatgacagttgtacaagatacatatggattaatgatgaaagtatataatgtaagtagtaa<br>attgtacgtagcatatgcccatatcaatttgcccgtatgtcccaaattgggtactgtaaaagtcaaaatacctgc<br>aagtgcaaaaggaacagctccataaataagataacttttttgtacttaccatgctttggattcattctctctgcaata<br>atacccatggtagggtcccatatcatatcccatcctctagatataagaaacataacagaaacttctgcagcagt<br>taatccataaacatcagtataataaaatgtcaaaaacattaaaattgactgaaaaactaaattcattccaccatct<br>acaagggaatatcccactacttctttggtaggaagtttataaaagccaggattatcaccactttttttcatacaaat<br>ttattgttttttgcctccat |
| *Clostridium acetobutylicum* | atgaataaaaaaatatctccagcactaatttatttctttggagccttcggtggatttatgtttggatatgatattgga<br>ataattaatggtgcttacctggaattaatgcaacttggcacgtaagttcttggttagaaggatttatcacttctgg<br>attgtttgttggagctatgataggagcctcattaatggcttcactagcagataggtttggtcgtcgtagaatgatt<br>atgtggagtgcaattgtgtttgcacttggtgcattaggttctgccgtttctactagtactaatcttttaatcggtgct<br>cgtgttattttaggagtagctgtaggtggagcttctgctttagttccaatgtatatgggagaaattagccctgctg<br>aaaacacgtggaaaactatctggtttaaatcaattaatgataactgttggaatgcttttctcatatggtgtaaatttg<br>cgtttgctggtgcatttgaaggatggcgttggatgctttggaaggagctatggtacctgcaatggtactattaattg<br>gaacatttatacttccagagtcaccaagattttttagctagaataggaaagacagaattagcaaaacaagtactt<br>cagactttacgttcaaaggaagaggcagaaactgaatatcaagagattattaattcaaaacatactgaaacag<br>gttcttttggagatttatttgcaaaacaggctttgccagctgtaattgcaggctgtgggttaacacttcttcaaca<br>aattcaaggtgcaaacactattttctactattcatcacaaattttcatccaatgtttttggatcagcaaatggtggaa<br>ctattagtactgttggaattggtgtggttctagtattagcaactattgtaactttattggttgtagacaattcaaac<br>gtcgtacattatttatgactggttctattggaatgggcgcatctctattattagttggattaatttatccatactctga<br>agctaaacatgcgtgggcaacttggttagtattcttcttcatatgtttatacgttgttttctatgcatactcttgggc<br>agctactacatggattgttgttggagaattattcccaagtaatgttagaggacttgcaacaggtattgcatcagc<br>agtaaactgttttggtaacattttagttgcttttattcttcccagtatttacttgaaactgtaggtttatctgtaatcctct<br>tcggttttgctgcaatttgtatcataggattttttatttgcaaaatatgttctttatgaaacaaaaggaaaatctttaga<br>agaaattgagacatatttgtacaatcgttctattggaaaagttagaggattaaatgagtag |
| *Clostridium acetobutylicum* | atgataggaagttttaaaattaaaatgagggaaaaaataggctatgcatctggagatttagcaagtaacttgat<br>atatcaaaccatttcaatttatttgctattttctatactaacgttttcggcttatctgctggtcaggccggtgtaatgt<br>ttcttgtggtaagatttatcgacgcaattaatgacccaattattggaacttagtcgacaaaaccaatacgcgtttt<br>ggaagatttagaccatacttattatatggagctgctccttttgcagttttagcttttctgtgttttaccactcctaattt<br>ttcagcaacgagataattaatttacgcttatgctacttacgtaggccttttcaattacttatacttgtataaatgttcctt<br>atggtgcattgacatcagctattacagatgataatcaggaaattgttagcttgacctcagtaagaatgtttttgct<br>aatctaggcggtgtaatcgttctacttttgttcctgtactttcggcatatttcacaaaatcatttggtctttcaggtg<br>gttggcaaataactatgagtattctaggtatagcaggtgccttcctattgctattttgttttcaagtactaaggaa<br>agagtaaaaagcgttaaccaagatcataagattaaattctctgatctctttgaacaattcaaaactaatagacct<br>cttattgtattaagtattttctagtactgatatttggaataaattcaattaatagttcaataggcatatattacattacc<br>tataacgttggtcgtgctgacttagtacaatggtatacggtattagggtctctccctgcatttgtttgtataccact<br>aataccaaaaatcaacagaaaaattggaaaaaagcctttattaattagttctctttttaataacagtgcttggtacc<br>ttatctctgttagtaattccaactcatgcagtagcatattagttttctcgtgtgattacatcaataggttcattga<br>ctgccggagcatttatgtggtcattaattccagaaacaattgaatatggtgaatacacaacaggaaaacgttta<br>agcggcttaatttatgctattatcggattctttttcaagtgcggaatggcattaggcggagctgtaccaggaata<br>atactcggtaactttgggtatgtagccaataaaacccaaactcctcatgccctaacgggtatacttctaactgc<br>cacagtcgttcctgccgtactcatgatattagctttaatagatattaccttctacaacttagatgataaaaatata<br>atcatattatagctactttaaaagaaagagctaaattaaatagaggggagaatttaaatttatga |

TABLE 4-continued

DNA sequences of xylose transporter genes expressed in
*Thermoanaerobacterium saccharolyticum*

| Organism | Sequence |
|---|---|
| *Thermoanaerobacterium thermosaccharolyticum* | atgaaaaattttgaaacaacttggaaagaaaggatcagttatgggcttagacactgcttctaatttagtttatc<br>agatgattaccacttatttaatgttttttttacactgatgttttttggaataagtgctgcagctgtcggaacacttttttta<br>gtagcaaggatcatcgacgcatttgatggaccattttttggcattctaatagatcatacaaatacaaagtgggg<br>aaaatgcagaccatacttttctttggttatcaattccatatggagtattagcaatactagcatttacgactccaagtt<br>ttaatgcttctggtaaattaatttatgcttatgttacatatattcttttaggaattatctactctggaattaatatacca<br>attcatcaattttaccgagtttaacagataatttagaagaaagaaatatattggttagtaccagaatgattttagct<br>acagttggtgctacgattgtcagtgtaggaacgttgcctctagttaaagtattcggcaatggtaatcagcaaaa<br>aggctttatgatgactatgactttgtttgctgtgttagctgttatattattcctagtaacctttttcaatactagagaa<br>aaagtaaacgaagcaaaagatcaatcaattacttttaaaagaagaactaaaagcattgaaaggaaatactcctt<br>ggtttatacttttctttgtagcttttataaatttcatagctttttataatgaaagctcaaacgacagtttattatttgaca<br>tataatttaaagatgcctaacttaatcagtatagctttaggattaggctcactgaatgttgtttcattacttatcatgc<br>catttttagcaaagaaaataggaaaaagaaatgtcatgattacgggatttacttttttcaatattagcacaatttata<br>ttgtatttatcatcattgacatcaagtgcatttatattttagtaggcactgtaattgcagcttttggaaatggatttgt<br>tatgggagcaatgttttctatgacagcagatacagttgactacggtgagtggaaatcgggtgttagagctcaa<br>ggacttctttcagctacaccagcttttggggtcaaagcaggaatgggaataggtggggcttagcaggttgg<br>atattatcaattggtaaatatgttccagatcatccgcaaaccttatccgcattaaaagcgatagaaattaactttat<br>ttggctaccgttaattggttttattatcagtgctgtattacttctattctataatttagataaacaacaagaacagatg<br>actaaagaattaaatgaaagaagagctaagttaagcgcatga |
| *Thermodesulfobium narugense* | atggttgagaaaaatttagacgaactaaaactaagcaagcaccacttaaaagcgatgtttgtttcaggaatgg<br>ggttttttactgatgcatatgatctcttcattattggtgtagctttatctttaattgctccggtgtgggacttacaag<br>ttcagaaattgcactccttggtagtagttctctttggctgctttgtttggttcgatttttttttggtagatttgcagata<br>atttggtagaaagaagatttatggtttagaagctctgataatgacaattggcgctttaatgtcagcattttcgcc<br>aaaatttgtttcttctcttctcaagattcattttgggtttaggcattggtggagattatcctgttagtgctgttattat<br>gagtgaatattcaaatagatctgatcgagggaaattggtgggttagttttttctatgcaagcacttggtcttataa<br>ttggtcctcttgttgccttaagcttattattgttacacattccacttgactttgcatggcgtttaatgcttgggttagg<br>agcgcttccttcvacttatggttatttatttaaggagaaaattaccagaatctcctcgctatctttcacaaatagttg<br>gcgataaaaaagcagcttttaactgcttttgtaaattttactggtaatggtaataagagctatgaaccgatacattt<br>aaatccgaaaattaatcataggttaaaagatttttttttcaaacaaacaacatactttgacttttatttgggacagctg<br>gtagctggttttgcttgattgggcttattatggtaacacaattctactccaattgtaatgaatgcaatttgtgata<br>gttcttcttagaactgaagatgatttattctcttgtaatatttgttgttttcgctttaccaggatatattttatcaataa<br>tatttatggatataattggaagaaaatatattcagcttatgggtttggcattatggcattttcatttttattattaggat<br>taataccgatatagaaagtaatgttacaggattttcttatactttatgggcttagctatctttttactgagtttggacc<br>taatactaccacttttgtccttccctcagagcttttcccaaccgaatataggacaacaggtcatggcttgtctgca<br>ggaattgggaaacttggagctttttggagtgttattttttccctattaccgagtcttttttgggactaaatatgaca<br>tttgttattgtttcgattatatgttttatgggaattataaccacgtctgttctgactgaaccaagggaaagagcct<br>cgaagactgttcgtattctaaaatagtaggcaaataa |

TABLE 5

Protein sequences of xylose transporters expressed in
*Thermoanaerobacterium saccharolyticum*

| Organism | Sequence |
|---|---|
| *Thermoanaerobacterium thermosaccharolyticum* | mgknakkallsvililsmlftfsacattnpnqsksnnqttntsdnsgkikigfsfdtlnlerwqhdrdyf<br>vqrakelgadvlvqsansdsqtqysqcqnliaqgikvlviiphdgsaiapiveeahkagvkvlaydrlim<br>nadvdayvsfdnekvgelqaeaitklvpkgnyfllegsptdnnaklfeqqkkvlqplvdkgdikivge<br>qwaqdwltqnaynimqnaltannnkidavvdandstalgairalqeqnlagkvaisgqdadlancqliv<br>egkqsmtvykpvkeeatkgadvavalakgedinangkvnngkidvpsvlltpvavdknnmvdtiik<br>dgfhsldevyknvpkdqwpkq |
| *Thermoanaerobacterium thermosaccharolyticum* | mdmgdfilemknitkdfsgvkaldnvnlkvkkgeihglcgengagkstlmkilsgvypygtfsgeiif<br>dgkelklnnikdaedagigiiyqelslvkelsvsenifignepnkngiidfdrmyyetkilldklnlninpn<br>vpvknlgigqqqlveiakalsknvsllildeptssltdadveilfnilrqlkdngvtciyishklnevmeitdr<br>itvqrdgktigsedtknlteseiikmmvgreltnlfpkeehqigkeilevknfsvydsksssskivdnvsft<br>lkegeilgiagligagrtelvssifgsypgrhegeiylegkkinirnpdealdygiamvpedrkgqglinils<br>vrdnmtlsniesyknnfgsvdvnkeivdvkkyiemlkikvshfdlavknlsggnqqkvvlaknllrnp<br>kilildeptrgidvgakyeiykliyelvksgisiimvsselpeiiglsdrivvmhegkkkgefvnkdvtqe<br>mimqcaiggk |
| *Thermoanaerobacterium thermosaccharolyticum* | mvnskgfkennvsinkkfsfnlklytmiialvgiwiifaiatkgdfltsrnmsnlfrqmvstavlaigmv<br>fviiagqidlsvgsllgltggiaaianvwfhingilsiiialaiglilgtwngwvvayknvpsfivtlagmlv<br>frgiligitngytiaplssdfqfigqayltpvsgyllgiivllvgaytiysqrkskikyglevspfyldiakiilm<br>ivliglfvftlnsyngipfsvlilailvaiftyiasktvfgrrvyalggnieaaklsginvkkitlilfaingllaav<br>sgvvltstlnagstsagqnaemdaiascviggaslmggvgsvigaiigalvmasinngmsllnsapfwq<br>yvvkglillllavyvdvasknke |
| *Thermoanaerobacter mathranii* | mvkskkllafflvlmiltlsvvlagctssktnettnttssngssstetkkikigfslptmreeryqrdrdafvee<br>aeklgaevlvqganndenlqnsqvenlitqgidvlvldpqnaasaatlvekahqagikvisydrlilnsep<br>dvyisfdnervgelqgefltklvpkgtyfifagaptdnnatlfkkgamkyiqplvdkgdikiafdqaikd |

TABLE 5-continued

Protein sequences of xylose transporters expressed in
*Thermoanaerobacterium saccharolyticum*

| Organism | Sequence |
| --- | --- |
| | wdpnealklaenaltanknkvdailapndgtaggiiqalaeqklagkvpitgqdaelaavkrivegtqsm<br>tvfkdvrvlarkaaqiavmlaqgkevkdipeinktvnnqkidvpsllltpvvitkdnidkelidsgwftre<br>qvygk |
| *Thermoanaerobacter ethanolicus* | mseyilemrnitkefpgvkaldnvnfkvkrgeihalvgengagkstlmkilsgvypygtykgdiiidge<br>vkqfrnikdseksgiaiiyqeltlvkymtvgeniflgeepvkggiidwmkvysetyrllkelqinvnpyt<br>kvmnlgighqqmveiakalskkarilildeptsaltesetehllnilkdlkkngvtciyishklnevfeiads<br>itvlrdgktimtdkkenftenkvislmvgreltqrfprakhtpgevvfevknytvydheipgkkiidnvsf<br>karrgeilgiaglmgagrtelaasifgafkgrkegeiylngkkieintpsdaikhgiaylsedrkrfglvtlm<br>dvqenialpnydrlskfsiinnnakikhaekyvkelkiktptirqrvanlsggnqqkvviakwlmsdpk<br>vlildeptrgidvgakfeiynlmnklvdmgvcvimisselpeilgmsdrilvihegkingefpieeadqe<br>kimycatggk |
| *Thermoanaerobacter ethanolicus* | mmeskvskttekrilnhfkidirsytmilallgiwiifsilthgdflsprnlsmlarqmsitailasgmvlvi<br>vaghidlsvgsvagftgaiaailqviyhwdtvptiivtlmaglaigvwqgfwiayrkvpafivtlssmlvf<br>rggillitkgvtisplkqdftvvgqgyipplfsvilavvagvlyvimdlknrnsrikyglsvsswgielakia<br>gvlifialftsvmisyegipvpvllvlvivilltfvaqnttfgryvyaiggnkeaaaysginiaktnmtiflim<br>gvlsaiagivltsrlnaattsagnlfeldaiasaiiggtstlggegtvpgailgalimasidngmslmnidysil<br>tivkglvlvlavwvdistkkrg |
| *Clostridium beijerinckii* | mkikisnsviyifaalsgllfgydtgvisgailfiqeqmhldswqqgwvvssvllgailgaaiigpmsdk<br>ygrikliltsaviffvgalgsafapeiwsliifriilgvavgassaliptylaelspsekrgtisslfqlmvmsgil<br>layitnyafsdlytgwrvmlgfaaipaavlligalvlpesprflvkdgradearsilehmnkhdkgavnye<br>laqikkqaeiksggvkelfsefvrpalvigfglavfqqimgcntvlyyaptiftdvgfgvqaallahigigv<br>fniiitaiavaimdkidrkkmliygaigmgvsllimsismkfsngsfvasiicvialtiyiaffsatwgpv<br>mwvmvgevfplnirglgnsfssvinwsanmmvsltfpvllnyfgtgslfigygvicfaaiwfvqskvf<br>etrnrsledieaelrsykgveklqkdictqdattka |
| *Clostridium carboxidivorans* | meaktinlyeksgdnpgfyklptkevvgyslvdggmnlvfqsilmfltfyytdvygltaaevsvmflis<br>rgwdmiwdptmgiiaermnpkhgkyksyliygavpfalagiltftvpnlghtgkliwayatynllltlyt<br>fiinpyvscttvmtadpmetrlnsirmmfaqsggvivalfipilsqvfgrgdsakgyqmtiillsvicasil<br>lysyttlherirvkshldpvtfkgfinqithnqpgvilflffvgvyafssiqsasgiyymtynvnrkdlvalfs<br>mlnvlpsvvavpfvpalfrhikkkktvvlglslgalgsaalyiipvsqitvmmiaksvaafgygilmgsl<br>wsiipdaveyaeyntgkrhaavvyslitlglkvslavggviptlilanvgyipnvtqtakslngilimtsilp<br>avvevvtllifmifynlteervadimaeldirhkndkenclvelveeipdqsikl |
| *Clostridium acetobutylicum* | mnkkispaliyffgafggfmfgydigiingalpginatwhvsswlegfitsglfvgamigaslmasladr<br>fgrrrmimwsaivfalgalgsavststnlligarvilgvavggasalvpmymgeispaetrgklsglnql<br>mitvgmlfsygvnfafagafegwrwmlggamvpamvlligtfilpesprflarigktelakqvlqtlrsk<br>eeaeteyqeiinskhtetgsfgdlfakqalpaviagcgltllqqiqgantifyyssqilsnvfgsanggtistv<br>gigvvlvlativtlllvvdkfkrrtlfmtgsigmgaslllvgliypyseakhawatwlvffficlyvvfyays<br>waattwivvgelfpsnvrglatgiasavnwfgnilvalffpvlletvglsviffgfaaiciigf<br>lfakyvlyetkgksleeietylynrsigkvrglne |
| *Clostridium acetobutylicum* | migsfkikmrekigyasgdlasnliyqtisiyllffytnvfglsagqagvmflvvrfidaindpiigtlvdkt<br>ntrfgrfrpyllygaapfavlaflcftttpnfsatgkliyayvtyvglsitytcinvpygaltsaitddnqeivslt<br>svrmffanlggvivsyfvpvlsayftksfglsggwqitmsilgiagaflllfcfsstkervksvnqdhkikfs<br>dlfeqfktnrplivlsiffvlifginsinssigiyyitynvgradlvqwytvlgslpafvciplipkinrkigkk<br>pllissllitvlgtlsllviptthavalilvsrvitsigsltagafmwslipetieygeyttgkrlsgliyaiigfffkc<br>gmalggavpgiilgnfgyvanktqtphalgillltatvvpavlmilaliditfynlddkkynhiiatlkerak<br>lnrgenlnl |
| *Thermoanaerobacterium thermosaccharolyticum* | mknfettwkerisyglsdtasnlvyqmittylmffytdvfgisaaavgtlflvariidafdgpffgilidhtn<br>tkwgkerpyflwlsipygvlailafttpsfnasgkliyayvtyillgiiysginipitsilpsltdnleernilvst<br>rmilatvgativsvgtlplvkvfgngnqqkgfmmtmtlfavlavilflvtffntrekvneakdqsitlkeel<br>kalkgntpwfilffvafinfiafimkaqttvyyltynlkmpnlisialglgslnvvsllimpflakkigkrnv<br>mitgftfsilaqfilylssltssafiflvgtviaafgngfvmgamfsmtadtvdygewksgvraqgllsatpa<br>fgvkagmgiggalagwilsigkyvpdhpqtlsalkaieinfiwlpligfiisavllllfynldkqqeqmtkel<br>nerraklsa |
| *Thermodesulfobium narugense* | mveknldelklskhhlkamfvsgmgfftdaydlfiigvalsliapvwgltsseiallgssslllaalfgsiffg<br>rfadnfgrkkiyglealimtigalmsafspnflfllfsrfilglgiggdypvsavimseysnrsdrgklvglv<br>fsmqalgliigplvalslllhipldfawrlmlglgalpslmviylrrklpesprylsqivgdkkaaltafvnft<br>gngnksyepihlnpkinhrlkdffsnkqhtltlfgtagswflldwayygntistpivmnaicdssslelkm<br>iyslvifvvfalpgyilsiifmdiigrkyiqlmgfgimafsflllglipdiesnvtgflilyglsylftefgpnttt<br>fvlpselfpteyrttghglsagigklgaffgvlffpitesflglnmtfvivsiicfmgiittsvltepkgksledc<br>syskivgk |

In certain embodiments of the invention, the xylose metabolizing enzyme can be a xylose isomerase, xylulokinase, xylose reductase, xylose dehydrogenase, xylitol dehydrogenase, xylonate dehydratase, a transketolase, and a transaldolase paralog or ortholog. In one particular embodiment, the xylose metabolizing enzyme comprises an amino acid sequence selected from SEQ ID NOs: 3-4. In certain other embodiments, the xylose metabolizing enzyme comprises an amino acid sequence that is at least about 70, about 80, about 90, about 95, about 96, about 97, about 98, about 99, or 100% identical to an amino acid sequence selected from SEQ ID NOs: 3-4. In another embodiment, the source organism for the xylose isomerase includes, but is not limited to, *Ciona intestinalis*, *Thermus thermophilus*, *Escherichia coli* K-12, *Cereus pterogonus*, *Streptonyces corchorusii*, *Thermus caldophilus*, *Arthrobacter nicotinae*, *Pectobacterium atrosepticum*, *Bacillus licheniformis*, *Thermoanaerobacterium thermosulurigenes*, *Thermotoga naepolitana*, *Lactococcus lactis*, *Actinoplanes nmissouriensis*, *Thermoanaerobacterium saccharolvticum*, *Hordeum vulgare*, *Bifidobacterium adloescentis*, *Bacillus sp.*, *Thermus aquaticus*, *Streptomyces violaceoruber*, *Geobacillus stearothermophilus*, *Streptomyces olivochromogenes*, *Streptomyces albus*, and *Caldicellulosiruptor* sp.

In another embodiment, the source organism for the xylulokinase includes, but is not limited to *Pinchia angusta*, *Arabidopsis thaliana*, *Geobacillus caldoxylosilyticus*, *Schef fersomyces stiptis*, *Lactobacillus pentosus*, and *Caldicellulosiruptor* sp.

As a practical matter, whether any polypeptide is at least 70%, 80%, 85%, 90%, 95%, 96%, 97%, 98%, 99% or 100% identical to a polypeptide of the present invention can be determined conventionally using known computer programs. Methods for determining percent identity, as discussed in more detail below in relation to polynucleotide identity, are also relevant for evaluating polypeptide sequence identity.

In some particular embodiments of the invention, amino acid and nucleic acid sequences are readily determined for a gene, protein or other element by a accession number upon consulting the proper database, for example Genebank. However, sequences for the genes and proteins of the present invention are also disclosed herein (SEQ ID NOs: 1-4). See Table 6 and Table 7 below.

TABLE 6

DNA sequence of xylose isomerase and xylulokinase of
*Thermoanaerobacterium saccharolyticum*

| Gene | DNA sequence |
| --- | --- |
| Xylose isomerase | atgaataaatatttgagaacgtatctaaaataaaatatgaaggaccaaaatcaaacaatccttattcttttaa<br>attttacaatccagaagaagtaatcgatggcaagacgatggaggagcatctacgcttttctatagcttactg<br>gcacacttttactgctgatggaacagatcaatttggcaaagctaccatgcaaagaccatggaaccactac<br>acagatcctatggacatagcaaaggcaagggtagaagcagcatttgagtttttgataagataaatgcacc<br>tttcttctgcttccatgacagggatattgcacctgaaggagacactcttagagagacaaacaaaaacttag<br>atacaatagttgccatgataaaggattacttgaagaccagcaagacgaaagttttgtggggcaccgcaaa<br>tctttctccaatccgagatttgtacatggtgcatcaacatcctgcaatgctgatgttttcgcatattctgcagc<br>tcaagttaaaaaagctcttgagattactaaggagcttggcggcgaaaactacgtattctggggtggcaga<br>gaaggatatgaaacacttctcaatacagacatggagtttgagcttgacaactttgcaagattttttgcacatg<br>gctgttgactacgcgaaggaaatcggctttgaaggccagttcttgattgagccgaagccaaaggagcct<br>acgaaacaccaatacgactttgacgtggcaaatgtattggcattcttgagaaaatacggccttgacaaata<br>tttcaaagtgaatatcgaggcaaaccatgcgacattggcattccacgacttccaacatgagctaagatacg<br>ccagaataaacggtgtattaggatcaattgacgcaaatacaggcgatatgcttttaggatgggatacaga<br>ccagttccctacagatatacgcatgacaacgcttgctatgtatgaagtcataaagatgggtggatttgaca<br>aaggcggccttaacttcgatgcaaaagtaagacgtgcttcatttgaaccagaagatcttttcttaggtcatat<br>agccggaatggatgcctttgcaaaaggcttcaaagttgcttacaaacttgtgaaagatggcgtatttgaca<br>agttcatcgaggaaagatacgcaagctacaaagacggcattggcgctgacattgtaagcgggaaagct<br>gacttcaagagccttgaaaagtacgcattagagcacagccagattgtcaacaaatcaggcaggcaaga<br>gctgttagaatcaatcctaaatcagtatttgtttgcagaataatga |
| Xylulokinase | atgtatttttagggatagatttagggacatcatcagttaagataatactgatgaatgaaagcggcaatgtgg<br>tatcaagcgtttcaaaagaatatcctgtgtactatccagagccaggctgggctgagcaaaatccagaaga<br>ttggtggaatggcacaagggatggaataagagagattattgcgaaaagcggcgtaaatggcgatgaaat<br>aaagggtgttggcttaagcgggcagatgcatggactggtgcttttagacaaagacaataacgttttaacg<br>ccagccatactttggtgtgaccagaggacacaggaagaatgcgactacatcacagagaaaataggaaa<br>agaaggccttttgaagtacacagggaataaagcattgacaggttttactgcaccaaagatattatgggtaa<br>agaagcaccttaaagacgtatatgaaagaatcgctcatatccttttgccaaaagattatataaggtttaaatt<br>gacaggtgagtacgctacagaagtttcagatgcatcaggtacacttcttttcgatgtggaaaatagaagat<br>ggtcaaaggaaatgatagacatatttgaaataccggaaaaagcccttcctaagtgctacgaatcaacaga<br>tgtcacagggtatgtcaccaaagaggcagcagatttgacagggcttcatgaagggactattgtcgtaggc<br>ggtggtggtgaccaagccagcggcgctgtaggcactggcacggtgaaaagcggcatagtgtccatcg<br>cattaggaacttcaggcgtcgtatttgcatcacaggacaagtacgcagcagatgatgagcttaggcttca<br>ctcattctgccatgcaaacggcaaatggcatgtgatgggtgtcatgctttcggctgcatcatgtcttaaatg<br>gtgggtagatgatgtaaataattacaagaccgatgttatgacatttgatggactcttagaagaagcagaga<br>aggtgaagccaggcagtgatggattgatattcttgccatacctgatgggtgaaaggacccttacagcga<br>tccttatgcgagaggcagctttgtaggtttaacaattacacacaatagaagccacatgacaagatctatatt<br>agaaggcgtcgcatttggacttagggattcgctggagcttataaaggctttaaatatacctgtaaatgaag<br>ccagggtaagtggtggtggtgctaaaagcaggcttttggaggcaaatacttgccgatgtattcaatgtaag<br>gatagacatgataaatgctacagaaggaccttcatttggtgcagcaataatggcgtctgtgggatatggcc<br>tttacaaaaatgtagatgatgcatgcaatagtttaataaaagttacagacagcgtatatccaatcaaagaaa<br>acgtcgaaaagtacaacaaactgtatccaatctacgtgagcttgtattcaaggcttaaaggcgcctttgaa<br>gaaattgggaagttggatttgtaa |

TABLE 7

Protein sequence of xylose isomerase and xylulokinase of
*Thermoanaerobacterium saccharolyticum*

| Gene | Protein sequence |
|---|---|
| Xylose isomerase | mnkyfenvskikyegpksnnpysfkfynpecvidgktmeehlrfsiaywhtftadgtdqfgkatmqr pwnhytdpmdiakarveaafeffdkinapffefhdrdiapegdtlretnknldtivamikdylktsktk vlwgtanlfsnprfvhgastscnadvfaysaaqvkkaleitkelggenyvfwggregyetllntdmefe ldnfarflhmavdyakeigfegqfliepkpkeptkhqydfdvanvlaftrkygldkyfkvnieanhatl afhdfqhelryaringvlgsidantgdmllgwdtdqfptdirmttlamyevikmggfdkgglnfdakv rrasfepedlflghiagmdafakgfkvayklvkdgvfdkfieeryasykdgigadivsgkadfksleky alehsqivnksgrqellesilnqylfae |
| Xylulokinase | myflgidlgtssvkiilmnesgnvvssvskeypvyypepgwaeqnpedwwngtrdgireiiaksgv ngdeikgvglsgqmhglvlldkdnnvltpailwcdqrtqeecdyitekigkegllkytgnkaltgftapk ilwvkkhlkdvyeriahillpkdyirfkltgeyatevsdasgtllfdvenrrwskemidifeipekalpkc yestdvtgyvtkeaadltglhegtivvggggdqasgavgtgtvksgivsialgtsgvvfasqdkyaadd elrlhsfchangkwhvmgvmlsaasclkwwvddynnyktdvmtfdglleeaekvkpgsdgliflp ylmgertpysdpyargsfvgltithnrshmtrsilegvafglrdslelikalnipvnearvsgggaksrlwr qiladvfnvridminategpsfgaaimasvgyglyknvddacnslikvtdsvypikenvekynklypi yvslysrlkgafeeigkldl |

Some embodiments of the invention encompass a polypeptide comprising at least 10, 20, 30, 40, 50, 60, 70, 80, 90, 100, 200, 300, 400, or 500 or more consecutive amino acids of any of SEQ ID NOs: 3-4, or domains, fragments, variants, or derivatives.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%. 99% similar to the polypeptide of any of SEQ ID NOs: 3-4 and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 3-4.

Fragments or portions of the polypeptides of the present invention can be employed for producing the corresponding full-length polypeptide by peptide synthesis. Therefore, the fragments can be employed as intermediates for producing the full-length polypeptides.

Fragments of xylose metabolizing enzymes of the invention encompass domains, proteolytic fragments, deletion fragments and fragments of any of the genes which retain any specific biological activity of the xylose isomerase, xylulokinase, xylose reductase, xylose dehydrogenase, xylitol dehydrogenase, xylonate dehydratase, transketolase, and transaldolase proteins. Polypeptide fragments further include any portion of the polypeptide which retains a catalytic activity of the xylose isomerase, xylulokinase, xylose reductase, xylose dehydrogenase, xylitol dehydrogenase, xylonate dehydratase, transketolase, and transaldolase proteins.

Fragments of xylanases of the invention encompass domains, proteolytic fragments, deletion fragments and fragments of any of the genes which retain any specific biological activity of xylanases. Polypeptide fragments further include any portion of the polypeptide which retains a catalytic activity of xylanases.

The variant, derivative or analog of the polypeptide of xylose metabolizing enzymes or xylanases of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the xylose metabolizing enzymes of the invention. The allelic variants, the conservative substitution variants, and members of the xylose metabolizing enzymes can have an amino acid sequence having at least 75%, at least 80%, at least 90%, at least 95% amino acid sequence identity with the xylose metabolizing enzymes of the invention, and, particularly, with the amino acid sequence set forth in any one of SEQ ID NOs: 3-4. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, in one aspect the proteins and peptides of the present invention include molecules comprising the amino acid sequence of SEQ ID NOs: 3-4 or fragments thereof having a consecutive sequence of at least about 3, 4, 5, 6, 10, 15, 20, 25, 30, 35 or more amino acid residues of the xylose isomerase, xylulokinase, xylose reductase, xylose dehydrogenase, xylitol dehydrogenase, xylonate dehydratase, transketolase, or transaldolase polypeptide sequences; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to bacterial, fungal, insect, rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the polypeptides encoding the xylose metabolizing enzymes. For instance, one or more amino acids can be deleted from the N-terminus or C-terminus of the secreted protein without substantial loss of biological function.

Thus, in another aspect the invention further includes xylose isomerase, xylulokinase, xylose reductase, xylose dehydrogenase, xylitol dehydrogenase, xylonate dehydratase, transketolase, and transaldolase polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala. Val, Leu and lie; replacement of the hydroxyl residues Ser and Thr; replacement of the acidic residues Asp and Glu; replacement of the amide residues Asn and Gin, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the xylose metabolizing enzymes of the invention, but retaining essential properties thereof. Generally, derivatives and analogs are overall closely similar, and, in many regions, identical to the xylose metabolizing enzymes of the invention. The terms "derivative" and "analog" when referring to xylose isomerase, xylulokinase, xylose reductase, xylose dehydrogenase, xylitol dehydrogenase, xylonate dehydratase, transketolase, and transaldolase polypeptides include any polypeptides which retain at least some of the activity of the corresponding native polypeptide, e.g., the xylose isomerase activity, or the activity of the its catalytic domain.

Derivatives of the xylose metabolizing enzymes disclosed herein, are polypeptides which have been altered so as to exhibit features not found on the native polypeptide. Derivatives can be covalently modified by substitution, chemical, enzymatic, or other appropriate means with a moiety other than a naturally occurring amino acid (e.g., a detectable moiety such as an enzyme or radioisotope). Examples of derivatives include fusion proteins.

An "analog" is another form of a xylose isomerase, xylulokinase, xylose reductase, xylose dehydrogenase, xylitol dehydrogenase, xylonate dehydratase, transketolase, and transaldolase polypeptide of the present invention. An analog also retains substantially the same biological function or activity as the polypeptide of interest, e.g., functions as a xylose isomerase. An analog includes a proprotein which can be activated by cleavage of the proprotein portion to produce an active mature polypeptide.

The polypeptide of the present invention may be a recombinant polypeptide, a natural polypeptide or a synthetic polypeptide. In some particular embodiments, the polypeptide is a recombinant polypeptide.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-2, or other xylose metabolizing enzymes using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homolog.

Combinations of Xylose Metabolizing Enzymes or Xylanases

In some embodiments of the present invention, the host cell expresses a combination of heterologous xylose metabolizing enzymes. In other embodiments, the host cell expresses a combination of heterologous xylanases. For example, the host cell can contain at least two heterologous xylose metabolizing enzymes or at least two heterologous xylanases, at least three heterologous xylose metabolizing enzymes or at least three heterologous xylanases, at least four heterologous xylose metabolizing enzymes or at least four heterologous xylanases, at least five heterologous xylose metabolizing enzymes or at least five heterologous xylanases, at least six heterologous xylose metabolizing enzymes or at least six heterologous xylanases, at least seven heterologous xylose metabolizing enzymes or at least seven heterologous xylanases, or at least eight heterologous xylose metabolizing enzymes or at least eight heterologous xylanases. The heterologous xylose metabolizing enzymes in the host cell can be from the same or from different species. In one embodiment, the one or more heterologous xylose metabolizing enzymes are contained in an operon. The heterologous xylanases in the host cell can be from the same or from different species.

Fusion Proteins Comprising Xylose Metabolizing Enzymes or Xylanases

The present invention also encompasses fusion proteins. For example, the fusion proteins can be a fusion of a heterologous xylose metabolizing enzyme and a second peptide. The heterologous xylose metabolizing enzyme and the second peptide can be fused directly or indirectly, for example, through a linker sequence. The fusion protein can comprise for example, a second peptide that is N-terminal to the heterologous xylose metabolizing enzyme and/or a second peptide that is C-terminal to the heterologous xylose metabolizing enzyme. Thus, in certain embodiments, the polypeptide of the present invention comprises a first polypeptide and a second polypeptide, wherein the first polypeptide comprises a heterologous xylose metabolizing enzyme.

In other embodiments, the fusion proteins can be a fusion of a heterologous xylanase and a second peptide. The heterologous xylanase and the second peptide can be fused directly or indirectly, for example, through a linker sequence. The fusion protein can comprise for example, a second peptide that is N-terminal to the heterologous xylanase and/or a second peptide that is C-terminal to the heterologous xylanase. Thus, in certain embodiments, the polypeptide of the present invention comprises a first polypeptide and a second polypeptide, wherein the first polypeptide comprises a heterologous xylanase.

According to one aspect of the present invention, the fusion protein can comprise a first and second polypeptide wherein the first polypeptide comprises a heterologous xylose metabolizing enzyme or a xylanase, and the second polypeptide comprises a signal sequence. According to another embodiment, the fusion protein can comprise a first and second polypeptide, wherein the first polypeptide comprises a heterologous xylose metabolizing enzyme or a xylanase, and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, or a MYC-tag.

According to another embodiment, the fusion protein can comprise a first and second polypeptide, wherein the first polypeptide comprises a heterologous xylose metabolizing enzyme or a xylanase, and the second polypeptide comprises a fluorescent protein. In one aspect, the fluorescent protein is used to detect the heterologous xylose metabolizing enzyme fusion protein or the heterologous xylanase fusion protein.

According to yet another embodiment, the fusion protein can comprise a first and second polypeptide, wherein the first polypeptide comprises a heterologous xylose metabolizing enzyme or a xylanase, and the second polypeptide comprises an anchoring peptide.

According to still another embodiment, the fusion protein can comprise a first and second polypeptide, wherein the first polypeptide comprises a heterologous xylose metabolizing enzyme or a xylanase, and the second polypeptide comprises a cellulose binding module (CBM).

In certain other embodiments, the first polypeptide and the second polypeptide are fused via a linker sequence. The linker sequence can, in some embodiments, be encoded by a codon-optimized polynucleotide. (Codon-optimized polynucleotides are described in more detail below).

Co-Cultures

In another aspect, the present invention is directed to co-cultures comprising at least two host cells wherein the at least two host cells each comprise one or more isolated polynucleotides encoding one or more xylose metabolizing enzymes. In one embodiment, the co-culture can comprise two or more strains of host cells and the heterologous xylose metabolizing enzymes can be expressed in any combination in the two or more strains of host cells. In one aspect, the at least two host cells express the same xylose metabolizing enzyme. In another aspect, the at least two host cell express different xylose metabolizing enzymes. In yet another aspect, the at least two host cell express at least one common xylose metabolizing enzyme. In one aspect, the xylose metabolizing enzymes are heterologous xylose metabolizing enzymes. In one embodiment, one of the host cells is a *Clostridium* host cell. In one aspect, one of the host cells is a recombinant *Clostridiunm thermocellum* host cell.

In other aspects, the present invention is directed to co-cultures comprising at least two host cells wherein the at least two host cells each comprise one or more isolated polynucleotides encoding one or more xylanases. In one embodiment, the co-culture can comprise two or more strains of host cells and the heterologous xylanases can be expressed in any combination in the two or more strains of host cells. In one aspect, the at least two host cells express the same xylanase. In another aspect, the at least two host cell express different xylanase. In yet another aspect, the at least two host cell express at least one common xylanase. In one aspect, the xylanases are heterologous xylanases. In one embodiment, one of the host cells is a *Clostridium* host cell. In one aspect, one of the host cells is a recombinant *Clostridium thermocellum* host cell.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells may be present in equal or unequal numbers.

Polynucleotides Encoding Heterologous Xylose Metabolizing Enzymes or Heterologous Xylanases In another aspect, the present invention includes isolated polynucleotides encoding xylose metabolizing enzymes or xylanases of the present invention. The polynucleotides can encode a xylose isomerase, xylulokinase, xylose reductase, xylose dehydrogenase, xylitol dehydrogenase, xylonate dehydratase, a transketolase, and a transaldolase.

The present invention also encompasses an isolated polynucleotide comprising a nucleic acid that is at least about 70%, 75%, or at least about 80% identical, at least about 90% to about 95% identical, or at least about 96%, 97%, 98%, 99% or 100% identical to a nucleic acid encoding a xylose isomerase, xylulokinase, xylose reductase, xylose dehydrogenase, xylitol dehydrogenase, xylonate dehydratase, a transketolase, and a transaldolase. The present invention further encompasses an isolated polynucleotide comprising a nucleic acid that is at least about 70%, 75%, or at least about 80% identical, at least about 90% to about 95% identical, or at least about 96%, 97%, 98%, 99% or 100% identical to a nucleic acid encoding a xylanase.

The present invention also encompasses variants of the xylose metabolizing enzyme genes or xylanase genes. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments xylose isomerase, xylulokinase, xylose reductase, xylose dehydrogenase, xylitol dehydrogenase, xylonate dehydratase, transketolase, and transaldolase polynucleotide variants can be produced for a variety of reasons, e.g., to optimize codon expression for a particular host. In other embodiments, xylanase polynucleotide variants can be produced for a variety of reasons, e.g., to optimize codon expression for a particular host. Codon-optimized polynucleotides of the present invention are discussed further below.

The present invention also encompasses an isolated polynucleotide encoding a fusion protein. In further embodiments, the first and second polynucleotides are in the same orientation, or the second polynucleotide is in the reverse orientation of the first polynucleotide. In additional embodiments, the first polynucleotide encodes a polypeptide that is either N-terminal or C-terminal to the polypeptide encoded by the second polynucleotide. In certain other embodiments, the first polynucleotide and/or the second polynucleotide are encoded by codon-optimized polynucleotides, for example, polynucleotides codon-optimized for *Clostridium thermocellum*.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-2, or other xylose metabolizing enzymes using information from the sequences disclosed herein or the clones deposited with the ATCC or otherwise publically available. For example, allelic variants and/or species homologs may be isolated and identified by making suitable probes or primers from the sequences provided herein and screening a suitable nucleic acid source for allelic variants and/or the desired homolog. Procedures known in the art can also be used to obtain full-length genes, allelic variants, splice variants, full-length coding portions, orthologs, and/or species homologs of genes corresponding to any xylanases using information from the sequences disclosed herein or the clones deposited with the ATCC or otherwise publically available.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. In one embodiment, the query sequence may be an entire sequence shown of any of SEQ ID NOs: 1-2, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs: 1-2, or domains, fragments, variants, or derivatives thereof. Other embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of known xylanases or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded can be the coding strand or non-coding (anti-sense) strand. In one embodiment, the coding sequence which encodes the mature polypeptide can be identical to the coding sequence encoding SEQ ID NO: 3-4, or may be a different coding sequence which coding sequence, as a result of the redundancy or degeneracy of the genetic code, encodes the same mature polypeptide as the nucleic acid sequences of any one of SEQ ID NOs: 3-4. In another embodiment, the coding sequence which encodes the mature polypeptide can be identical to the coding sequence encoding a known xylanase, or may be a different coding sequence which coding sequence, as a result of the redundancy or degeneracy of the genetic code, encodes the same mature xylanase.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 1-2. In other embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of a known xylanase.

The polynucleotide encoding for the mature polypeptide of SEQ ID NOs: 3-4 may include: only the coding sequence for the mature polypeptide; the coding sequence of any domain of the mature polypeptide; and the coding sequence for the mature polypeptide (or domain-encoding sequence) together with non coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

Due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs: 1-2, or fragments thereof, will encode polypeptides having functional activity. In fact, since degenerate variants of any of these nucleotide sequences encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having functional activity.

The polynucleotides of the present invention also comprise nucleic acids encoding xylose metabolizing enzyme or domain, fragment, variant, or derivative thereof, fused to a polynucleotide encoding a marker sequence which allows for detection of the polynucleotide of the present invention. In one embodiment of the invention, expression of the marker is independent from expression of the xylose metabolizing enzyme. The polynucleotides of the present invention further comprise nucleic acids encoding xylanases or a domain, fragment, variant, or derivative thereof, fused to a polynucleotide encoding a marker sequence which allows for detection of the polynucleotide of the present invention. In one embodiment of the invention, expression of the marker is independent from expression of the xylanase.

In one embodiment, the one or more polynucleotides of the present invention are stably integrated into the genome of the host cell. In one aspect, the polynucleotides are randomly integrated into the genome of the host cell. In another aspect, multiple copies of polynucleotides are randomly integrated into the genome of the host cell. In one aspect, at least two copies of polynucleotides are randomly integrated into the genome of the host cell.

In another embodiment, the one or more polynucleotides are not integrated into the genome of the host cell. In one aspect, the one or more polynucleotides are present in the host cell in a extrachromosomal plasmid.

In one embodiment, one or more polynucleotides of the present invention are stably integrated at a specific site in the genome of the host cell. In one aspect, the one or more polynucleotides are stably integrated at the site of one or more specific genes in the genome of the host cell. In one embodiment, the one or more specific genes are disrupted as a result of the one or more integration events. In another aspect, the one or more specific genes are deleted as a result of the one or more integration events. In one embodiment, the host cell cannot make the protein product(s) of the one or more specific disrupted genes. In another aspect, the host cell cannot make the protein product(s) of the one or more specific deleted genes. In a preferred embodiment, the one or more polynucleotides are stably integrated at the site of the lactate dehydrogenase gene in the genome of the host cell.

In one embodiment, the start codon of a polynucleotide of the present invention is integrated in frame with the promoter of a specific gene in the genome of the host cell. In another embodiment, the stop codon of a polynucleotide of the invention is integrated in frame with the terminator of a specific gene in the genome of the host cell. In one embodiment, the start codon of a polynucleotides is integrated in frame with the promoter of a specific gene in the genome of the host cell, and the terminator of the same polynucleotide is also integrated in frame with the terminator of the specific gene.

In one embodiment, the one or more polynucleotides are part of an operon. In one aspect, the start codon of the first polynucleotides in the operon is integrated in frame with the promoter of a specific gene in the genome of the host cell. In another aspect, the stop codon of the last polynucleotides in the operon is integrated in frame with the terminator of a specific gene in the genome of the host cell. In one embodiment, the start codon of the first polynucleotide in the operon is integrated in frame with the promoter of a specific gene in the genome of the host cell, and the stop codon of the last polynucleotide in the operon is integrated in frame with the terminator of the specific gene.

Codon Optimized Polynucleotides

The polynucleotides of the invention can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 8. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 8

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://www.kazusa.or.jp/codon/ (visited Dec. 21, 2011), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for *Clostridium thermocellum* are reproduced below as Table 9. This table uses mRNA nomenclature, and so instead of thymine (T) which is found in DNA, the table uses uracil (U) which is found in RNA. The table has been adapted so that frequencies are calculated for each amino acid, rather than for all 64 codons.

TABLE 9

Codon Usage Table for *Clostridium thermocellum* Genes

| Amino Acid | Codon | Number | Frequency per thousand |
|---|---|---|---|
| Phe | UUU | 33708 | 31.4 |
| Phe | UUC | 11609 | 10.8 |
| Leu | UUA | 14541 | 13.6 |
| Leu | UUG | 22069 | 20.6 |
| Leu | CUU | 29310 | 27.3 |
| Leu | CUC | 5946 | 5.5 |
| Leu | CUA | 3307 | 3.1 |
| Leu | CUG | 17685 | 16.5 |

TABLE 9-continued

Codon Usage Table for *Clostridium thermocellum* Genes

| Amino Acid | Codon | Number | Frequency per thousand |
|---|---|---|---|
| Ile | AUU | 138715 | 36.1 |
| Ile | AUC | 12546 | 11.7 |
| Ile | AUA | 39530 | 36.9 |
| Met | AUG | 26236 | 24.5 |
| Val | GUU | 27407 | 25.6 |
| Val | GUC | 8318 | 7.8 |
| Val | GUA | 22260 | 20.8 |
| Val | GUG | 18418 | 17.2 |
| Ser | UCU | 8481 | 7.9 |
| Ser | UCC | 11589 | 10.8 |
| Ser | UCA | 12797 | 11.9 |
| Ser | UCG | 6968 | 6.5 |
| Ser | AGU | 11506 | 10.7 |
| Ser | AGC | 13305 | 12.4 |
| Pro | CCU | 11646 | 10.9 |
| Pro | CCC | 7085 | 6.6 |
| Pro | CCA | 5359 | 5.0 |
| Pro | CCG | 12219 | 11.4 |
| Thr | ACU | 12643 | 11.8 |
| Thr | ACC | 14186 | 13.2 |
| Thr | ACA | 17970 | 16.8 |
| Thr | ACG | 9132 | 8.5 |
| Ala | GCU | 15775 | 14.7 |
| Ala | GCC | 16131 | 15.0 |
| Ala | GCA | 24707 | 23.0 |
| Ala | GCG | 11699 | 10.9 |
| Tyr | UAU | 30600 | 28.5 |
| Tyr | UAC | 14622 | 13.6 |
| His | CAU | 10285 | 9.6 |
| His | CAC | 4968 | 4.6 |
| Gln | CAA | 11015 | 10.3 |
| Gln | CAG | 16436 | 15.3 |
| Asn | AAU | 34401 | 32.1 |
| Asn | AAC | 23283 | 21.7 |
| Lys | AAA | 55999 | 52.2 |
| Lys | AAG | 30476 | 28.4 |
| Asp | GAU | 35175 | 32.8 |
| Asp | GAC | 25798 | 24.1 |
| Glu | GAA | 54980 | 51.3 |
| Glu | GAG | 26502 | 24.7 |
| Cys | UGU | 6020 | 5.6 |
| Cys | UGC | 6488 | 6.0 |
| Trp | UGG | 9460 | 8.8 |
| Arg | CGU | 4135 | 3.9 |
| Arg | CGC | 2988 | 2.8 |
| Arg | CGA | 1989 | 1.9 |
| Arg | CGG | 3581 | 3.3 |
| Arg | AGA | 20471 | 19.1 |
| Arg | AGG | 13476 | 12.6 |
| Gly | GGU | 18094 | 16.9 |
| Gly | GGC | 15050 | 14.0 |
| Gly | GGA | 29764 | 27.7 |
| Gly | GGG | 8599 | 8.0 |
| Stop | UAA | 1762 | 1.6 |
| Stop | UAG | 633 | 0.6 |
| Stop | UGA | 796 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 9 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 9 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTl Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Dec. 18, 2009) and the "backtranseq" function available at http://emboss.bioinformatics.nl/cgi-bin/emboss/backtranseq (visited Dec. 18, 2009). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be, for example, versions encoding a xylose metabolizing enzyme of the invention, or domains, fragments, variants, or derivatives thereof.

Codon optimization is carried out for a particular species by methods described herein, for example, in certain embodiments codon-optimized coding regions encoding polypeptides disclosed in the present application or domains, fragments, variants, or derivatives thereof are optimized according to codon usage in bacteria (e.g., *Clostridium thermocellum*). In certain embodiments described herein, a codon-optimized coding region encoding any of SEQ ID NOs: 3-4 or domain, fragment, variant, or derivative thereof, is optimized according to codon usage in *Clostridium*. In some embodiments, the sequences are codon-optimized specifically for expression in *Clostridium thermocellum*. Alternatively, a codon-optimized coding region encoding any of SEQ ID NOs: 3-4 can be optimized according to codon usage in any plant, animal, or microbial species.

Also provided are polynucleotides, vectors, and other expression constructs comprising codon-optimized coding regions encoding polypeptides disclosed herein, or domains, fragments, variants, or derivatives thereof, and various methods of using such polynucleotides, vectors and other expression constructs.

Vectors and Methods of Using Vectors in Host Cells

In another aspect, the present invention relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Any suitable promoter to drive gene expression in the host cells of the invention may be used.

In addition, the expression vectors may contain one or more selectable marker genes to provide a phenotypic trait for selection of transformed host cells such as URA3, HIS3, LEU2, TRPI, LYS2 or ADE2, dihydrofolate reductase, neomycin (G418) resistance or zeocin resistance for eukaryotic cell culture, or tetracycline or ampicillin resistance in prokaryotic cell culture, e.g., *Clostridium thermocellum*.

The expression vector may also contain a ribosome binding site for translation initiation and/or a transcription terminator. The vector may also include appropriate sequences for amplifying expression, or may include additional regulatory regions.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a host cell as described elsewhere in the application. The host cell can be, for example, a lower eukaryotic cell, such as a yeast cell, e.g., *Saccharomyces* cerevisiae or Kluyveromvces, or the host cell can be a prokaryotic cell, such as a bacterial cell, e.g., Clostridium thermocellum.

The selection of an appropriate host is deemed to be within the scope of those skilled in the art from the teachings herein. In one embodiment, the vector is integrated into the genome of the host cell. In another embodiment, the vector is present in the host cell as an extrachromosomal plasmid.

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce less ethanol, or more lactic acid and/or more acetate.

Methods of Using Host Cells to Produce Ethanol or Other Fermentation Products

Microorganisms produce a diverse array of fermentation products, including organic acids, such as lactate (the salt form of lactic acid), acetate (the salt form of acetic acid), pyruvate, succinate, and butyrate, and neutral products, such as ethanol, butanol, acetone, and butanediol. Fermentive products include biofuels, chemicals, compounds suitable as liquid fuels, gaseous fuels, reagents, chemical feedstocks, chemical additives, processing aids, food additives, and other products. For example, see International Publication No. WO 2010/105194, International Application No. PCT/US2010/046172, and U.S. Provisional Application Nos. 61/331,657 and 61/351,133.

In one aspect, the present invention is directed to use of host cells and co-cultures to produce ethanol or other products from the xylose portion of biomass substrates. Such methods can be accomplished, for example, by contacting a xylose-containing lignocellulosic substrate with a host cell or a co-culture of the present invention. In another aspect, the present invention is directed to use of host cells and co-cultures to produce ethanol or other products from the xylan portion of biomass substrates. Fermentation products include, but are not limited to products such as ethanol, propanol, isoamyl alcohol, butanol, acetate, amino acids, and vitamins.

In one embodiment, the end products of xylose fermentation by the host strain comprise pyruvate, acetate, and ethanol. In another embodiment, the end products of xylose fermentation by the host strain comprises acetate, and ethanol. In one aspect, the ratio of acetate to ethanol formed can be at least about 10:1, at least about 5:1, at least about 2:1, at least about 1:1, at least about 1:2, at least about 1:5, at least about 1:10, at least 1:100, at least 1:1000, or at least 1:10,000. In one embodiment, the end products of xylan fermentation by the host strain contain no detectable acetate. In another embodiment, the end products of xylan fermentation by the host strain comprise ethanol. In one embodiment, the host cell is further engineered in order to increase ethanol production from xylose fermentation by the host cell. In one embodiment, the PTA gene is deleted in order to increase ethanol production from xylose fermentation by the host cell. In one aspect, the deletion of the PTA gene results in ethanol being the major end product of xylose fermentation by the host cell. In another aspect, the deletion of the PTA gene results in the production of ethanol as theend product of xylose fermentation by the host cell, with the virtual elimination of one or more undesirable end products (e.g. end products other than ethanol or carbon dioxide). In another aspect, the deletion of the PTA gene results in the production of ethanol as the end product and the production of no undesirable end product. In another embodiment, no, or significantly no lactate or acetate, or both, is produced.

The production of ethanol can, according to the present invention, be performed at temperatures of at least about 25° C., about 28° C., about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments of the present invention, the thermotolerant host cell can produce ethanol from a xylose-containing or a xylan-containing cellulosic substrate at temperatures above about 30° C., about 31° C., about 32° C., about 33° C., about 34° C., about 35° C., about 36° C., about 37° C., about 38° C. about 39° C. about 40° C. about 41° C. about 42° C. or about 50° C. In some embodiments of the present invention, the thermotolterant host cell can produce ethanol from a xylose-containing or a xylan-containing cellulosic substrate at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a xylose-containing and/or xylan-containing lignocellulosic substrate with a host cell or co-culture of the invention and additionally contacting the xylose-containing lignocellulosic substrate with externally produced xylose metabolizing enzymes and/or xylanases. Exemplary externally produced xylose metabolizing enzymes are commercially available and are known to those of skill in the art. Exemplary externally produced xylanases are also commercially available and are known to those of skill in the art.

In some embodiments, the recombinant host cell of the invention is further selected by growth on a medium containing xylose as the only sugar source for at least 2, 5, 10, 15, 20, or 100 generations to generate a second recombinant host cell which utilizes xylose more efficiently than an otherwise identical cell that has not undergone the selection.

The invention is also directed to methods of reducing the amount of externally produced xylose metabolizing enzymes required to produce a given amount of ethanol from a xylose-containing cellulosic substrate comprising contacting the xylose-containing cellulosic substrate with externally produced xylose metabolizing enzymes and with a host cell or co-culture of the invention. In some embodiments, the same amount of ethanol production can be achieved using at least about 5%. 10%, 15%, 20%, 25%, 30%, or 50% fewer externally produced xylose metabolizing enzymes. In other embodiments, ethanol production can be achieved without the addition of externally produced xylose metabolizing enzymes.

The invention is further directed to methods of reducing the amount of externally produced xylanases required to produce a given amount of ethanol from a xylan-containing cellulosic substrate comprising contacting the xylan-containing cellulosic substrate with externally produced xylanases and with a host cell or co-culture of the invention. In some embodiments, the same amount of ethanol production can be achieved using at least about 5%, 10%, 15%, 20%, 25%, 30%, or 50% fewer externally produced xylanases. In other embodiments, ethanol production can be achieved without the addition of externally produced xylanases.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter more than a control strain (lacking heterologous xylose metabolizing enzymes) and grown under the same conditions. In some embodiments, the ethanol can be produced in the absence of any externally added xylose metabolizing enzymes.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

The U.S. Department of Energy (DOE) provides a method for calculating theoretical ethanol yield. Accordingly, if the weight percentages are known of C6 sugars (i.e., glucan, galactan, mannan), the theoretical yield of ethanol in gallons per dry ton of total C6 polymers can be determined by applying a conversion factor as follows:

> (1.11 pounds of $C6$ sugar/pound of polymeric sugar)×(0.51 pounds of ethanol/pound of sugar)×(2000 pounds of ethanol/ton of $C6$ polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

And if the weight percentages are known of C5 sugars (i.e., xylan, arabinan), the theoretical yield of ethanol in gallons per dry ton of total C5 polymers can be determined by applying a conversion factor as follows:

> (1.136 pounds of $C5$ sugar/pound of $C5$ polymeric sugar)×(0.51 pounds of ethanol/pound of sugar)×(2000 pounds of ethanol/ton of $C5$ polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.:

It follows that by adding the theoretical yield of ethanol in gallons per dry ton of the total C6 polymers to the theoretical yield of ethanol in gallons per dry ton of the total C5 polymers gives the total theoretical yield of ethanol in gallons per dry ton of feedstock.

In one embodiment, the invention provides for a method of making a pentose sugar fermentation product comprising incubating a reaction mixture comprising a biomass comprising one or more pentose sugars and a microorganism capable of fermenting one or more pentose sugars. In one aspect, the microorganism capable of fermenting one or more pentose sugars is a *Clostridium* species. In one aspect, the *Clostridium* species is *Clostridium thermocellum*. In one embodiment, the *Clostridium thermocellum* is the recombinant *Clostridium thermocellum* host cell of the invention. In one embodiment, the pentose sugar is xylose. In one embodiment, the xylose fermentation product comprises ethanol, acetate, and/or pyruvate. In one embodiment, the xylose fermentation end product is ethanol.

In one embodiment, the invention provides for a method of fermenting xylose comprising incubating a reaction mixture comprising a biomass comprising one or more pentose sugars and a microorganism capable of fermenting the one or more pentose sugars. In one aspect, the pentose sugar is xylose. In one aspect, the microorganism capable of fermenting one or more pentose sugars is a *Clostridium* species. In one aspect, the *Clostridium* species is *Clostridium thermocellum*. In one embodiment, the *Clostridium thermocellum* is the recombinant *Clostridium thermocellum* host cell of the invention.

In yet another embodiment, the invention provides a fermentation broth comprising: a microorganism capable of fermenting one or more pentose sugars and a media. In one aspect, the pentose sugar is xylose. In one aspect, the microorganism capable of fermenting one or more pentose sugars is a *Clostridium* species. In one aspect, the *Clostridium* species is *Clostridium thermocellum*. In one aspect, the *Clostridium thermocellum* is the recombinant *Clostridium thermocellum* host cell of the invention. In one embodiment, the media comprises one or more pentose sugars. In one aspect, the pentose sugar is xylose. In one embodiment, the media is capable of supporting the growth of the microorganism capable of fermenting one or more pentose sugars.

EXEMPLIFICATION

The invention now being generally described, it will be more readily understood by reference to the following examples, which are included merely for purposes of illustration of certain aspects and embodiments of the present invention, and are not intended to limit the invention.

Example 1

Creation of Δldh::XI/XK (T2) Strain

Figure 1:
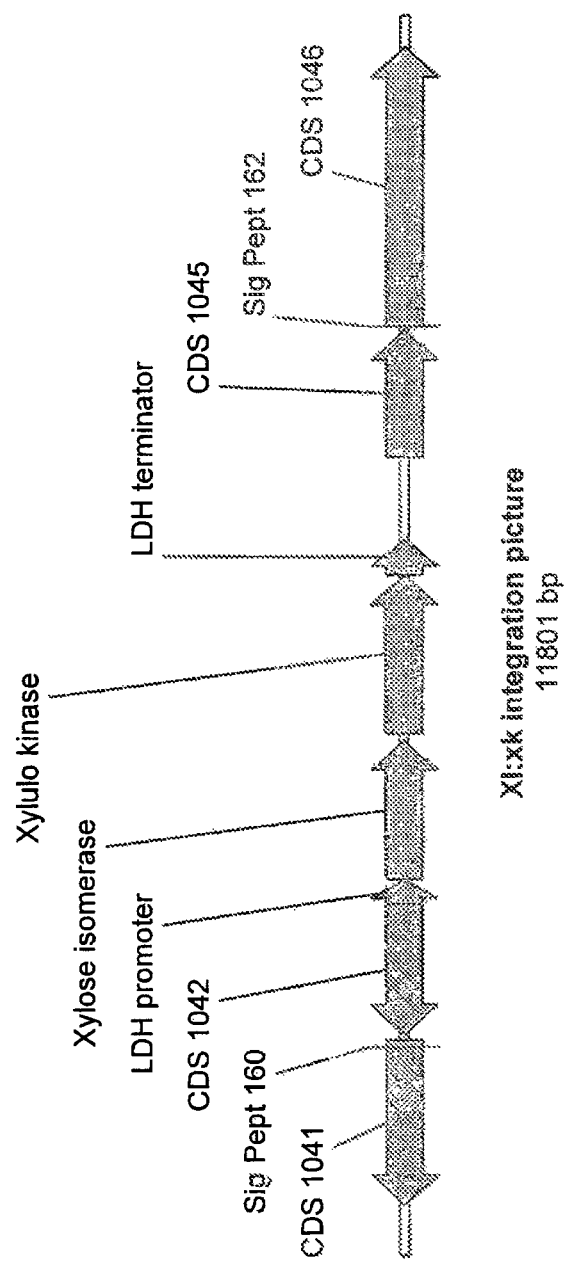
FIG. 1 depicts the integration of xylose isomerase/xylulokinase at the LDH locus.

The present invention provides methods for generating C. thermocellum expressing the enzymes XI and XK. To do this, a molecular cassette was designed to fuse the XI/XK operon with the LDH promoter and terminator sequences on the chromosome of C. thermocellum (FIG. 1). In the process of seamless integration the LDH open reading frame is deleted and the resulting strain cannot make lactate.

In order to integrate the XI/XK operon on the chromosome, plasmid pMU1793 was designed and built (FIG. 2). This plasmid was transformed into a C. thermocellum containing a deletion of the hypoxanthine phosphoribosyl transferase (HPT) gene. This background is required to facilitate the genetic selections for the integration event and is not relevant to the invention. Two rounds of genetic selections were conducted. The first round selected against the plasmid and for integration of the XI/XK operon and selectable markers. In the second round, the markers were removed resulting in a seamless integration of the XI/XK operon in frame with the LDH promoter and terminator. The seamless integration was confirmed by diagnostic PCR (FIG. 3).

Example 2

Growth of Δldh::XI/XK (T2) Strain on Xylose

The resulting strain from Example 1 was inoculated in several tubes of CTFUD medium containing xylose concentrations ranging from 5-100 g/l. After 7 days an increase in OD as observed in 10, 20, 50 g/l xylose. These strains were further analyzed by diagnostic PCR and 16S sequencing. Both results indicated the sample was a pure culture of C. thermocellum. End point samples were taken and analyzed by HPLC. After 156 hrs, significant xylose consumption was observed (FIG. 4). No turbidity was observed in medium that had been inoculated with wild type C. thermocellum and the samples were not analyzed by HPLC.

Example 3

Xylose Fermentation by the Δldh::XI/XK (T2) Strain

C. thermocellum makes ethanol, lactate and acetate as the primary fermentation end products. The T2 Δldh::XI/XK strain was observed to produce small amounts of acetate, ethanol and pyruvate (FIG. 5). No lactate was observed, a result which is expected given the deletion of the LDH gene. The relatively large amount of pyruvate observed in the medium indicated the cells were likely under stress.

The Δldh::Xi/Xk culture grown in 20 g/l was serially transferred two times in the same medium creating T3 and T4 culture. The OD of these transfers was monitored and analyzed by microscopy. A pattern was observed that begins with no growth in the first 24 hrs post innoculation. After 48 hrs a slight increase in OD was observed and high frequency sporulation was observed (FIG. 6). Sporulation is a phenomenon that is not easy to produce in C. thermocellum and has only been observed at this frequency in the early stages of directed evolution of the ΔldhΔpta strain. Given the metabolic perturbation introduced to both Δldh::Xi/XK and ΔldhΔpta strains, this data may indicate C. thermocellum sporulates in response to redox stress. After 72 hrs, the sporulation phenomenon observed in the T3 and T4 cultures was replaced by long stressed out cells (FIG. 7).

Example 4

Xylose Fermentation by the Δldh::XI/XK (T6) Strain

Serial transfer of the Δldh::XI/XK culture was continued for two more generations, thereby creating a T6 strain. Endpoint analysis was done on the T6 culture grown in both 10 and 20 g/l xylose. The results indicated the culture was evolving to make acetate preferentially since a 5:1 acetate to ethanol ratio was observed (FIG. 8).

Molecular QC was performed on the T6 strain and again confirmed the strain was a pure culture of C. thermocellum. The T6 strain was inoculated into medium containing 10 g/l avicel to further support that the culture was indeed C. thermocellum. Growth on avicel was rapid, indicating the organism that had been transferred was highly cellulolytic. Interesting, the acetate:ethanol remained at 5:1 even on a cellulose based carbon source (FIG. 9). No lactate was observed which is expected because of the LDH deletion.

Example 5

Creation of Δhpt, Δldh:XI/XdΔpta Strain

The T6 strain described above was able to grow on xylose, however acetate was still produced. In order to generate a high yielding strain, production of acetate should be eliminated, which can be accomplished by deletion of the PTA gene.

Thus, to create a strain capable of converting xylose into ethanol as the end product, with the virtual elimination of other undesirable end products or with the production of no undesirable end product, it was necessary to delete the PTA gene. Since, the Δldh::XI/XK strain evolved to make a 5:1 acetate to ethanol, the unevolved strain was chosen as a background for this mutation. The procedure to delete PTA in the Δldh:XI/XK background was as disclosed in Argyros et al., *Appl. Environ. Microbiol.*, 77:8288-8294, 2011. Briefly, the Δldh:XiXK strain was transformed with plasmid pMU1817 which has been used previously to delete PTA. The genetic selections were performed as above and a Δpta, Δldh:XI/XK strain was confirmed by diagnostic PCR. This strain was transferred on minimal medium 10 times and frozen down for further analysis.

Additionally, from the resulting strain of Example 1, strain M2236 was constructed. Strain M2236 further contains a deletion of the PTA gene, resulting in a strain that is Δhpt, Δldh:XI/XKΔpta. A MI570 strain is used as a control strain of C. thermocellum. M1570 has both LDH and PTA deletions but does not contain the *T. saccharolyticunm* XI/XK genes and is unable to ferment xylose into ethanol.

Example 6

Xylose Fermentation by the Δhpt, Δldh::XU/XKΔpta Strain

The M1570 (ΔhptΔldhΔpta) and M2236 strains were grown in CM3 medium containing xylose as the only sugar source. The concentrations of xylose and ethanol were measured using HPLC at both 24 hrs. and 48 hrs. FIG. 10 shows that xylose is consumed and ethanol is produced by the M2236 strain. In contrast, the M1570 strain is unable to convert significant amounts of xylose to ethanol. No lactate or acetate was detected in either fermentation.

INCORPORATION BY REFERENCE

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant *Clostridium thermocellum* host cell capable of fermenting xylan, wherein the host cell comprises one or more heterologous polynucleotides encoding one or more xylanase enzymes, wherein the polynucleotide comprises a nucleotide sequence from any one of the nucleotide sequences of SEQ ID NOs: 5-21,
wherein the host cell further comprises one or more additional heterologous polynucleotides encoding a xylose isomerase and/or a xylulokinase, and
wherein the heterologous polynucleotide that encodes the xylose isomerase comprises the nucleotide sequence of SEQ ID NO: 1 and the heterologous polynucleotide that encodes the xylulokinase comprises the nucleotide sequence of SEQ ID NO: 2.

2. The recombinant *Clostridium* thermocellum host cell of claim 1, wherein one or more heterologous polynucleotides are integrated at a specific site in the genome of the host cell.

3. The recombinant *Clostridium thermocellum* host cell of claim 2, wherein the integration of at least one of the heterologous polynucleotides occurs at the site of a specific gene in the genome of the host cell.

4. The recombinant *Clostridium thermocellum* host cell of claim 3, wherein the specific gene is disrupted as a result of integration of the heterologous polynucleotide.

5. The recombinant *Clostridium thermocellum* host cell of claim 3, wherein the specific gene is deleted as a result of integration of the heterologous polynucleotide.

6. The recombinant *Clostridium thermocellum* host cell of claim 4, wherein the host cell cannot make the protein product of the disrupted gene.

7. The recombinant *Clostridium thermocellum* host cell of claim 5, wherein the host cell cannot make the protein product of the deleted gene.

8. The recombinant *Clostridium thermocellum* host cell of claim 1, wherein one or more heterologous polynucleotides are present in the host cell in an extrachromosomal plasmid.

9. The recombinant *Clostridium thermocellum* host cell of claim 1, wherein one or more heterologous polynucleotides are randomly integrated into the genome of the host cell.

10. The recombinant *Clostridium thermocellum* host cell of claim 1, wherein the host cell ferments xylan to ethanol.

11. A co-culture comprising the recombinant *Clostridium thermocellum* host cell of claim 1 and at least one other host cell.

12. The co-culture of claim 11, wherein the host cells express the same xylan metabolizing enzymes.

13. The co-culture of claim 11, wherein the host cells express different xylan metabolizing enzymes.

14. The co-culture of claim 11, wherein the host cells express at least one common xylan metabolizing enzyme.

15. The recombinant *Clostridium thermocellum* host cell of claim 1, wherein the one or more heterologous polynucleotides that encode a xylanase enzyme encode a polypeptide comprising an amino acid sequence from any one of the amino acid sequences of SEQ ID NOs: 22-38.

16. The recombinant *Clostridium thermocellum* host cell of claim 1, further comprising one or more heterologous polynucleotides encoding one or more xylose transporters, wherein the polynucleotide comprises a nucleotide sequence from any one of the nucleotide sequences of SEQ ID NOs: 39-50.

17. The recombinant *Clostridium thermocellum* of claim 16, wherein the one or more heterologous polynucleotides that encode a xylose transporter encode a polypeptide comprising an amino acid sequence from any one of the amino acid sequences of SEQ ID NOs: 51-62.

18. The recombinant *Clostridium thermocellum* host cell of claim 1, wherein the host cell further comprises a lactate dehydrogenase promoter and terminator.

19. The recombinant *Clostridium thermocellum* host cell of claim 1, wherein one or more heterologous polynucleotides encoding one or more xylanse enzymes are expressed.

20. The recombinant *Clostridium thermocellum* host cell of claim 19, wherein expression of one or more heterologous polynucleotides confers to the recombinant host cell the ability to ferment xylan.

21. The recombinant *Clostridium thermocellum* host cell of claim 1, further comprising a deletion of one or more genes endogenous to the host cell.

22. The recombinant *Clostridium thermocellum* host cell of claim 21, wherein the deletion of one or more genes endogenous to the host cell comprises the hypoxanthine phosphoribosyl transferase (HPT) gene.

23. The recombinant *Clostridium thermocellum* host cell of claim 21, wherein the deletion of one or more genes endogenous to the host cell comprises the phosphotransacetylase (PTA) gene.

24. The recombinant *Clostridium thermocellum* of claim 1, wherein the heterologous polynucleotide that encodes a xylose isomerase encodes a polypeptide comprising the amino acid sequence of SEQ ID NO: 3.

25. The recombinant *Clostridium thermocellum* host cell of claim 1, wherein expression of the heterologous polynucleotide encoding the xylose isomerase confers to the recombinant host cell the ability to ferment xylose.

26. The recombinant *Clostridium thermocellum* of claim 1, wherein the heterologous polynucleotide that encodes a xylulokinase encodes a polypeptide comprising the amino acid sequence of SEQ ID NO: 4.

* * * * *